United States Patent [19]
Bemis et al.

[11] Patent Number: 6,103,711
[45] Date of Patent: Aug. 15, 2000

[54] INHIBITORS OF INTERLEUKIN-1β CONVERTING ENZYME

[75] Inventors: Guy W. Bemis, Arlington, Mass.; Julian M. C. Golec, Swindon, United Kingdom; David J. Lauffer, Stow, Mass.; Michael D. Mullican, Needham, Mass.; Mark A. Murcko, Holliston, Mass.; David J. Livingston, Newtonville, Mass.

[73] Assignee: Vertex Pharmaceuticals, Incorporated, Cambridge, Mass.

[21] Appl. No.: 08/465,216

[22] Filed: Jun. 5, 1995

Related U.S. Application Data

[60] Division of application No. 08/440,898, May 25, 1995, Pat. No. 5,847,135, which is a continuation-in-part of application No. 08/261,452, Jun. 17, 1994, Pat. No. 5,756,466.

[51] Int. Cl.$^7$ .................................................. A01N 43/00
[52] U.S. Cl. ........................... 514/183; 514/19; 514/214; 514/221; 514/248; 514/299; 514/306; 540/567
[58] Field of Search ..................................... 530/331, 332; 514/16–18, 183, 19, 214, 221, 248, 299, 306; 540/567

[56] References Cited

U.S. PATENT DOCUMENTS

| | | | |
|---|---|---|---|
| 4,276,298 | 6/1981 | Jones et al. | 424/270 |
| 4,369,183 | 1/1983 | Jones et al. | 424/263 |
| 4,499,295 | 2/1985 | Mueller et al. | 560/53 |
| 4,551,279 | 11/1985 | Mueller et al. | 260/404 |
| 4,584,397 | 4/1986 | Mueller et al. | 560/75 |
| 4,968,607 | 11/1990 | Dower et al. | 435/69.1 |
| 5,008,245 | 4/1991 | Digenis et al. | 514/18 |
| 5,055,451 | 10/1991 | Krantz et al. | 514/19 |
| 5,081,228 | 1/1992 | Dower et al. | 530/35.1 |
| 5,158,936 | 10/1992 | Krantz et al. | 514/19 |
| 5,180,812 | 1/1993 | Dower et al. | 530/351 |
| 5,374,623 | 12/1994 | Zimmerman et al. | 514/17 |
| 5,411,985 | 5/1995 | Bills et al. | 514/460 |
| 5,416,013 | 5/1995 | Black et al. | 435/226 |
| 5,430,128 | 7/1995 | Chapman et al. | 530/330 |
| 5,434,248 | 7/1995 | Chapman et al. | 530/330 |
| 5,462,939 | 10/1995 | Dolle et al. | 514/231.5 |
| 5,486,623 | 1/1996 | Zimmerman et al. | 549/417 |
| 5,498,616 | 3/1996 | Mallamo et al. | 514/300 |
| 5,498,695 | 3/1996 | Daumy et al. | 530/331 |
| 5,552,400 | 9/1996 | Dolle | 514/221 |
| 5,565,430 | 10/1996 | Dolle | 514/19 |
| 5,585,357 | 12/1996 | Dolle et al. | 514/18 |
| 5,585,486 | 12/1996 | Dolle | 444/182 |
| 5,585,537 | 12/1996 | Dolle | 514/18 |
| 5,639,745 | 6/1997 | Dolle | 514/183 |
| 5,670,494 | 9/1997 | Dolle | 514/86 |

FOREIGN PATENT DOCUMENTS

| | | | |
|---|---|---|---|
| 64514/94 | 12/1994 | Australia | C07F 9/32 |
| 0 275 101 | 7/1988 | European Pat. Off. | C07K 5/02 |
| 0 410 411 | 1/1991 | European Pat. Off. | C07K 5/04 |
| 0 417 721 | 3/1991 | European Pat. Off. | C07K 5/10 |
| 0 479 489 | 4/1992 | European Pat. Off. | C07K 5/08 |
| 0 504 938 | 9/1992 | European Pat. Off. | A61K 37/02 |
| 0 519 748 | 12/1992 | European Pat. Off. | C07K 5/04 |
| 0 525 420 | 2/1993 | European Pat. Off. | C07D 307/56 |
| 0 528 487 | 2/1993 | European Pat. Off. | C07K 5/10 |
| 0 529 713 | 3/1993 | European Pat. Off. | B01J 20/32 |
| 0 533 226 | 3/1993 | European Pat. Off. | C07K 5/10 |
| 0533 350 A1 | 3/1993 | European Pat. Off. | C12N 15/57 |
| 547 699 | 6/1993 | European Pat. Off. | C07K 5/02 |
| 0 618 223 | 10/1994 | European Pat. Off. | C07K 5/02 |
| 0 623 592 | 11/1994 | European Pat. Off. | C07C 271/22 |
| 0 623 606 | 11/1994 | European Pat. Off. | C07D 307/60 |
| 0 628 550 | 12/1994 | European Pat. Off. | C07D 237/24 |
| 0 644 198 | 3/1995 | European Pat. Off. | C07K 5/02 |
| WO 91/15577 | 10/1991 | WIPO | C12N 9/64 |
| WO 93/05071 | 3/1993 | WIPO | C07K 15/00 |
| WO 93/09135 | 5/1993 | WIPO | C07K 5/04 |
| WO 93/14777 | 8/1993 | WIPO | A61K 37/00 |
| WO 93/16710 | 9/1993 | WIPO | A61K 37/00 |
| WO 93/25683 | 12/1993 | WIPO | C12N 15/12 |
| WO 93/25685 | 12/1993 | WIPO | C12N 15/12 |
| WO 93/25694 | 12/1993 | WIPO | C12N 15/57 |
| WO 94/00154 | 1/1994 | WIPO | A61K 39/395 |
| WO 94/03480 | 2/1994 | WIPO | C07K 5/02 |
| WO 95/00160 | 1/1995 | WIPO | A61K 37/02 |
| WO 95/05192 | 2/1995 | WIPO | A61K 38/06 |

OTHER PUBLICATIONS

Elfond Buit J Pharm 1995, 115 601.

Spatola, Chem, Biochem Amino Acids & Peptides 268, 1983.

T. Graybill, et al. "Preparation and Evaluation of Peptidic Aspartyl hemiacetals as reversible inhibitors of interleukin–1β converting enzyme (ICE)", *Intl J. Peptide Protein Res.*, 44, pp. 173–182 (1994).

Ator, M.A. and Dolle, R. E., "Interleukin–1b Converting Enzyme: Biology and the Chemistry of Inhibitors" *Curr. Pharm. Design*, 1, pp. 191–210 (1995).

Elfond, P.R. et al., "Reduction of Inflammation and Pyrexia in the Rat by Oral Administration of SDZ 224–015, and Inhibitor of the Interleukin–1β Converting Enzyme", *British Journal of Pharmacology*, vol. 115, pp. 601–606 (Jun. 1995).

(List continued on next page.)

*Primary Examiner*—Cecilia J. Tsang
*Assistant Examiner*—David Lukton
*Attorney, Agent, or Firm*—Fish & Neave; James F. Haley, Jr.; Lisa A. Dixon

[57] ABSTRACT

The present invention relates to novel classes of compounds which are inhibitors of interleukin-1β converting enzyme. The ICE inhibitors of this invention are characterized by specific structural and physicochemical features. This invention also relates to pharmaceutical compositions comprising these compounds. The compounds and pharmaceutical compositions of this invention are particularly well suited for inhibiting ICE activity and consequently, may be advantageously used as agents against interleukin-1 mediated diseases, including inflammatory diseases, autoimmune diseases and neurodegenerative diseases. This invention also relates to methods for inhibiting ICE activity and methods for treating interleukin-1 mediated diseases using the compounds and compositions of this invention.

13 Claims, No Drawings

OTHER PUBLICATIONS

Fan, T.-P.D. et al., "Stimulation of Angiogenesis by Substance P and Interleukin–1 in the Rat and Its Inhibition by NK1 or Interleukin–1 Receptor Antagonists" *Br. J. Pharmacol.*, 110, 43–49 (1993).

Fauszt, I. et al., "Inhibition of Interleukin–1β Converting Enzyme by Peptide Derivatives," *Proc. of the 13th Am. Peptide Symp.*, Jun. 20–25, 1993; Hodges, R.S. and Smith, J.A., Eds., *Peptides*, pp. 589–591 (1994).

Fletcher, D.S. et al., "A Synthetic Inhibitor of Interleukin–1β Converting Enzyme Prevents Endotoxin–Induced Interleukin–1β Production In Vitro and In Vivo," *J. Interfer. Cytokin Res.*, 15, pp. 243–248 (1995).

Hanessian, S. et al., "Design and Synthesis of a Prototype Model Antagonist of Tachykinin NK–2 Receptor" *Bioorg. Med. Chem. Lett.*, 11, 1397–1400 (1994).

Mjalli, A.M.M. et al., "Phenylalkyl Ketones as Potent Reversible Inhibitors of Interleukin–1β Converting Enzyme," *Bioorg. Med. Chem. Lett.*, 3, pp. 2689–2692 (1993).

Mullican, M.D. et al., "The Synthesis and Evaluation of Peptidyl Aspartyl Aldehydes as Inhibitors of ICE" *Bioorg. Med. Chem. Lett.*, 4, 2359–2364 (1994).

Nalin, C.M., "Apoptosis Research Enters the ICE Age," *Structure*, 3, pp. 143–145 (1995).

Robinson, R.P. and Donahue, K.M., "Synthesis of a Peptidyl Difluoro Ketone Bearing the Aspartic Acid Side Chain: An Inhibitor of Interleukin–1β Converting Enzyme" J. Org. Chem., 57, 7309–7314 (1992).

Salvatore, M.J. et al., "L–741,494, A Fungal Metabolite that is an Inhibitor of Interleukin–1β Converting Enzyme," *J. Nat. Prods.*, 57, 755–760 (1994).

Spatola, A.F., in "Chemistry and Biochemistry of Amino Acids, Peptides, and Proteins," ch. 5, pp. 267–281, Weinstein, B., ed., Marcel Dekker, Inc., New York (1983).

D. Alberg & S. Schreiber, "Structure–Based Design of a Cyclophilin–Calcineurin Bridging Ligand", *Science*, 262, pp. 248–250 (1993).

P. Andrews, "Functional Groups, Drug–Receptor Interactions and Drug Design", *Trends Pharmacol. Sci.*, 7, pp. 148–151 (1986).

K. Appelt et al., "Design of Enzyme Inhibitors Using Iterative Protein Crystallographic Analysis", *J. Med. Chem.*, 34, pp. 1925–1934 (1991).

M. Ator, "Peptide and Non–peptide Inhibitors of Interleukin–1β Converting Enzyme", *Cambridge Healthtech Institute (Inflammatory Cytokine Antagonists Targets, Strategies, and Indication)*, (1994).

E. Baker & J. Drenth, "The Thiol Proteases: Structure and Mechanism", in *Biological Macromolecules and Assemblies*, 3, pp. 313–368 (F. Jurnak & A. McPherson eds., 1987).

J. Baldwin et al., "Thienothiopyran–2–sulfonamides: Novel Topically Active Carbonic Anhydrase Inhibitors for the Treatment of Glaucoma", *J. Med. Chem.*, 32, pp. 2510–2513 (1989).

M. Barinaga, "Death Gives Birth to the Nervous System. But How?", *Science*, 259, pp. 762–763 (1993).

P. Bartlett et al., "Caveat: A Program to Facilitate the Structure–derived Design of Biologically Active Molecules", *Molecular Recognition: Chemical and Biochemical Problems*, 78, pp. 182–196 (1989).

P. Bender & J. Lee, "Pharmacological Modulation of Interleukin–1", *Annu. Rep. Med. Chem.*, 25, pp. 185–193 (1989).

R. Black et al., "Activation of Interleukin–1β by a Co–induced Protease", *FEBS Lett*, 247, pp. 386–390 (1989).

H. Böhm, "The Computer Program LUDI: A New Method for the De Novo Design of Enzyme Inhibitors", *J. Comput. Aided Mol. Des.*, 6, pp. 61–78 (1992).

J. Breitner et al., "Inverse Association of Anti–inflammatory Treatments and Alzheimer's Disease: Initial Results of a Co–twin Control Study", *Neurology*, 44, pp. 227–232 (1994).

B. Brooks et al., "CHARMM: A Program for Macromolecular Energy, Minimization, and Dynamics Calculations", *J. Comput. Chem.*, 4, pp. 187–217 (1983).

A. Brünger, "Extension of Molecular Replacement: A New Search Strategy Based on Patterson Correlation Refinement", *Acta Crystallogr. A*, 46, pp. 46–57 (1990).

A. Brënger & A. Krukowski, "Slow–Cooling Protocols for Crystallographic Refinement by Simulated Annealing", *Acta Crystallogr. A*, 46, pp. 585–593 (1990).

U. Brukett & N. Allinger, "Methods for the Computation of Molecular Geometry" in *Molecular Mechanics*, pp. 59–78 (1982).

M. Carson, "Ribbons 2.0", *J. App. Crystallogr.*, 24, pp. 958–961 (1991).

F. Casano et al., "The Structure and Complete Nucleotide Sequence of the Murine Gene Encoding Interleukin–1β Converting Enzyme (ICE)", *Genomics*, 20, pp. 474–481 (1994).

D. Cerretti et al., "Molecular Cloning of the Interleukin–1β Converting Enzyme", *Science*, 256, pp. 97–100 (1992).

K. Chapman, "Synthesis of a Potent, Reversible Inhibitor of Interleukin–1β Converting Enzyme", *Bioorg. Med. Chem. Lett.*, 2, pp. 613–618 (1992).

N. Cohen, "Drug Design in Three Dimensions", *Advances in Drug Research*, 14, pp. 41–145 (1985).

N. Cohen, "Rational Drug Design and Molecular Modeling", *Drugs of the Future*, 10, pp. 311–328 (1985).

N. Cohen et al., "Molecular Modeling Software and Methods for Medicinal Chemistry", *J. Med. Chem.*, 33, pp. 883–894 (1990).

D. Davies & D. Segal, "Protein Crystallization: Micro Techniques Involving Vapor Diffusion", *Methods Enzymol.*, 22, pp. 266–269 (1971).

K. Dill, "Dominant Forces in Protein Folding", *Biochemistry*, 29, pp. 7133–7155 (1990).

C. Dinarello, "Role of Interleukin–1 in Infectious Diseases", *Immunol. Rev.*, 127, pp. 119–146 (1992).

C. Dinarello et al., "Anticytokine Strategies in the Treatment of the Systemic Inflammatory Response Syndrome", *J. Am. Med. Assoc.*, 269, pp. 1829–1835 (1993).

R. Dolle et al., "Aspartyl α–((1–Phenyl–3–(trifluoromethyl)–pyrazol–5–yl)oxy)methyl Ketones as Interleukin–1β Converting Enzyme Inhibitors. Significance of the $P_1$ and $P_3$ Amido Nitrogens for Enzyme-–Peptide Inhibitor Binding", *J. Med. Chem.*, 37, pp. 3863–3865 (1994).

R. Dolle et al., "Aspartyl α–((Diphenylphosphinyl)oxy)methyl Ketones as Novel Inhibitors of Interleukin–1β Converting Enzyme. Utility of the Diphenylphosphinic Acid Leaving Group for the Inhibition of Cysteine Proteases", *J. Med. Chem.*, 38, pp. 220–222 (1995).

R. Dolle et al., "$P_1$ Aspartate–Based Peptide α–((2, 6–Dichlorobenzoyl)oxy)methyl Ketones as Potent Time–Dependent Inhibitors of Interleukin–1β–Converting Enzyme" *J. Med. Chem.*, 37, pp. 563–564 (1994).

S. Ealick et al., "Application of Crystallographic and Modeling Methods in the Design of Purine Nucleoside Phosphorylase Inhibitors", *Proc. Natl. Acad. Sci. USA*, 88, pp. 11540–11544 (1991).

P. Edwards et al., "Design, Synthesis, and Kinetic Evaluation of a Unique Class of Elastase Inhibitors, the Peptidyl α–Ketobenzoxazoles, and the X–ray Crystal Structure of the Covalent Complex between Porcine Pancreatic Elastase and Ac–Ala–Pro–Val–2–Benzoxazole", *J. Am. Chem. Soc.*, 114, pp. 1854–1863 (1992).

H. Eklund et al., "Three–dimensional Structure of Horse Liver Alcohol Dehydrogenase at 2.4 Å Resolution", *J. Mol. Biol.*, 102, pp. 27–50 (1976).

J. Erickson et al., "Design, Activity, and 2.8 Å Crystal Structure of a $C_2$ Symmetric Inhibitor Complexed to HIV–1 Protease", *Science*, 249, pp. 527–533 (1990).

V. Gagliardini et al., "Prevention of Vertebrate Neuronal Death by the crmA Gene", *Science*, 263, pp. 826–828 (1994).

T. Geiger et al., "Neutralization of Interleukin–1β Activity in vivo with a Monoclonal Antibody Alleviates Collagen–induced Arthritis in DBA/1 Mice and Prevents the Associated Acute–phase Response", *Clin. Exp. Rheumatol.*, 11, pp. 515–522 (1993).

A. Giannis & T. Kolter, "Peptidomimetics for Receptor Ligands–Discovery, Development, and Medical Perspectives", *Angew. Chem. Int. Ed. Engl.* 32, pp. 1244–1267 (1993).

P. Goodford, "A Computational Procedure for Determining Energetically Favorable Binding Sites on Biologically Important Macromolecules", *J. Med. Chem.*, 28, pp. 849–857 (1985).

D. Goodsell & A. Olson, "Automated Docking of Substrates to Proteins by Simulated Annealing", *Proteins: Structure, Function, and Genetics*, 8, pp. 195–202 (1990).

T. Graybill et al., "The Preparation and Evaluation of Peptidic Aspartyl Hemiacetals as Reversible Inhibitors of ICE", *Am. Chem. Soc. Abs.* (*206th Natl. Mtg.*), MEDI 235 (1993).

W. Griffin et al., "Brain Interleukin 1 and S–100 Immunoreactivity are Elevated in Down Syndrome and Alzheimer Disease", *Proc. Natl. Acad. Sci. USA*, 86, pp. 7611–7615 (1989).

C. Hammerberg et al., "Interleukin–1 Receptor Antagonist in Normal and Psoriatic Epidermis", *J. Clin. Invest.*, 90, pp. 571–583 (1992).

E. Harris, "Rheumatoid Arthritis: Pathophysiology and Implications for Therapy", *N. Eng. J. Med.*, 322, pp. 1277–1289 (1990).

W. Hendrickson et al., "Selenomethionyl Proteins Produced for Analysis by Multiwavelength Anomalous Diffraction (MAD): A Vehicle for Direct Determination of Three–dimensional Structure", *EMBO J.*, 9, pp. 1665–1672 (1990).

R. Hirschmann et al., "The First Design and Synthesis of a Steroidal Peptidomimetic. The Potential Value of Peptidomimetics in Elucidating the Bioactive Conformation of Peptide Ligands", *J. Am. Chem. Soc.*, 114, pp. 9699–9701 (1992).

R. Hirschmann et al., "Nonpeptidal Peptidomimetics with a β–D–Glucose Scaffolding. A Partial Somatostatin Agonist Bearing a Close Structural Relationship to a Potent, Selective Substance P Antagonist", *J. Am. Chem. Soc.*, 114, pp. 9217–9218 (1992).

A. Holmgren et al., "Three–dimensional Structure of *Escherichia coli* Thioredoxin–$S_2$ to 2.8Å Resolution", *Proc. Natl. Acad. Sci. USA*, 72, pp. 2305–2309 (1975).

A. Hopfinger, "Computer–Assisted Drug Design", *J. Med. Chem.*, 28, pp. 1133–1139 (1985).

A. Hopfinger & B. Burke, "Molecular Shape Analysis: A Formalism to Quantitatively Establish Spatial Molecular Similarity", in *Concepts and Applications of Molecular Similarity*, pp. 173–209 (M. Johnson & G. Maggiora eds., 1990).

A. Howard et al., "High–Level Production and Characterization of Functional Human Interleukin–1β Converting Enzyme in Baculovirus and *E.coli* Expression Systems", *J. Cell. Biochem. Suppl.*, 17B, p. 146 (1993).

A. Howard et al., "Human Interleukin–1β Converting Enzyme: A Mutational Analysis of Proenzyme Activation", *J. Cell. Biochem. Suppl.*, 17B, p. 113 (1993).

A. Howard et al., "IL–1–Converting Enzyme Requires Aspartic Acid Residues for Processing of the IL–1β Precursor at Two Distinct Sites and Does Not Cleave 31–kDa IL–1α", *J. Immunol.*, 147, pp. 2964–2969 (1991).

J. Kamphuis et al., "Thiol Proteases: Comparative Studies Based on the High–rsolution Structures of Papain and Actinidin, and on Amino Acid Sequence Information for Cathepsins B and H, and Stem Bromelain", *J. Mol. Biol.*, 182, pp. 317–329 (1985).

J. Knowles, "Tinkering with Enzymes: What are We Learning?", *Science*, 236, pp. 1252–1258 (1987).

M. Kostura et al., "Identification of a Monocyte Specific Pre–Interleukin 1β Convertase Activity", *Proc. Natl. Acad. Sci. USA*, 86, pp. 5227–5231 (1989).

K. Kuida et al., "Altered Cytokine Export and Apoptosis in Mice Deficient in Interleukin–1β Converting Enzyme", *Science*, 267, pp. 2000–2003 (1995).

I. Kuntz et al., "A Geometric Approach to Macromolecule––Ligand Interactions", *J. Mol. Biol.*, 161, pp. 269–288 (1982).

E. Lattman, "Use of the Rotation and Translation Functions", *Methods Enzymol.*, 115, pp. 55–77 (1985).

P. Li et al., Mice Deficient in IL–1β–Converting Enzyme are Defective in Production of Mature IL–1β and Resistant to Endotoxic Shock, *Cell*, 80, pp. 401–411 (1995).

C. Lipinski, "Bioisosterism in Drug Design", *Annu. Rep. Med. Chem.*, 21, pp. 283–291 (1986).

G. Lonnemann et al., "Differences in the Synthesis and Kinetics of Release of Interleukin 1α, Interleukin 1β and Tumor Necrosis Factor from Human Mononuclear Cells", *Eur. J. Immunol.*, 19, pp. 1531–1536 (1989).

A. MacKenzie et al., "An Inhibitor of the Interleukin–1β–Processing Enzyme Blocks IL–1 Release and Reduces Pyrexia and Acute Inflammation", *Inflammation Research Association* (*7th Internat. Conf.*), W42 (1994).

T. Mandrup–Poulsen et al. "Involvement of Interleukin 1 and Interleukin 1 Antagonist in Pancreatic β–Cell Destruction in Insulin–dependent Diabetes Mellitus", *Cytokine*, 5, pp. 185–191 (1993).

C. March et al., "Cloning, Sequence and Expression of Two Distinct Human Interleukin–1 Complementary DNAs", *Nature*, 315, pp. 641–647 (1985).

G. Marshall, "Computer–Aided Drug Design", *Annu. Rev. Pharmacol. Toxicol.*, 27, pp. 193–213 (1987).

G. Marshall & I. Motoc, "Approaches to the Conformation of the Drug Bound to the Receptor", in *Molecular Graphics and Drug Design*, pp. 115–156 (A. Burgen et al. eds., 1986).

Y. Martin, "3D Database Searching in Drug Design", *J. Med. Chem.*, 35, pp. 2145–2154 (1992).

J. Marx, "Cell Death Studies Yield Cancer Clues", *Science*, 259, pp. 760–761 (1993).

D. Mayer et al., "A Unique Geometry of the Active Site of Angiotensin–Converting Enzyme Consistent with Structure– Activity Studies", *J. Comput. Aided Mol. Des.*, 1, pp. 3–16 (1987).

R. Ménard et al., "Contribution of the Glutamine 19 Side Chain to Transition–State Stabilization in the Oxyanion Hole of Papain", *Biochemistry*, 30, pp. 8924–8928 (1991).

R. Ménard et al., "Importance of Hydrogen–Bonding Interactions Involving the Side Chain of Asp 158 in the Catalytic Mechanism of Papain", *Biochemistry*, 30, pp. 5531–5538 (1991).

E. Meng et al., "Automated Docking with Grid–Based Energy Evaluation", *J. Comput. Chem.*, 13, pp. 505–524 (1992).

D. Miller et al., "The IL–1β Converting Enzyme as a Therapeutic Target", *Ann. N. Y. Acad. Sci.*, 696, pp. 133–148 (1993).

S. Miller et al., "The Accessible Surface Area and Stability of Oligomeric Proteins", *Nature*, 328, pp. 834–836 (1987).

B. Miller et al., "Inhibition of Mature IL–1β Production in Murine Macrophages and a Murine Model of Inflammation by WIN 67694, an Inhibitor of IL–1β Converting Enzyme", *J. Immunol.*, 154, pp. 1331–1338 (1995).

A. Miranker & M. Karplus, "Functionality Maps of Binding Sites: A Multiple Copy Simultaneous Search Method", *Proteins: Structure, Function, and Genetics*, 11, pp. 29–34 (1991).

M. Miura et al., "Induction of Apoptosis in Fibroblasts by IL–1β–Converting Enzyme, a Mammalian Homolog of the *C.elegans* Cell Death Gene ced–3", *Cell*, 75, pp. 653–660 (1993).

A. Mjalli et al., "Activated Ketones as Potent Reversible Inhibitors of Interleukin–1β Converting Enzyme", *Bioorg. Med. Chem. Lett.*, 4, pp. 1965–1968 (1994).

S. Molineaux et al., "Interleukin 1β(IL–1β) Processing in Murine Macrophages Requires a Structurally Conserved Homologue of Human IL–1β Converting Enzyme", *Proc. Natl. Acad. Sci. USA*, 90, pp. 1809–1813 (1993).

B. Mosley et al., "Determination of the Minimum Polypeptide Lengths of the Functionally Active Sites of Human Interleukins 1α and 1β", *Proc. Natl. Acad. Sci. USA*, 84, pp. 4572–4576 (1987).

M. Navia & M. Murcko, "Use of Structural Information in Drug Design", *Curr. Opin. Struc. Biol.*, 2, pp. 202–210 (1992).

M. Nett et al., "Molecular Cloning of the Murine IL–1β Converting Enzyme cDNA", *J. Immunol.*, 149, pp. 3254–3259 (1992).

M. Nett–Fiordalisi et al., "Characterization and Activation of the Murine Interleukin–1β (IL–1β) Converting Enzyme", *J. Cell. Biochem. Suppl.*, 17B, p. 117 (1993).

Y. Nishibata & A. Itai, "Automatic Creation of Drug Candidate Structures Based on Receptor Structure. Starting Point for Artificial Lead Generation", *Tetrahedron*, 47, pp. 8985–8990 (1991).

C. Noren et al., A General Method for Site–Specific Incorporation of Unnatural Amino Acids into Proteins, *Science*, 244, pp. 182–188 (1989).

I. Noronha et al., "In situ Production of TNF–α, IL–1β and IL–2R in ANCA–positive Glomerulonephritis", *Kidney Int.*, 43, pp. 682–692 (1993).

K. Ohlsson et al., "Interleukin–1 Receptor Antagonist Reduces Mortality from Endotoxin Shock", *Nature*, 348, pp. 550–552 (1990).

J. Oppenheim et al., "There is More than One Interleukin 1", *Immunol. Today*, 7, pp. 45–55 (1986).

M. Pennington & N. Thornberry, "Synthesis of a Fluorogenic Interleukin–1β Converting Enzyme Substrate Based on Resonance Energy Transfer", *Pept. Res.*, 7, pp. 72–76 (1994).

R. Peters & R. McKinstry, "Three–Dimensional Modeling and Drug Development: Has "Rational" Drug Design Arrived?" *Biotechnology (N Y)*, 12 pp. 147–150 (1994).

J. Plattner & D. Norbeck, "Obstacles to Drug Development from Peptide Leads", in *Drug Discovery Technologies*, pp. 92–126 (C. Clark & W. Moos eds., 1990).

L. Polgár, "On the Mode of Activation of the Catalytically Essential Sulfhydryl Group of Papain", *Eur. J. Biochem.*, 33, pp. 104–109 (1973).

C. Prasad et al., "$P_1$ Aspartate–Based Peptide α–arylacyloxy– and α–Aryloxymethyl Ketones as Potent Time–Dependent Inhibitors of Interleukin 1β Converting Enzyme", *Am. Chem. Soc. Abs.* (*24th Med. Chem. Symp.*), 66 (1994).

C. Ray et al., "Viral Inhibition of Inflammation: Cowpox Virus Encodes an Inhibitor of the Interleukin–1β Converting Enzyme", *Cell*, 69, pp. 597–604 (1992).

L. Reiter, "Peptidic p–Nitroanilide Substrates of Interleukin–1β–Converting Enzyme", *Int. J. Pept. Protein Res.*, 43, pp. 87–96 (1994).

L. Revesz et al., "Synthesis of P1 Aspartate–Based Peptide Acyloxymethyl and Fluoromethyl Ketones as Inhibitors of Interleukin–1β–Converting Enzyme", *Tetrahedron Lett.*, 35, pp. 9693–9696 (1994).

C. Ring et al., "Structure–based Inhibitor Design by Using Protein Models for the Development of Antiparasitic Agents," *Proc. Natl. Acad. Sci. USA*, 90, pp. 3583–3587 (1993).

J. Sandberg et al., "Treatment with an Interleukin–1 Receptor Antagonist Protein Prolongs Mouse Islet Allograft Survival", *Diabetes*, 42, pp. 1845–1851 (1993).

I. Schecter & A. Berger, "On the Size of the Active Site in Proteases. I. Papain", *Biochem. Biophys. Res. Commun.*, 27, pp. 157–162 (1967).

S. Schmidt et al., "Synthesis and Evaluation of Aspartyl α–Chloro–, α–Aryloxy–, and α–Arylacyloxymethyl Ketones as Inhibitors of Interleukin–1β Converting Enzyme", *Am. Chem. Soc. Abs.* (*208th Natl. Mtg.*), MEDI 4, (1994).

B. Shivers et al., "Molecular Cloning of Rat Interleukin–1β–Converting Enzyme: Distribution and Regulation", *J. Cell. Biochem. Suppl.*, 17B, p. 119 (1993).

I. Singer et al., "Interleukin 1β is Localized in the Cytoplasmic Ground Substance but is Largely Absent from the Golgi Apparatus and Plasma Membranes of Stimulated Human Monocytes", *J. Exp. Med.*, 167, pp. 389–407 (1988).

P. Sleath et al., "Substrate Specificity of the Protease that Processes Human Interleukin–1β", *J. Biol. Chem.*, 265, pp. 14526–14528 (1990).

R. Taylor & O. Kennard, "Hydrogen–Bond Geometry in Organic Crystals", *Acc. Chem. Res,*. 17, pp. 320–326 (1984).

C. Thornber, "Isosterism and Molecular Modification in Drug Design", *Chem. Soc. Rev.*, 8, pp. 563–580 (1979).

N. Thornberry et al., "A Novel Heterodimeric Cysteine Protease is Required for Interleukin–1β Processing in Monocytes", *Nature*, 356, pp. 768–774 (1992).

N. Thornberry et al., "Inactivation of Interleukin–1β Converting Enzyme by Peptide (Acyloxy)methyl Ketones", *Biochemistry*, 33, pp. 3934–3940 (1994).

J. Travis, "Proteins and Organic Solvents Make an Eye–Opening Mix", *Science*, 262, p. 1374 (1993).

J. Uhl et al., "Secretion of Human Monocyte Mature IL–1β: Optimization of Culture Conditions and Inhibition by ICE Inhibitors", *Inflammation Research Association (7th Internat. Conf.)*, W41 (1994).

P. Warner, et al., "Pyridone HLE Inhibitors: Variation of the 3 and 5 Substituents", *Royal Soc. Chem. Abs. (7th RSC–SCI Med. Chem. Symp.)*, P23 (1993).

S. Weiner et al., "A New Force Field for Molecular Mechanical Simulation of Nucleic Acids and Proteins", *J. Am. Chem. Soc.*, 106, pp. 765–784 (1984).

C. Wong & J. McCammon, "Dynamics and Design of Enzymes and Inhibitors", *J. Am. Chem. Soc.*, 108, pp. 3830–3832 (1986).

P. Wooley et al., "The Effect of an Interleukin–1 Receptor Antagonist Protein on Type II Collagen–induced Arthritis and Antigen–induced Arthritis in Mice", *Arthritis Rheum.*, 36, pp. 1305–1314 (1993).

J. Yuan et al., "The *C.elegans* Cell Death Gene ced–3 Encodes a Protein Similar to Mammalian Interleukin–1β–Converting Enzyme", *Cell*, 75, pp. 641–652 (1993).-

INHIBITORS OF INTERLEUKIN-1β CONVERTING ENZYME

This is a division, of application Ser. No. 08/440,898, filed May 25, 1995 entitled Inhibitors of Interleukin-1β Converting Enzyme which is a continuation in part application of application Ser. No. 08/261,452, filed on Jun. 17, 1994, entitled Inhibitors of Interleukin-1β Converting Enzyme, now U.S. Pat. No. 5,756,466.

TECHNICAL FIELD OF THE INVENTION

The present invention relates to novel classes of compounds which are inhibitors of interleukin-1β converting enzyme ("ICE"). The ICE inhibitors of this invention are characterized by specific structural and physicochemical features. This invention also relates to pharmaceutical compositions comprising these compounds. The compounds and pharmaceutical compositions of this invention are particularly well suited for inhibiting ICE activity and consequently, may be advantageously used as agents against interleukin-1 ("IL-1") mediated diseases, including inflammatory diseases, autoimmune diseases and neurodegenerative diseases. This invention also relates to methods for inhibiting ICE activity and methods for treating interleukin-1 mediated diseases using the compounds and compositions of this invention.

BACKGROUND OF THE INVENTION

Interleukin 1 ("IL-1") is a major pro-inflammatory and immunoregulatory protein that stimulates fibroblast differentiation and proliferation, the production of prostaglandins, collagenase and phospholipase by synovial cells and chondrocytes, basophil and eosinophil degranulation and neutrophil activation. Oppenheim, J. H. et al, *Immunology Today*, 7, pp. 45–56 (1986). As such, it is involved in the pathogenesis of chronic and acute inflammatory and autoimmune diseases. IL-1 is predominantly produced by peripheral blood monocytes as part of the inflammatory response and exists in two distinct agonist forms, IL-1α and IL-1β. Mosely, B. S. et al., *Proc. Nat. Acad. Sci.*, 84, pp. 4572–4576 (1987); Lonnemann, G. et al., *Eur. J. Immunol.*, 19, pp. 1531–1536 (1989).

IL-1β is synthesized as a biologically inactive precursor, pIL-1β. pIL-1β lacks a conventional leader sequence and is not processed by a signal peptidase. March, C. J., *Nature*, 315, pp. 641–647 (1985). Instead, pIL-1β is cleaved by interleukin-1β converting enzyme ("ICE") between Asp-116 and Ala-117 to produce the biologically active C-terminal fragment found in human serum and synovial fluid. Sleath, P. R., et al., *J. Biol. Chem.*, 265, pp. 14526–14528 (1992); A. D. Howard et al., *J. Immunol.*, 147, pp. 2964–2969 (1991). Processing by ICE is also necessary for the transport of mature IL-1β through the cell membrane.

ICE is a cysteine protease localized primarily in monocytes. It converts precursor IL-1β to the mature form. Black, R. A. et al., *FEBS Lett.*, 247, pp. 386–390 (1989); Kostura, M. J. et al., *Proc. Natl. Acad. Sci. USA*, 86, pp. 5227–5231 (1989). ICE, or its homologues, also appears to be involved in the regulation of cell death or apoptosis. Yuan, J. et al., *Cell*, 75, pp. 641–652 (1993); Miura, M. et al., *Cell*, 75, pp. 653–660 (1993); Nett-Fiordalisi, M. A. et al., *J. Cell Biochem.*, 17B, p. 117 (1993). In particular, ICE or ICE homologues are thought to be associated with the regulation of apoptosis in neurogenerative diseases, such as Alzheimer's and Parkinson's disease. Marx, J. and M. Baringa, *Science*, 259, pp. 760–762 (1993); Gagliardini, V. et al., *Science*, 263, pp. 826–828 (1994).

ICE has been previously described as a heterodimer composed of two subunits, p20 and p10 (20 kDa and 10 kDa molecular weight, respectively). These subunits are derived from a 45 kDa proenzyme (p45) by way of a p30 form, through an activation mechanism that is autocatalytic. Thornberry, N. A. et al., *Nature*, 356, pp. 768–774 (1992). The ICE proenzyme has been divided into several functional domains: a prodomain (p14), a p22/20 subunit, a polypeptide linker and a p10 subunit. Thornberry et al., supra; Casàno et al., *Genomics*, 20, pp. 474–481 (1994).

Full length p45 has been characterized by its cDNA and amino acid sequences. PCT patent applications WO 91/15577 and WO 94/00154. The p20 and p10 cDNA and amino acid sequences are also known. Thornberry et al., supra. Murine and rat ICE have also been sequenced and cloned. They have high amino acid and nucleic acid sequence homology to human ICE. Miller, D. K. et al., Ann. N.Y. Acad. Sci., 696, pp. 133–148 (1993); Molineaux, S. M. et al., *Proc. Nat. Acad. Sci.*, 90, pp. 1809–1813 (1993). Knowledge of the primary structure of ICE, however, does not allow prediction of its tertiary structure. Nor does it afford an understanding of the structural, conformational and chemical interactions of ICE and its substrate pIL-1β or other substrates or inhibitors.

ICE inhibitors represent a class of compounds useful for the control of inflammation or apoptosis or both. Peptide and peptidyl inhibitors of ICE have been described. PCT patent applications WO 91/15577; WO 93/05071; WO 93/09135; WO 93/14777 and WO 93/16710; and European patent application 0 547 699. However, due to their peptidic nature, such inhibitors are typically characterized by undesirable pharmacologic properties, such as poor oral absorption, poor stability and rapid metabolism. Plattner, J. J. and D. W. Norbeck, in *Drug Discovery Technologies*, C. R. Clark and W. H. Moos, Eds. (Ellis Horwood, Chichester, England, 1990), pp. 92–126. This has hampered their development into effective drugs.

Accordingly, the need exists for compounds that can effectively inhibit the action of ICE, for use as agents for preventing and treating chronic and acute forms of IL-1 mediated diseases, including various cancers, as well as inflammatory, autoimmune or is neurodegenerative diseases.

SUMMARY OF THE INVENTION

The present invention provides novel classes of compounds, and pharmaceutically acceptable derivatives thereof, that are useful as inhibitors of ICE. These compounds can be used alone or in combination with other therapeutic or prophylactic agents, such as antibiotics, immunomodulators or other anti-inflammatory agents, for the treatment or prophylaxis of diseases mediated by IL-1. According to a preferred embodiment, the compounds of this invention are capable of binding to the active site of ICE and inhibiting the activity of that enzyme.

It is a principal object of this invention to provide novel classes of inhibitors of ICE. These novel classes of ICE inhibitors are characterized by the following structural and physicochemical features:

a) a first and a second hydrogen bonding moiety, each of said moieties being capable of forming a hydrogen bond with a different backbone atom of ICE, said backbone atom being selected from the group consisting of the carbonyl oxygen of Arg-341, the amide —NH— group of Arg-341, the carbonyl oxygen of Ser-339 and the amide —NH— group of Ser-339;

b) a first and a second moderately hydrophobic moiety, said moieties each being capable of associating with a separate binding pocket of ICE when the inhibitor is bound thereto, said binding pocket being selected from the group consisting of the P2 binding pocket, the P3 binding pocket, the P4 binding pocket and the P' binding pocket; and c) an electronegative moiety comprising one or more electronegative atoms, said atoms being attached to the same atom or to adjacent atoms in the moiety and said moiety being capable of forming one or more hydrogen bonds or salt bridges with residues in the P1 binding pocket of ICE.

It is also an object of this invention to provide a method for identification, design or prediction of ICE inhibitors comprising the steps of:

a) selecting a candidate compound of defined chemical structure comprising at least two hydrogen bonding moieties, at least two moderately hydrophobic moieties and one electronegative moiety comprising one or more electronegative atoms attached either to the same atom or to adjacent atoms in the electronegative moiety;

b) determining a low-energy conformation for binding of said compound to the active site of ICE;

c) evaluating the capability of said compound in said conformation to form at least two hydrogen bonds with the non-carbon backbone atoms of Arg-341 and Ser-339 of ICE;

d) evaluating the capability of said compound in said conformation to associate with at least two of the binding pockets of ICE selected from the group consisting of the P2 binding pocket, the P3 binding pocket, the P4 binding pocket and the P' binding pocket;

e) evaluating the capability of said compound in said conformation to interact with the P1 binding pocket of ICE; and f) accepting or rejecting said candidate compound as an ICE inhibitor based on the determinations and evaluations carried out in the preceding steps.

It is a further object of this invention to provide novel classes of ICE inhibitors represented by formulas:

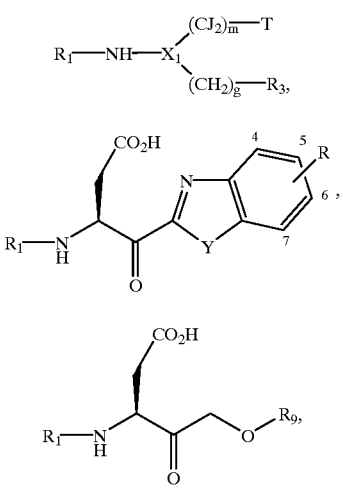

-continued

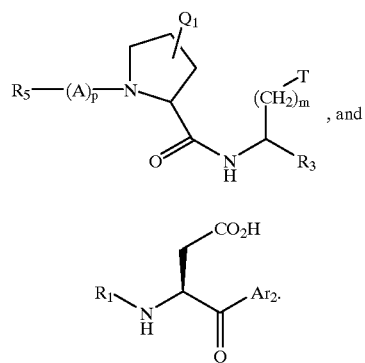

ABBREVIATIONS AND DEFINITIONS

Abbreviations

| Designation | Reagent or Fragment |
|---|---|
| Ala | alanine |
| Arg | arginine |
| Asn | asparagine |
| Asp | aspartic acid |
| Cys | cysteine |
| Gln | qlutamine |
| Glu | glutamic acid |
| Gly | glycine |
| His | histidine |
| Ile | isoleucine |
| Leu | leucine |
| Lys | lysine |
| Met | methionine |
| Phe | phenylalanine |
| Pro | proline |
| Ser | serine |
| Thr | threonine |
| Trp | tryptophan |
| Tyr | tyrosine |
| Val | valine. |

Definitions

The following terms are employed herein:

The term "active site" refers to any or all of the following sites in ICE: the substrate binding site, the site where an inhibitor binds and the site where the cleavage of substrate occurs. The active site is characterized by at least amino acid residues: 173, 176, 177, 178, 179, 180, 236, 237, 238, 239, 244, 248, 283, 284, 285, 290, 338, 339, 340, 341, 342, 343, 344, 345, 348, 352, 381, 383, using the sequence and numbering according to Thornberry et al., supra.

The terms "P binding pocket", "S subsite", "S pocket", and the like, refer to binding subsites, or portions of the substrate binding site on the ICE molecule. The amino acid residues of the substrate are given designations according to their position relative to the scissile bond, i.e. the bond which is broken by the protease. The residues are designated P1, P2, etc., for those extending toward the N-terminus of the substrate and P1', P2', etc., for those extending toward the C-terminus of the substrate. The portions of an inhibitor which correspond to the P or P' residues of the substrate are also labeled P1, P1', etc., by analogy with the substrate. The binding subsites of the ICE molecule which receive the residues labeled P1, P1', etc., are designated S1, S1', etc., or may alternately be designated "the P1 binding pocket", "the P1' binding pocket", etc. [I. Schechter and A. Berger, "On the Size of the Active Site in Proteases", *Biochem. Biophys. Res. Commun.*, vol. 27, pp. 157–162 (1967).]

The terms "P2 binding pocket" or "S2 subsite" of the ICE active site are equivalent and are defined as the space surrounded by amino acid residues Pro-290, Val-338 or Trp-340.

The terms "P3 binding pocket" or "S3 subsite" of the ICE active site are equivalent and are defined as the space surrounded by amino acid residues Pro-177, Arg-178, Thr-180, Arg-341 or Pro-343.

The terms "P4 binding pocket" or "S4 subsite" of the ICE active site are equivalent and are defined as the space surrounded by amino acid residues His-342, Met-345, Val-348, Arg-352, Asp-381, Arg-383 or Trp-340.

The terms "P1 binding pocket" or "S1 subsite" of the ICE active site are equivalent and are defined as the space surrounded by amino acid residues Arg-179, His-237, Gln-283, or Arg-341.

The terms "P' binding pocket" or "S' subsite" of the ICE active site are equivalent and are defined as the space surrounded by amino acid residues Phe-173, Ile-176, His-237, Gly-238, Ile-239, Cys-244 or His-248.

The term "hydrophobic" refers to a moiety which tends not to dissolve in water and is fat-soluble. Hydrophobic moieties include, but are not limited to, hydrocarbons, such as alkanes, alkenes, alkynes, cycloalkanes, cycloalkenes, cycloalkynes and aromatic compounds, such as aryls, certain saturated and unsaturated heterocycles and moieties that are substantially similar to the side chains of hydrophobic natural and unnatural α-amino acids, including valine, leucine, isoleucine, methionine, phenylanine, α-amino isobutyric acid, alloisoleucine, tyrosine, and tryptophan.

The term "moderately hydrophobic" refers to a hydrophobic moiety in which one or two carbon atoms have been replaced with more polar atoms, such as oxygen or nitrogen.

The term "heterocycle" or "heterocyclic" refers to a stable mono- or polycyclic compound which may optionally contain one or two double bonds or may optionally contain one or more aromatic rings. Each heterocycle consists of carbon atoms and from one to four heteroatoms independently selected from a group including nitrogen, oxygen, and sulfur. As used herein, the terms "nitrogen heteroatoms" and "sulphur heteroatoms" include any oxidized form of nitrogen or sulfur and the quaternized form of any basic nitrogen. Heterocycles defined above include, for example, pyrimidinyl, tetrahydroquinolyl, tetrahydroisoquinonlinyl, purinyl, pyrimidyl, indolinyl, benzimidazolyl, imidazolyl, imidazolinoyl, imidazolidinyl, quinolyl, isoquinolyl, indolyl, pyridyl, pyrrolyl, pyrrolinyl, pyrazolyl, pyrazinyl, quinoxolyl, piperidinyl, morpholinyl, thiamorpholinyl, furyl, thienyl, triazolyl, thiazolyl, β-carbolinyl, tetrazolyl, thiazolidinyl, benzofuranoyl, thiamorpholinyl sulfone, benzoxazolyl, oxopiperidinyl, oxopyrroldinyl, oxoazepinyl, azepinyl, isoxazolyl, tetrahydropyranyl, tetrahydrofuranyl, thiadiazolyl, benzodioxolyl, benzothienyl, tetrahydrothiophenyl and sulfolanyl. Further heterocycles are described in A. R. Katritzky and C. W. Rees, eds., *Comprehensive Heterocyclic Chemistry: The Structure, Reactions, Synthesis and Use of Heterocyclic Compounds*, Vol. 1–8, Pergamon Press, N.Y. (1984).

The term "cycloalkyl" refers to a mono- or polycyclic group which contains 3 to 15 carbons and may optionally contain one or two double bonds. Examples include cyclohexyl, adamantyl and norbornyl.

The term "aryl" refers to a mono- or polycyclic group which contains 6, 10, 12, or 14 carbons in which at least one ring is aromatic. Examples include phenyl, naphthyl and biphenyl.

The term "heteroaromatic" refers to a mono- or polycyclic group which contains 1 to 15 carbon atoms and from 1 to 4 heteroatoms, each of which is selected independently from a group including sulphur, nitrogen and oxygen, and which additionally contains from 1 to 3 five or six membered rings, at least one of which is aromatic.

The term "alpha-amino acid" (α-amino acid) refers to both the naturally occurring amino acids and other "non-protein" α-amino acids commonly utilized by those in the peptide chemistry arts when preparing synthetic analogues of naturally occurring peptides, including D and L forms. The naturally occurring amino acids are glycine, alanine, valine, leucine, iso-leucine, serine, methionine, threonine, phenylalanine, tyrosine, tryptophan, cysteine, proline, histidine, aspartic acid, asparagine, glutamic acid, glutamine, γ-carboxyglutamic acid, arginine, ornithine and lysine. Examples of "non-protein" alpha-amino acids include hydroxylysine, homoserine, homotyrosine, homophenylalanine, citrulline, kynurenine, 4-aminophenylalanine, 3-(2-naphthyl)-alanine, 3-(1-naphthyl)-alanine, methionine sulfone, t-butyl-alanine, t-butylglycine, 4-hydroxyphenylglycine, aminoalanine, phenylglycine, vinylalanine, propargyl-glycine, 1,2,4-triazolo-3-alanine, 4,4,4-trifluoro-threonine, thyronine, 6-hydroxytryptophan, 5-hydro-xytryptophan, 3-hydroxykynurenine, 3-aminotyrosine, trifuoromethylalanine, 2-thienylalanine, (2-(4-pyridyl)ethyl)-cysteine, 3,4-dimethoxy-phenylalanine, 3-(2-thiazolyl)-alanine, ibotenic acid, 1-amino-1-cyclopentanecarboxylic acid, 1-amino-1-cyclohexanecarboxylic acid, quisqualic acid, 3-trifuoromethylphenylalanine, 4-trifuoromethylphenylalanine, cyclohexylalanine, cyclohexylglycine, thiohistidine, 3-methoxytyrosine, elastatinal, norleucine, norvaline, alloisoleucine, homoarginine, thioproline, dehydroproline, hydroxyproline, isonipectotic acid, homoproline, cyclohexylglycine, α-amino-n-butyric acid, cyclohexylalanine, aminophenylbutyric acid, phenylalanines substituted at the ortho, meta, or para position of the phenyl moiety with one or two of the following: a $(C_1–C_4)$ alkyl, a $(C_1–C_4)$ alkoxy, halogen or nitro groups or substituted with a methylenedioxy group; β-2- and 3-thienylalanine, β2- and 3-furanylalanine, β2-, 3- and 4-pyridylalanine, β-(benzothienyl-2- and 3-yl)alanine, β-(1- and 2-naphthyl)alanine, O-alkylated derivatives of serine, threonine or tyrosine, S-alkylated cysteine, S-alkylated homocysteine, O-sulfate, O-phosphate and O-carboxylate esters of tyrosine, 3-sulfo-tyrosine, 3-carboxy-tyrosine, 3-phospho-tyrosine, 4-methane sulfonic acid ester of tyrosine, 4-methane phosphonic acid ester of tyrosine, 3,5-diiodotyrosine, 3-nitro-tyrosine, ε-alkyl lysine, and delta-alkyl ornithine. Any of these α-amino acids may be substituted with a methyl group at the alpha position, a halogen at any aromatic residue on the α-amino side chain, or an appropriate protective group at the O, N, or S atoms of the side chain residues. Appropriate protective groups are disclosed in "Protective Groups In Organic Synthesis," T. W. Greene and P. G. M. Wuts, J. Wiley & Sons, NY, N.Y., 1991.

The term "α-amino acid side chain residue" refers to a chemical moiety which is attached to the α-carbon of an alpha-amino acid.

The term "bioisosteric replacement for —$CO_2H$" refers to group which may substitute for a carboxylic acid group in bioactive molecules. Examples of such groups are disclosed in Christopher A. Lipinski, "Bioisosteres in Drug Design" *Annual Reports In Medical Chemistry*, 21, pp. 286–88 (1986), and in C. W. Thornber, "Isosterism and Molecular Modification in Drug Design" *Chemical Society Reviews*, pp. 563–580 (1979).

The term "association" is used in reference to a condition of proximity between an inhibitor or portions thereof to an ICE molecule or portions thereof wherein the juxtaposition is energetically favored by electrostatic or van der Waals interactions.

The term "hydrogen bond" refers to a favorable interaction that occurs whenever a suitable donor atom, X, bearing a proton, H, and a suitable acceptor atom, Y, have a separation of between 2.5 Å and 3.5 Å and where the angle X-H - - - Y is greater than 90 degrees. Suitable donor and acceptor atoms are well understood in medicinal chemistry (G. C. Pimentel and A. L. McClellan, *The Hydrogen Bond*, Freeman, San Francisco, 1960; R. Taylor and O. Kennard, "Hydrogen Bond Geometry in Organic Crystals", *Accounts of Chemical Research*, 17, pp. 320–326 (1984)).

The term "salt bridge" refers to the non-covalent attractive interaction between a positively charged moiety (P) and a negatively charged moiety (N) when the distance between the centers of mass of P and N is between 2 and 6 Angstroms. In calculating the center of mass, atoms which may contain a formal charge and atoms immediately adjacent to these are included. For example, a salt bridge may be formed between the positively charged guanidinium side chain of an arginine residue and the negative charged carboxylate side chain of a glutamate residue. Salt bridges are well understood in medicinal chemistry (L. Stryer, *Biochemistry*, Freeman, San Francisco, (1975); K. A. Dill, "Dominant Forces in Protein Folding", *Biochemistry*, 29, No. 31, pp. 7133–7155, (1990)).

The term "center of mass" refers to a point in three-dimensional space which represents a weighted average position of the masses that make up an object.

The terms "backbone chain" and "backbone" refer to the portion of a polypeptide which comprises the repeating unit —CO—CH—NH—.

The term "scaffold" refers to a structural building block which forms the basis of an ICE inhibitor according to this invention. Various moieties and functional groups are intended to be appended to the scaffold. The scaffolds of this invention are thus depicted having open valences. Various scaffolds of ICE inhibitors according to this invention include the portions:

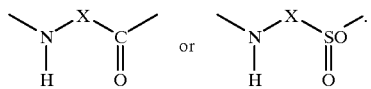

In those scaffolds, the NH and CO or $SO_2$ moieties represent a first and a second hydrogen bonding moiety, said moieties each being capable of forming a hydrogen bond with a backbone atom of ICE, said backbone atom being selected from the group consisting of the carbonyl oxygen of Arg-341, the amide —NH— of Arg-341, the carbonyl oxygen of Ser-339 and the amide —NH— of Ser-339.

The term "substitute" refers to the replacement of a hydrogen atom in a compound with a substituent group. In the present invention, those hydrogen atoms which form a part of a hydrogen bonding moiety which is capable of forming a hydrogen bond with the carbonyl oxygen of Arg-341 of ICE or the carbonyl oxygen of Ser-339 of ICE are excluded from substitution. These excluded hydrogen atoms include those which comprise an —NH— group which is alpha to a Z or a —CO— group and are depicted as —NH— rather than an X group or some other designation in the following diagrams: (a) through (t), (v) through (y), and (I) through (VIID).

The term "straight chain" refers to a contiguous unbranching string of covalently bound members, i.e. atoms, which form a portion of a ring. The straight chain and the ring of which it forms a part may be substituted, but these substituents are not a part of the straight chain.

The term "$K_i$" refers to a numerical measure of the effectiveness of a compound in inhibiting the activity of a target enzyme such as ICE. Lower values of $K_i$ reflect higher effectiveness. The $K_i$ value is a derived by fitting experimentally determined rate data to standard enzyme kinetic equations (see I. H. Segel, *Enzyme Kinetics*, Wiley-Interscience, 1975).

The term "minimize" refers to the systematic altering of the atomic geometry of a molecule or molecular complex so that any further minor perturbation of the atomic geometry would cause the total energy of the system as measured by a molecular mechanics force-field to increase. Minimization and molecular mechanics force-fields are well understood in computational chemistry [U. Burkert and N. L. Allinger, *Molecular Mechanics*, ACS Monograph 177, American Chemical Society, Washington, D.C. 1982 pages 59–78].

The term "strain energy" is used in this application to refer to the difference between the free conformation energy of a compound and the bound conformation energy of that compound when bound to ICE. The strain energy can be determined by the following steps: Evaluate the energy of the molecule when it has the conformation necessary for binding to ICE. Then minimize and reevaluate the energy—this is the free conformation energy. The strain energy for binding of a potential inhibitor to ICE is the difference between the free conformation energy and the bound conformation energy. In a preferred embodiment, the strain energy of an inhibitor of the present invention is less than about 10 kcal/mol.

The term "patient" as used in this application refers to any mammal, especially humans.

The term "pharmaceutically effective amount" refers to an amount effective in treating or ameliorating an IL-1 mediated disease in a patient. The term "prophylactically effective amount" refers to an amount effective in preventing or substantially lessening IL-1 mediated disease in a patient.

The term "pharmaceutically acceptable carrier or adjuvant" refers to a non-toxic carrier or adjuvant that may be administered to a patient, together with a compound of this invention, and which does not destroy the pharmacological activity thereof.

The term "pharmaceutically acceptable derivative" means any pharmaceutically acceptable salt, ester, or salt of such ester, of a compound of this invention or any other compound which, upon administration to a recipient, is capable of providing (directly or indirectly) a compound of this invention or an anti-ICE active metabolite or residue thereof.

Pharmaceutically acceptable salts of the compounds of this invention include, for example, those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, formic, benzoic, malonic, naphthalene-2-sulfonic and benzene-sulfonic acids. Other acids, such as oxalic, while not in themselves pharmaceutically acceptable, may be employed in the preparation of salts useful as intermediates in obtaining the compounds of the invention and their pharmaceutically acceptable acid addition salts. Salts derived from appropriate bases include alkali metal (e.g., sodium), alkaline earth metal (e.g., magnesium), ammonium and N-($C_{1-4}$ alkyl)$_4^+$ salts.

This invention also envisions the "quaternization" of any basic nitrogen-containing groups of the compounds disclosed herein. The basic nitrogen can be quaternized with any agents known to those of ordinary skill in the art including, for example, lower alkyl halides, such as methyl, ethyl, propyl and butyl chloride, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides including benzyl and phenethyl bromides. Water or oil-soluble or dispersible products may be obtained by such quaternization.

The ICE inhibitors of this invention may contain one or more "asymmetric" carbon atoms and thus may occur as racemates and racemic mixtures, single enantiomers, diastereomeric mixtures and individual diastereomers. All such isomeric forms of these compounds are expressly included in the present invention. Each stereogenic carbon may be of the R or S configuration. Although specific compounds and scaffolds exemplified in this application may be depicted in a particular stereochemical configuration, compounds and scaffolds having either the opposite stereochemistry at any given chiral center or mixtures thereof are also envisioned.

The ICE inhibitors of this invention may comprise ring structures which may optionally be substituted at carbon, nitrogen or other atoms by various substituents. Such ring structures may be singly or multiply substituted. Preferably, the ring structures contain between 0 and 3 substituents. When multiply substituted, each substituent may be picked independently of any other substituent as long as the combination of substituents results in the formation of a stable compound.

Combinations of substituents and variables envisioned by this invention are only those that result in the formation of stable compounds. The term "stable", as used herein, refers to compounds which possess stability sufficient to allow manufacture and administration to a mammal by methods known in the art. Typically, such compounds are stable at a temperature of 40° C. or less, in the absence of moisture or other chemically reactive conditions, for at least a week.

DETAILED DESCRIPTION OF THE INVENTION

In order that the invention herein described may be more fully understood, the following detailed description is set forth.

We have discovered that compounds possessing the following novel combination of features are surprisingly effective ICE inhibitors:

a) a first and a second hydrogen bonding moiety, each of said moieties being capable of forming a hydrogen bond with a different backbone atom of ICE, said backbone atom being selected from the group consisting of the carbonyl oxygen of Arg-341, the amide —NH— group of Arg-341, the carbonyl oxygen of Ser-339 and the amide —NH— group of Ser-339;

b) a first and a second moderately hydrophobic moiety, said moieties each being capable of associating with a separate binding pocket of ICE when the inhibitor is bound thereto, said binding pocket being selected from the group consisting of the P2 binding pocket, the P3 binding pocket, the P4 binding pocket and the P' binding pocket; and c) an electronegative moiety comprising one or more electronegative atoms, said atoms being attached to the same atom or to adjacent atoms in the moiety and said moiety being capable of forming one or more hydrogen bonds or salt bridges with residues in the P1 binding pocket of ICE.

Preferably, any moderately hydrophobic moiety associating with the P2 binding pocket of ICE does so in such a way that:

a) the distance from the center of mass of the moderately hydrophobic moiety in the P2 binding pocket to the carbonyl oxygen of Arg-341 of ICE is between about 7.1 Å and about 12.5 Å;

b) the distance from the center of mass of the moderately hydrophobic moiety in the P2 binding pocket to the amide nitrogen of Arg-341 of ICE is between about 6.0 Å and about 12 Å; and c) the distance from the center of mass of the moderately hydrophobic moiety in the P2 binding pocket to the carbonyl oxygen of Ser-339 of ICE is between about 3.7 Å and about 9.5 Å.

Preferably, any moderately hydrophobic moiety associating with the P3 binding pocket of ICE does so in such a way that:

a) the distance from the center of mass of the moderately hydrophobic moiety in the P3 binding pocket to the carbonyl oxygen of Arg-341 of ICE is between about 3.9 Å and about 9.5 Å;

b) the distance from the center of mass of the moderately hydrophobic moiety in the P3 binding pocket to the amide nitrogen of Arg-341 of ICE is between about 5.4 Å and about 11 Å; and c) the distance from the center of mass of the moderately hydrophobic moiety in the P3 binding pocket to the carbonyl oxygen of Ser-339 of ICE is between about 7.0 Å and about 13 Å.

Preferably, any moderately hydrophobic moiety associating with the P4 binding pocket of ICE does so in such a way that:

a) the distance from the center of mass of the moderately hydrophobic moiety in the P4 binding pocket to the carbonyl oxygen of Arg-341 of ICE is between about 4.5 Å and about 7.5 Å;

b) the distance from the center of mass of the moderately hydrophobic moiety in the P4 binding pocket to the amide nitrogen of Arg-341 of ICE is between about 5.5 Å and about 8.5 Å; and c) the distance from the center of mass of the moderately hydrophobic moiety in the P4 binding pocket to the carbonyl oxygen of Ser-339 of ICE is between about 8 Å and about 11 Å.

Preferably, any moderately hydrophobic moiety associating with the P' binding pocket of ICE does so in such a way that:

a) the distance from the center of mass of the moderately hydrophobic moiety in the P' binding pocket to the carbonyl oxygen of Arg-341 of ICE is between about 11 Å and about 16 Å;

b) the distance from the center of mass of the moderately hydrophobic moiety in the P' binding pocket to the amide nitrogen of Arg-341 of ICE is between about 10 Å and about 15 Å; and c) the distance from the center of mass of the moderately hydrophobic moiety in the P' binding pocket to the carbonyl oxygen of Ser-339 of ICE is between about 8 Å and about 12 Å.

More preferably, all of the above associative conditions are met in the compounds of this invention.

The practitioner skilled in the art will appreciate that there are a number of means to design the inhibitors of the present invention. These same means may be used to select a candidate compound for screening as an ICE inhibitor. This design or selection may begin with selection of the various moieties which fill binding pockets.

There are a number of ways to select moieties to fill individual binding pockets. These include visual inspection of a physical model or computer model of the active site and manual docking of models of selected moieties into various binding pockets. Modeling software that is well known and available in the art may be used. These include QUANTA [Molecular Simulations, Inc., Burlington, Mass., 19923], SYBYL [Molecular Modeling Software, Tripos Associates, Inc., St. Louis, Mo., 1992], AMBER [S. J. Weiner, P. A. Kollman, D. A. Case, U. C. Singh, C. Ghio, G. Alagona, and P. Weiner, *J. Am. Chem. Soc.*, vol. 106, pp. 765–784 (1984)], or CHARMM [B. R. Brooks, R. E. Bruccoleri, B. D. Olafson, D. J. States, S Swaminathan, and M. Karplus, *J. Comp. Chem.* vol. 4, pp. 187–217 (1983)]. This modelling step may be followed by energy minimization with standard molecular mechanics forcefields such as CHARMM and AMBER. In addition, there are a number of more specialized computer programs to assist in the process of selecting the binding moieties of this invention. These include:

1. GRID (Goodford, P. J. A Computational Procedure for Determining Energetically Favorable Binding Sites on Biologically Important Macromolecules. *J. Med. Chem.*, 28, pp. 849–857 (1985)). GRID is available from Oxford University, Oxford, UK.

2. MCSS (Miranker, A.; Karplus, M. Functionality Maps of Binding Sites: A Multiple Copy Simultaneous Search Method. *Proteins: Structure, Function and Genetics*, 11, pp. 29–34 (1991)). MCSS is available from Molecular Simulations, Burlington, Mass.

3. AUTODOCK (Goodsell, D.S.; Olsen, A. J. Automated Docking of Substrates to Proteins by Simmulated Annealing. *PROTEINS: Structure. Function and Genetics*, 8, pp. 195–202 (1990)). AUTODOCK is available from the Scripps Research Institute, La Jolla, Calif.

4. DOCK (Kuntz, I. D.; Blaney, J. M.; Oatley, S. J.; Langridge, R.; Ferrin, T. E. A Geometric Approach to Macromolecule-Ligand Interactions. *J. Mol. Biol.*, 161, pp. 269–288 (1982)). DOCK is available from the University of California, San Francisco, Calif.

Once suitable binding moieties have been selected, they can be assembled into a single inhibitor. This assembly may be accomplished by connecting the various moieties to a central scaffold. The assembly process may, for example, be done by visual inspection followed by manual model building, again using software such as Quanta or Sybyl. A number of other programs may also be used to help select ways to connect the various moieties. These include:

1. CAVEAT (Bartlett, P. A.; Shea, G. T.; Telfer, S. J.; Waterman, S. CAVEAT: A Program to Facilitate the Structure-Derived Design of Biologically Active Molecules. In "Molecular Recognition in Chemical and Biological Problems," Special Pub., Royal Chem. Soc., 78, pp. 182–196 (1989)). CAVEAT is available from the University of California, Berkeley, Calif.

2. 3D Database systems such as MACCS-3D (MDL Information Systems, San Leandro, Calif.). This area has been recently reviewed by Martin (Martin, Y. C. 3D Database Searching in Drug Design. *J. Med. Chem.*, 35, pp. 2145–2154 (1992)).

3. HOOK (available from Molecular Simulations, Burlington, Mass.).

In addition to the above computer assisted modeling of inhibitor compounds, the inhibitors of this invention may be constructed "de novo" using either an empty active site or optionally including some portions of a known inhibitor. Such methods are well known in the art. They include, for example:

1. LUDI (Bohm, H. J. The Computer Program LUDI: A New Method for the De Novo Design of Enzyme Inhibitors. *J. Comp. Aid. Molec. Design.*, 6, 61–78 (1992)). LUDI is available from Biosym Technologies, San Diego, Calif.

2. LEGEND (Nishibata, Y., Itai, A., *Tetrahedron*, 47, 8985 (1991)). LEGEND is available from Molecular Simultations, Burlington, Mass.

3. LeapFrog (available from Tripos associates, St. Louis, Mo.).

A number of techniques commonly used for modeling drugs may be employed (For a review, see: Cohen, N. C.; Blaney, J. M.; Humblet, C.; Gund, P.; Barry, D. C., "Molecular Modeling Software and Methods for Medicinal Chemistry", *J. Med. Chem.*, 33, pp. 883–894 (1990)). There are likewise a number of examples in the chemical literature of techniques that can be applied to specific drug design projects. For a review, see: Navia, M. A. and Murcko, M. A., "The Use of Structural Information in Drug Design", *Current Opinions in Structural Biology*, 2, pp. 202–210 (1992). Some examples of these specific applications include: Baldwin, J. J. et al., "Thienothiopyran-2-sulfonamides: Novel Topically Active Carbonic Anhydrase Inhibitors for the Treatment of Glaucoma", *J. Med. Chem.*, 32, pp. 2510–2513 (1989); Appelt, K. et al., "Design of Enzyme Inhibitors Using Iterative Protein Crystallographic Analysis", *J. Med. Chem.*, 34, pp. 1925–1934 (1991); and Ealick, S. E. et al., "Application of Crystallographic and Modeling Methods in the Design of Purine Nucleotide Phosphorylase Inhibitors" *Proc. Nat. Acad. Sci. USA*, 88, pp. 11540–11544 (1991).

Using the novel combination of steps of the present invention, the skilled artisan can advantageously avoid time consuming and expensive experimentation to determine enzymatic inhibition activity of particular compounds. The method also is useful to facilitate rational design of ICE inhibitors and therapeutic and prophylactic agents against IL-1-mediated diseases. Accordingly, the present invention relates to such inhibitors.

A variety of conventional techniques may be used to carry out each of the above evaluations as well as the evaluations necessary in screening a candidate compound for ICE inhibiting activity. Generally, these techniques involve determining the location and binding proximity of a given moiety, the occupied space of a bound inhibitor, the deformation energy of binding of a given compound and electrostatic interaction energies. Examples of conventional techniques useful in the above evaluations include: quantum mechanics, molecular mechanics, molecular dynamics, Monte Carlo sampling, systematic searches and distance geometry methods (G. R.

Marshall, *Ann. Rev. Pharmacol. Toxicol.*, 27, p. 193 (1987)). Specific computer software has been developed for use in carrying out these methods. Examples of programs designed for such uses include: Gaussian 92, revision E.2 (M. J. Frisch, Gaussian, Inc., Pittsburgh, Pa. ©1993); AMBER, version 4.0 (P. A. Kollman, University of California at San Francisco, ©1993); QUANTA/CHARMM [Molecular Simulations, Inc., Burlington, Mass. ©1992]; and Insight II/Discover (Biosysm Technologies Inc., San Diego, Calif. ©1992). These programs may be implemented, for instance, using a Silicon Graphics Indigo 2 workstation or IBM RISC/6000 workstation model 550. Other hardware systems and software packages will be known and of evident applicability to those skilled in the art.

Different classes of active ICE inhibitors, according to this invention, may interact in similar ways with the various binding pockets of the ICE active site. The spatial arrangement of these important groups is often referred to as a pharmacophore. The concept of the pharmacophore has been well described in the literature (D. Mayer, C. B. Naylor, I. Motoc, and G. R. Marshall, *J. Comp. Aided Molec. Design* vol. 1, pp. 3–16 (1987); A. Hopfinger and B. J. Burke, in *Concepts and Applications of Molecular Similarity*, M. A. Johnson and G. M. Maggiora, ed., Wiley (1990)).

Different classes of ICE inhibitors of this invention may also use different scaffolds or core structures, but all of these cores will allow the necessary moieties to be placed in the active site such that the specific interactions necessary for binding may be obtained. These compounds are best defined in terms of their ability to match the pharmacophore, i.e., their structural identity relative to the shape and properties of the active site of ICE.

The ICE inhibitors of one embodiment of this invention comprise a first and a second hydrogen bonding moiety, a first and a second moderately hydrophobic moiety, and an electronegative moiety which comprise or are covalently bound to one of the following scaffolds:

(I)

(II)

(III)

(IV)

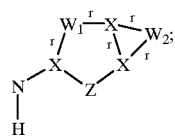

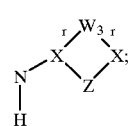

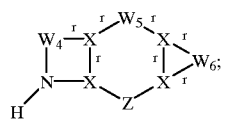

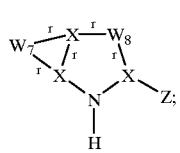

(V)

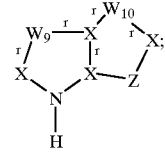

(VI)

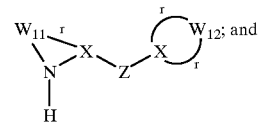

(VII)

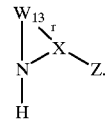

The ICE inhibitors of another embodiment (A) of this invention are those of formula α:

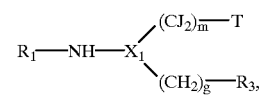

wherein:

$X_1$ is CH or N;

g is 0 or 1;

each J is independently selected from the group consisting of —H, —OH, and —F, provided that when a first and second J are bound to a C and said first J is —OH, said second J is —H;

m is 0, 1, or 2;

T is —$Ar_3$, —OH, —$CF_3$, —CO—$CO_2$H, —$CO_2$H or any bioisosteric replacement for —$CO_2$H;

$R_1$ is selected from the group consisting of the following formulae, in which any ring may optionally be singly or multiply substituted at any carbon by $Q_1$, at any nitrogen by $R_5$, or at any atom by =O, —OH, —$CO_2$H, or halogen, and in which any saturated ring may optionally be unsaturated at one or two bonds:

(a)

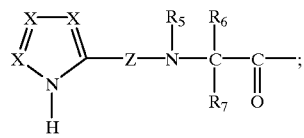

(b)

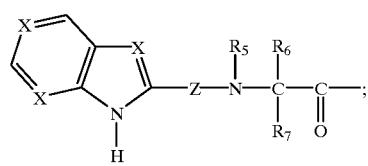

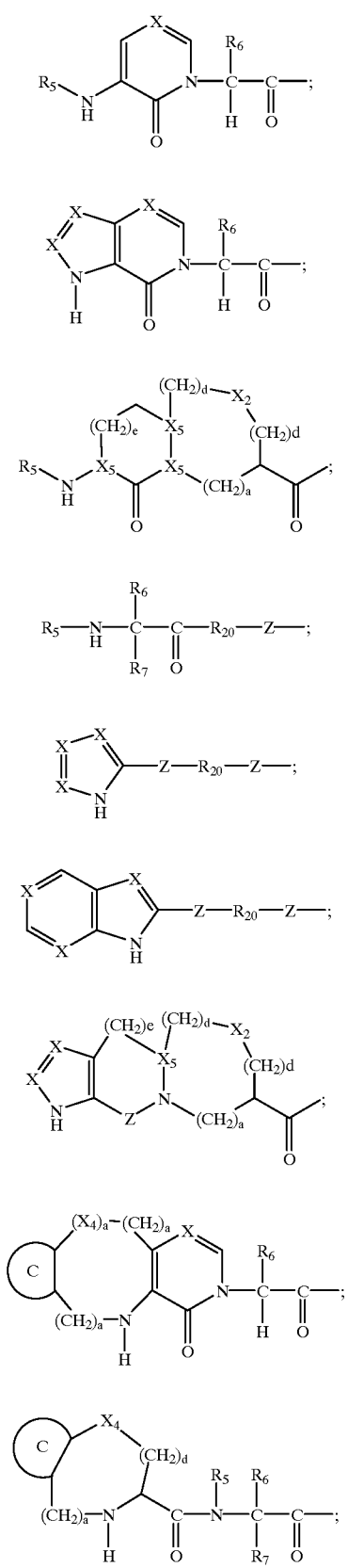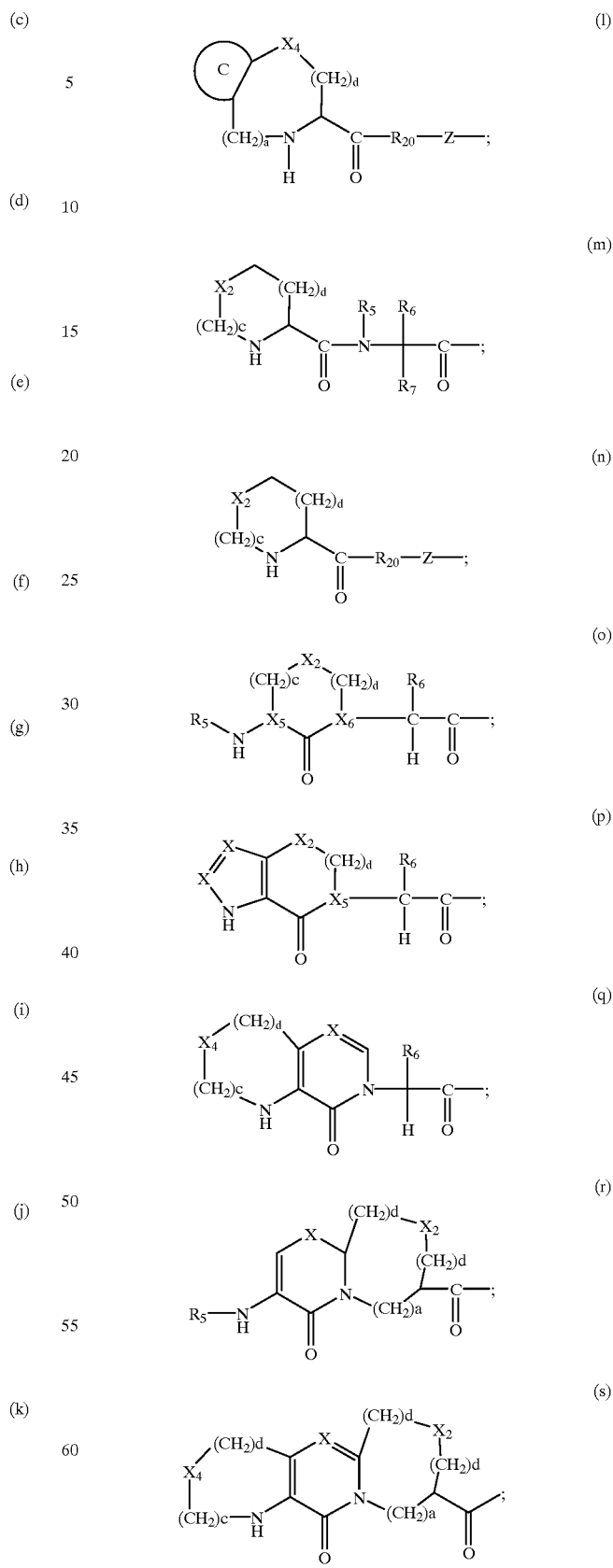

-continued
(t) 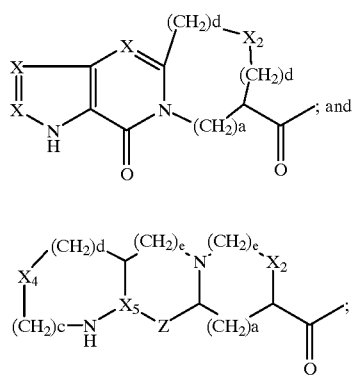; and
(v) 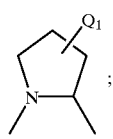;
$R_{20}$ is selected from the group consisting of:
(aa1) 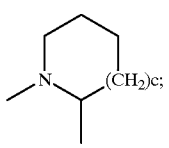;
(aa2) 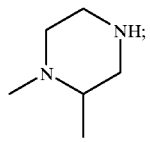;
(aa3) 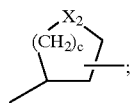;
(aa4) 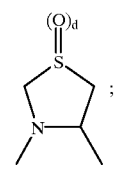;
(aa5) 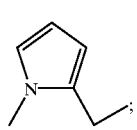;
(bb) 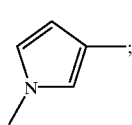;
(cc) 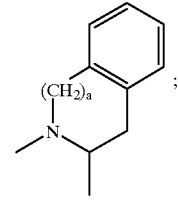;
-continued
(dd) 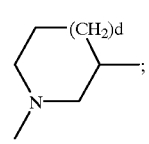;
(ee) 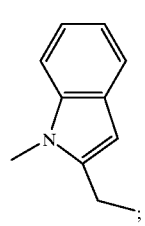;
(ff) 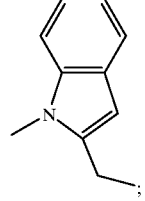;
(gg) 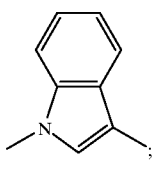;
(gga) 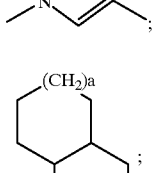;
(ggb) 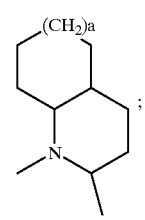; and
(ggc) 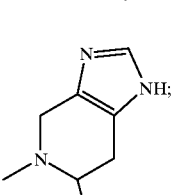;
wherein each ring C is independently chosen from the group consisting of benzo, pyrido, thieno, pyrrolo, furano, thiazolo, isothiazolo, oxazolo, isoxazolo, pyrimido, imidazolo, cyclopentyl, and cyclohexyl;
$R_3$ is
—CN,
—CH=CH—$R_9$,
—CH=N—O—$R_9$, —(CH$_2$)$_{1-3}$—T$_1$—R$_9$,
—CJ$_2$—R$_9$,
—CO—R$_{13}$, or

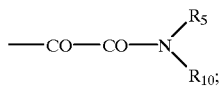

each R$_4$ is independently selected from the group consisting of:
—H,
—Ar$_1$,
—R$_9$,
—T$_1$—R$_9$, and
—(CH$_2$)$_{1,2,3}$—T$_1$—R$_9$, each T$_1$ is independently selected from the group consisting of:
—CH=CH—,
—O—,
—S—,
—SO—,
—SO$_2$—,
—NR$_{10}$—,
—NR$_{10}$—CO—,
—CO—,
—O—CO—,
—CO—O—,
—CO—NR$_{10}$—,
—O—CO—NR$_{10}$—,
—NR$_{10}$—CO—O—,
—NR$_{10}$—CO—NR$_{10}$—,
—SO$_2$—NR$_{10}$—,
—NR$_{10}$—SO$_2$—, and
—NR$_{10}$—SO$_2$—NR$_{10}$—, each R$_5$ is independently selected from the group consisting of:
—H,
—Ar$_1$,
—CO—Ar$_1$,
—SO$_2$—Ar$_1$,
—R$_9$,
—CO—R$_9$,
—CO—O—R$_9$,
—SO$_2$—R$_9$,

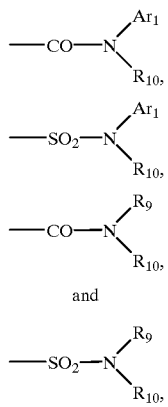

and

R$_6$ and R$_7$ taken together form a saturated 4–8 member carbocyclic ring or heterocyclic ring containing —O—, —S—, or —NH—, or R$_7$ is —H and R$_6$ is —H
—Ar$_1$,
—R$_9$, or
—(CH$_2$)$_{1,2,3}$—T$_1$—R$_9$;

each R$_9$ is a C$_{1-6}$ straight or branched alkyl group optionally singly or multiply substituted by —OH, —F, or =O and optionally substituted with one or two Ar$_1$ groups;

each R$_{10}$ is independently selected from the group consisting of —H or a C$_{1-6}$ straight or branched alkyl group;

each R$_{13}$ is independently selected from the group consisting of —Ar$_2$ and —R$_4$;

each Ar$_1$ is a cyclic group independently selected from the set consisting of an aryl group which contains 6, 10, 12, or 14 carbon atoms and between 1 and 3 rings, a cycloalkyl group which contains between 3 and 15 carbon atoms and between 1 and 3 rings, said cycloalkyl group being optionally benzofused, and a heterocycle group containing between 5 and 15 ring atoms and between 1 and 3 rings, said heterocycle group containing at least one heteroatom group selected from —O—, —S—, —SO—, —SO$_2$—, =N—, and —NH—, said heterocycle group optionally containing one or more double bonds, said heterocycle group optionally comprising one or more aromatic rings, and said cyclic group optionally being singly or multiply substituted by =O, —OH, perfluoro C$_{1-3}$ alkyl, or —Q$_1$;

each Ar$_2$ is independently selected from the following group, in which any ring may optionally be substituted by —Q$_1$:

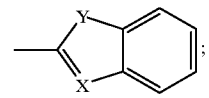

(hh)

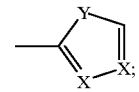

(ii)

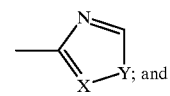

(jj)

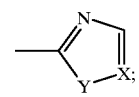

(kk)

Ar$_3$ is a cyclic group selected from the set consisting of a phenyl ring, a 5-membered heteroaromatic ring, and a 6-membered heteroaromatic ring, said heteroaromatic rings comprising 1–3 heteroatom groups selected from —O—, —S—, —SO—, —SO$_2$—, =N—, and —NH—, said cyclic group optionally being singly or multiply substituted with =O, —OH, halogen, perfluoro C$_{1-3}$ alkyl, or —CO$_2$H;

each Q$_1$ is independently selected from the group consisting of:
—Ar$_1$
—R$_9$, —T₁—R₉, and

—(CH₂)₁,₂,₃—T₁—R₉, provided that when —Ar₁ is substituted with a Q₁ group which comprises one or more additional —Ar₁ groups, said additional —Ar₁ groups are not substituted with Q₁;

each X is independently selected from the group consisting of =N— and =CH—;

each X₂ is independently selected from the group consisting of —O—, —CH₂—, —NH—, —S—, —SO—, and —SO₂;

each X₃ is independently selected from the group consisting of —CH₂—, —S—, —SO—, and —SO₂—;

each X₄ is independently selected from the group consisting of —CH₂— and —NH—;

each X₅ is independently selected from the group consisting of $$-\overset{|}{\underset{|}{C}}H-  \text{ and } -\overset{|}{N}-;$$

X₆ is CH or N, provided that when X₆ is N in the R₁ group labeled (o) and X₅ is CH and X₂ is CH₂ the ring of the R₁ group labeled (o) must be substituted by Q₁ or benzofused;

each Y is independently selected from the group consisting of —O— and —S—;

each Z is independently CO or SO₂, each a is independently 0 or 1, each c is independently 1 or 2, each d is independently 0, 1, or 2, and each e is independently 0, 1, 2, or 3.

The ICE inhibitors of another embodiment (B) of this invention are those of formula α:

α

$$R_1-NH-X_1\begin{matrix}(CJ_2)_{\overline{m}}-T\\(CH_2)_{\overline{g}}-R_3,\end{matrix}$$

wherein:

X₁ is —CH;

g is 0 or 1;

each J is independently selected from the group consisting of —H, —OH, and —F, provided that when a first and second J are bound to a C and said first J is —OH, said second J is —H;

m is 0, 1, or 2;

T is —OH, —CO—CO₂H, —CO₂H or any bioisosteric replacement for —CO₂H;

R₁ is selected from the group consisting of the following formulae, in which any ring may optionally be singly or multiply substituted at any carbon by Q₁, at any nitrogen by R₅, or at any atom by =O, —OH, —CO₂H, or halogen, any saturated ring may optionally be unsaturated at one or two bonds; and wherein R₁ (e) and R₁ (y) are optionally benzofused;

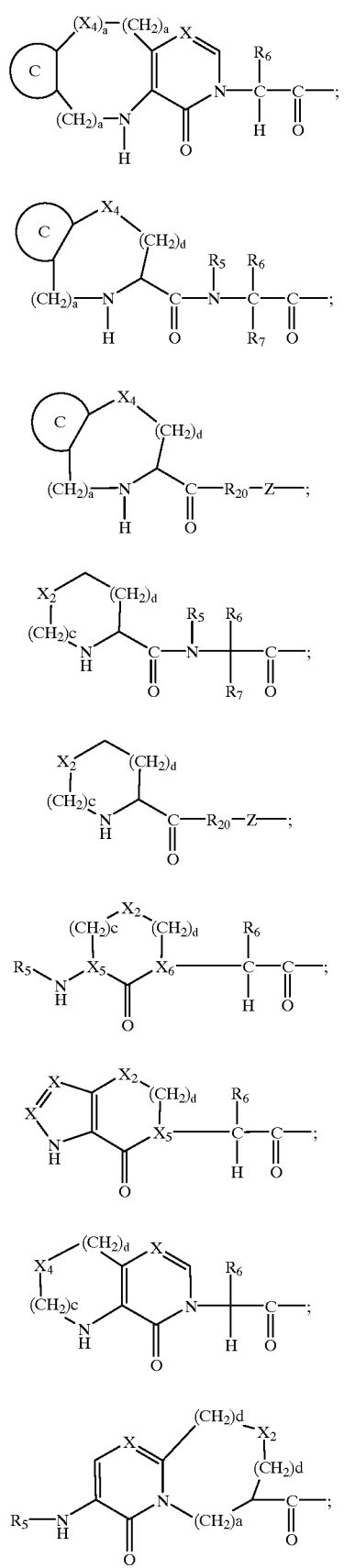
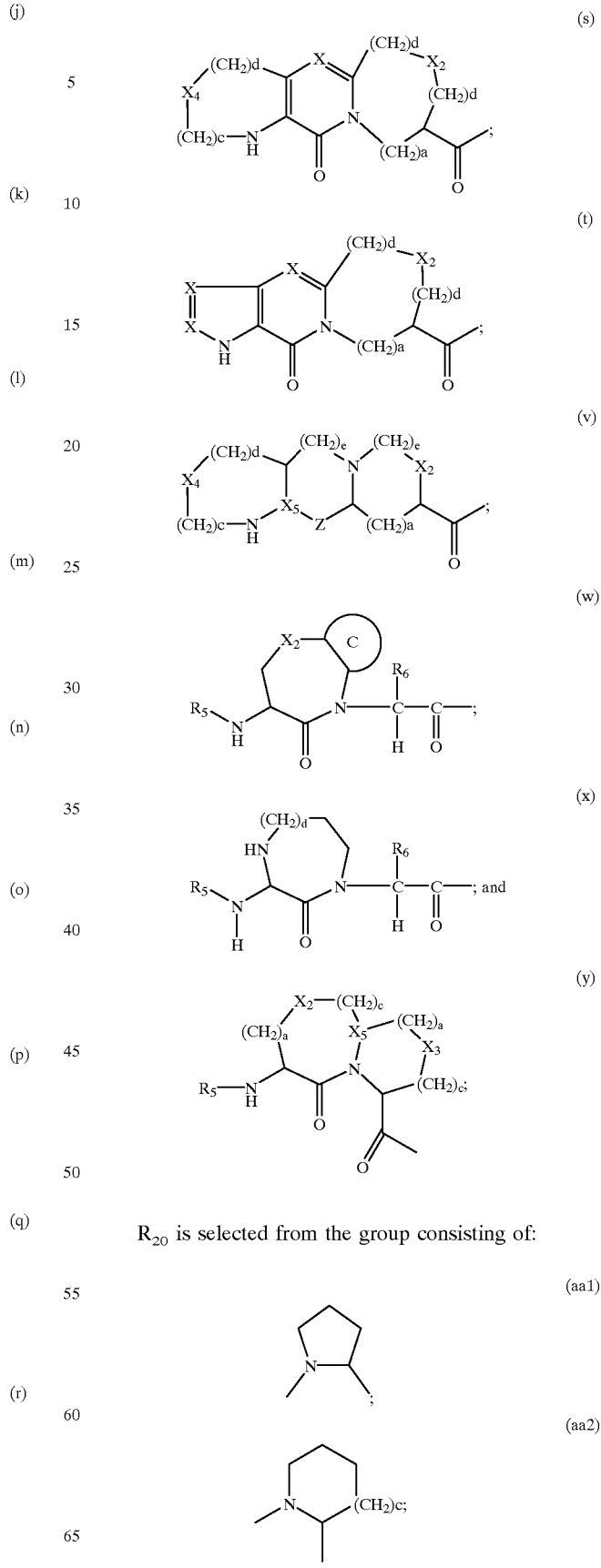
$R_{20}$ is selected from the group consisting of:

-continued (aa3) 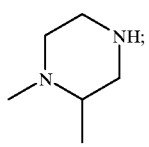

(aa4) 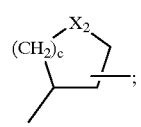

(aa5) 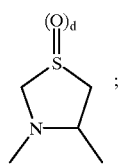

(bb) 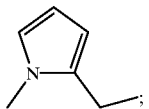

(cc) 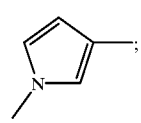

(dd) 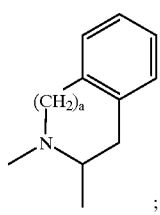

(ee) 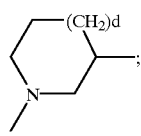

(ff) 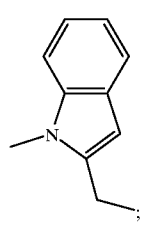

(gg) 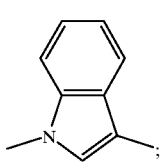

-continued (gga) 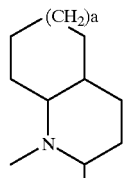

(ggb) 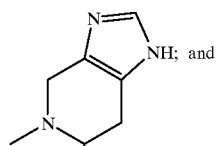

(ggc) 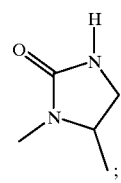

wherein each ring C is independently chosen from the group consisting of benzo, pyrido, thieno, pyrrolo, furano, thiazolo, isothiazolo, oxazolo, isoxazolo, pyrimido, imidazolo, cyclopentyl, and cyclohexyl;

$R_3$ is
—CN,
—CH=CH—$R_9$,
—CH=N—O—$R_9$,
—(CH$_2$)$_{1-3}$—$T_1$—$R_9$,
—CJ$_2$—$R_9$,
—CO—$R_{13}$, or

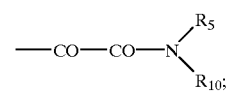

each $R_4$ is independently selected from the group consisting of:
—H,
—Ar$_1$,
—$R_9$,
—$T_1$—$R_9$, and
—(CH$_2$)$_{1,2,3}$—$T_1$—$R_9$, each $T_1$ is independently selected from the group consisting of:
—CH=CH—,
—O—,
—S—,
—SO—,
—SO$_2$—,
—NR$_{10}$—,
—NR$_{10}$—CO—,
—CO—,
—O—CO—,
—CO—O—,
—CO—NR$_{10}$—,
—O—CO—NR$_{10}$—,
—NR$_{10}$—CO—O—,
—NR$_{10}$—CO—NR$_{10}$—, —SO$_2$—NR$_{10}$—,
—NR$_{10}$—SO$_2$—, and
—NR$_{10}$—SO$_2$—NR$_{10}$—, each R$_5$ is independently selected from the group consisting of:
—H,
—Ar$_1$,
—CO—Ar$_1$,
—SO$_2$—Ar$_1$,
—CO—NH$_2$,
—SO$_2$—NH$_2$,
—R$_9$,
—CO—R$_9$,
—CO—O—R$_9$,
—SO$_2$—R$_9$,

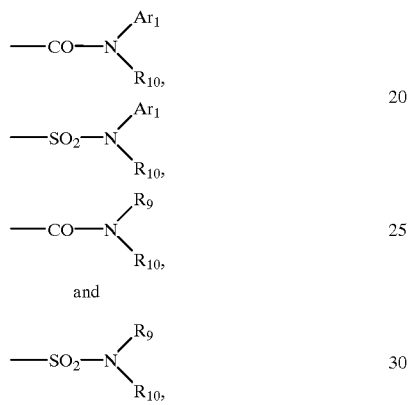

and

R$_6$ and R$_7$ taken together form a saturated 4–8 member carbocyclic ring or heterocyclic ring containing —O—, —S—, or —NH—; or R$_7$ is —H and R$_6$ is:
—H,
—Ar$_1$,
—R$_9$,
—(CH$_2$)$_{1,2,3}$—T$_1$—R$_9$, or
an α-amino acid side chain residue;

each R$_9$ is a C$_{1-6}$ straight or branched alkyl group optionally singly or multiply substituted by —OH, —F, or =O and optionally substituted with one or two Ar$_1$ groups;

each R$_{10}$ is independently selected from the group consisting of —H or a C$_{1-6}$ straight or branched alkyl group;

each R$_{13}$ is independently selected from the group consisting of —Ar$_2$, —R$_4$ and $$\begin{array}{c} -\text{N}-\text{OH;} \\ | \\ \text{R}_5 \end{array}$$

each Ar$_1$ is a cyclic group independently selected from the set consisting of an aryl group which contains 6, 10, 12, or 14 carbon atoms and between 1 and 3 rings, a cycloalkyl group which contains between 3 and 15 carbon atoms and between 1 and 3 rings, said cycloalkyl group being optionally benzofused, and a heterocycle group containing between 5 and 15 ring atoms and between 1 and 3 rings, said heterocycle group containing at least one heteroatom group selected from —O—, —S—, —SO—, —SO$_2$—, =N—, and —NH—, said heterocycle group optionally containing one or more double bonds, said heterocycle group optionally comprising one or more aromatic rings, and said cyclic group optionally being singly or multiply substituted by —NH$_2$, —CO$_2$H, —Cl, —F, —Br, —I, —NO$_2$, —CN, =O, —OH, -perfluoro C$_{1-3}$ alkyl

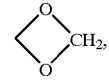

each Ar$_2$ is independently selected from the following group, in which any ring may optionally be singly or multiply substituted by —Q$_1$ and —Q$_2$:

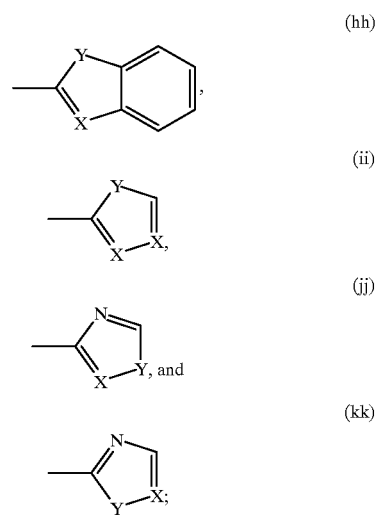

each Q$_1$ is independently selected from the group consisting of
—Ar$_1$
—O—Ar$_1$
—R$_9$,
—T$_1$—R$_9$, and
—(CH$_2$)$_{1,2,3}$—T$_1$—R$_9$;

each Q$_2$ is independently selected from the group consisting of —OH, —NH$_2$, —CO$_2$H, —Cl, —F, —Br, —I, —NO$_2$, —CN, —CF$_3$, and

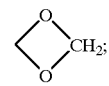

provided that when —Ar$_1$ is substituted with a Q$_1$ group which comprises one or more additional —Ar$_1$ groups, said additional —Ar$_1$ groups are not substituted with Q$_1$;

each X is independently selected from the group consisting of =N— and =CH—;

each X$_2$ is independently selected from the group consisting of —O—, —CH$_2$—, —NH—, —S—, —SO—, and —SO$_2$—;

each X$_3$ is independently selected from the group consisting of —CH$_2$—, —S—, —SO—, and —SO$_2$—;

each X$_4$ is independently selected from the group consisting of —CH$_2$— and —NH—;

each X$_5$ is independently selected from the group consisting of

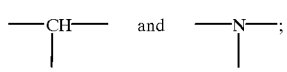

$X_6$ is CH or N, provided that when $X_6$ is N in the $R_1$ group labeled (o) and $X_5$ is CH and $X_2$ is $CH_2$ the ring of the $R_1$ group labeled (o) must be substituted by $Q_1$ or benzofused;

each Y is independently selected from the group consisting of —O— and —S—, and —NH;
each Z is independently CO or $SO_2$,
each a is independently 0 or 1,
each c is independently 1 or 2,
each d is independently 0, 1, or 2, and
each e is independently 0, 1, 2, or 3,
provided that when
  $R_1$ is (f),
  $R_6$ is an α-amino acid side chain residue, and
  $R_7$ is —H,
then (aa1) and (aa2) must be substituted with $Q_1$;
also provided that when
  $R_1$ is (o),
  g is 0,
  J is —H,
  m is 1,
  $R_6$ is an α-amino acid side chain residue,
  $R_7$ is —H,
  $X_2$ is —$CH_2$—,
  $X_5$ is

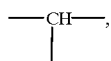

$X_6$ is

and
$R_3$ is

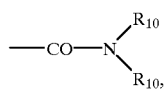

or —CO—$R_{13}$, when
$R_{13}$ is:
  —$CH_2$—O—CO—$Ar_1$,
  —$CH_2$—S—CO—$Ar_1$,
  —$CH_2$—O—$Ar_1$,
  —$CH_2$—S—$Ar_1$ or
  —$R_4$ when —$R_4$ is —H;
then the ring of the $R_1$(o) group must be substituted with $Q_1$ or benzofused; and
provided that when
  $R_1$ is (w),
  g is 0,
  J is —H,
  m is 1,
  T is —$CO_2$H or —CO—NH—OH,
  $X_2$ is O,
  $R_5$ is benzyloxycarbonyl, and
  ring C is benzo, then $R_3$ cannot be —CO—$R_{13}$ when:
  $R_{13}$ is —$CH_2$—O—$Ar_1$ and
  $Ar_1$ is 1-phenyl-3-chloro- or 3-trifluoromethyl-pyrazole-5-yl; or when
  $R_{13}$ is —$CH_2$—O—CO—$Ar_1$ and
  $Ar_1$ is 2,6-dichlorophenyl.

Preferred forms of the $R_1$ group (a) for embodiments A and B are:

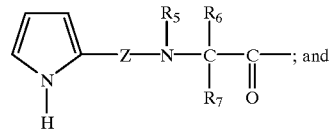

(a1)

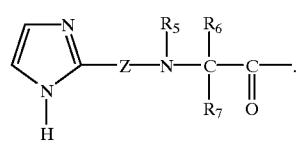

(a2)

Preferred forms of the $R_1$ group (c) are:

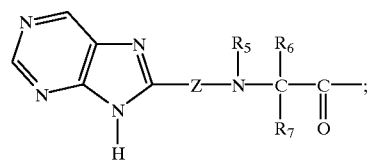

(b1)

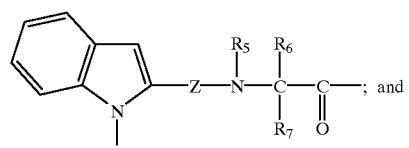

(b2)

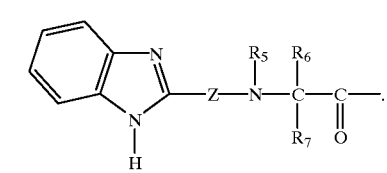

(b3)

Preferred forms of the $R_1$ group (c) are:

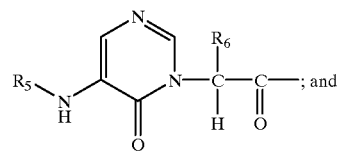

(c1)

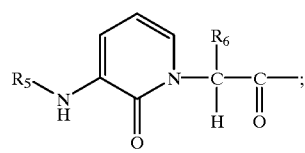

(c2)

provided that when $R_1$ is (c1),
g is 0,

J is —H,
m is 1,
T is —CO$_2$H,
X is N,
R$_5$ is benzyloxycarbonyl, and
R$_6$ is —H, then R$_3$ cannot be —CO—R$_{13}$ when
R$_{13}$ is —CH$_2$—O—Ar$_1$ and
Ar$_1$ is a chloro-substituted 1-phenyl-3-trifluoromethyl-pyrazole-5-yl, or when
R$_{13}$ is —CH$_2$—O—CO—Ar$_1$ and
Ar$_1$ is 2,6-dichlorophenyl,
and when the 2-position of the scaffold ring is substituted with para-fluoro-phenyl;

Preferred forms of the R$_1$ group (d) are:

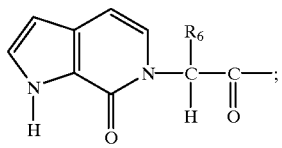
(d1)

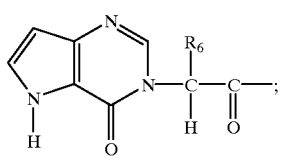
(d2)

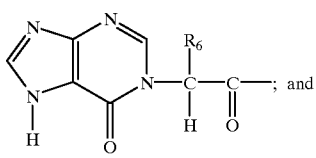
(d3)

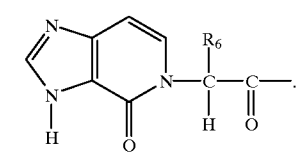
(d4)

Preferred forms of the R$_1$ group (e) are:

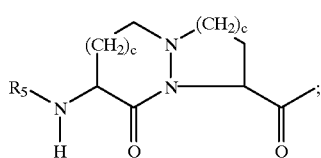
(e1)

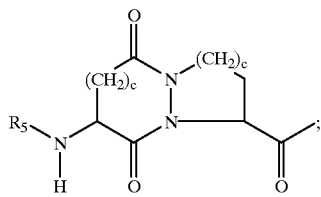
(e2)

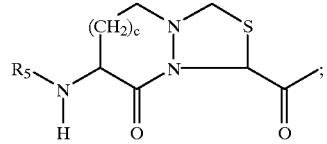
(e3)

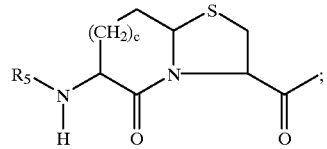
(e4)

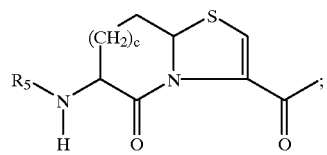
(e5)

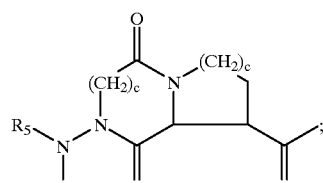
(e6)

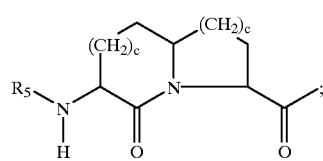
(e7)

which is optionally benzofused;

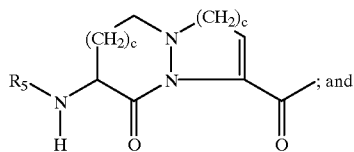
(e8)

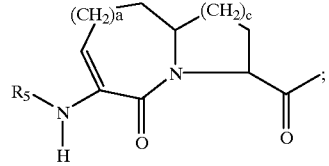
(e9)

provided that when R$_1$ is (e4),
g is 0,
J is —H,
m is 1,
T is —CO$_2$H,
R$_5$ is benzyloxycarbonyl, and
c is 1,
then R$_3$ cannot be —CO—R$_{13}$ when
R$_{13}$ is —CH$_2$—O—Ar$_1$ and Ar$_1$ is 1-phenyl-3-trifluoromethyl-pyrazole-5-yl, wherein the phenyl is optionally substituted with a chlorine atom; or when R$_{13}$ is —CH$_2$—O—CO—Ar$_1$ and
Ar$_1$ is 2,6-dichlorophenyl, and when the 2-position of the scaffold ring is substituted with para-fluoro-phenyl; and also provided that when R$_1$ is (e7),
g is 0,
J is —H,
m is 1,
T is —CO$_2$H or —CO—NH—OH,
R$_5$ is a protective group for the N atom of an amino acid side chain residue, and
each c is 1, then R$_3$ cannot be —CO—R$_{13}$ when R$_{13}$ is:
—CH$_2$—O—CO—Ar$_1$,
—CH$_2$—S—CO—Ar$_1$,
—CH$_2$—O—Ar$_1$, or
—CH$_2$—S—Ar$_1$.

Preferred forms of the R$_1$ group (g) are:

(g1)

(g2)

Preferred forms of the R$_1$ group (h) are:

(h1)

(h2)

(h3)

Preferred forms of the R$_1$ group (i) are:

(i1)

(i2)

(i3)

(i4)

Preferred forms of the R$_1$ group (j) are:

(j1)

(j2)

(j3)

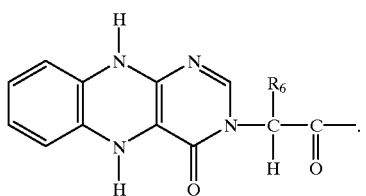
(j4)
Preferred forms of the $R_1$ group (k) are:
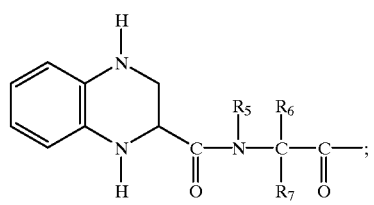
(k1)
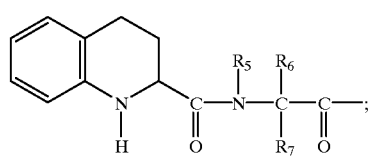
(k2)
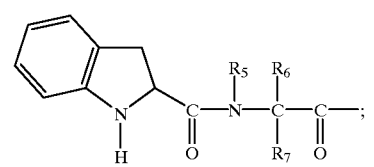
(k3)
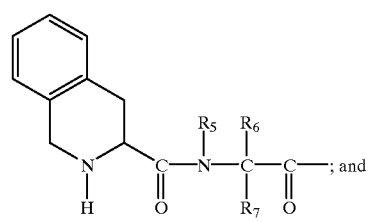
(k4)
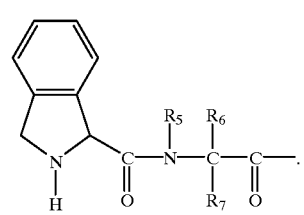
(k5)
Preferred forms of the $R_1$ group (l) are:
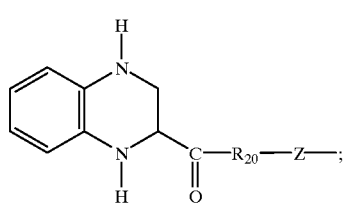
(l1)
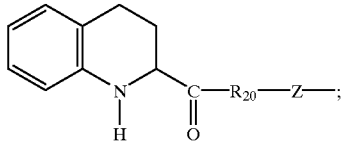
(l2)
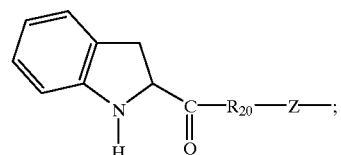
(l3)
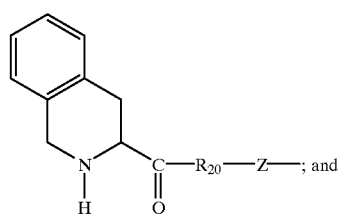
(l4)
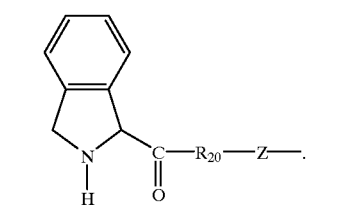
(l5)
Preferred forms of the $R_1$ group (m) are:
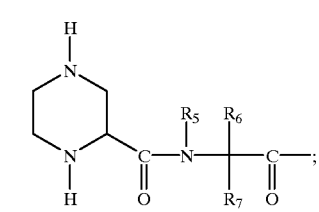
(m1)
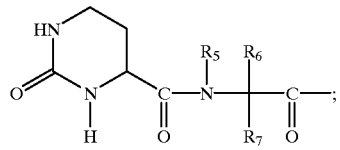
(m2)
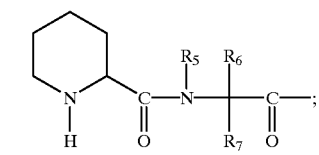
(m3)
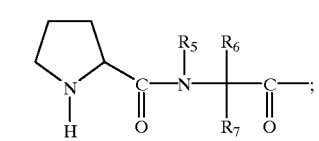
(m4)

-continued (m5)

(m6)

Preferred forms of the R₁ group (n) are:

(n1)

(n2)

(n3)

(n4)

(n5)

(n6)

Preferred forms of the R₁ group (o) are:

(o1)

(o2)

(o3)

(o4)

(o5)

A preferred form of the R₁ group (o) of embodiment B is:

(o6)

wherein X₂ is —O—, —S—, —SO₂—, or —NH—.
For embodiments A and B, preferred forms of the R₁ group (p) are:

(p1)

(p2)
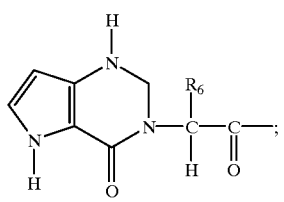
(p3)
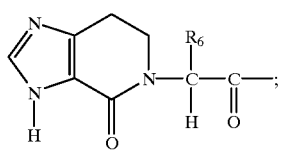
(p4)
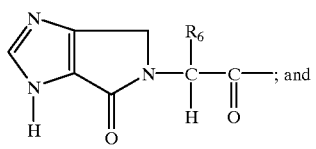; and
(p5)
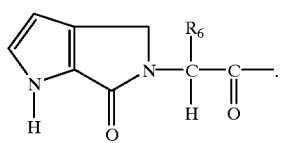.
Preferred forms of the $R_1$ group (q) are:
(q1)
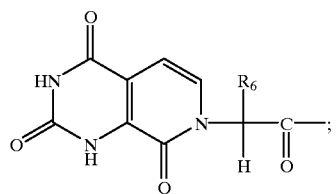
(q2)
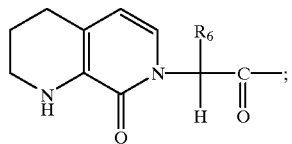
(q3)
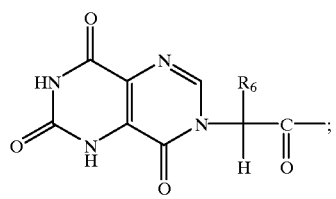
(q4)
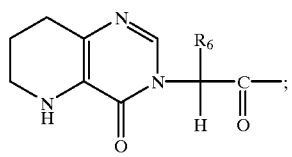
(q5)
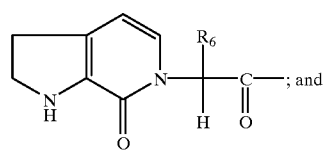; and
(q6)
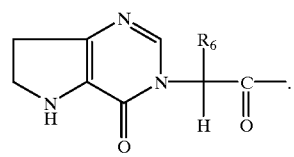.
Preferred forms of the $R_1$ group (r) are:
(r1)
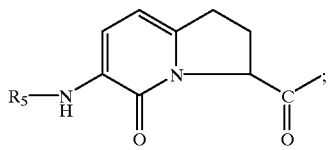
(r2)
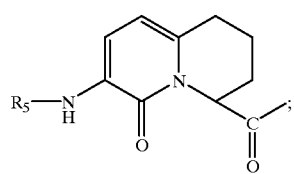
(r3)
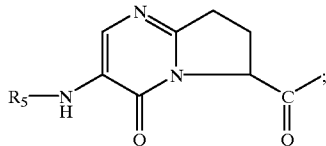
(r4)
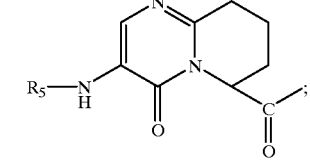
(r5)
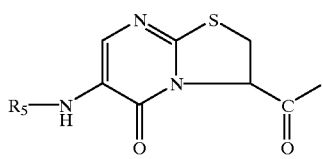
(r6)
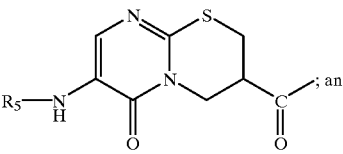; and

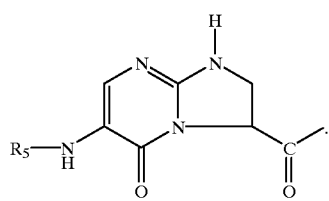 (r7)
Preferred forms of the R₁ group (s) are:
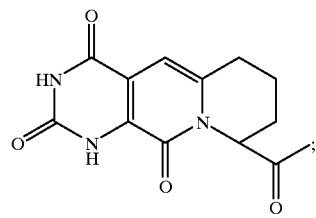 (s1)
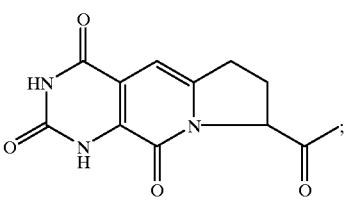 (s2)
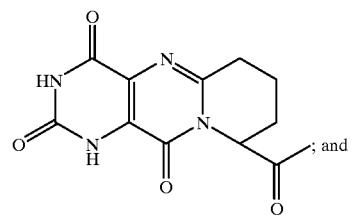 (s3)
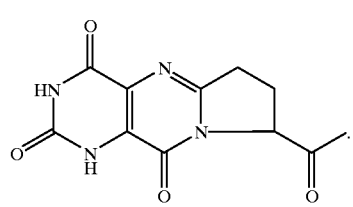 (s4)
Preferred forms of the R₁ group (t) are:
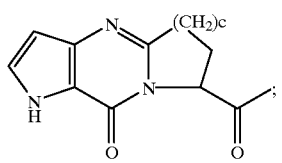 (t1)
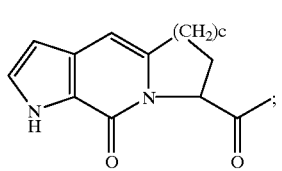 (t2)
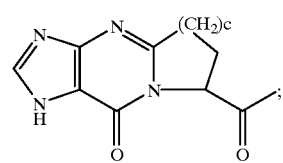 (t3)
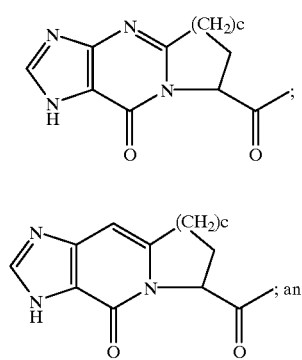 (t4)
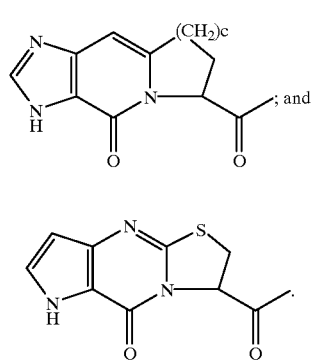 (t5)
Preferred forms of the R₁ group (v) are:
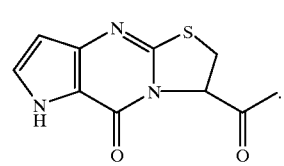 (v1)
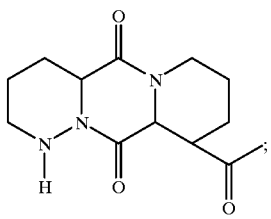 (v2)
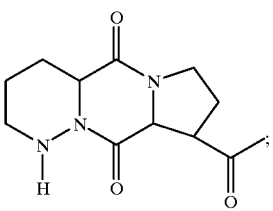 (v3)
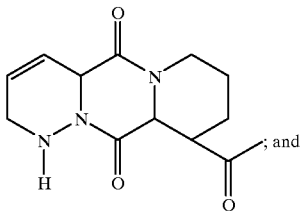 (v4)
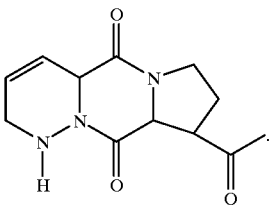

A preferred form of the $R_1$ group (w) of embodiment B is:

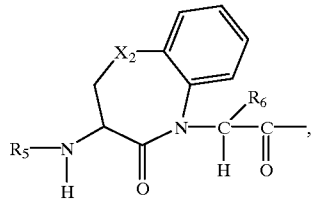
(w1)

wherein $X_2$ is —O—, —S—, —SO$_2$— or —NH—.

The preferred compounds of embodiments A and B of this invention are those which employ formula α, wherein:

$X_1$ is CH;

g is 0;

J is —H;

m is 0 or 1 and T is —Ar$_3$, —CO—CO$_2$H, —CO$_2$H or any bioisosteric replacement for —CO$_2$H, or m is 1 or 2 and T is —OH, —CF$_3$, or —CO$_2$H;

more preferably m is 1 and T is —CO$_2$H;

$R_1$ is

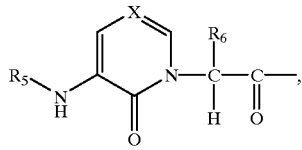
(c)

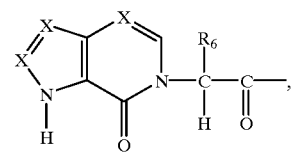
(d)

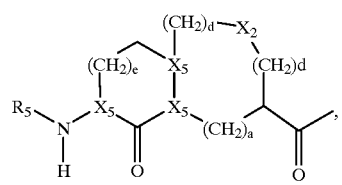
(e)

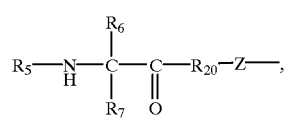
(f)

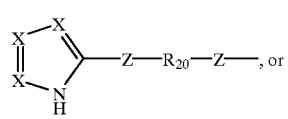
(g)

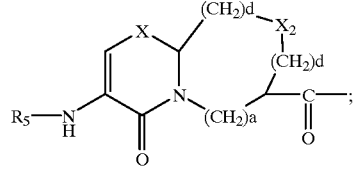
(r)

$R_{20}$ is

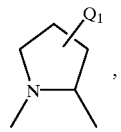
(aa1)

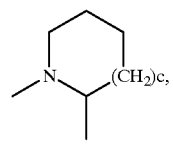
(aa2)

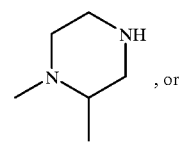
(aa3)

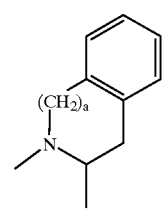
(dd)

wherein ring C is benzo;
$R_3$ is
—CO—R$_{13}$, or

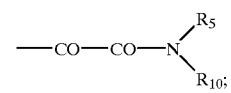

most preferably $R_3$ is any one of 1), 2) or 3) as follows:
1) —CO—Ar$_2$, 2) —CO—R$_9$ where R$_9$ is C$_{3-6}$ alkyl substituted with two Ar$_1$ groups or one Ar$_1$ group itself substituted with an Ar$_1$ group, —C$_{1-2}$—Ar$_1$, —Cl, —CH$_3$, or —CF$_3$, or 3) —(CH$_2$)$_{1,2}$—T$_1$—R$_9$ where T$_1$ is —O— or —S— and R$_9$ is C$_{1-2}$ alkyl substituted with two Ar$_1$ groups or one Ar$_1$ group itself substituted with an Ar$_1$ group, C$_{1-2}$—Ar$_1$, —Cl, —CH$_3$, or —CF$_3$;

$R_4$ is —H or —R$_9$;

$T_1$ is
—O—,
—S—,
—CO—,
—O—CO—, or
—SO$_2$—;

when $R_1$ is (a), (b), (k), or (m), $R_5$ is preferably —$Ar_1$ or $C_{1-4}$—$Ar_1$;

when $R_1$ is (c), (e), (f), (o), or (r), $R_5$ is preferably —$SO_2$—$Ar_1$, —$SO_2$—$R_9$, or —CO—$C_{1-4}$—$Ar_1$;

$R_7$ is —H and $R_6$ is $C_{1-4}$—$Ar_1$;

$R_{10}$ is —H or a $C_{1-3}$ straight or branched alkyl group;

$R_{13}$ is —$Ar_2$;

$Ar_1$ is phenyl, naphthyl, pyridyl, benzothiazolyl, thienyl, benzothienyl, benzoxazolyl, 2-indanyl, or indolyl;

$Ar_2$ is preferably substituted with —$Ar_1$, or —$C_{1-4}$—$Ar_1$;

$Ar_3$ is phenyl, thiophene, thiazole, pyridine, or oxazole; and $Q_1$ is —$R_9$ or —$(CH_2)_{1,2}$—$T_1$—$(CH_2)_{1-3}$—$Ar_1$ where $T_1$ is —O— or —S—.

In connection with this continuation-in-part, we now prefer the compounds of embodiment B of this invention which employ formula α, wherein:

$X_1$ is —CH;

g is O;

J is —H;

m is 0 or 1 and T is —CO—$CO_2H$, or any bioisosteric replacement for —$CO_2H$; or m is 1 and T is —$CO_2H$;

$R_1$ is selected from the group consisting of the following formulae, in which any ring may optionally be singly or multiply substituted at any carbon by $Q_1$, at any nitrogen by $R_5$, or at any atom by =O, —OH, —$CO_2H$, or halogen, and wherein (e) is optionally benzofused:

(a)

(b)

(c)

(e)

(f)

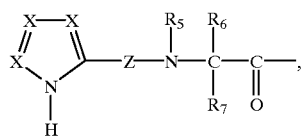

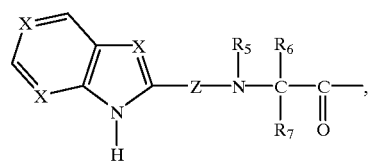

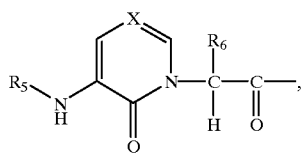

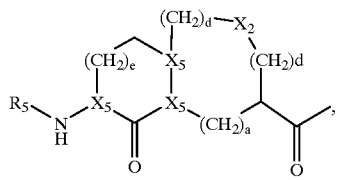

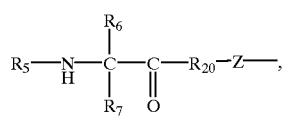

-continued (g)

(h)

(o)

(r)

(w)

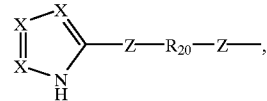

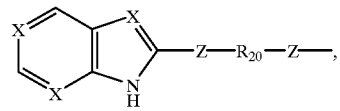

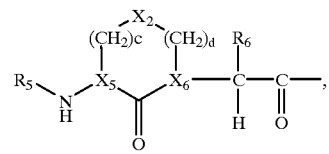

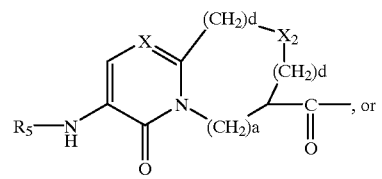

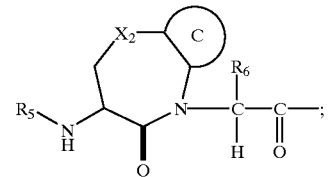

$R_{20}$ is (aa1)

(aa2)

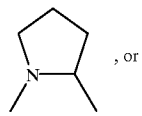

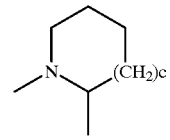

and c is 1;

ring C is benzo optionally substituted with —$C_{1-3}$ alkyl, —O—$C_{1-3}$ alkyl, —Cl, —F or —$CF_3$;

$R_3$ is:
—CO—$R_{13}$, or

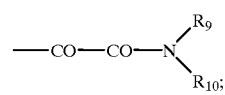

more preferably $R_3$ is any one of 1), 2) or 3) as follows: 1) —CO—$Ar_2$; 2) —CO—$R_9$ where $R_9$ is $C_{1-5}$ alkyl substituted with an $Ar_1$; or 3) —$CH_2$—$T_1$—$R_9$ where $T_1$ is —O— or —S— and $R_9$ is $C_{1-2}$ alkyl substituted with one $Ar_1$ group;

$R_4$ is —H or —$R_9$;
$T_1$ is:
 —S—,
 —CO—,
 —O—CO—, or
 —$SO_2$—;
when $R_1$ is (a) or (b), $R_5$ is preferably —H, and when $R_1$ is (c), (e), (f), (o), (r), (w), (x) or (y), $R_5$ is preferably:
 —CO—$Ar_1$,
 —$SO_2$—$Ar_1$,
 —CO—$NH_2$,
 —CO—NH—$Ar_1$,
 —CO—$R_9$,
 —CO—O—$R_9$,
 —$SO_2$—$R_9$, or
 —CO—NH—$R_9$,
$R_7$ is —H and $R_6$ is
 —H,
 —$R_9$ or
 —$Ar_1$;
$R_9$ is $C_{1-6}$ straight or branched alkyl group optionally substituted with =O and optionally substituted with —$Ar_1$;
$R_{10}$ is —H or a $C_{1-3}$ straight or branched alkyl group;
$R_{13}$ is:
 —H,
 —$R_9$,
 —$Ar_2$, or
 —$CH_2$—$T_1$—$R_9$,
more preferably where —$Ar_2$ is (hh) and where (hh) is optionally substituted singly or multiply with —$C_{1-6}$ alkyl, —O—$C_{1-6}$ alkyl, —NH—$C_{1-6}$ alkyl, —N—($C_{1-6}$ alkyl)$_2$, —S—$C_{1-6}$ alkyl, —Cl, —F, —$CF_3$, or

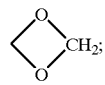

$Ar_1$ is phenyl, naphthyl, pyridyl, benzothiazolyl, thienyl, benzothienyl, benzoxazolyl, 2-indanyl, or indolyl substituted with —O—$C_{1-3}$ alkyl, —NH—$C_{1-3}$ alkyl, —N—($C_{1-3}$ alkyl)$_2$, —Cl, —F, —$CF_3$, —$C_{1-3}$ alkyl, or

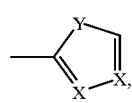

preferably where $Ar_2$ is:

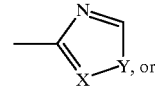
(ii)

(jj)

-continued

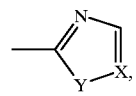
(kk)

each X is independently selected from the group consisting of =N— and =CH—;
each $X_2$ is independently selected from the group consisting of —O—, —$CH_2$—, —NH—, —S—, —SO—, and —$SO_2$—;
each $X_5$ is independently selected from the group consisting of

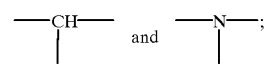
and $X_6$ is

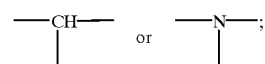
or and
Z is C=O;
provided that when
 $R_1$ is (f),
 $R_6$ is an α-amino acid side chain residue, and
 $R_7$ is —H,
then (aa1) and (aa2) must be substituted with $Q_1$;
also provided that when
 $R_1$ is (o),
 g is 0,
 J is —H,
 m is 1,
 $R_6$ is an α-amino acid side chain residue,
 $R_7$ is —H,
 $X_2$ is —$CH_2$—,
 $X_5$ is

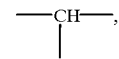

$X_6$ is

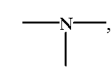

and
$R_3$ is

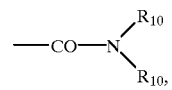

or —CO—$R_{13}$, when
$R_{13}$ is:
 —$CH_2$—O—CO—$Ar_1$,
 —$CH_2$—S—CO—$Ar_1$,
 —$CH_2$—O—$Ar_1$,
 —$CH_2$—S—$Ar_1$, or
 —$R_4$ when —$R_4$ is —H;

then the ring of the $R_1(o)$ group must be substituted with $Q_2$ or benzofused; and provided that when
$R_1$ is (w),
g is 0,
J is —H,
m is 1,
T is —$CO_2H$,
$X_2$ is O,
$R_5$ is benzyloxycarbonyl, and
ring C is benzo,
then $R_3$ cannot be —CO—$R_{13}$ when:
$R_{13}$ is —$CH_2$—O—$Ar_1$ and
$Ar_1$ is 1-phenyl-3-trifluoromethyl-pyrazole-5-yl, wherein the phenyl is optionally substituted with a chlorine atom;
or when $R_{13}$ is —$CH_2$—O—CO—$Ar_1$, wherein $Ar_1$ is 2,6-dichlorophenyl.

A preferred form of $R_{13}$ is —$CH_2$—O—$R_9$, wherein $R_9$ is a $C_{1-6}$ straight or branched alkyl group optionally substituted with =O and optionally substituted with $Ar_1$;

another preferred form of $R_{13}$ is $CH_2$—S—$R_9$, wherein $R_9$ is a $C_{1-6}$ straight or branched alkyl group optionally substituted with $Ar_1$;

another preferred form of $R_{13}$ is $CH_2$—O—$R_9$ wherein $R_9$ is a $C_{1-6}$ straight or branched alkyl group optionally substituted with $Ar_1$;

another preferred form of $R_{13}$ is H.

A more preferred form of the $R_1$ group (a) is:

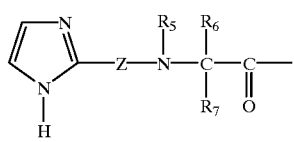

(a2)

optionally substituted with $Q_1$, wherein
$R_5$ is —H;
$R_7$ is —H; and
Z is C=O;

a more preferred form of the $R_1$ group (b) is:

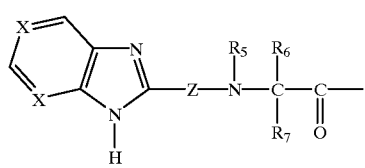

(b)

optionally substituted with $Q_1$, wherein
$R_5$ is —H;
$R_7$ is —H; and
Z is C=O;

more preferred forms of the $R_1$ group (c) are:

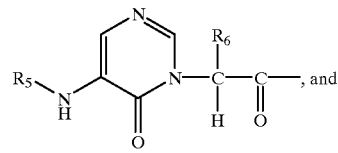

(c1)

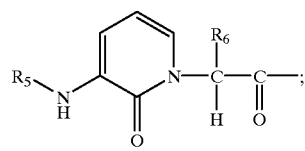

(c2)

provided that when $R_1$ is (c1),
g is 0,
J is —H,
m is 1,
T is —$CO_2H$,
X is N,
$R_5$ is benzyloxycarbonyl, and
$R_6$ is —H,
then $R_3$ cannot be —CO—$R_{13}$ when
$R_{13}$ is —$CH_2$—O—$Ar_1$ and
$Ar_1$ is 1-phenyl-3-trifluoromethyl-pyrazole-5-yl wherein the phenyl is optionally substituted with a chlorine atom; or when
$R_{13}$ is —$CH_2$—O—CO—$Ar_1$, wherein
$Ar_1$ is 2,6-dichlorophenyl, and wherein the 2-position of the scaffold ring is substituted with para-fluorophenyl;

more preferred forms of the $R_1$ group (e) are:

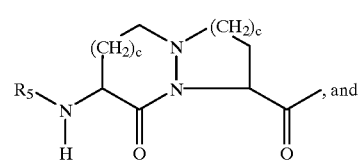

(e1)

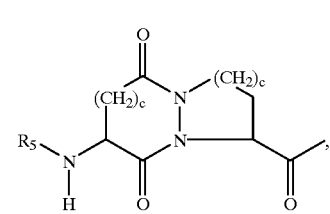

(e2)

wherein c is 2; and

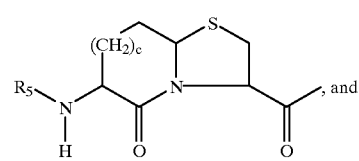

(e4)

-continued

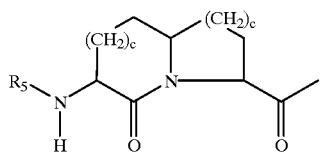
(e7)

which is optionally benzofused,
wherein c is 1 or 2;
provided that when $R_1$ is (e4),
  g is 0,
  J is —H,
  m is 1,
  T is —$CO_2H$,
  $R_5$ is benzyloxycarbonyl, and
  c is 1,
then $R_3$ cannot be —CO—$R_{13}$ when
  $R_{13}$ is —$CH_2$—O—$Ar_1$ and
  $Ar_1$ is 1-phenyl-3-trifluoromethyl-pyrazole-5-yl wherein the phenyl is optionally substituted with a chlorine atom; or when
  $R_{13}$ is —$CH_2$—O—CO—$Ar_1$, wherein
  $Ar_1$ is 2,6-dichlorophenyl,
and wherein the 2-position of the scaffold ring is substituted with para-fluoro-phenyl; and
also provided that when
  $R_1$ is (e7),
  g is 0,
  J is —H,
  m is 1,
  T is —$CO_2H$, —CO—NH—OH, or a bioisosteric replacement for —$CO_2H$,
  $R_5$ is a protective group for the N atom of an α-amino acid side chain residue, and
  each c is 1,
then $R_3$ cannot be —CO—$R_{13}$ when $R_{13}$ is:
  —$CH_2$—O—CO—$Ar_1$,
  —$CH_2$—S—CO—$Ar_1$,
  —$CH_2$—O—$Ar_1$, or
  —$CH_2$—S—$Ar_1$ —.

a more preferred form of the $R_1$ group (f) is

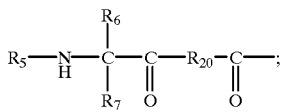
(f1)

a more preferred form of the $R_1$ group (g) is:

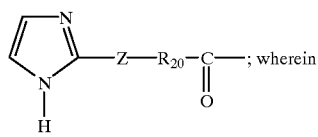
(g2)

$R_{20}$ is (aa1) optionally substituted singly or multiply with $Q_1$; and

Z is C=O;

a more preferred form of the $R_1$ group (h) is:

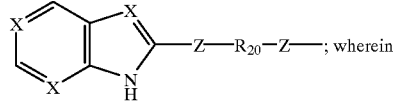
(h)

$R_{20}$ is (aa1) optionally substituted singly or multiply with $Q_1$; and
Z is C=O;

more preferred forms of the $R_1$ group (o) are:

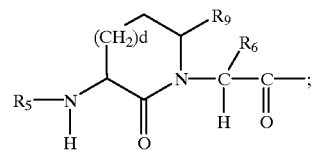
(o1)

wherein d is 1 or 2; and

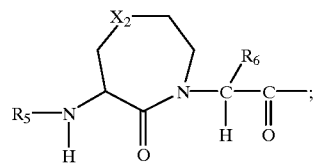
(o6)

more preferred forms of the $R_1$ group (r) are:

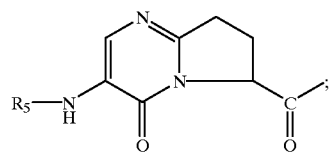
(r3)

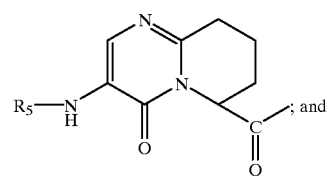
(r4)
; and

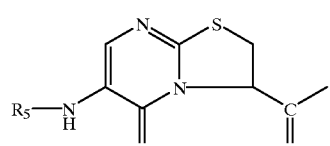
(r5)

optionally substituted with $Q_1$;

a more preferred form of the $R_1$ group (w) is:

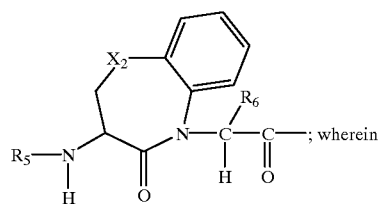

(w1)

$X_2$ is:
—NH—,
—S—,
—O—, or
—SO$_2$—;
optionally substituted with $R_5$ or $Q_1$ at $X_2$ when $X_2$ is —N—; and
ring C is benzo substituted with —$C_{1-3}$ alkyl, —O—$C_{1-3}$ alkyl, —Cl, —F or —CF$_3$.
When $R_1$ is:

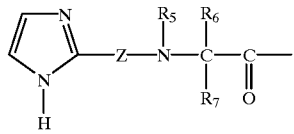

(a2)

preferred compounds of this invention include but are not limited to:

A preferred compound of embodiment B of this invention employs formula α, wherein the $R_1$ is:

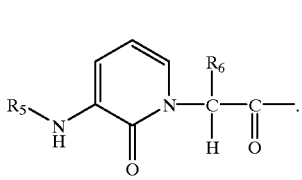

(c2)

Preferred compounds of this embodiment include but are not limited to:

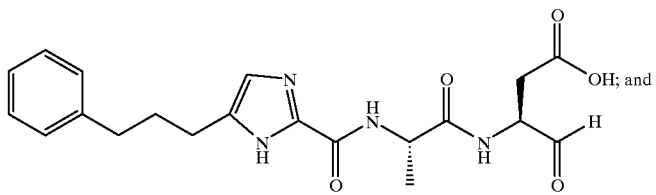

20d

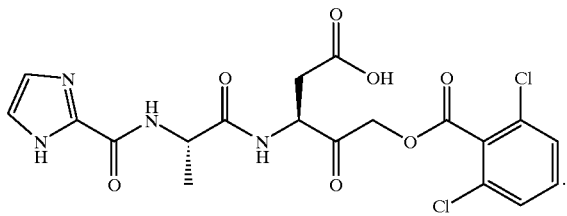

142

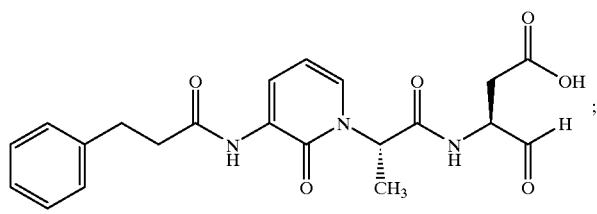
54a
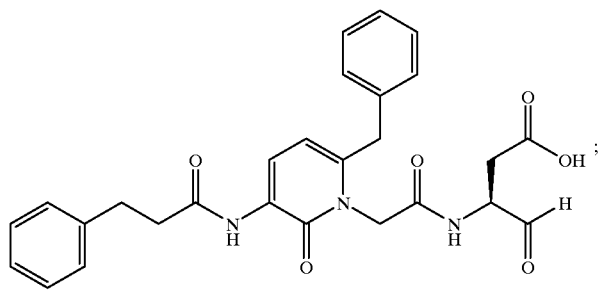
54b
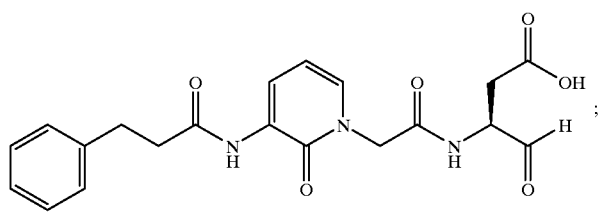
54g
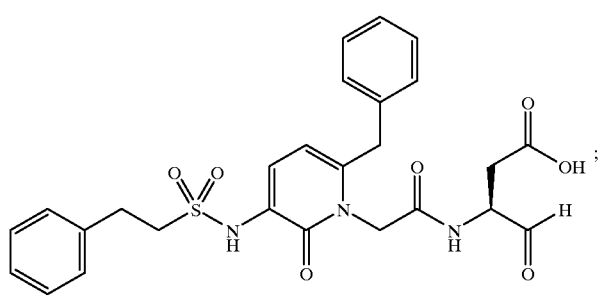
54j
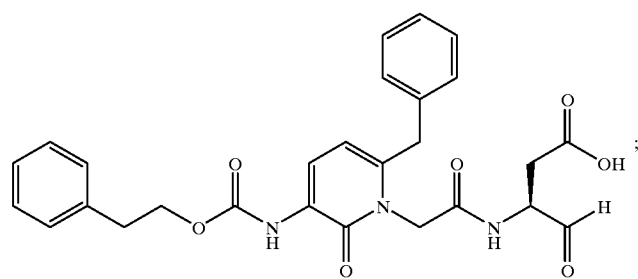
54k

57b
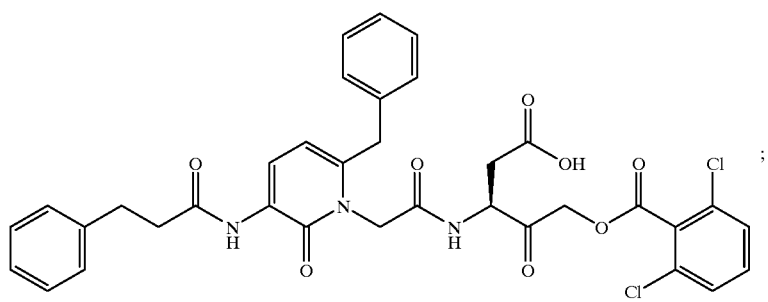
88
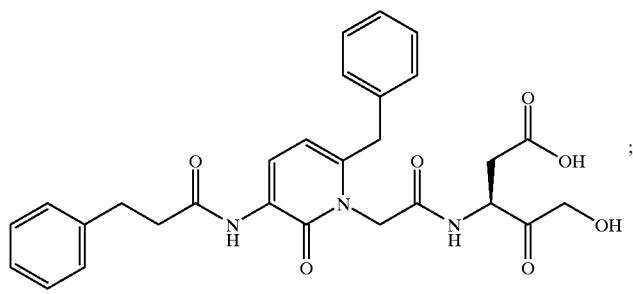
90
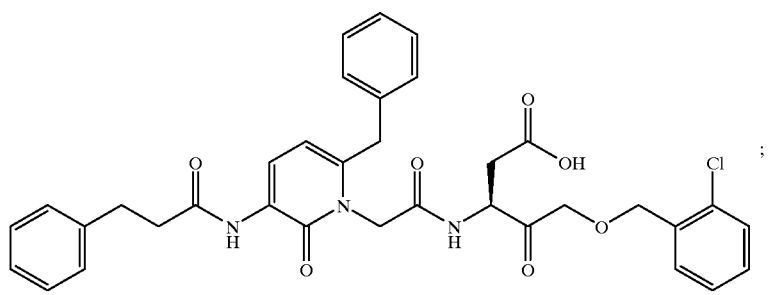
91
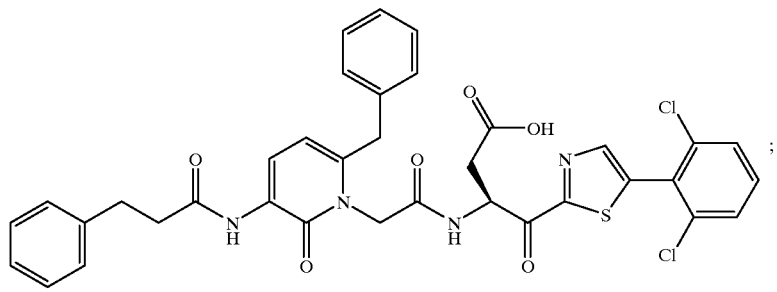
125a
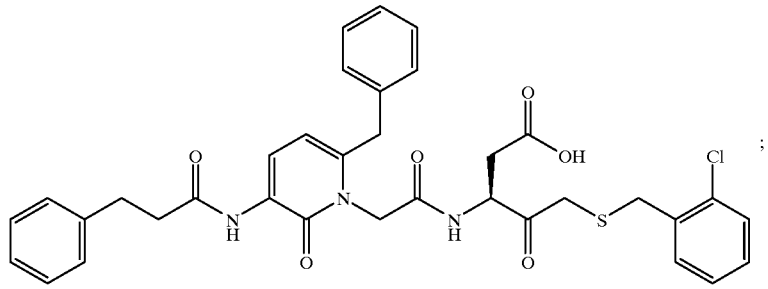

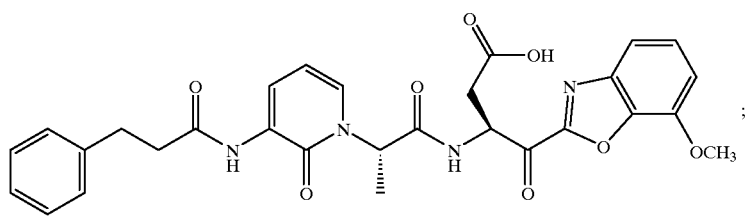
126
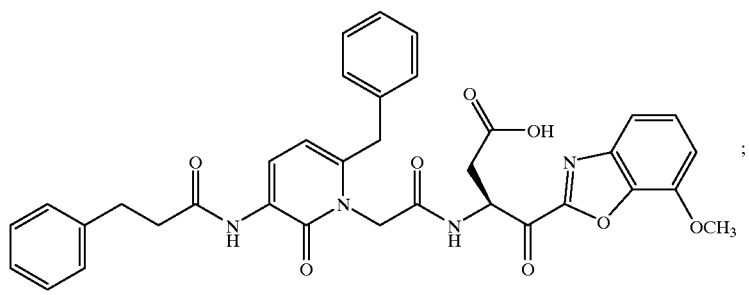
127
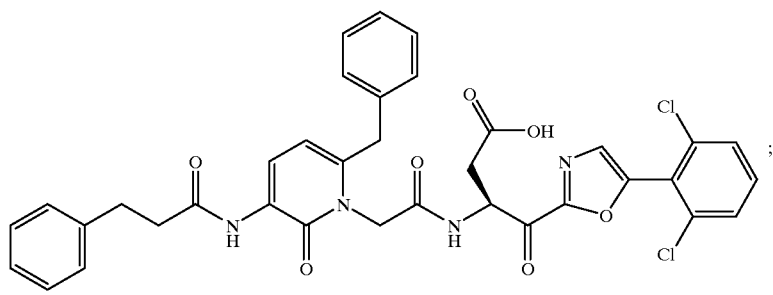
128
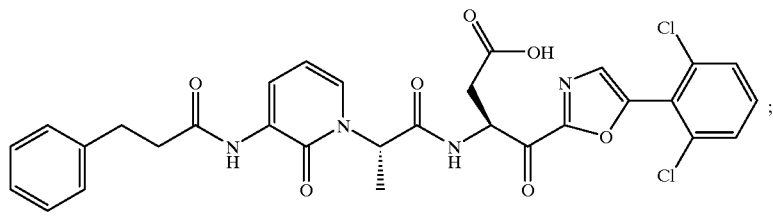
129
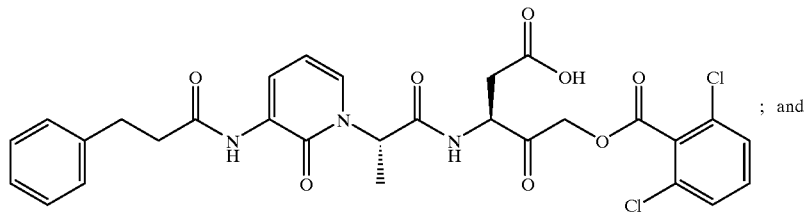
130
; and

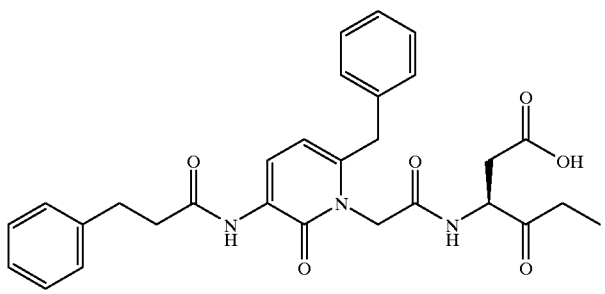
131
When R₁ is:
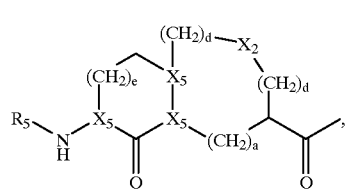
(e)
preferred compounds of this invention include but are not limited to:
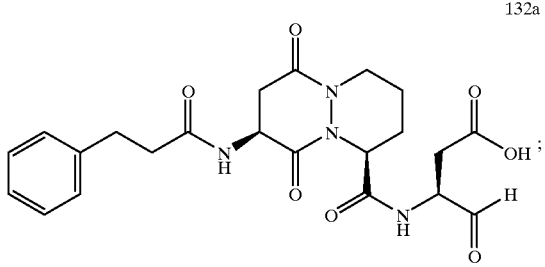
132a
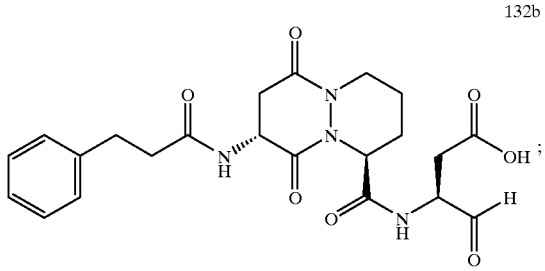
132b
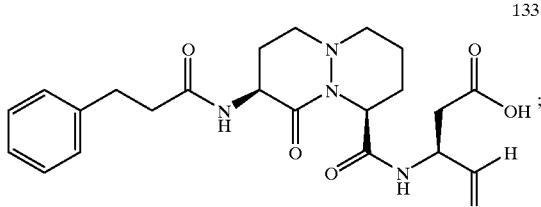
133
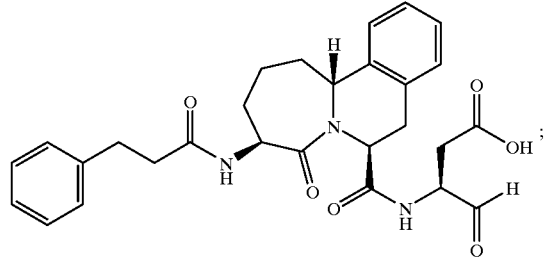
140
and
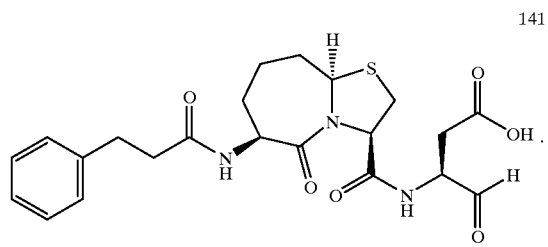
141
A preferred compound of embodiment B of this invention employs formula α, wherein:
R₁ is:
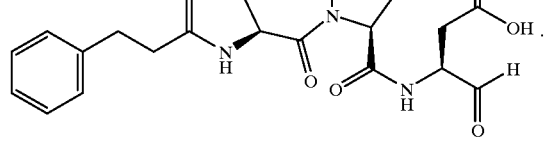
(e1)
, or
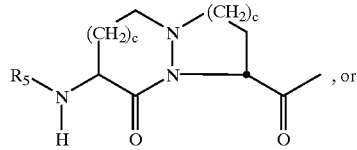
(e2)
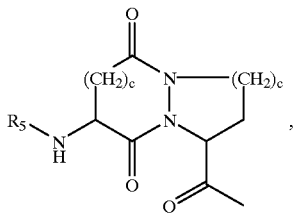
and c is 2;
m is 1;

T is —CO₂H; and
R₃ is —CO—R₁₃.
Preferred compounds of this embodiment include but are not limited to:
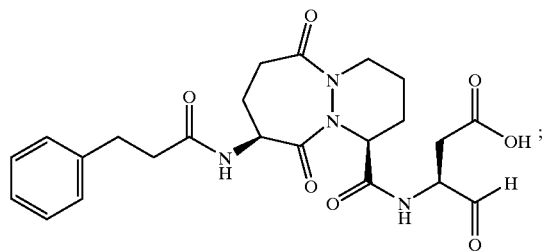
47a
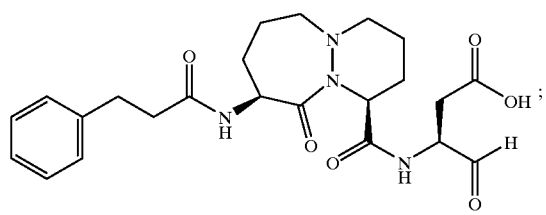
47b
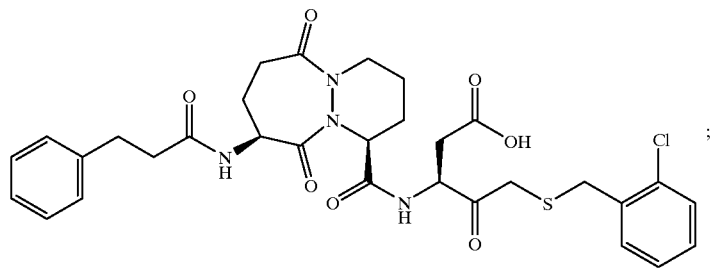
125b
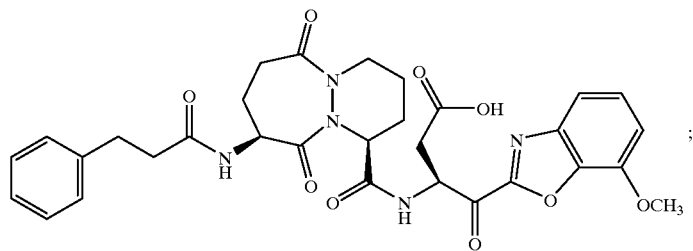
135a
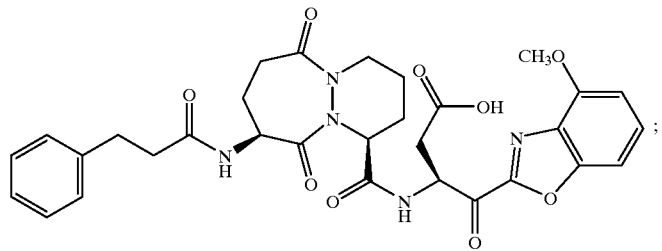
135b -continued
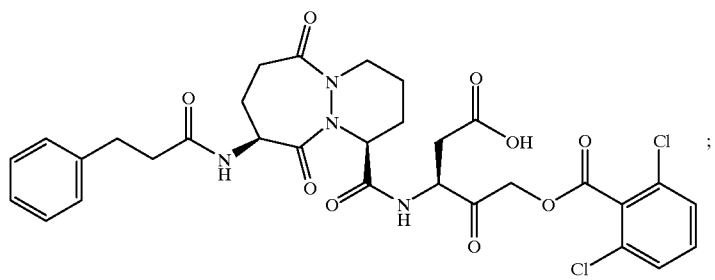
136
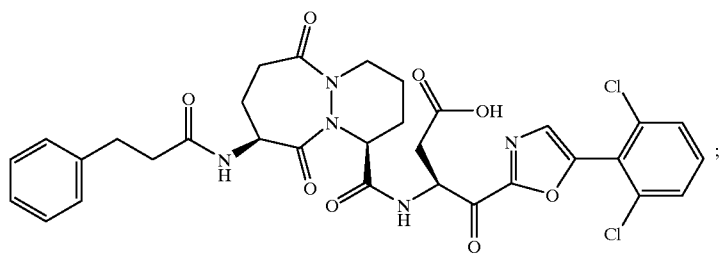
137
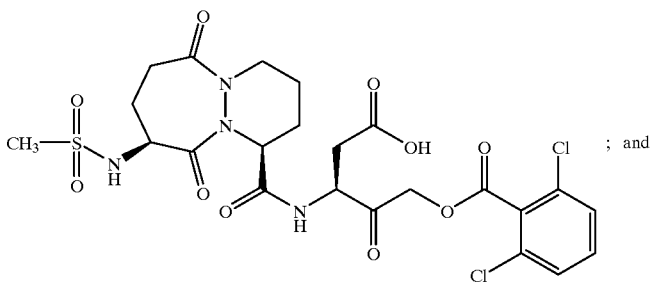
138
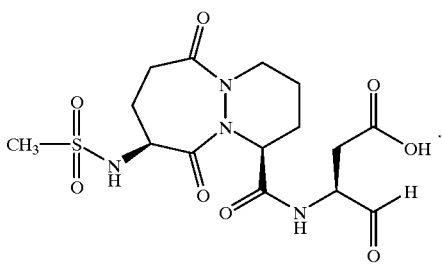
139
When R₁ is:
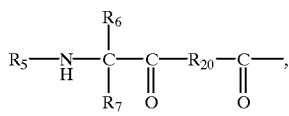
(f1)
preferred compounds of this invention include but are not limited to:
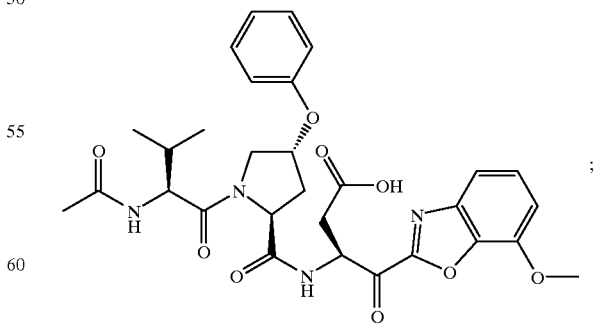
86

87
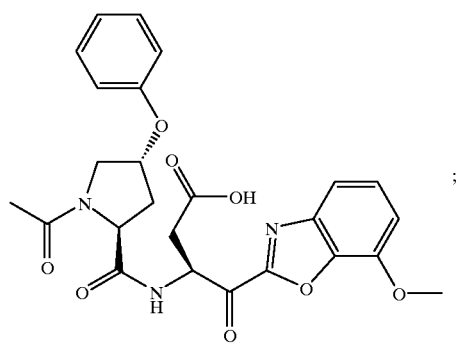
158
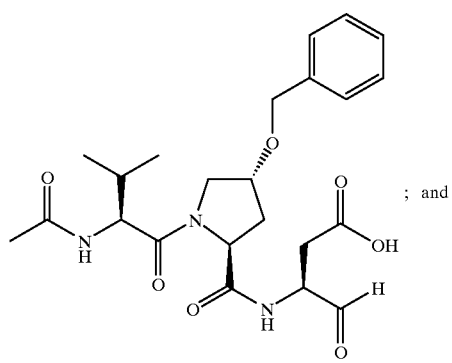
; and
160
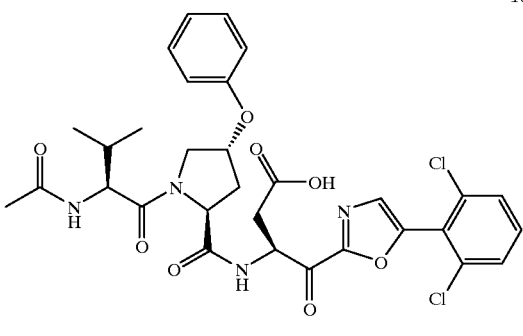
.
When R₁ is:
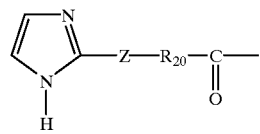
(g2)
preferred compounds of this invention include but are not limited to:
21d
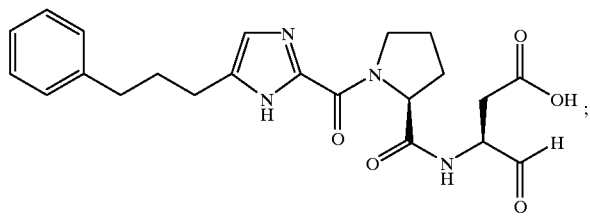
21e
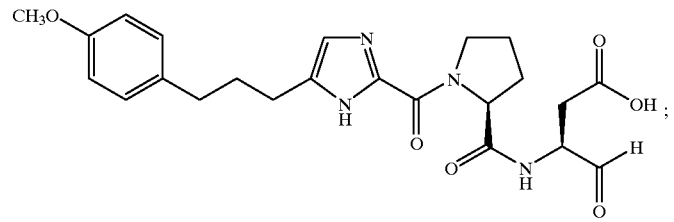
21f
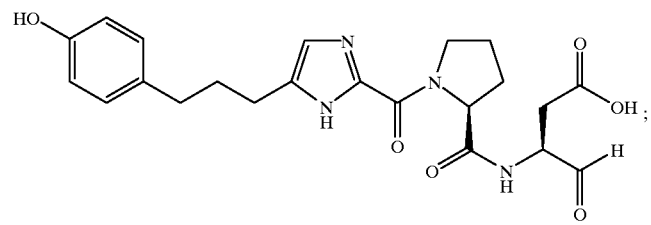

-continued
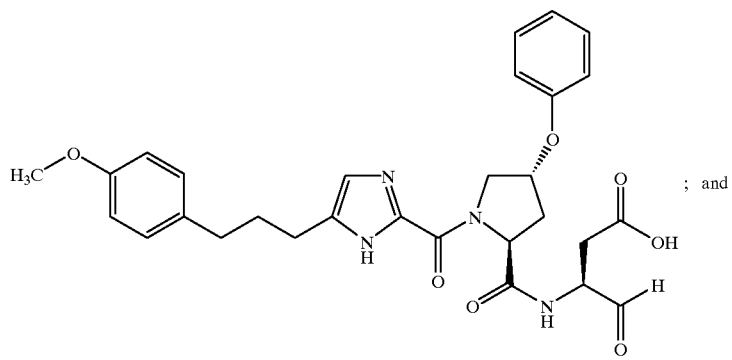
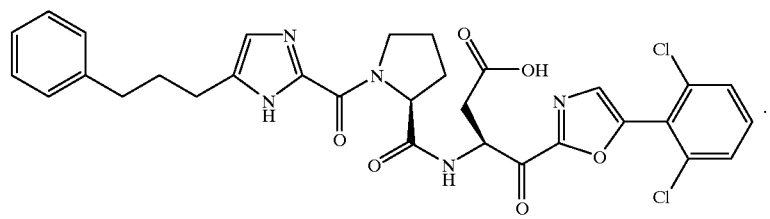
When $R_1$ is:
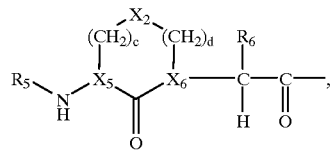
(o)
preferred compounds of this invention include but are not limited to:
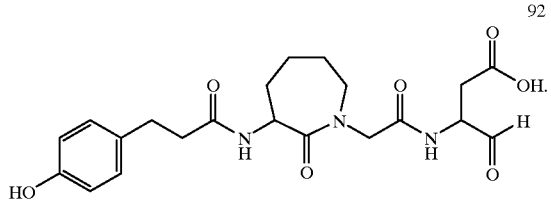
92
A preferred compound of embodiment B of this invention employs formula α, wherein:
$R_1$ is:
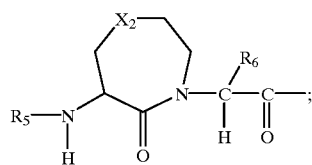
(o6)
$X_2$ is —NH—;
m is 1;
T is —CO$_2$H;
$R_3$ is —CO—$R_{13}$.
Preferred compounds of this embodiment include but are not limited to:
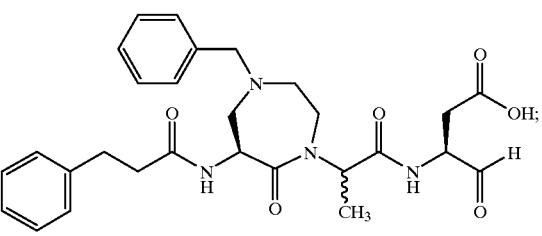
114a
114b
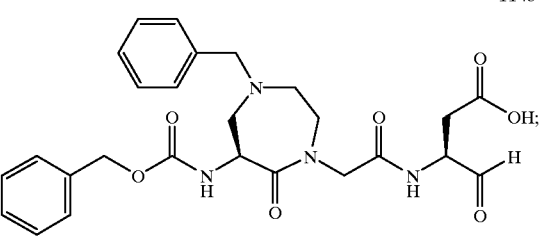
115
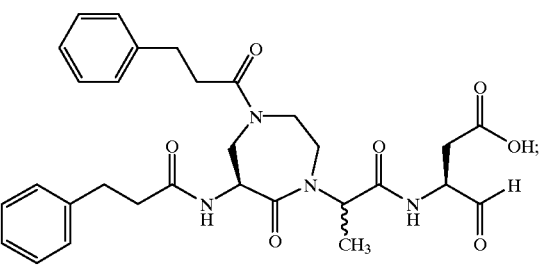
and

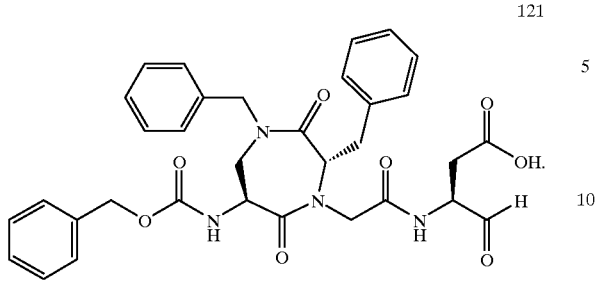
121
When R₁ is:
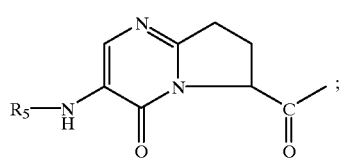
(r3)
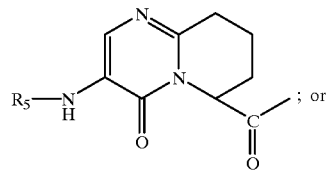
(r4)
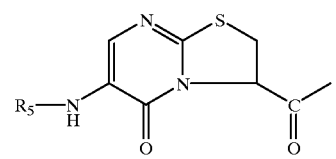
(r5)
optionally substituted with Q₁;
preferred compounds of embodiment B of this invention include but are not limited to:
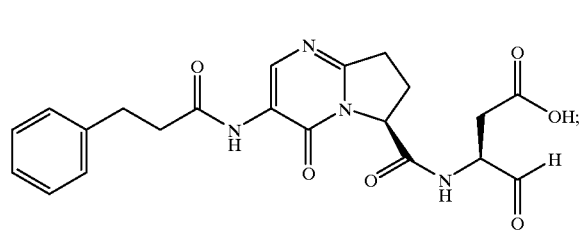
98
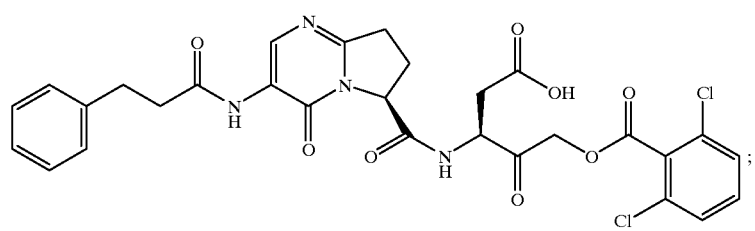
102a
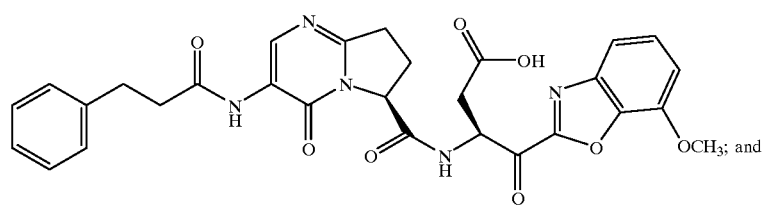
102b
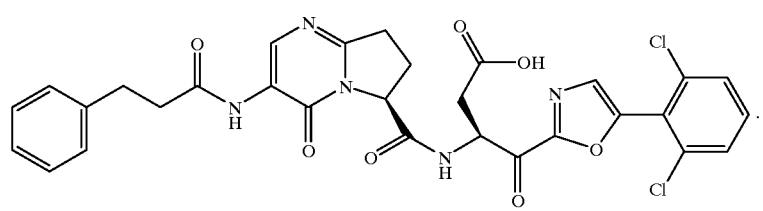
102c When R₁ is:
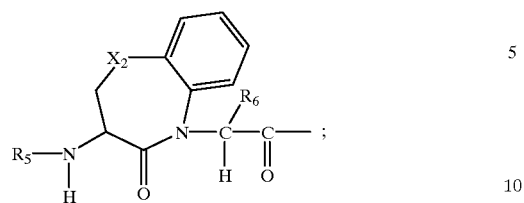 (w1)
preferred compounds of this invention include but are not limited to:
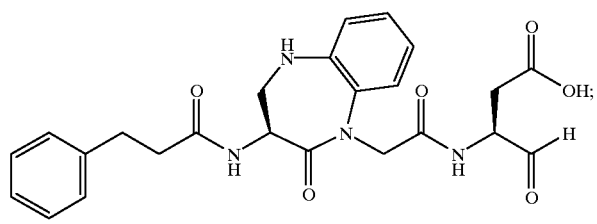
106a
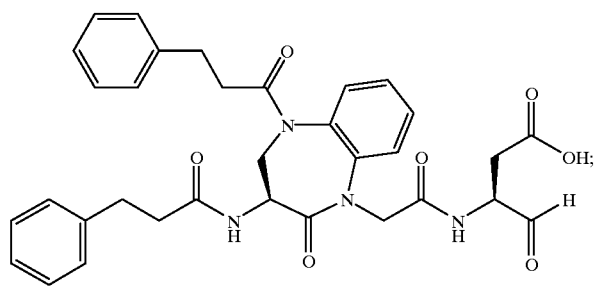
106b
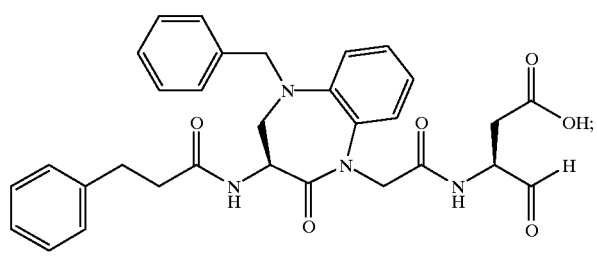
106c
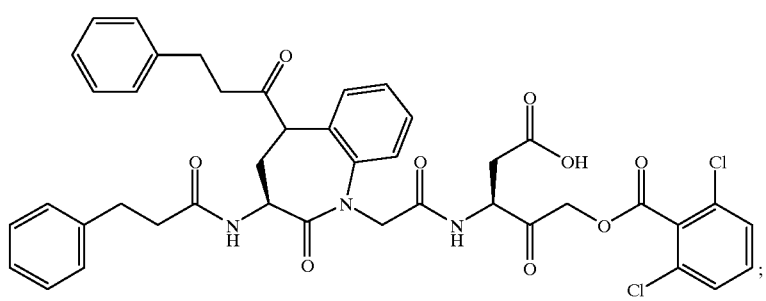
108a

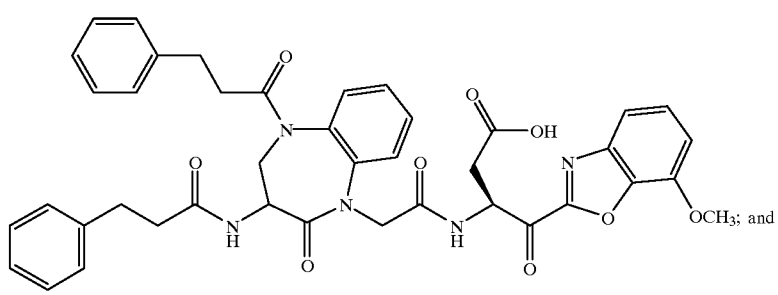

108b

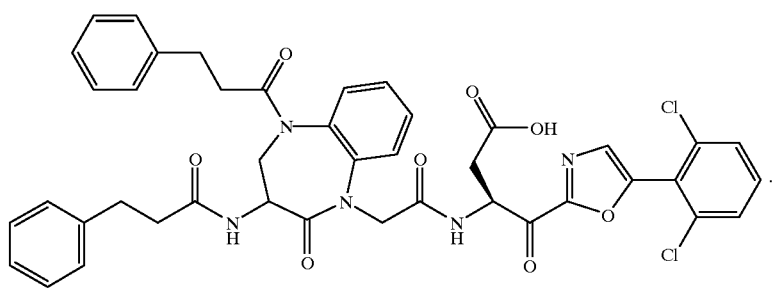

108c

The ICE inhibitors of another embodiment (C) of this invention are represented by the formula σ:

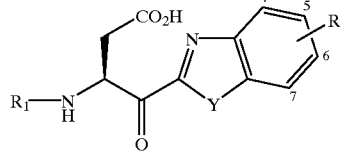

σ wherein the ring is optionally substituted with one or more R groups, preferably 0, 1 or 2; and wherein:

$R_1$ is $R_5—(A)_p—$;

$R_5$ is selected from the group consisting of:
- —H,
- —$Ar_1$,
- —CO—$Ar_1$,
- —$SO_2$—$Ar_1$,
- —$R_9$,
- —CO—$R_9$,
- —CO—O—$R_9$,

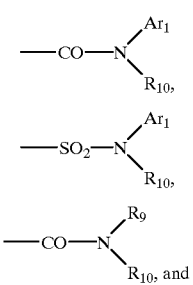

-continued

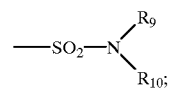

each A is independently selected from the group consisting of any α-amino acid;

p is 0, 1, 2, 3 or 4;

Y is:
- —S— or
- —NH;

R is:
- —H,
- —O—$C_{1-6}$ alkyl,
- —NH($C_{1-6}$ alkyl),
- —N($C_{1-6}$ alkyl)$_2$,
- —S—$C_{1-6}$ alkyl,
- —$C_{1-6}$ alkyl, or
- —$Q_2$;

each $R_9$ is a $C_{1-6}$ straight or branched alkyl group optionally singly or multiply substituted by —OH, —F, or =O and optionally substituted with one or two $Ar_1$ groups;

each $R_{10}$ is independently selected from the group consisting of —H or a $C_{1-6}$ straight or branched alkyl group;

each $T_1$ is independently selected from the group consisting of:
- —CH=CH—,
- —O—,
- —S—,
- —SO—,
- —$SO_2$—,
- —$NR_{10}$—,
- —$NR_{10}$—CO—,
- —CO—,
- —O—CO—,
- —CO—O—,
- —CO—$NR_{10}$—, —O—CO—NR$_{10}$—,
—NR$_{10}$—CO—O—,
—NR$_{10}$—CO—NR$_{10}$—,
—SO$_2$—NR$_{10}$—,
—NR$_{10}$—SO$_2$—, and
—NR$_{10}$—SO$_2$—NR$_{10}$—, each Ar$_1$ is a cyclic group independently selected from the set consisting of an aryl group which contains 6, 10, 12, or 14 carbon atoms and between 1 and 3 rings, a cycloalkyl group which contains between 3 and 15 carbon atoms and between 1 and 3 rings, said cycloalkyl group being optionally benzofused, and a heterocycle group containing between 5 and 15 ring atoms and between 1 and 3 rings, said heterocycle group containing at least one heteroatom group selected from —O—, —S—, —SO—, —SO$_2$—, =N—, and —NH—, said heterocycle group optionally containing one or more double bonds, said heterocycle group optionally comprising one or more aromatic rings, and said cyclic group optionally being singly or multiply substituted by: —NH$_2$, —CO$_2$H, —Cl, —F, —Br, —I, —NO$_2$, —CN, =O, —OH, -perfluoro C$_{1-3}$ alkyl,

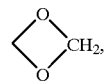

or —Q$_1$;
each Q$_1$ is independently selected from the group consisting of:
—Ar$_1$
—R$_9$,
—T$_1$—R$_9$, and
—(CH$_2$)$_{1,2,3}$—T$_1$—R$_9$;
each Q$_2$ is independently selected from the group consisting of —OH, —NH$_2$, —CO$_2$H, —Cl, —F, —Br, —I, —NO$_2$, —CN, —CF$_3$, and

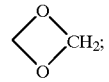

provided that when —Ar$_1$ is substituted with a Q$_1$ group which comprises one or more additional —Ar$_1$ groups, said additional —Ar$_1$ groups are not substituted with Q$_1$.

Preferred compounds of embodiment C of this invention include but are not limited to:

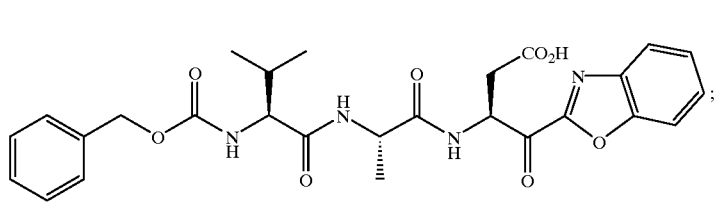

(O)

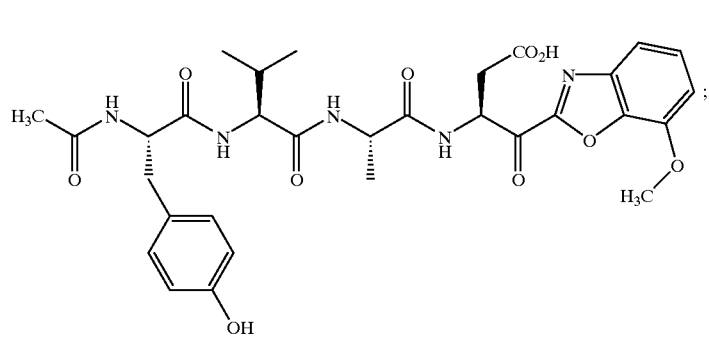

(R)

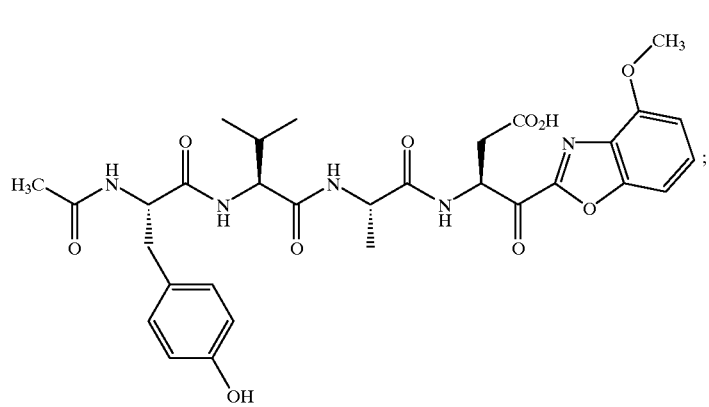

(S)

(T)

(V)

Preferred compounds of embodiment C of this invention are also those in which each A is independently selected from the group consisting of the α-amino acids:
alanine,
histidine,
lysine,
phenylalanine,
proline,
tyrosine,
valine,
leucine,
isoleucine,
glutamine,
methionine,
homoproline,
3-(2-thienyl) alanine, and
3-(3-thienyl) alanine.

The ICE inhibitors of another embodiment (D) of this invention are represented by the formula π:

π wherein:
$R_1$ is $R_5$—$(A)_p$—;
each $T_1$ is independently selected from the group consisting of:
—CH=CH—,
—O—,
—S—,
—SO—,
—$SO_2$—,
—$NR_{10}$—,
—$NR_{10}$—CO—,
—CO—,
—O—CO—,
—CO—O—,
—CO—$NR_{10}$—,
—O—CO—$NR_{10}$—,
—$NR_{10}$—CO—O—,
—$NR_{10}$—CO—$NR_{10}$—,
—$SO_2$—$NR_{10}$—,
—$NR_{10}$—$SO_2$—, and
—$NR_{10}$—$SO_2$—$NR_{10}$—, $R_5$ is selected from the group consisting of:
—H,
—$Ar_1$,
—CO—$Ar_1$,
—$SO_2$—$Ar_1$,
—$R_9$,
—CO—$R_9$,
—CO—O—$R_9$,
—$SO_2$—$R_9$, —CO—N(Ar$_1$)(R$_{10}$), —SO$_2$—N(Ar$_1$)(R$_{10}$), —CO—N(R$_9$)(R$_{10}$), and -continued

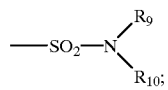

each A is independently selected from the group consisiting of any α-amino acid;
p is 0, 1, 2, 3 or 4;
each $R_9$ is a $C_{1-6}$ straight or branched alkyl group optionally singly or multiply substituted by —OH, —F, or =O and optionally substituted with an $Ar_1$ group;
each $R_{10}$ is independently selected from the group consisting of —H or a $C_{1-6}$ straight or branched alkyl group;
$Ar_1$ is a cyclic group independently selected from the set consisting of an aryl group which contains 6, 10, 12, or 14 carbon atoms and between 1 and 3 rings, a cycloalkyl group which contains between 3 and 15 carbon atoms and between 1 and 3 rings, said cycloalkyl group being optionally benzofused, and a heterocycle group containing between 5 and 15 ring atoms and between 1 and 3 rings, said heterocycle group containing at least one heteroatom group selected from —O—, —S—, —SO—, —SO$_2$—, =N—, and —NH—, said heterocycle group optionally containing one or more double bonds, said heterocycle group optionally comprising one or more aromatic rings, and said cyclic group optionally being singly or multiply substituted by —NH$_2$, —CO$_2$H, —Cl, —F, —Br, —I, —NO$_2$, —CH, =O, —OH, -perfluoro $C_{1-3}$ alkyl, or

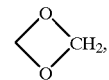

—$R_9$, or —$T_1$—$R_9$.

Preferred compounds of embodiment D of this invention are those in which $R_9$ is a $C_{1-4}$ straight or branched alkyl substituted with $Ar_1$ when $Ar_1$ is phenyl.

Preferred compounds of embodiment D of this invention include but are not limited to:

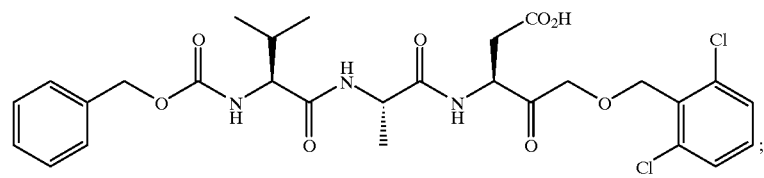

(W)

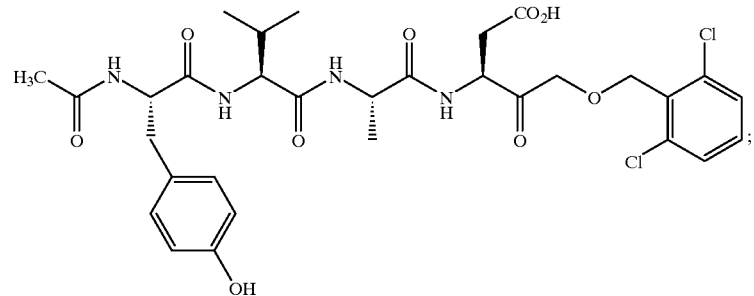

(X)

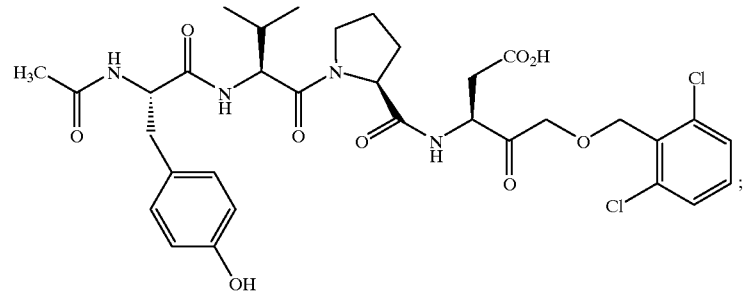

(Y)

-continued

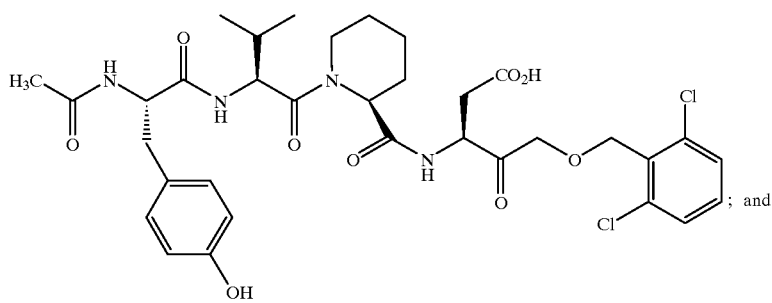

(Z)

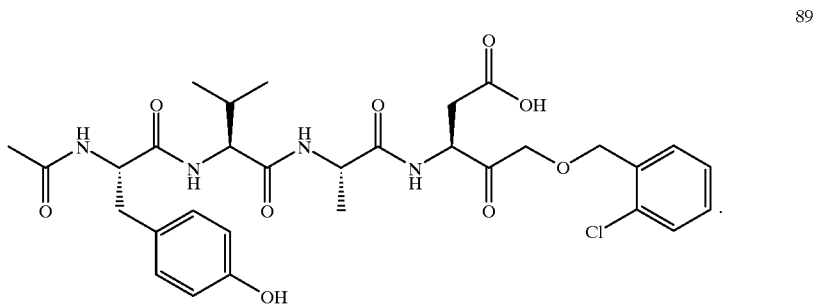

89

Preferred compounds of embodiment D of this invention are also those in which A is independently selected from the group consisting of the α-amino acids:
- alanine,
- histidine,
- lysine,
- phenylalanine,
- proline,
- tyrosine,
- valine,
- leucine,
- isoleucine,
- glutamine,
- methionine,
- homoproline,
- 3-(2-thienyl) alanine, and
- 3-(3-thienyl) alanine.

The ICE inhibitors of another embodiment (E) of this invention are represented by formula γ:

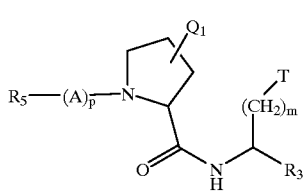

γ wherein:
m is 0, 1, or 2;
T is —CO$_2$H, or any bioisosteric replacement for —CO$_2$H,
R$_3$ is
—CN,
—COR$_{13}$, or

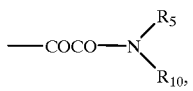

R$_5$ is selected from the group consisting of:
—H,
—Ar$_1$,
—CO—Ar$_1$,
—SO$_2$—Ar$_1$,
—R$_9$,
—CO—R$_9$,
—CO—O—R$_9$,
—SO$_2$—R$_9$,

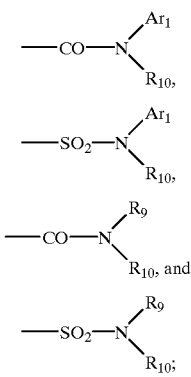

each A is independently selected from the group consisting of any α-amino acid;
p is 2 or 3;
each R$_9$ is a C$_{1-6}$ straight or branched alkyl group optionally singly or multiply substituted by —OH, —F, or =O and optionally substituted with one Ar$_1$ group;

each $T_1$ is independently selected from the group consisting of:
—CH=CH—,
—O—,
—S—,
—SO—,
—SO$_2$—,
—NR$_{10}$—,
—NR$_{10}$—CO—,
—CO—,
—O—CO—,
—CO—O—,
—CO—NR$_{10}$—,
—O—CO—NR$_{10}$—,
—NR$_{10}$—CO—O—,
—NR$_{10}$—CO—NR$_{10}$—,
—SO$_2$—NR$_{10}$—,
—NR$_{10}$—SO$_2$—, and
—NR$_{10}$—SO$_2$—NR$_{10}$—;

each $R_{10}$ is independently selected from the group consisting of —H or a —C$_{1-6}$ straight or branched alkyl group;

each $R_{13}$ is independently selected from the group consisting of H, $R_9$, $Ar_2$, and $CH_2T_1R_9$;

each $Ar_1$ is a cyclic group independently selected from the set consisting of an aryl group which contains 6, 10, 12, or 14 carbon atoms and between 1 and 3 rings, a cycloalkyl group which contains between 3 and 15 carbon atoms and between 1 and 3 rings, said cycloalkyl group being optionally benzofused, and a heterocycle group containing between 5 and 15 ring atoms and between 1 and 3 rings, said heterocycle group containing at least one heteroatom group selected from —O—, —S—, —SO—, —SO$_2$—, =N—, and —NH—, said heterocycle group optionally containing one or more double bonds, said heterocycle group optionally comprising one or more aromatic rings, and said cyclic group optionally being singly or multiply substituted by —NH$_2$, —CO$_2$H, —Cl, —F, —Br, —I, —NO$_2$, —CN, =O, —OH, -perfluoro C$_{1-3}$ alkyl,

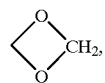

or —Q$_1$; and each $Ar_2$ is independently selected from the following group, in which any ring may optionally be singly or multiply substituted by —Q$_1$ and —Q$_2$:

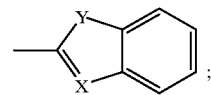

(hh)

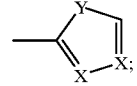

(ii)

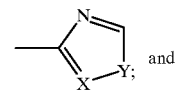
and (jj)

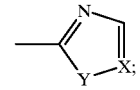

(kk)

each $Q_1$ is independently selected from the group consisting of:
—Ar$_1$
—O—Ar$_1$
$R_9$,
—T$_1$—R$_9$, and
—(CH$_2$)$_{1,2,3}$—T$_1$—R$_9$;

each $Q_2$ is independently selected from the group consisting of —OH, —NH$_2$, —CO$_2$H, —Cl, —F, —Br, —I, —NO$_2$, —CN, —CF$_3$, and

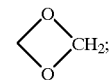

provided that when —Ar$_1$ is substituted with a Q$_1$ group which comprises one or more additional —Ar$_1$ groups, said additional —Ar$_1$ groups are not substituted with Q$_1$.

Preferred compounds of embodiment E of this invention include but are not limited to:

I

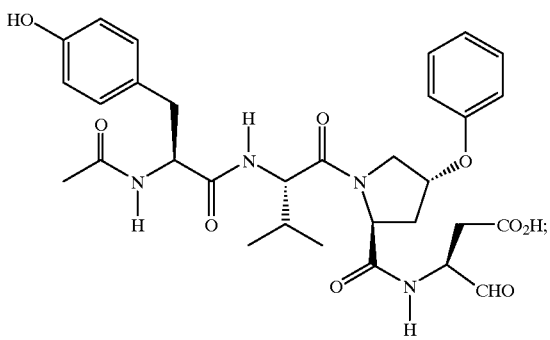

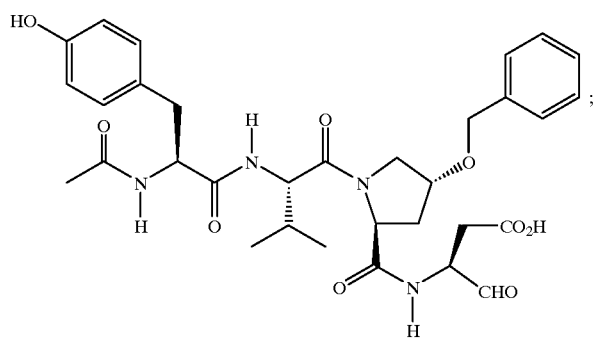
K
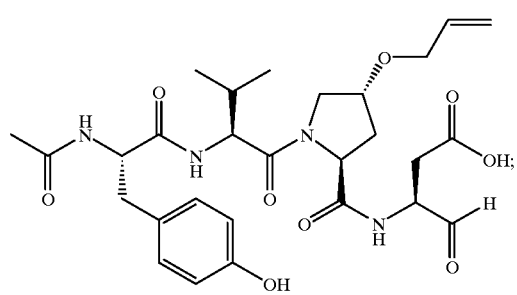
85
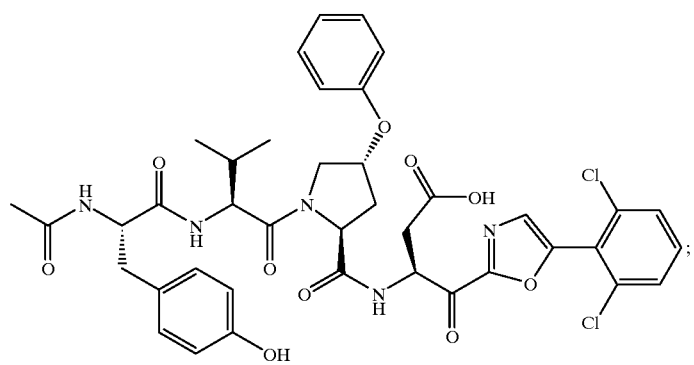
156
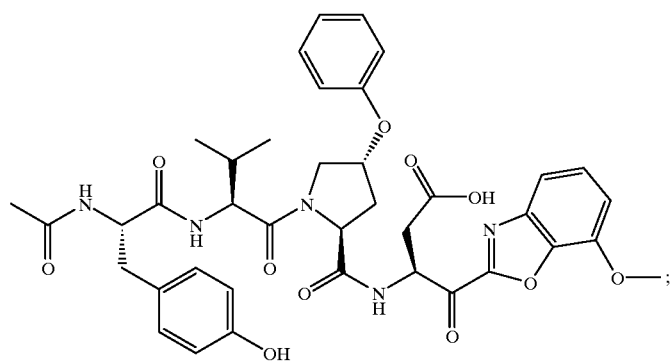
159

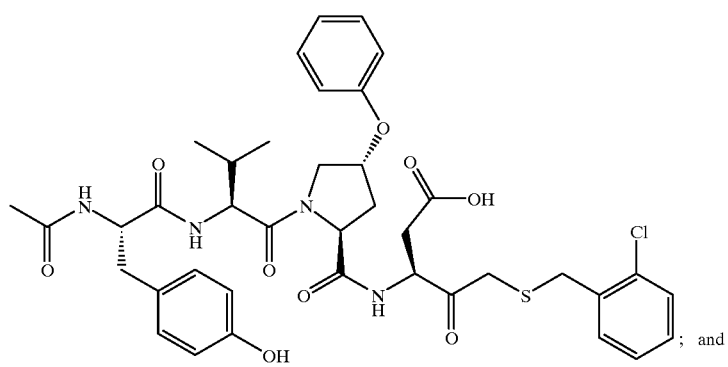

161

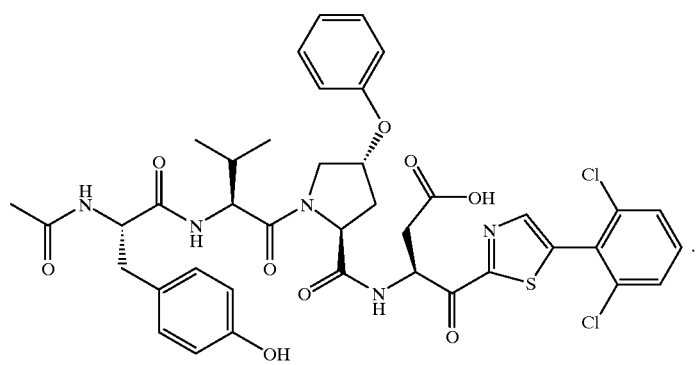

162

Preferred compounds of embodiment E of this invention are also those in which A is independently selected from the group consisting the α-amino acids:

alanine,
histidine,
lysine,
phenylalanine,
proline,
tyrosine,
valine,
leucine,
isoleucine,
glutamine,
methionine,
homoproline,
3-(2-thienyl) alanine, and
3-(3-thienyl) alanine.

The ICE inhibitors of another embodiment (F) of this invention are represented by formula δ:

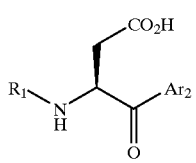

δ wherein:

$R_1$ is $R_5$—(A)$_p$—;
$R_5$ is selected from the group consisting of:

—H,
—Ar$_1$,
—CO—Ar$_1$,
—SO$_2$—Ar$_1$,
—R$_9$,
—CO—R$_9$,
—CO—O—R$_9$,
—SO$_2$—R$_9$,

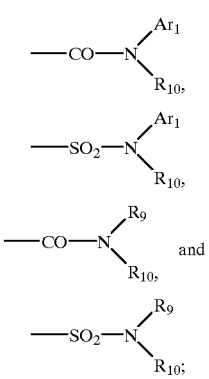

each A is independently selected from the group consisting of any α-amino acid;
p is 0, 1, 2, 3 or 4;
each $R_9$ is a $C_{1-6}$ straight or branched alkyl group optionally singly or multiply substituted by —OH, —F, or =O and optionally substituted with one Ar$_1$ group;
each $R_{10}$ is independently selected from the group consisting of —H or a $C_{1-6}$ straight or branched alkyl group;

each $T_1$ is independently selected from the group consisting of:
—CH=CH—,
—O—,
—S—,
—SO—, each $Ar_1$ is a cyclic group independently selected from the set consisting of an aryl group which contains 6, 10, 12, or 14 carbon atoms and between 1 and 3 rings, a cycloalkyl group which contains between 3 and 15 carbon atoms and between 1 and 3 rings, said cycloalkyl group being optionally benzofused, and a heterocycle group containing between 5 and 15 ring atoms and between 1 and 3 rings, said heterocycle group containing at least one heteroatom group selected from —O—, —S—, —SO—, —SO$_2$—, =N—, and —NH—, said heterocycle group optionally containing one or more double bonds, said heterocycle group optionally comprising one or more aromatic rings, and said cyclic group optionally being singly or multiply substituted by —NH$_2$, —CO$_2$H, —Cl, —F, —Br, —I, —NO$_2$, —CN, =O, —OH, -perfluoro $C_{1-3}$ alkyl,

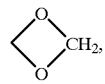

or —$Q_1$; and each $Ar_2$ is independently selected from the following group, in which any ring may optionally be singly or multiply substituted by —$Q_1$ and —$Q_2$:

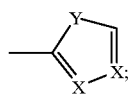 (ii)

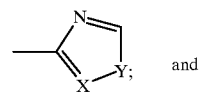 (jj)

and

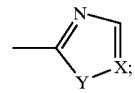 (kk)

each $Q_1$ is independently selected from the group consisting of:
—$Ar_1$
—O—$Ar_1$
—$R_9$,
—$T_1$—$R_9$, and
—(CH$_2$)$_{1,2,3}$—$T_1$—$R_9$;

each $Q_2$ is independently selected from the group consisting of —OH, —NH$_2$, —CO$_2$H, —Cl, —F, —Br, —I, —NO$_2$, —CN, —CF$_3$, and

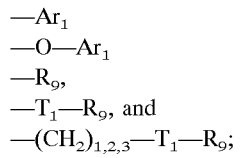

provided that when —$Ar_1$ is substituted with a $Q_1$ group which comprises one or more additional —$Ar_1$ groups, said additional —$Ar_1$ groups are not substituted with $Q_1$;

each X is independently selected from the group consisting of =N—, and =CH—; and each Y is independently selected from the group consisting of —O—, —S—, and —NH.

Preferred compounds of emvodiment F of this invention include but are not limited to:

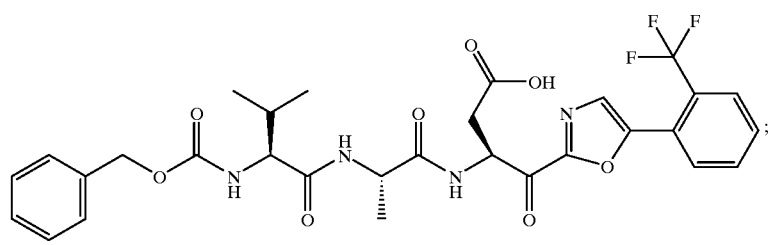

144

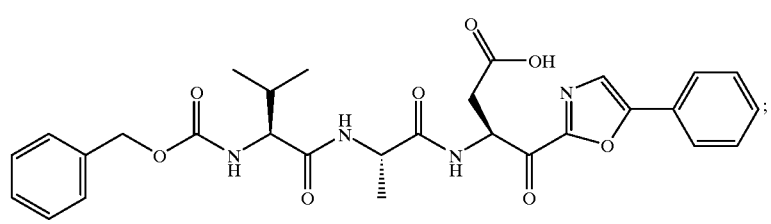

145

146
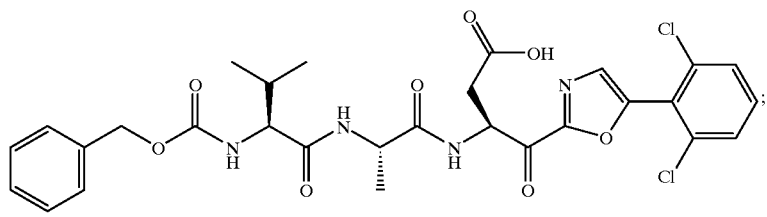
147
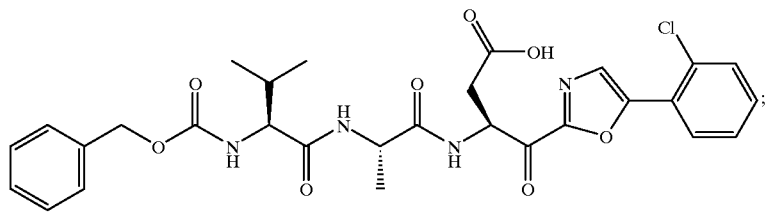
148
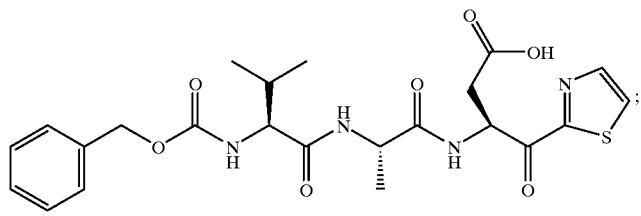
149
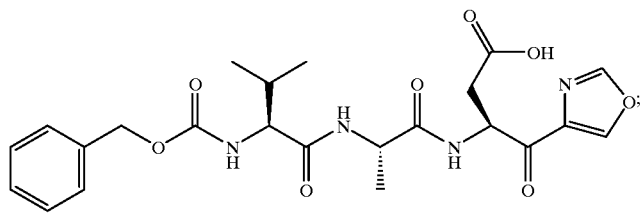
150
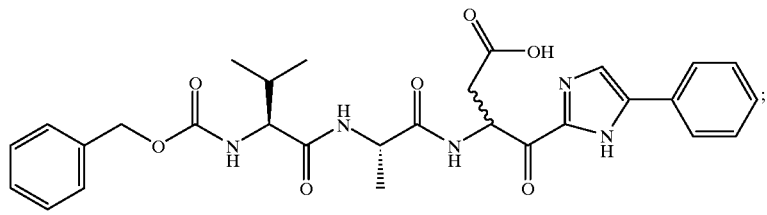
151
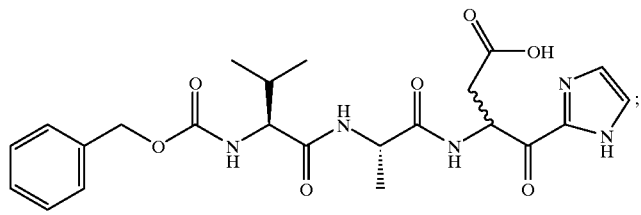
152
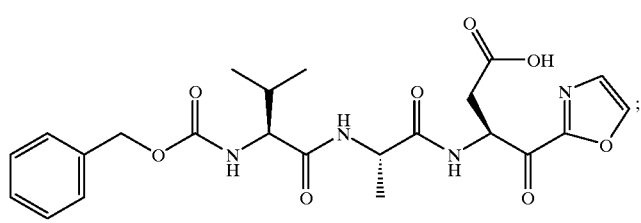

153

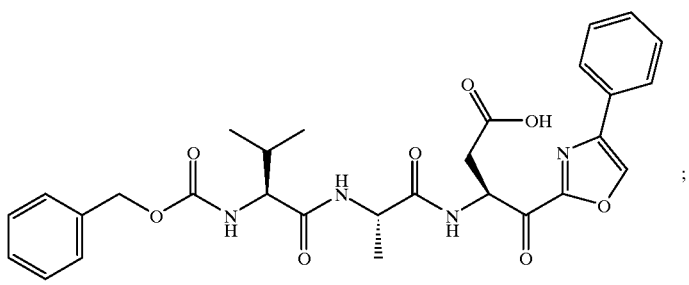

154

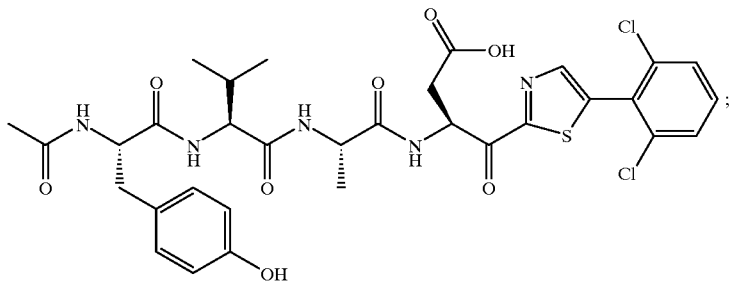

155

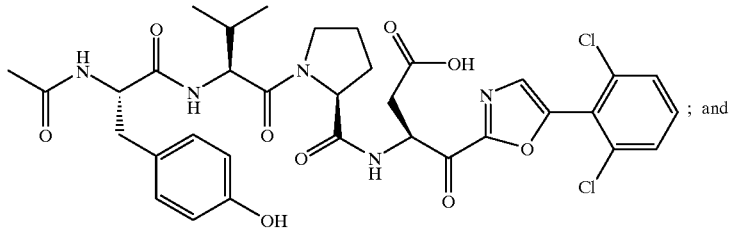

; and

163

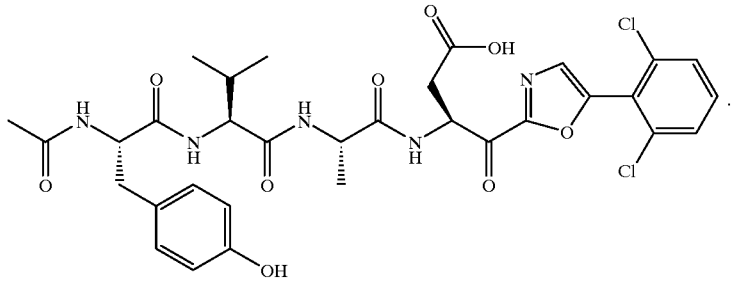

Preferred compounds of embodiment F of this invention are also those in which A is independently selected from the group consisting the α-amino acids:

alanine,
histidine,
lysine,
phenylalanine,
proline,
tyrosine,
valine,
leucine,
isoleucine,
glutamine,
methionine,
homoproline,
3-(2-thienyl) alanine, and
3-(3-thienyl) alanine.

The compounds of this invention having a molecular weight of less than or equal to about 700 Daltons, and more preferably between about 400 and 600 Daltons, are preferred. These preferred compounds may be readily absorbed by the bloodstream of patients upon oral administration. This oral availability makes such compounds excellent agents for orally-administered treatment and prevention regimens against IL-1 mediated diseases.

The ICE inhibitors of this invention may be synthesized using conventional techniques. Advantageously, these compounds are conveniently synthesized from readily available starting materials.

The compounds of this invention are among the most readily synthesized ICE inhibitors known. Previously described ICE inhibitors often contain four or more chiral centers and numerous peptide linkages. The relative ease with which the compounds of this invention can be synthesized represents an enormous advantage in the large scale production of these compounds.

It should be understood that the compounds of this invention may exist in various equilibrium forms, depending on conditions including choice of solvent, pH, and others known to the practitioner skilled in the art. All such forms of these compounds are expressly included in the present invention. In particular, many of the compounds of this invention, especially those which contain aldehyde or ketone groups in $R_3$ and carboxylic acid groups in T, may take hemi-ketal (or hemi-acetal) or hydrated forms, as depicted below:

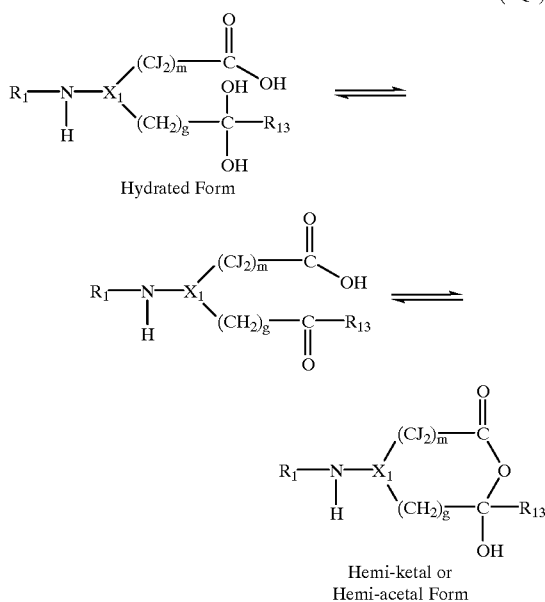

Hydrated Form

Hemi-ketal or Hemi-acetal Form (EQ1)

Depending on the choice of solvent and other conditions known to the practitioner skilled in the art, compounds of this invention may also take acyloxy ketal, acyloxy acetal, ketal or acetal form:

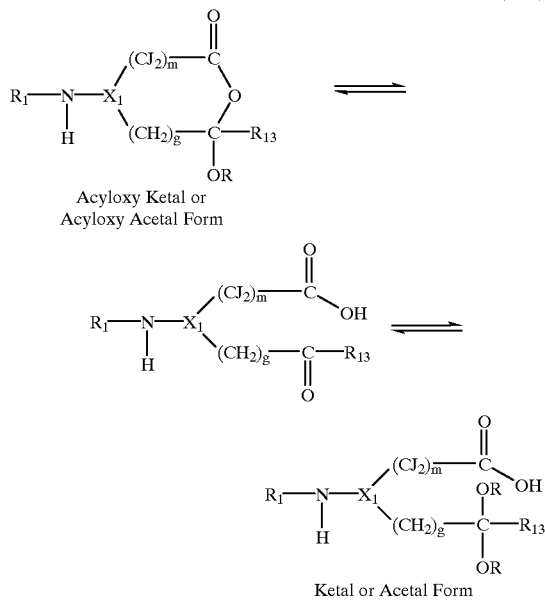

Acyloxy Ketal or Acyloxy Acetal Form

Ketal or Acetal Form (EQ2)

In addition, it should be understood that the equilibrium forms of the compounds of this invention may include tautomeric forms. All such forms of these compounds are expressly included in the present invention.

It should be understood that the compounds of this invention may be modified by appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion. In addition, the compounds may be altered to pro-drug form such that the desired compound is created in the body of the patient as the result of the action of metabolic or other biochemical processes on the pro-drug. Some examples of pro-drug forms include ketal, acetal, oxime, and hydrazone forms of compounds which contain ketone or aldehyde groups, especially where they occur in the $R_3$ group of the compounds of this invention.

The compounds of this invention are excellent ligands for ICE. Accordingly, these compounds are capable of targeting and inhibiting events in IL-1 mediated diseases, such as the conversion of precursor IL-1β to mature IL-1β and, thus, the ultimate activity of that protein in inflammatory diseases, autoimmune diseases and neurodegenerative diseases. For example, the compounds of this invention inhibit the conversion of precursor IL-1β to mature IL-1 β by inhibiting ICE. Because ICE is essential for the production of mature IL-1, inhibition of that enzyme effectively blocks initiation of IL-1 mediated physiological effects and symptoms, such as inflammation, by inhibiting the production of mature IL-1. Thus, by inhibiting IL-1β precursor activity, the compounds of this invention effectively function as IL-1 inhibitors.

The compounds of this invention may be employed in a conventional manner for the treatment of diseases which are mediated by IL-1. Such methods of treatment, their dosage levels and requirements may be selected by those of ordinary skill in the art from available methods and techniques. For example, a compound of this invention may be combined with a pharmaceutically acceptable adjuvant for administration to a patient suffering from an IL-1 mediated disease in a pharmaceutically acceptable manner and in an amount effective to lessen the severity of that disease.

Alternatively, the compounds of this invention may be used in compositions and methods for treating or protecting individuals against IL-1 mediated diseases over extended periods of time. The compounds may be employed in such compositions either alone or together with other compounds of this invention in a manner consistent with the conventional utilization of ICE inhibitors in pharmaceutical compositions. For example, a compound of this invention may be combined with pharmaceutically acceptable adjuvants conventionally employed in vaccines and administered in prophylactically effective amounts to protect individuals over an extended period time against IL-1 mediated diseases.

The compounds of this invention may also be co-administered with other ICE inhibitors to increase the effect of therapy or prophylaxis against various IL-1-mediated diseases.

In addition, the compounds of this invention may be used in combination either conventional anti-inflammatory agents or with matrix metalloprotease inhibitors, lipoxygenase inhibitors and antagonists of cytokines other than IL-1β.

The compounds of this invention can also be administered in combination with immunomodulators (e.g., bropirimine, anti-human alpha interferon antibody, IL-2, GM-CSF, methionine enkephalin, interferon alpha, diethyldithiocarbamate, tumor necrosis factor, naltrexone and rEPO) or with prostaglandins, to prevent or combat IL-1-mediated disease symptoms such as inflammation.

When the compounds of this invention are administered in combination therapies with other agents, they may be administered sequentially or concurrently to the patient. Alternatively, pharmaceutical or prophylactic compositions according to this invention may be comprised of a combination of an ICE inhibitor of this invention and another therapeutic or prophylactic agent.

Pharmaceutical compositions of this invention comprise any of the compounds of the present invention, and pharmaceutically acceptable salts thereof, with any pharmaceutically acceptable carrier, adjuvant or vehicle. Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of this invention may be administered orally, parenterally, by inhalation spray, topically, rectally, nasally, buccally, vaginally or via an implanted reservoir. We prefer oral administration. The pharmaceutical compositions of this invention may contain any conventional non-toxic pharmaceutically-acceptable carriers, adjuvants or vehicles. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as Ph. Helv or a similar alcohol.

The pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxy-ethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The IL-1 mediated diseases which may be treated or prevented by the compounds of this invention include, but are not limited to, inflammatory diseases, autoimmune diseases and neurodegenerative diseases.

Inflammatory diseases which may be treated or prevented include, for example, septic shock, septicemia, and adult respiratory distress syndrome. Target autoimmune diseases include, for example, rheumatoid, arthritis, systemic lupus erythematosus, scleroderma, chronic thyroiditis, Graves' disease, autoimmune gastritis, insulin-dependent diabetes mellitus, autoimmune hemolytic anemia, autoimmune neutropenia, thrombocytopenia, chronic active hepatitis, myasthenia gravis and multiple sclerosis. And target neurodegenerative diseases include, for example, amyotrophic lateral sclerosis, Alzheimer's disease, Parkinson's disease, and primary lateral sclerosis. The ICE inhibitors of this invention may also be used to promote wound healing. And the ICE inhibitors of this invention may be used to treat infectious diseases.

Although this invention focuses on the use of the compounds disclosed herein for preventing and treating IL-1-mediated diseases, the compounds of this invention can also be used as inhibitory agents for other cysteine proteases.

The compounds of this invention are also useful as commercial reagents which effectively bind to ICE or other cysteine proteases. As commercial reagents, the compounds of this invention, and their derivatives, may be used to block proteolysis of a target peptide or may be derivatized to bind to a stable resin as a tethered substrate for affinity chromatography applications. These and other uses which characterize commercial cysteine protease inhibitors will be evident to those of ordinary skill in the art.

In order that this invention be more fully understood, the following examples are set forth. These examples are for the purpose of illustration only and are not to be construed as limiting the scope of the invention in any way.

EXAMPLE 1

The following example demonstrates a process of drug design which embodies the present invention:

Step 1) Pick 2 hydrogen bonding moieties of ICE, here, the backbone C=O and N—H of Arg-341.

Step 2) Pick a scaffold, here, a pyridone derivative, and confirm that the hydrogen bonding moieties of the scaffold are capable of forming satisfactory hydrogen bonds with the hydrogen bonding moieties selected in step 1. This confirmation is performed by using molecular mechanics techniques to minimize the scaffold fragment intext of the active site of ICE.

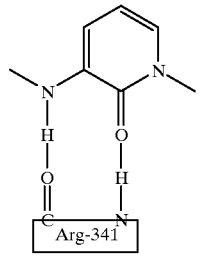

(Z1)

Step 3) Pick a hydrophobic pocket, here, S2, as next target and a hydrophobic moiety, here, benzene. Minimize the benzene group within the S2 pocket to assure that substantial hydrophobic overlap is obtained.

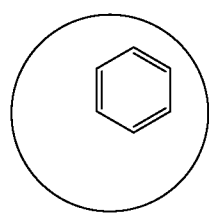

(Z2)

Step 4) Pick another hydrophobic pocket, here, S4, as the next target and a hydrophobic moiety, here, benzene. Minimize the benzene group within the S4 pocket to ensure that substantial hydrophobic overlap is obtained.

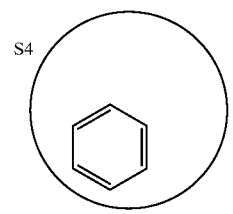

(Z3)

Step 5) Fill the S1 polar pocket with an electronegative moiety, here, a carboxylate sidechain provided by aspartic acid in which the C-terminus has been reduced to an aldehyde. Minimize to ensure that the carboxylate sidechain retains a favorable electrostatic interaction with the S1 polar pocket.

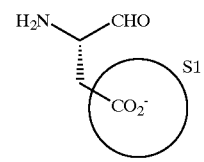

(Z4)

Step 6) Link the scaffold with the moieties from steps 3, 4, and 5, preferably using the minimum number of bonds consistent with a chemically reasonable structure. Minimize the entire composite molecule in the active site of ICE.

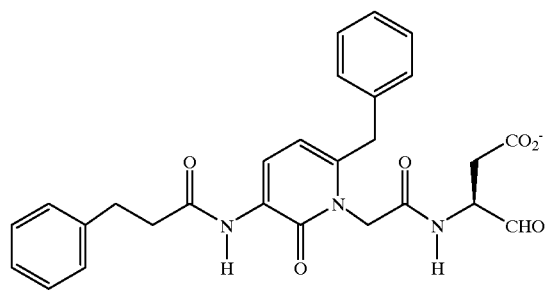

(Z5)

Step 7) Evaluate the energy of the molecule when it has the conformation necessary for binding to ICE. Then minimize and reevaluate the energy—this is the free conformation energy. The strain energy for binding of the potential inhibitor to ICE is the difference between the free conformation energy and the bound conformation energy. The strain energy should be less than about 10 kcal/mol. In this case the bound conformation energy is −1.6 kcal/mol and the free conformation energy is −11.7 kcal/mol, for a strain energy of 10.1 kcal/mol.

Step 8) The inhibitor designed using the above steps has been made and has been show to have a $K_i$ of 150 nM.

EXAMPLE 2

We obtained inhibition constants ($K_i$) and $IC_{50}$ values for several compounds of this invention using the three methods described below:

1. Enzyme Assay with UV-visible Substrate

This assay is run using an Succinyl-Tyr-Val-Ala-Asp-pNitroanilide substrate (SEQ ID no:1). Synthesis of analogous substrates is described by L. A. Reiter (Int. J. Peptide Protein Res. 43, 87–96 (1994)). The assay mixture contains:

65 μl buffer (10 mM Tris, 1 mM DTT, 0.1% CHAPS @pH 8.1)

10 μl ICE (50 nM final concentration to give a rate of ~1 mOD/min)

5 μl DMSO/Inhibitor mixture

20 μl 400 μM Substrate (80 μM final concentration)

100 μl total reaction volume

The visible ICE assay is run in a 96-well microtiter plate. Buffer, ICE and DMSO (if inhibitor is present) are added to the wells in the order listed. The components are left to incubate at room temperature for 15 minutes starting at the time that all components are present in all wells. The microtiter plate reader is set to incubate at 37° C. After the 15 minute incubation, substrate is added directly to the wells and the reaction is monitored by following the release of the chromophore (pNA) at 405–603 nm at 37° C. for 20 minutes. A linear fit of the data is performed and the rate is calculated in mOD/min. DMSO is only present during experiments involving inhibitors, buffer is used to make up the volume to 100 μl in the other experiments.

2. Enzyme Assay with Fluorescent Substrate

This assay is run essentially according to Thornberry et al. (Nature 356: 768–774 (1992)), using substrate 17 referenced in that article. The substrate is: Acetyl-Tyr-Val-Ala-Asp-amino-4-methylcoumarin (AMC) (SEQ ID no:2). The following components are mixed:

65 μl buffer(10 mM Tris, 1 mM DTT, 0.1% CHAPS @pH8.1)

10 μl ICE (2–10 nM final concentration)

5 μl DMSO/inhibitor solution

20 μl 150 μM Substrate (30 μM final)

100 μl total reaction volume

The assay is run in a 96 well microtiter plate. Buffer and ICE are added to the wells. The components are left to incubate at 37° C. for 15 minutes in a temperature-controlled wellplate. After the 15 minute incubation, the reaction is started by adding substrate directly to the wells and the reaction is monitored @37° C. for 30 minutes by following the release of the AMC fluorophore using an excitation wavelength for 380 nm and an emission wavelength of 460 nm. A linear fit of the data for each well is performed and a rate is determined in fluorescence units per second.

For determination of enzyme inhibition constants ($K_i$) or the mode of inhibition (competitive, uncompetitive or noncompetitive), the rate data determined in the enzyme assays at varying inhibitor concentrations are computer-fit to standard enzyme kinetic equations (see I. H. Segel, *Enzyme Kinetics*, Wiley-Interscience, 1975).

3. Cell Assay

IL-1β Assay with a Mixed Population of Human Peripheral Blood Mononuclear Cells (PBMC) or Enriched Adherent Mononuclear Cells Processing of pre-IL-1β by ICE can be measured in cell culture using a variety of cell sources. Human PBMC obtained from healthy donors provides a mixed population of lymphocyte subtypes and mononuclear cells that produce a spectrum of interleukins and cytokines in response to many classes of physiological stimulators. Adherent mononuclear cells from PBMC provides an enriched source of normal monocytes for selective studies of cytokine production by activated cells.

Experimental Procedure:

An initial dilution series of test compound in DMSO or ethanol is prepared, with a subsequent dilution into RPMI-10% FBS media (containing 2 mM L-glutamine, 10 mM HEPES, 50 U and 50 ug/ml pen/strep) respectively to yield drugs at 4× the final test concentration containing 0.4% DMSO or 0.4% ethanol. The final concentration of DMSO is 0.1% for all drug dilutions. A concentration titration which brackets the apparent $K_i$ for a test compound determined in an ICE inhibition assay is generally used for the primary compound screen.

We generally test 5–6 compound dilutions and have performed the cellular component of the assay in duplicate, with duplicate ELISA determinations on each cell culture supernatant.

PBMC Isolation and IL-1 Assay:

Buffy coat cells isolated from one pint human blood (yielding 40–45 ml final volume plasma plus cells) are diluted with media to 80 ml and LeukoPREP separation tubes (Becton Dickinson) are each overlaid with 10 ml of cell suspension. After 15 min centrifugation at 1500–1800× g, the plasma/media layer is aspirated and then the mononuclear cell layer is collected with a Pasteur pipette and transferred to a 15 ml conical centrifuge tube (Corning). Media is added to bring the volume to 15 ml, gently mix the cells by inversion and centrifuge at 300×g for 15 min. Resuspend the PBMC pellet in a small volume of media, count cells and adjust to $6 \times 10^6$ cells/ml.

For the cellular assay, add 1.0 ml of the cell suspension to each well of a 24-well flat bottom tissue culture plate (Corning), 0.5 ml test compound dilution and 0.5 ml LPS solution (Sigma #L-3012; 20 ng/ml solution prepared in complete RPMI media; final LPS concentration 5 ng/ml). The 0.5 ml additions of test compound and LPS are usually sufficient to mix the contents of the wells. Three control mixtures are run per experiment, with either LPS alone, solvent vehicle control, and/or additional media to adjust the final culture volume to 2.0 ml. The cell cultures are incubated for 16–18 hr at 37° C. in the presence of 5% $CO_2$.

At the end of the incubation period, cells are harvested and transferred to 15 ml conical centrifuge tubes. After centrifugation for 10 min at 200×g, supernatants are harvested and transferred to 1.5 ml Eppendorf tubes. It may be noted that the cell pellet may be utilized for a biochemical evaluation of pre-IL-1β and/or mature IL-1β content in cytosol extracts by western blotting or ELISA with pre-IL-1β specific antisera.

Isolation of Adherent Mononuclear Cells:

PBMC are isolated and prepared as described above. Media (1.0 ml) is first added to wells followed by 0.5 ml of the PBMC suspension. After a one hour incubation, plates are gently shaken and nonadherent cells aspirated from each well. Wells are then gently washed three times with 1.0 ml of media and final resuspended in 1.0 ml media. The enrichment for adherent cells generally yields $2.5-3.0 \times 10^5$ cells per well. The addition of test compounds, LPS, cell incubation conditions and processing of supernatants proceeds as described above.

ELISA:

We have used Quantikine kits (R&D Systems) for measurement of mature IL-1β. Assays are performed according to the manufacturer's directions. Mature IL-1β levels of about 1–3 ng/ml in both PBMC and adherent mononuclear cell positive controls are observed. ELISA assays are performed on 1:5, 1:10 and 1:20 dilutions of supernatants from LPS-positive controls to select the optimal dilution for supernatants in the test panel.

The inhibitory potency of the compounds can be represented by an $IC_{50}$ value, which is the concentration of inhibitor at which 50% of mature IL-1β is detected in the supernatant as compared to the positive controls.

The following $K_i$ and $IC_{50}$ values were determined for compounds A through N using the indicated assays. Structures for compounds A through N follow this table.

|          | $K_i$ (μM), by indicated assay: | | |
|----------|---------------------|----------------------|-------------------|
| Compound | UV-visible $K_i$ (μM) | Fluorescence $K_i$ (μM) | Cell $IC_{50}$ (μM) |
| A | 5.5 | | 25.0 |
| B | 8.6 | | 20.0 |
| C | 10 | | <30 |
| D | 4.7 | | |
| E | 3.2 | | |
| F | 0.15 | | 2–4 |
| G | 4.8 | | |
| H | 0.023 | 0.0047 | 6–11 |
| I | 0.0072 | 0.0052 | 2.6 |
| J | 0.012 | 0.0039 | 5–7 |
| K | 0.010 | 0.002 | 2–11 |
| L | 0.014 | | |
| M | 0.15 | | |
| N | 0.95 | | |

Structures of Compounds A Through N:

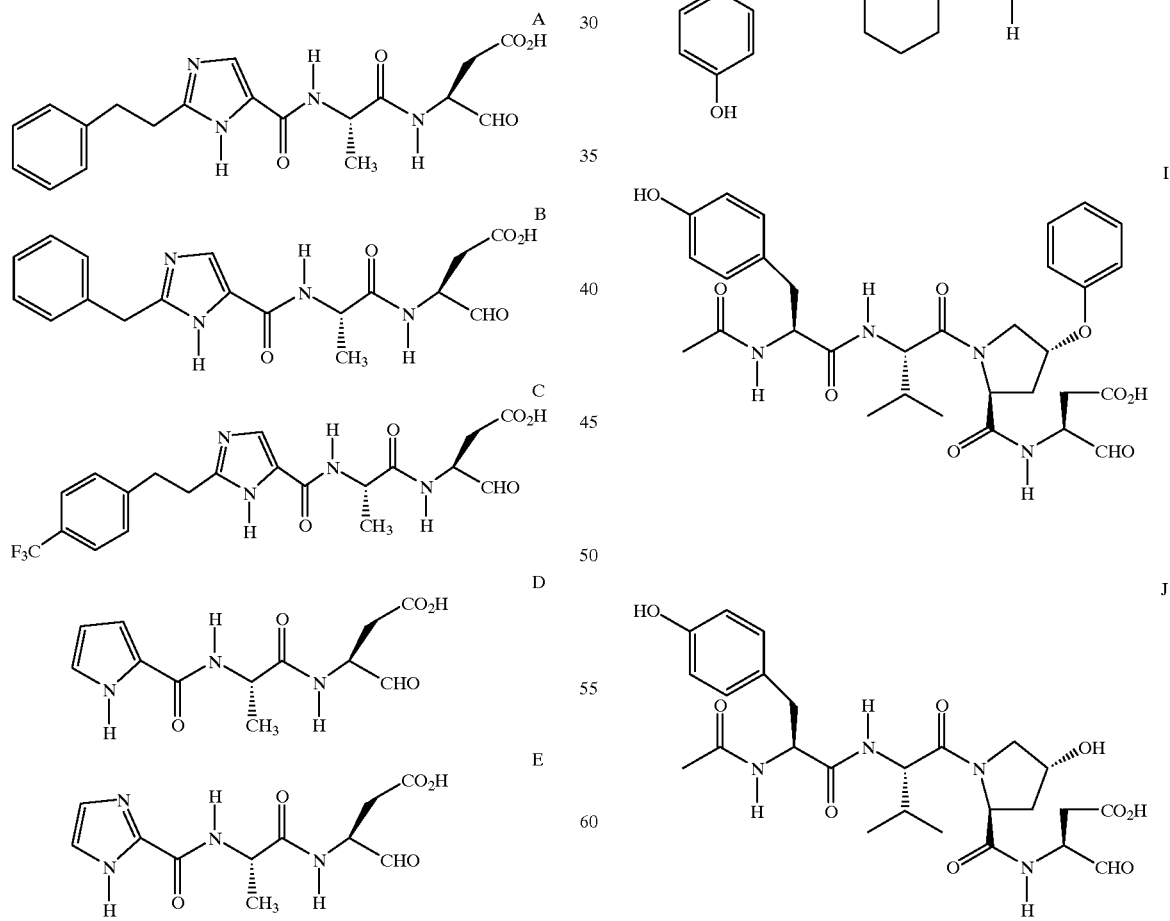

K

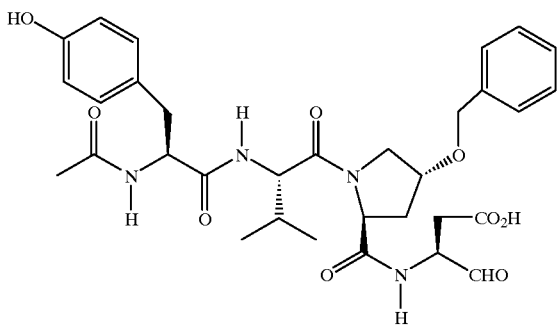

L

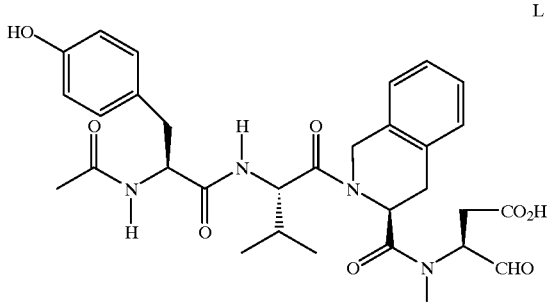

M

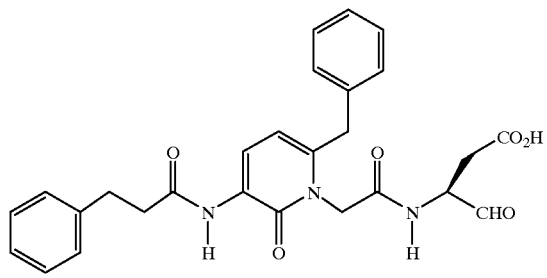

N

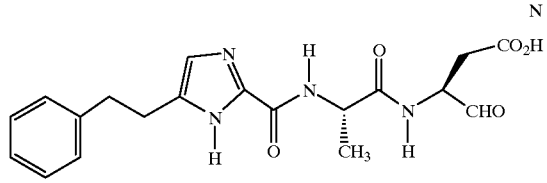

EXAMPLE 3

Compounds of Example 2 were synthesized as follows:

H. N-(N-Acetyl-tyrosinyl-valinyl-pipecolyl)-3-amino-4-oxobutanoic acid

Step A. N-(N-tert-Butoxycarbonylpipecolyl)-4-amino-5-benzyloxy-2-oxotetrahydrofuran.

Reaction of N-tert-butoxycarbonylpipecolic acid (460 mg, 2.0 mmol) and N-allyloxycarbonyl-4-amino-5-benzyloxy-2-oxotetrahydrofuran (530 mg, 1.82 mmol) was carried out by a method analogous to that reported by Chapman (Bioorg. & Med. Chem. Lett. 1992, 2, 613–618.) to give 654 mg of the title compound.

$^1$H NMR (500 MHz, CDCl$_3$ (existing as rotamers)) δ 7.35 (m, 5H), 6.88 (br. s, 1H), 4.9–4.45(m, 4H), 3.95 (br. m, 2H), 3.06 (m, 1H), 2.9 (m, 1H), 2.7 (br. m, 1H), 2.45 (m, 1H), 2.2 (m, 1H), 1.7–1.5 (m, 3H), 1.45 (two s, 9H).

Step B. N-Pipecolyl-4-amino-5-benzyloxy-2-oxotetrahydrofuran.

N-(N-tert-Butoxycarbonylpipecolyl)-4-amino-5-benzyloxy-2-oxo-tetrahydrofuran (654 mg) was dissolved in 15 ml of 25% trifluoroacetic acid in dichloromethane and stirred at room temperature. The mixture was concentrated to give a gummy residue. The residue was dissolved in dichloromethane and washed with 10% sodium bicarbonate. The organic layer was dried over anhydrous sodium sulfate, filtered, and concentrated to give 422 mg of the title compound as a beige solid.

$^1$H NMR (500 MHz, CDCl$_3$) δ 7.38 (m, 5H), 7.15 (d, 1H), 5.55 (d, 1H), 4.95–4.8 (m, 1H), 4.78 (m, 1H), 4.65 (d, 1H), 4.45 (m, 1H), 3.2 (m, 0.5H), 3.05 (m, 0.5H), 2.95 (m, 0.5H), 2.85 (m, 0.5H), 2.65 (m, 1H), 2.55–2.38(m, 1H), 1.95 (m, 1H), 1.8 (m, 1H), 1.6 (m, 2H), 1.38 (m, 2H).

Step C. N-(N-Acetyl-tyrosinyl-valinyl-pipecolyl)-4-amino-5-benzyloxy-2-oxotetrahydrofuran.

N-Acetyl-tyrosinyl-valine (464 mg, 1.44 mmol) and N-Pipecolyl-4-amino-5-benzyloxy-2-oxotetrahydrofuran (412 mg, 1.3 mmol) were dissolved in 5 ml each of dimethylformamide and dichloromethane and cooled to 0° C. To the cooled solution was added 1-hydroxybenzotriazole (HOBT; 210 mg, 1.56 mmol) followed by the addition of 1-(3-dimethylaminopropyl)-3-ethyl carbodiimide hydrochloride (EDC; 326 mg, 1.7 mmol). After stirring for 18 hours, the mixture was diluted with ethyl acetate and washed with water, 10% sodium hydrogen sulfate, 10% sodium bicarbonate, and water. The organic layer was concentrated to give a crude solid that was purified by flash chromatography (SiO$_2$) eluting with 94:6:1 (dichloromethane:isopropanol: pyridine) to give 370 mg of the title compound.

$^1$H NMR (500 MHz, CD$_3$OD (existing as diastereomers as well as rotamers)) δ 7.35 (m, 5H), 7.05 (m, 2H), 6.68 (m, 2H), 5.65 & 5.25 (m, 1H), 4.9–3.95 (m, 8H), 3.4–2.6 (m, 4H), 2.5–2.1 (m, 1H), 1.98 (s, 1H), 1.9 (s, 1H), 1.85 (s, 1H), 1.8–1.6 (m, 2H), 1.55–1.3 (m, 4H), 0.95–0.85 (m, 6H).

Step D. N-(N-Acetyl-tyrosinyl-valinyl-pipecolyl)-3-amino-4-oxobutanoic acid.

To a solution of 100 mg of N-(N-Acetyl-tyrosinyl-valinyl-pipecolyl)-4-amino-5-benzyloxy-2-oxotetrahydrofuran in 10 ml of methanol was added 60 mg of Pd(OH)$_2$ on carbon and the mixture placed under an atmosphere of hydrogen via a balloon. The mixture was filtered through Celite and concentrated providing a white solid. This crude solid was dissolved in 2 ml of methanol and triturated with diethyl ether affording 26 mg of the title compound.

$^1$H NMR (500 MHz, CD$_3$OD(existing as diastereomers as well as rotamers)) δ 7.1 (m, 2H), 6.7 (m, 2H), 5.2 (br. m, 1H), 4.8–3.6 (m, 6H), 3.2–2.5 (m, 4H), 2.5–2.1 (m, 1H), 1.95 (three s, 3H), 1.9–1.3 (m, 6H), 1.1–0.7 (m, 6H).

The following compounds were prepared by a method analogous to that reported for H:

J. N-[N-Acetyl-tyrosinyl-valinyl-(4-hydroxyprolinyl)]-3-amino-4-oxobutanoic acid Substitute N-tert-butoxycarbonyl-4-benzyloxyproline for N-tert-butoxycarbonylpipecolic acid.

L. N-[2-(N-Acetyl-tyrosinyl-valinyl)-(S)-1,2,3,4-tetrahydroisoquinoline-3-carbonyl]-3-amino-oxobutanoic acid Substitute (S)-N-tert-butoxycarbonyl-1,2,3,4-tetrahydroisoquinoline-3-carboxylic acid for N-tert-butoxycarbonylpipecolic acid.

I. N-(N-Acetyl-tyrosinyl-valinyl-(4-phenoxyprolinyl))-3-amino-4-oxobutanoic acid Step A. N-tert-Butoxycarbonyl-4-phenoxyproline methyl ester.

To a cooled solution (0° C.) of N-tert-butoxy-cis-4-hydroxyproline (2–0 g, 8.15 mmol), phenol (0.77 g, 8.15 mmol), and triphenylphosphine (2.14 g, 8.15 mmol) in 20 ml of tetrahydrofuran was added diethyl azodicarboxylate (1.4 ml, 9 mmol) dropwise over 30 minutes. The reaction was stirred at room temperature for 16 hrs. then concentrated to give a viscous residue. The crude residue was purified by flash chromatography (SiO$_2$) eluting with 3:7 (ethyl acetate:hexane) to give 1.89 g of the title compound.

$^1$H NMR (500 MHz, CDCl$_3$) δ 7.3 (m, 2H), 6.95 (m, 1H), 6.85 (d, 2H), 4.9 (m br., 1H), 4.55–4.15 (m, 2H), 3.88–3.65 (m, 1H), 3.70 (s, 3H), 2.58 (m, 1H), 2.22 (m, 1H.), 1.4 (3×s, 9H).

Step B. 4-Phenoxyproline methyl ester hydrochloride.

To a cooled solution (ice bath) of N-tert-Butoxycarbonyl-4-phenoxyproline methyl ester (0.6 g) in 20 ml of ethyl acetate was bubbled anhydrous hydrogen chloride until saturated. The mixture was warmed to room temperature and stirred for 3 hrs. then concentrated to give 480 mg of the title compound.

$^1$H NMR (500 MHz, CDCl$_3$) δ 7.22 (m,2H), 6.95 (m 1 H), 6.83 (m, 2H), 5.1 (br., 1H), 4.6 (br. m, 1H), 4.06 (br. m, 1H), 3.75 (s, 3H), 3.55 (br. m, 1H), 2.58 (m, 2H).

Step C. N-Acetyl-tyrosinyl-valinyl-(4-phenoxy)proline methyl ester.

N-Acetyl-tyrosinyl-valine (0.524 g, 1.63 mmol) and 4-phenoxyproline methyl ester (0.381 g, 1.48 mmol) were dissolved in 4 ml each of dimethylformamide and dichloromethane and cooled to 0° C. To the cooled solution was added diisopropylethylamine (258 ul, 1.86 mmol), HOBT (0.24 g, 1.78 mmol), and EDC (0.37 g, 1.92 mmol) and the reaction was stirred for 18 hrs. The mixture was diluted with 400 ml of ethyl acetate and washed with water, 10% sodium hydrogen sulfate, 10% sodium bicarbonate, and water. The organic layer was concentrated to give a residue that was purified by flash chromatography (SiO$_2$) eluting with 94:6:1 (CH$_2$Cl$_2$:i-PrOH:Pyridine) to afford 360 mg of the title compound.

$^1$H NMR (500 MHz, CDCl$_3$ (existing as rotamers)) δ 7.3 (m, 2H), 7.05 (m, 1H), 6.95 (d, 2H), 6.9–6.2 (4×d, 4H), 5.05 (br. s, 1H), 4.7–3.94 (m,5H), 2.93 (m, 1H), 2.82(m, 1H), 2.65 (m, 1H), 2.2 (m, 1H), 2.05 (m, 1H), 1.95 (s, 3H), 1.86, (m, 1H), 0.98 (d, 3H), 0.88 (d, 3H).

Step D. N-Acetyl-tyrosinyl-valinyl-(4-phenoxy)proline.

Lithium hydroxide (57 mg, 1.37 mmol) was added to a solution of N-Acetyl-tyrosinyl-valinyl-(4-phenoxy)proline methyl ester (360 mg, 0.685 mmol) dissolved in 8 ml of tetrahydrofuran/water (1:1) and stirred at room temperature for 1 hour. The mixture was acidified with 10% hydrochloric acid giving a white precipitate that was collected to give 175 mg of the title compound.

$^1$H NMR (500 MHz, DMSO-d6) δ 9.2 (br. s, 1H), 8.05–7.95 (m, 2H), 7.3 (m, 1H), 7.0–6.9 (m,4H), 6.65 (d, 2H), 4.42 (m, 1H), 4.35(m, 1H), 4.05–3.95 (m, 2H), 3.3 (br. s, 2H), 2.75 (m, 1H), 2.55–2.38 (m, 2H), 2.2 (m, 1H), 2.0 (m, 1H), 1.7 (s, 3H), 0.95 (d, 3H), 0.85 (d, 3H).

Step E. N-[N-Acetyl-tyrosinyl-valinyl-(4-phenoxy)-prolinyl]-4-amino-5-benzyloxy-2-oxotetrahydrofuran.

The title compound was prepared by the method reported for compound H, step A, by reaction of N-acetyl-tyrosinyl-valinyl-(4-phenoxy)proline and N-allyloxycarbonyl-4-amino-5-benzyloxytetrahydrofuran.

$^1$H NMR (500 MHz, CDCl$_3$ (existing as a 1:1 diastereomer mixture of the hemiacetal)) δ 7.8–6.3 (m, 17H), 5.6 (d, 1H), 5.1–4.15 (m, 5H), 4.15–3.75 (m, 2H), 2.95–2.15 (m, 5H), 2.15–1.95 (m, 1H), 1.9–1.85 (2×s, 3H), 1.1–0.75 (m, 6H).

Step F. N-[N-Acetyl-tyrosinyl-valinyl-(4-phenoxy) prolinyl]-3-amino-4-oxobutanoic acid.

The title compound was prepared by the hydrogenolysis procedure reported for compound H, step D.

$^1$H NMR (500 MHz, CD$_3$OD (existing as a 1:1 diastereomer mixture of the hemiacetal)) δ 7.25 (m, 2H), 7.10–6.85 (m, 5H), 6.65 (d, 2H), 5.1 (br. m, 1H), 4.65–4.05 (m, 5H), 4.0–3.40 (m, 2H), 2.95–2.35 (m, 5H), 2.25 (m, 1H), 2.05 (m, 1H), 1.85 (s, 3H), 1.0 (d, 3H), 0.95 (d, 3H).

K. N-[N-Acetyl-tyrosinyl-valinyl-(4-benzyloxy) prolinyl]-3-amino-4-oxobutanoic acid Step A. N-(N-Allyloxycarbonyl-4-benzyloxyprolinyl)-3-amino-4-oxobutanoic acid tert-butyl ester semicarbazone.

The title compound was prepared by the reaction of N-allyloxycarbonyl-4-benzyloxyproline and 3-amino-4-oxobutanoic acid tert-butyl ester semicarbazone (T. L. Graybill et. al., Abstracts of papers, 206th National Meeting of the American Chemical Society, Abstract MEDI-235. Chicago, Ill. (1993)) under similar peptide coupling conditions as reported above (compound H; Step C).

$^1$H NMR (500 MHz, CDCl$_3$) δ 9.05 (br. s, 1H), 7.85 (br. m, 1H), 7.4–7.2 (m, 5H), 7.15 (br. s, 1H), 6.55 (br. s, 1H), 5.9 (m, 1H), 5.1–4.9 (br. m, 2H), 4.65–4.4 (m, 4H), 4.2 (br. m, 1H), 3.75–3.5 (m, 2H), 2.75–2.55 (m, 2H), 2.5 (br. m, 1H), 2.25 (br. m, 1H) 1.4 (s, 9H).

Step B. N-(N-Acetyl-tyrosinyl-valinyl-(4-benzyloxyprolinyl))-3-amino-4oxobutanoic acid tert-butyl ester semicarbazone.

The title compound was prepared by reaction of N-acetyl-tyrosinyl-valine and N-(N-allyloxycarbonyl-4-benzyloxyprolinyl)-3-amino-4-oxobutanoic acid tert-butyl ester semicarbazone by reaction conditions reported for compound H, step A.

$^1$H NMR (500 MHZ, CD$_3$OD) δ 7.35–7.2 (m, 6H), 7.0 (d, 2H), 6.65(d, 2H), 4.85 (m, 1H), 4.6–4.45 (m, 4H), 4.3 (br. m, 1H), 4.15 (m, 1H), 3.7 (m, 1H), 2.95 (m, 1H), 2.75–2.6 (m, 3H), 2.35 (m, 1H), 2.1 (m, 1H), 1.9 (s, 3H), 1.4 (s, 9H), 0.95 (d, 3H), 0.90 (s, 3H).

Step C. N-(N-Acetyl-tyrosinyl-valinyl-(4-benzyloxyprolinyl))-3-amino-4oxobutanoic acid.

N-(N-Acetyl-tyrosinyl-valinyl-(4-benzyloxyprolinyl))-3-amino-4-oxobutanoic acid tert-butyl ester semicarbazone (270 mg) was dissolved into 10 ml of 25% trifluoroacetic acid in dichloromethane and stirred at room temperature for 3 hours. The mixture was concentrated to give a solid residue. The residue was dissolved into a 10 ml mixture of methanol:acetic acid:37% formaldehyde (3:1:1) and stirred at room temperature for 1 hour. The mixture was concentrated and the resulting residue purified by flash chromatography (SiO$_2$) eluting with dichloromethane/methanol/formic acid (100:5:0.5) to give 37 mg of the title compound.

$^1$H NMR (500 MHz, CD$_3$OD (existing as a 1:1 mixture of diastereomers of the hemiacetal)) δ 7.4–7.25 (m, 5H), 7.0 (d, 2H), 6.65 (d, 2H), 4.65–4.05 (m, 7H), 3.75–3.4 (m, 2H), 3.05–2.3 (m, 5H), 2.2–1.95 (m, 2H), 1.90 (s, 3H), 1.0 (d, 3H), 0.95 (d, 3H).

EXAMPLE 4

We obtained inhibition constants (K$_i$) and IC$_{50}$ values for several compounds of this invention using enzyme assays with UV-visible substrate and cell assays as described in Example 2. The following K$_i$ and IC$_{50}$ values were determined for compounds 7a, 7b, 20a–d, 21c–f, 22e, 25, 28, 33a–c, 36a, 36b, 39, 43, 47a, 47b, 54a–l, 63, 69a, 69b, 84a and 84b using the indicated assays. Corresponding lettered compound designations are indicated parenthetically. The compound structures are shown in Examples 2 and 5.

| Compound | Assay | |
|---|---|---|
| | UV-visible $K_i$ ($\mu M$) | Cell $IC_{50}$ ($\mu M$) |
| 7a | 35 | |
| 7b | 1.2 | |
| 20a (= E) | 3.2 | |
| 20b | 0.85 | 16.4 |
| 20c (= N) | 0.95 | |
| 20d | 0.1 | 6.2 |
| 21c | 0.64 | |
| 21d | 0.24 | 4.8 |
| 21e | 0.22 | 2.9 |
| 21f | 0.17 | 2.9 |
| 22e | 0.19 | |
| 25 | 6.2 | |
| 28 | 12.0 | |
| 33a (= A) | 5.5 | 25.0 |
| 33b (= C) | 10.0 | >30.0 |
| 33c (= B) | 8.6 | 20.0 |
| 36a (= D) | 4.7 | |
| 36b | 0.8 | 17.0 |
| 39 | 2.5 | |
| 43 | 20.0 | |
| 47a | 0.019 | 2.1 |
| 47b | 0.027 | 1.8 |
| 54a (= F) | 0.15 | 2.7 |
| 54b (= M) | 0.15 | 9.1 |
| 54c | 1.2 | >19.0 |
| 54d | | 1.0 |
| 54e | | 3.5 |
| 54f | | 0.9 |
| 54g (= G) | 4.8 | >20.0 |
| 54h | | 0.97 |
| 54i | 0.054 | 2.4 |
| 54j | | 0.28 |
| 54k | | 0.085 |
| 54l | 0.215 | 7.0 |
| 63 (= O) | 0.85 | 4.1 |
| 69a (= R) | 0.011 | 0.735 |
| 69b (= S) | 0.050 | 0.745 |
| 84a (= V) | 0.100 | 3.3 |
| 84b (= W) | 0.019 | 0.50 |

EXAMPLE 5

Compounds of Example 4 were synthesized as follows:

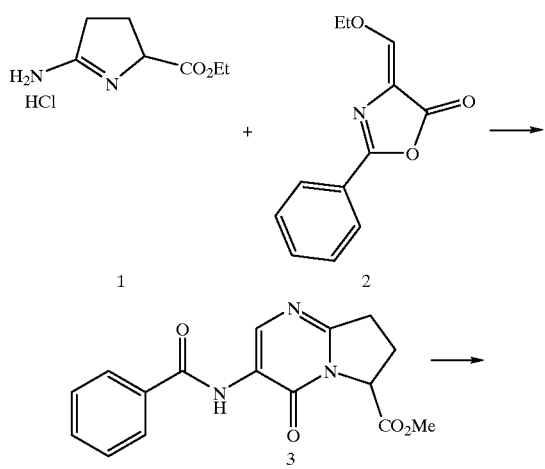

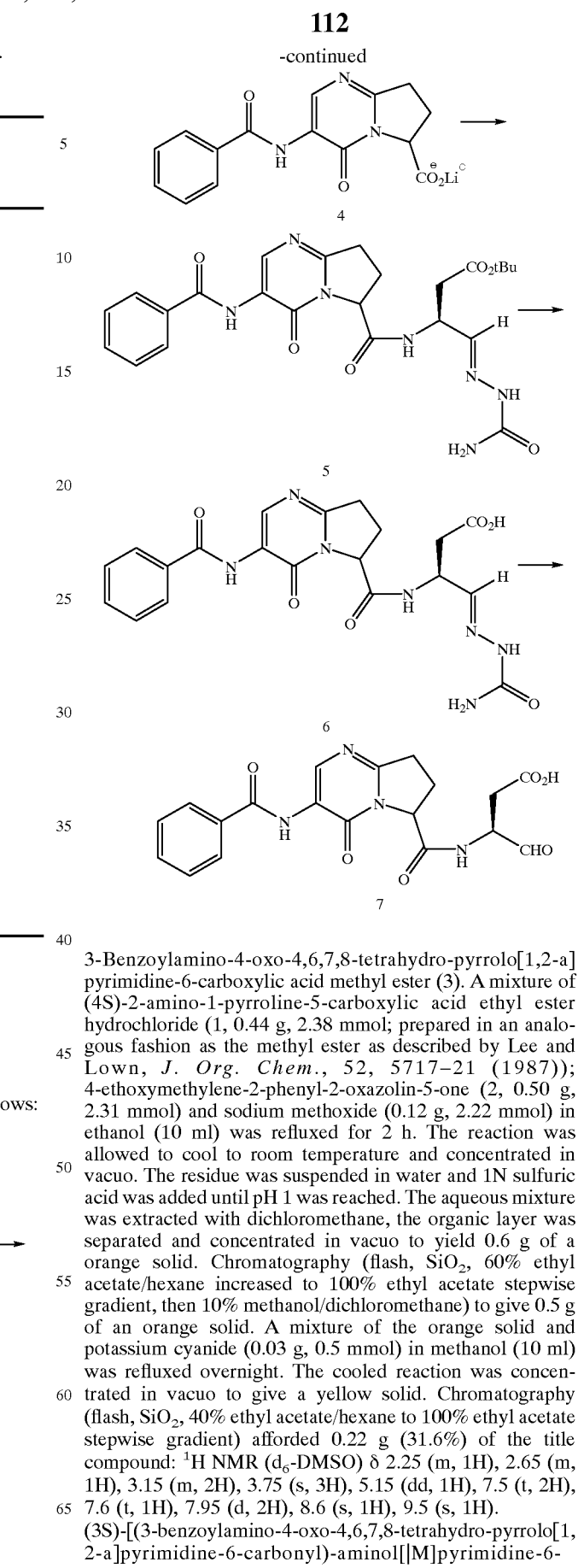

3-Benzoylamino-4-oxo-4,6,7,8-tetrahydro-pyrrolo[1,2-a]pyrimidine-6-carboxylic acid methyl ester (3). A mixture of (4S)-2-amino-1-pyrroline-5-carboxylic acid ethyl ester hydrochloride (1, 0.44 g, 2.38 mmol; prepared in an analogous fashion as the methyl ester as described by Lee and Lown, *J. Org. Chem.*, 52, 5717–21 (1987)); 4-ethoxymethylene-2-phenyl-2-oxazolin-5-one (2, 0.50 g, 2.31 mmol) and sodium methoxide (0.12 g, 2.22 mmol) in ethanol (10 ml) was refluxed for 2 h. The reaction was allowed to cool to room temperature and concentrated in vacuo. The residue was suspended in water and 1N sulfuric acid was added until pH 1 was reached. The aqueous mixture was extracted with dichloromethane, the organic layer was separated and concentrated in vacuo to yield 0.6 g of a orange solid. Chromatography (flash, $SiO_2$, 60% ethyl acetate/hexane increased to 100% ethyl acetate stepwise gradient, then 10% methanol/dichloromethane) to give 0.5 g of an orange solid. A mixture of the orange solid and potassium cyanide (0.03 g, 0.5 mmol) in methanol (10 ml) was refluxed overnight. The cooled reaction was concentrated in vacuo to give a yellow solid. Chromatography (flash, $SiO_2$, 40% ethyl acetate/hexane to 100% ethyl acetate stepwise gradient) afforded 0.22 g (31.6%) of the title compound: $^1$H NMR ($d_6$-DMSO) δ 2.25 (m, 1H), 2.65 (m, 1H), 3.15 (m, 2H), 3.75 (s, 3H), 5.15 (dd, 1H), 7.5 (t, 2H), 7.6 (t, 1H), 7.95 (d, 2H), 8.6 (s, 1H), 9.5 (s, 1H).

(3S)-[(3-benzoylamino-4-oxo-4,6,7,8-tetrahydro-pyrrolo[1,2-a]pyrimidine-6-carbonyl)-aminol[[M]pyrimidine-6- carboxylic acid ethyl ester (3, 0.22 g 0.70 mmol) and lithium hydroxide hydrate (0.032 g, 0.76 mmol) in methanol (5 ml) and tetrahydrofuran (5 ml) and was stirred 18 h at room temperature. The reaction was concentrated to give 3-benzoylamino-4-oxo-4,6,7,8-tetrahydro-pyrrolo[1,2-a]pryrimidine-6-carboxylic acid lithium salt (4) as a white solid. This was used without further purification in the subsequent reaction.

A 0° C. mixture of (3S)-amino-4-oxo-butanoic acid tert-butyl ester semicarbazone (0.163 g, 0.71 mmol; Graybill et al., *Int. J. Protein Res.*, 44, pp. 173–82 (1994)) and 3-benzoylamino-4-oxo-4,6,7,8-tetrahydro-pyrrolo[1,2-a] pyrimidine-6-carboxylic acid lithium salt (4) in dimethyl-formamide (5 ml) and dichloromethane (5 ml) was treated with hydroxybenzotriazole (0.104 g, 0.77 mmol) and 1-(3-dimethylaminopropyl)-3-ethyl carbodiimide hydrogen chloride (0.148 g. 0.37 mmol). The reaction was allowed to warm to room temperature and stirred 18 hr. The reaction was poured onto water (50 ml) and extracted with ethyl acetate (2×50 mL). The combined organic layers were washed with aqueous 1M sodium hydrogen sulfate solution, dilute aqueous sodium hydrogen carbonate (50 mL) and saturated aqueous sodium chloride. The organic layer was concentrated in vacuo to yield 0.43 g of a yellow solid. Chromatography (flash, $SiO_2$, ammonium hydroxide/methanol/di-chloromethane (1:1:99 to 1:10:90 stepwise gradient)) gave 0.11 g (30.9%) of the higher Rf diastereomer (5a):
$^1$H NMR (CD$_3$OD) δ 1.45 (s, 9H), 2.29–2.35 (m, 1H), 2.6–2.7 (m, 2H), 2.8 (dd, 1H), 3.1–3.15 (m, 1H), 3.2–3.3 (m, 1H), 4.9–4.95 (m, 1H), 5.2 (dd, 1H), 7.25 (d, 1H), 7.5–7.55 (m, 2H), 7.55–7.6 (m, 1H), 7.95 (d, 2H), 8.9 (s, 1H) and 0.11 g (30.9%) of the lower Rf diastereomer (5b): $^1$H NMR (CD$_3$OD) δ 1.45 (s,9H), 2.3–2.4 (m, 1H), 2.6–2.7 (m, 1H), 2.7–2.8 (m, 2H), 3.1–3.15 (m, 1H), 3.2–3.3 (m, 1H), 4.85–4.95 (m, 1H), 5.15 (dd, 1H), 7.25 (d, 1H), 7.55 (t, 2H), 7.6 (t, 1H), 7.95 (d, 2H), 8.9 (s, 1H). Diastereomer 5a and diastereomer 5b were taken on separately.

(3S)-[(3-benzoylamino-4-oxo-4,6,7,8-tetrahydro-pyrrolo[1,2-a]pyrimidine-6-carbonyl)-amino]-4-oxo-butanoic acid (7a). A suspension of (3S)-[(3-benzoylamino-4-oxo-4,6,7,8-tetrahydro-pyrrolo[1,2-a]pyrimidine-6-carbonyl)-amino]-4-oxo-butanoic acid tert-butyl ester semicarbazone (5a, 0.11 g, 0.22 mmol) in dichloromethane (7.5 ml) and trifluoroacetic acid (2.5 ml) was stirred for 5 h. The reaction was concentrated in vacuo, the residue was taken up in dichloromethane, concentrated in vacuo, suspended in toluene and concentrated in vacuo to give 0.07 g of (3S)-[(3-benzoylamino-4-oxo-4,6,7,8-tetrahydro-pyrrolo[1,2-a] pyrimidine-6-carbonyl)-amino]-4-oxo-butanoic acid semicarbazone (6a) as a white solid. The solid was suspended in a mixture of 37% aqueous formaldehyde/acetic acid/methanol (1:1:5) and stirred at room temperature for 18 hr. The reaction was concentrated in vacuo, the residue was suspended in acetonitrile and concentrated in vacuo to give 0.1 g of a white solid. Chromatography (HPLC, reverse phase C18, 1% to 75% acetonitrile/water (buffered with 0.1% trifluoroacetic acid) gradient elution) to give 0.05 g (60%) of 7a as a white solid: RT=7.9 min (HPLC, C18 reverse phase, 1 to 100% acetonitrile/water (0.1% trifluoroacetic acid buffer); 20 min gradient elution);
$^1$H NMR (CD$_3$OD (existing as a 1:1 mixture of anomers of the hemi-acyloxy acetal form)) δ 2.25–2.4 (m, 1H), 2.45–2.8 (m, 4H), 3.05–3.15 (m, 1H), 4.25–4.35 (m, 1H), 4.55–4.6 (m, 1H), 5.1–5.2 (m, 1H), 7.45–7.65 (m, 3H), 7.9–8.0 (m, 2H), 8.9 (s, 1H).

(3S)-[(3-benzylamino-4-oxo-4,6,7,8-tetrahydro-pyrrolo[1,2-a]pyrimidine-6-carbonyl)-amino]-4-oxo-butanoic acid (7b) was prepared as described for diastereomer 7a to give 0.03 g (35%) of 7b as a white solid: RT=8.1 min (HPLC, C18 reverse phase, 1 to 100% acetonitrile/water (0.1% trifluoroacetic acid buffer); 20 min gradient elution); $^1$H NMR (d$_6$-DMSO (existing as a 1:1 mixture of anomers of the hemi-acyloxy acetal form)) δ 2.1–2.2 (m, 1H), 2.4 (d, 1H), 2.7–2.8 (m, 1H), 3.0–3.2 (m, 3H), 5.0 (dd, 1H), 5.1–5.2 (m, 1H), 5.5 (s, 1H), 5.7–5.8 (m, 1H), 7.55 (t, 2H), 7.67 (t, 1H), 7.95 (d, 2H), 8.55 (s, 1H), 9.0–9.15 (m, 1H), 9.4–9.5 (m, 1H).

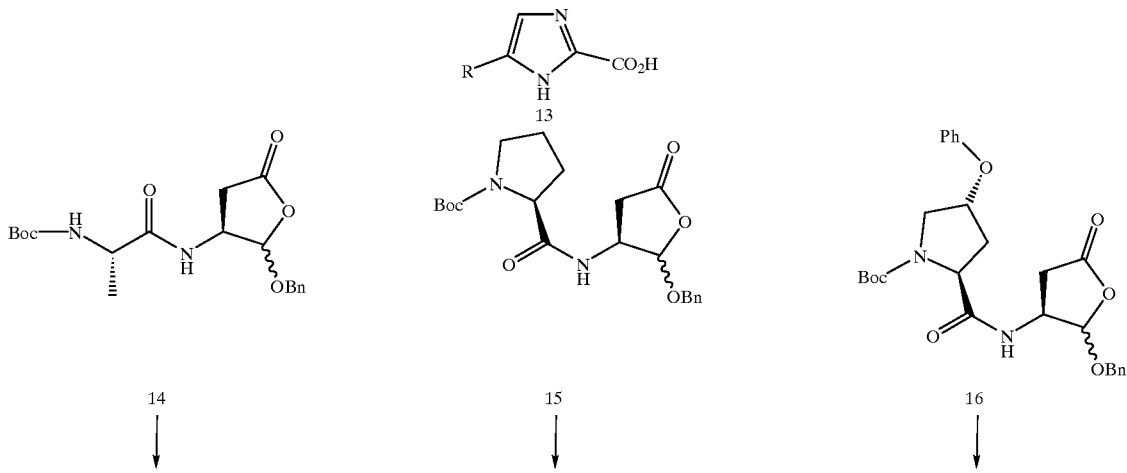

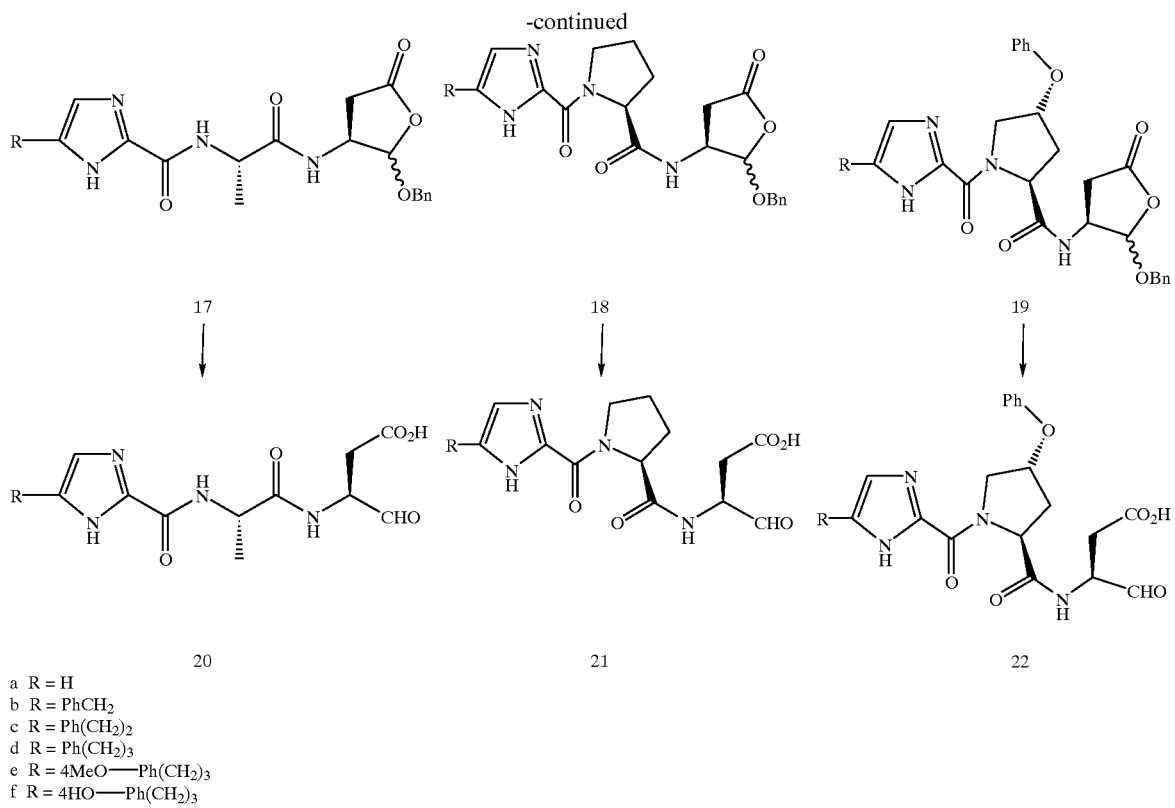

a R = H
b R = PhCH₂
c R = Ph(CH₂)₂
d R = Ph(CH₂)₃
e R = 4MeO—Ph(CH₂)₃
f R = 4HO—Ph(CH₂)₃

Imidazole-2-carboxylic acids 13 were prepared using modifications of described procedures (Yamanaka et al., *Chem. Pharm. Bull.*, 31, pp. 4549–53 (1983)); Suzuki et al., *J. Org. Chem.*, 38, pp. 3571–75 (1973)); and Oliver et al. (*J. Org. Chem.*, 38, pp. 1437–38 (1973)).

Imidazole-2-carboxylic acid (13a) was prepared according to Curtis and Brown, *J. Org. Chem.*, 45, pp. 4038–40 (1980).

4-Benzylimidazole-2-carboxylic acid (13b), was isolated as an off-white solid: mp. 153–155° C.; IR (KBr) 3026–2624, 1630, 1515, 1498, 1438, 1405; ¹H NMR(d₆-DMSO) δ 7.31 (5H, m), 7.14 (1H, s), 3.95 (2H, s).

4-(2-Phenylethyl) imdazole-2-carboxylic acid (13c), was isolated as a pale yellow solid: mp. 151–153° C.; IR (KBr) 3054–2617, 1637, 1497, 1376; ¹H NMR(d₆-DMSO) δ 7.27 (5H, m), 7.11 (1H, s), 2.92 (4H, s).

4-(3-Phenylpropyl)imidazole-2-carboxylic acid (13d), was isolated as a pale yellow solid: mp. 148–150° C.; IR (KBr) 3020–2615, 1636, 1509, 1498, 1383; ¹H NMR(d₆-DMSO) δ 7.35–7.22 (5H, m), 7.01 (1H, s), 2.62 (4H, m), 1.94 (2H, m).

4-[3-(4-Methoxyphenyl)propyl]imidazole-2-carboxylic acid (13e), was isolated as a white crystalline solid: mp. 155–156° C. (decomp.); IR (KBr) 3300–2300, 1633, 1513, 1376, 1244; ¹H NMR(d₆-DMSO) δ 9.50–7.50 (2H, bs), 7.15 (1H, s), 7.11 (2H, d, J=8.5), 6.84 (2H, d, J=8.5), 3.71 (3H, s), 2.60–2.50 (4H, m), 1.86 (2H, m). Anal. Calcd for C₁₄H₁₆N₂O₃: C, 64.60; H, 6.20; N, 10.76. Found: C, 64.45; H, 6.21; N, 10.70.

4-[3-(4-Hydroxyphenyl)propyl]imidazole-2-carboxylic acid (13f). A solution of the ethyl ester of 13e (1.15 g, 4.0 mmol) in dry dichloromethane (50 ml) was treated with boron tribromide (16 ml, 1.0M solution in CH₂Cl₂, 16.0 mmol) at 0° C. After 15 min at 0° C., the mixture was warmed to 25° C. and stirred for 16 h. The reaction mixture was cooled in an ice bath and quenched with a dropwise addition of water (20 ml). The resulting mixture was briefly stirred at 25° C. then filtered. The filtrate was carefully neutralised by the addition of solid NaHCO₃ to afford 13f (700 mg, 71%) as a white solid: m.p. 186–187° C. (decomp.) (recrystallised from MeOH); IR (KBr) 3500–2400, 2935, 1640, 1516, 1396, 1232; ¹H NMR(d₆-DMSO) δ 9.83 (3H, bs), 7.16 (1H, s), 6.98 (2H, d, J=8.2), 6.66 (2H, d, J=8.2), 2.60–2.40 (4H, m), 1.84 (2H, m). Anal. Calcd for C₁₃H₁₄N₂O₃: C, 63.40; H, 5.73; N, 11.38. Found: C, 62.96; H, 5.70; N, 11.27.

(2R,S, 3S) N²-Tert-butoxycarbonyl-N-(tetrahydro-2-benzyloxy-5-oxo-3-furanyl)-L-alaninamide (14). Tri-n-butyl tin hydride (4.0 ml, 14.9 mmol) was added dropwise to a solution of (2R,S, 3S) 3-(N-allyloxycarbonyl) amino-2-benzyloxy-5-oxotetrahydrofuran (Chapman, *Biorg. Med. Chem. Lett.*, 2, pp. 613–18 (1992); (2.91 g, 10 mmol)), N-tert-butoxycarbonyl-L-alanine (2.08 g, 11 mmol) and bis(triphenylphosphine)palladium (II) chloride (150 mg) in dichloromethane (75 ml) until the colour of the solution turned dark orange. Hydroxybenzotriazole (2.70 g, 20 mmol) was added, and the mixture cooled to 0° C. 1-(3-dimethylamino-propyl)-3-ethylcarbodiimide hydrochloride (2.30 g, 12 mmol) was added then the mixture was allowed to warm slowly to room temperature during 4 h. The mixture was diluted with ethyl acetate (250 ml) and washed with iN hydrochloric acid (3×150 ml), saturated aqueous sodium bicarbonate (3×150 ml) and brine (2×150 ml), then dried (MgSO₄), filtered and concentrated. The crude product was purified by column chromatography (50–70% ethyl acetate/hexane) to afford 3.17 g (84%) of a mixture of diastereomers. Recrystallization (ethyl acetate-hexane) gave colorless crystals: mp. 132–145° C.; IR (KBr) 3357, 3345, 1781, 1688, 1661, 1535, 1517, 1165; ¹H NMR(d₆-DMSO) δ 8.49 (d, J=6.8), 8.23 (d, J=7.4), 7.40 (5H, m), 7.01 (1H, m), 5.68 (d, J=5.0), 4.75 (m), 4.31 (m), 3.97 (1H, m), 2.82 (m), 3.11 (m), 2.82 (m), 2.59 (m), 2.45 (m), 1.40 (9H, s), 1.20 (d, J=7.2), 1.16 (d, J=7.2). Anal. Calcd for C₁₉H₂₆N₂O₆: C, 60.31; H, 6.92; N, 7.40. Found C, 60.30; H, 6.91; N, 7.38.

(2R, S, 3S) tert-Butoxycarbonyl-N-(tetrahydro-2-benzyloxy-5-oxo-3-furanyl)-L-prolinamide (15), was prepared by the method described for 14 to afford 1.64 g (81%) of a colorless glass. IR (KBr) 3317, 2978, 1797, 1697, 1670, 1546, 1400, 1366, 1164, 1121; $^1$H NMR(CDCl$_3$) δ 7.68 (1H, brm), 7.35 (5H, m); 5.53 (d, J=5.2), 5.43 (s), 4.93–4.61 (m), 4.44 (m), 4.25 (brm), 3.39 (2H, brm), 3.10–2.81 (1H, m), 2.44 (1H, m), 2.32 (brm), 1.88 (brm), 1.67 (brm), 1.42 (9H, s).

(2R, S, 3S) N-(N-tert-Butoxycarbonyl-(4(R)-phenoxy-L-prolinyl)-3-amino-2-benzyloxy-5-oxotetrahydrofuran (16) was prepared by the method described for 14 to afford 530 mg (84%) of a colorless amorphous solid: $^1$H NMR (CDCl$_3$) δ 7.65 (1H, m), 7.4–7.2 (7 H, m), 6.95 (1H, m), 6.85 (1H, m), 5.55(1H, d), 4.95 (1H, d), 4.8–4.7 (1H, brm), 4.65 (1H, d), 4.55–4.45 (1H, brm), 4.4–4.3 (0.5H, brm), 3.95–3.85 (0.5H, brm), 3.75–3.58 (2H, m), 2.95–2.8 (1H, m), 2.7–2.55 (1H, m), 2.54–2.4 (1H, m), 2.35–2.2 (1H, m), 1.4 (9H,s).

(2R,S, 3S) N$^2$-[4-(3-Phenylpropyl)imidazole-2-carbonyl]-N-(tetrahydro-2-benzyloxy-5-oxo-3-furanyl)-L-alaninamide (17d). Trifluoroacetic acid (7 ml) was added to a solution of (2R,S, 3S) N$^2$-tert-butoxycarbonyl-N-(tetrahydro-2-benzyloxy-5-oxo-3-furanyl)-L-alaninamide (14) (1.00 g, 2.64 mmol) in dichloromethane (7 ml) at 0° C. The mixture was stirred at 0° C. for 75 min. The mixture was concentrated, and the residue treated with diethyl ether then the ether was removed under vacuum. This procedure was repeated twice to yield a pale yellow glass. The solid was dissolved in DMF (20 ml). Diisopropylethylamine (1.38 ml, 7.92 mmol) followed by 4-(3-phenylpropyl) imidazole-2-carboxylic acid (13d) (0.67 g, 290 mmol), 1-(3-dimethylaminopropyl)-3-ethyl carbodiimide hydrochloride (0.56 g, 2.90 mmol) and hydroxybenzotriazole (0.71 g, 5.28 mmol) were then added to this solution. The mixture was stirred at room temperature for 20 h then poured into brine. The mixture was extracted with ethyl acetate (3×50 ml). The combined organic extracts were washed with saturated aqueous sodium bicarbonate (2×100 ml) then brine (2×100 ml), dried (MgSO$_4$), filtered and concentrated. The residue was purified by column chromatography (ethyl acetate) to afford 0.99 g (76%) of 17d as a mixture of diastereomers: IR (KBr) 3293, 3064, 2937, 1793, 1650, 1530, 1451, 1446, 1119; $^1$H NMR (CDCl$_3$) δ 7.96 (brm), 7.62 (brd), 7.36–7.10 (10H, m), 6.88 (s), 6.86 (s), 5.53 (d, J=5.2), 5.48 (s), 4.87–4.52 (4H, m), 3.11–2.38 (2H, m), 2.65 (4H, m), 1.99 (2H, m), 1.47 (d, J=6.9), 1.46 (d, J=7.0).

The following compounds were prepared in a similar manner:

(2R,S, 3S) N$^2$-(Imidazole-2-carbonyl)-N-(tetrahydro-2-benzyloxy-5-oxo-3-furanyl)-L-alaninamide (17a), was isolated (74%) as a pale yellow solid: IR (KBr) 3289, 3056, 2937, 1793, 1664, 1642, 1528, 1453, 1440, 1124; $^1$H NMR (d$_6$-DMSO) δ 13.13 (1H, brs), 8.67 (d, J=7.0), 8.48 (d, J=7.8), 8.29 (d, J=6.8), 8.25 (d, J=7.6), 7.40–7.34 (6H, m), 7.11 (1H, s), 5.69 (d, J=5.0), 5.49 (d, J=0.8), 4.85–4.31 (4H, m), 3.19–2.42 (2H, m), 1.38 (d, J=7.4), 1.34 (d, J=7.4).

(2R,S, 3S) N$^2$-(4-Benzylimidazole-2-carbonyl)-N-(tetrahydro-2-benzyloxy-5-oxo-3-furanyl)-L-alaninamide (17b), was isolated (75%) as a pale yellow glass: IR (KBr) 3294, 3031, 2937, 1792, 1650, 1530, 1453, 1444, 1119; $^1$H NMR(CDCl$_3$) δ 7.99 (brm), 7.75 (brd), 7.36–7.11 (10H, m), 6.81 (1H, s), 5.51, 5.45 (d, s, J=5.3), 4.85–4.47 (4H, m), 3.95 (2H, s), 3.04–2.72 (1H, m), 2.48–2.35 (1H, m), 1.44 (d, J=6.9), 1.43 (d, J=7.1).

(2R,S, 3S) N$^2$-[4-(2-Phenylethyl)imidazole-2-carbonyl]-N-(tetrahydro-2-benzyloxy-5-oxo-3-furanyl)-L-alaninamide (17c), was isolated (79%) as a pale yellow glass: IR (KBr) 3292, 3029, 2936, 1793, 1650, 1530, 1453, 1444, 1119; $^1$H NMR(CDCl$_3$) δ 8.06 (brm), 7.70 (brs), 7.39–7.15 (10H, m), 6.82 (s), 6.81 (s), 5.53 (d, J=5.2), 5.48 (s), 4.87–4.53 (4H, m), 2.95 (4H, m), 3.11–2.37 (2H, m), 1.48 (d, J=5.6), 1.45 (d, J=6.7).

(2R,5, 3S) 1-[4-(2-Phenylethyl)imidazole-2-carbonyl]-N-(tetrahydro-2-benzyloxy-5-oxo-3-furanyl)-L-prolinamide (18c), was isolated (79%) as a pale yellow glass: IR (CH$_2$Cl$_2$) 3422, 2959, 1795, 1685, 1611, 1497, 1116; $^1$H NMR(d$_6$-DMSO) δ 12.78–12.59 (1H, m), 8.61–8.34 (1H, m), 7.39–7.22 (10H, m), 6.99–6.61 (1H, m), 5.71–5.26 (1H, m), 4.85–4.02 (4H, m), 3.63 (1H, m), 3.18–1.74 (11H, m).

(2R,S, 3S) 1-[4-(3-Phenylpropyl)imidazole-2-carbonyl]-N-(tetrahydro-2-benzyl-oxy-5-oxo-3-furanyl)-L-prolinamide (18d), was isolated (87%) as a colorless glass: IR (CH$_2$Cl$_2$) 3422, 3214, 2945, 1794, 1685, 1604, 1496, 1117; $^1$H NMR (d$_6$-DMSO) δ 12.71 (1H, brm), 8.61–8.34 (1H, m), 7.45–7.18 (10H, m), 7.05–6.64 (1H, m), 5.70–5.28 (1H, m), 4.85–4.02 (4H, m), 3.62 (1H, m) 3.18–1.71 (13H, m).

(2R,S, 3S) 1-{4-[3-(4-Nothoxyphenyl)propyl]imidazole-2-carbonyl}-N-(tetra-hydro-2-benzyloxy-5-oxo-3-furanyl)-L-prolinamide (18e), was isolated (72%) as a white glassy solid: mp. 62–65° C.; IR (KBr) 3213, 2937, 1793, 1680, 1606, 1606, 1512, 1245; $^1$H NMR(d$_6$-DMSO) δ 12.71, 12.67, 12.58 (1H, 3×bs), 8.60–8.30 (1H, m), 7.40–7.20 (5H, m), 7.15–6.55 (5H, m), 5.66–5.20 (1H, m), 4.81–4.59 (2H, m), 4.55–4.05 (2H, m), 3.71 (3H, s), 3.65–3.45 (1H, m), 3.15–1.50 (13H, m). FABSMS m/e 547 (M$^+$, 100%), 439, 412, 340, 312, 243, 177, 154.

(2R,S, 3S) 1-{4-[3-(4-Hydroxyphenyl)propyl]imidazole-2-carbonyl)-N-(tetra-hydro-2-benzyloxy-5-oxo-3-furanyl)-L-prolinamide (18f), was isolated (70%) as a light yellow glassy solid: mp. 86–90° C.; IR (KBr) 3298, 1790, 1669, 1606, 1515, 1242; $^1$H NMR(d$_6$-DMSO) δ 12.66, 12.56 (1H, 2×bs), 9.14 (1H, s), 8.57–8.30 (1H, m), 7.36–7.30 (5H, m), 7.02–6.83 (3H, m), 6.70–6.57 (2H, m), 5.65–5.28 (1H, m), 4.80–4.49 (2H, m), 4.50–4.05 (2H, m), 3.65–3.45 (1H, m), 3.15–1.55 (13H, m). FABMS m/e 533 (M$^+$, 100%), 425, 298, 229, 176, 154.

1-{5-[3-(4-Methoxyphenyl)propyl]-1H-imiidazole-2-carbonyl}-4(R)-phenoxypyrrolidine-2(S)-carbonyl-(tetrahydro-2(R,S)-benzyloxy-5-oxofuran-3(S)-yl)amide (19e) was isolated (77%) as a clear colorless amorphous solid. $^1$H NMR (CDCl$_3$) δ 9.95–9.75 (1H, m), 7.95 (1H, brs), 7.40–7.2 (7H, m), 7.2–6.78 (7H, m), 5.65–5.6 (1H, m), 5.55–5.45 (1H, m), 5.3–5.2 (1H,m), 5.15–5.0 (1H, m), 4.95–4.75 (1H, m), 4.7–4.6 (1H, m), 4.5–4.4 (1H, m), 4.35–4.4.25 (1H, m), 3.8 (3H, s), 3.05–1.75 (10H, m).

(3S) 3-{N-[4-(3-Phenylpropyl)imidazole-2-carbonyl]-L-alaninyl}amino-4-oxo-butanoic acid (20d). A mixture of (2R,S, 3S) N$^2$-[4-(3-Phenylpropyl)imidazole-2-carbonyl)-N-(tetrahydro-2-benzyloxy-5-oxo-3-furanyl)-L-alaninamide (0.93 g, 1.90 mmol) and 10% palladium on activated carbon (0.93 g) in methanol (100 ml) was stirred under a hydrogen atmosphere for 5 h. The resulting mixture was filtered and concentrated to yield a colorless glass. Recrystallization from methanol-diethyl ether afforded 401 mg (53%) of 20d as a colorless solid: mp. 94–96° C.; [α]$_D^{27}$+16.4° (c 0.5, MeOH); IR (KBr) 3300, 3287, 1786, 1732, 1659, 1651, 1532, 1451; $^1$H NMR(CD$_3$OD) δ 7.19 (5H, m), 6.91 (1H, s), 4.60–4.46 (2H, m), 4.27 (1H, m), 2.63 (4H, m), 2.75–2.40 (2H, m), 1.96 (2H, m), 1.44 (3H, d, J=7.0).

The following compounds were prepared in a similar manner:

(3S) 3-[N-(Imidazole-2-carbonyl)-L-alaninyl]amino-4-oxobutanoic acid (20a; E), was isolated (83%) as a colorless solid: mp. 115° C.; [α]$_D^{25}$+4.4° (c 0.5, MeOH); IR (KBr) 3303, 1782, 1658, 1650, 1563, 1521, 1454; 1H NMR (CD$_3$OD) δ 7.18 (2H, s), 4.55 (2H, m), 4.27 (1H, m), 2.56 (2H, m), 1.45 (d, J=7.1), 1.44 (d, J=7.0).

(3S) 3-[N-(4-Benzylimidazole-2-carbonyl)-L-alaninyl] amino-4-oxobutanoic acid (20b), was isolated (56%) as a colorless solid: mp. 113–115° C.; [α]$_D^{29}$+18.2° (c 0.5 MeOH). IR (KBr) 3301, 3288, 1783, 1727, 1650, 1531, 1452; $^1$H NMR(CD$_3$OD) δ 7.25 (5H, m), 6.90 (1H, s), 4.59–4.45 (2H, m), 4.26 (1H, m), 3.95 (2H, s), 2.74–2.39 (2H, m), 1.42 (3H, d, J=7.0). Anal. Calcd for C$_{18}$H$_{20}$N$_4$O$_5$: C, 56.69; H, 5.55; N, 14.69. Found: C, 57.06; H, 5.54; N, 14.41.

(3S) 3-{N-[4-(2-Phenylethyl)imidazole-2-carbonyl]-L-alaninyl}amino-4-oxobutanoic acid (20c; N), was isolated (53%) as a colorless solid: mp. 102–104° C.; [α]$_D^{27}$+13.7° (c 0.5, MeOH); IR (KBr) 3299, 3289, 1785, 1732, 1650, 1531, 1452; $^1$H NMR(CD$_3$OD) δ 7.20 (5H, m), 6.82 (1H, s), 4.60–4.46 (2H, m), 4.29 (1H, m), 2.92 (4H, s), 2.76–2.41 (2H, m), 1.44 (3H, 2×d, J=7.1). Anal. Calcd for C$_{19}$H$_{22}$N$_4$O$_5$ H$_2$O: C, 56.43; H, 5.98; N, 13.85. Found: C, 56.65; H, 5.84; N, 13.91.

(3S) 3{N-[4-(2-Phenylethyl)imidazole-2-carbonyl]-L-prolinyl}amino-4-oxobutanoic acid (21c), was isolated (85%) as a colorless glass: mp. 101–103° C. (methanol-diethyl ether); [α]$_D^{27}$-63.8° (c 0.25, MeOH); IR (KBr) 3275, 1784, 1728, 1664, 1606, 1498, 1429; $^1$H NMR (CD$_3$OD) δ 7.24 (5H, m), 6.83 (s), 6.79 (s), 4.58–4.14 (3H, m), 3.69 (1H, m), 2.93 (4H, brs), 2.75–1.99 (6H, m). Anal. Calcd for C$_{21}$H$_{24}$N$_4$O$_5$ H$_2$O: C, 58.60; H, 6.09; N, 13.02. Found: C, 58.34; H, 5.96; N, 12.67.

(3S) 3-{N-[4-(3-Phenylpropyl)imidazole-2-carbonyl]-L-prolinyl}amino-4-oxo-butanoic acid (21d), was isolated (81%) as a colorless glass: mp. 91–94° C.; (methanol-diethyl ether); [α]$_D^{25}$-68° (c 0.25, MeOH); IR (KBr) 3277, 2939, 1784, 1727, 1662, 1606, 1498, 1429; H NMR(CD$_3$OD) δ 7.29–7.16 (5H, m), 6.92 (s), 6.86 (s), 4.58–4.16 (3H, m), 3.71 (1H, m), 2.75–1.92 (13H, m). Anal. Calcd for C$_{22}$H$_{26}$N$_4$O$_5$ H$_2$O: C, 59.45; H, 6.35; N, 12.60. Found: C, 59.75; H, 6.21; N, 12.41.

(3S) 3-{N-[4-[3-(4-Methoxyphenyl)propyl]imidazole-2-carbonyl]-L-prolinyl}amino-4-oxobutanoic acid (21e), was isolated (65%) as a white glassy solid: mp. 101–105° C.; [α]$_D^{23}$-60.6 (c 0.05, MeOH); IR (KBr) 3231, 1784, 1726, 1611, 1512, 1245; $^1$H NMR(CD$_3$OD) δ 7.09 (2H, d, J=8.6), 6.92, 6.85 (1H, 2×s), 6.81 (2H, d, J=8.6), 5.45–5.30 (1H, m), 4.64–4.46 (1H, m), 4.28–4.10 (2H, m), 3.75 (3H, s), 3.74–3.66 (1H, m), 2.67–1.84 (13H, m). Anal. Calcd for C$_{23}$H$_{28}$N$_4$O$_6$ H$_2$O: C, 58.22; H, 6.37; N, 11.81. Found: C, 58.39; H, 6.34; N, 11.45; FABMS m/e 457 (M$^+$), 405, 312, 243, 215, 176, 154 (100%).

(3S) 3-{N-[4-[3-(4-Hydroxyphenyl)propyl]imidazole-2-carbonyl]-L-prolinyl}amino-4-oxobutanoic acid (21f), was isolated (43%) as a white glassy solid: mp. 114–118° C.; [α]$_D^{25}$-55.7° (c 0.05, MeOH); IR (KBr) 3288, 2935, 1780, 1715, 1662, 1610, 1515, 1441; $^1$H NMR(CD$_3$OD) δ 6.99 (2H, d, J=8.5), 6.91, 6.85 (1H, 2×s), 6.68 (2H, d, J=8.5), 5.45–5.30 (1H, m), 4.60–4.47 (1H, m), 4.30–4.10 (2H, m), 3.80–3.55 (1H, m), 2.70–1.80 (13H, m). Anal. Calcd for C$_{22}$H$_{26}$N$_4$O$_6$ H$_2$O: C, 57.38; H, 6.13; N, 12.17. Found: C, 57.68; H, 6.25; N, 11.66. FABMS m/e 443 (M$^+$), 298, 229, 154 (100%).

3(S)-[(1-{5-[3-(4-Methoxyphenyl)propyl]-1H-imidazole-2-carbonyl}-4(R)-phenoxy pyrrolidine-2(S)-carbonyl)amino]-4-oxobutanoic acid (22e) was isolated (43%) as a beige solid: $^1$H NMR (CD$_3$OD) δ 7.35–7.2 (3H,m), 7.15–7.0 (2H,m), 6.98–6.85 (3H, m), 6.83–6.77 (2H,d), 5.4–5.1 (1H, m), 4.65–4.5 (1H,m), 4.35–4.2 (2H,m), 4.15–3.90 (1H,m), 3.78 (3H, s), 3.62–3.48 (1H, m), 2.78–2.25 (8H, m), 2.02–1.9 (2H,m).

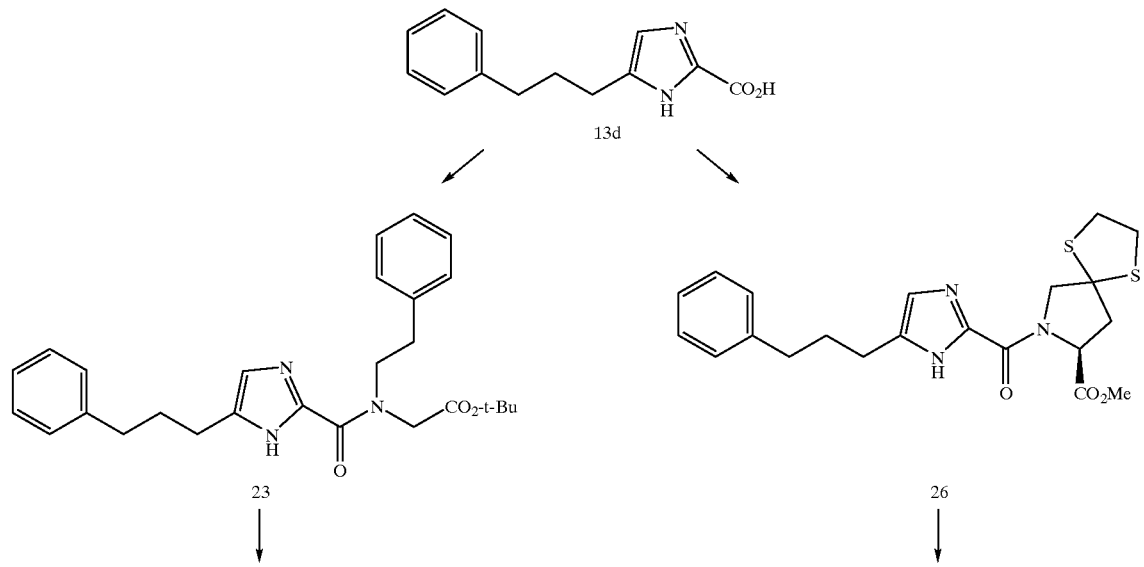

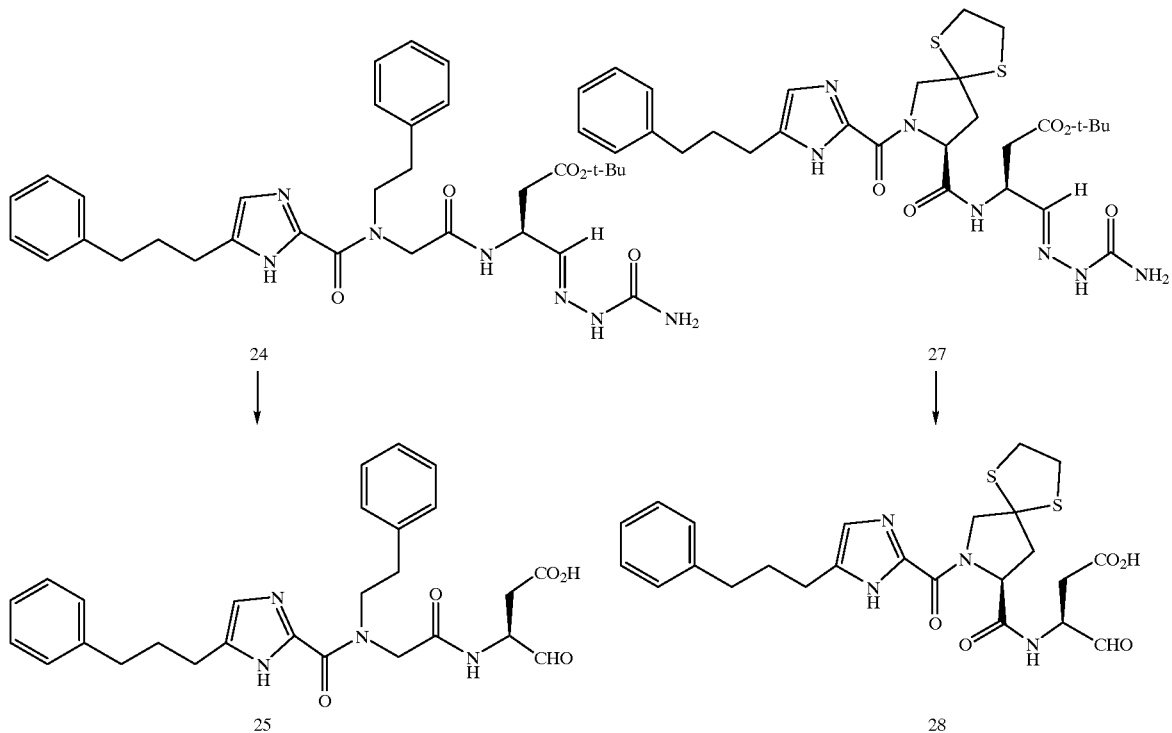

{Phenethyl-[5-(3-propyl)-1H-imidazole-2-carbonyl]amino}acetic acid tert-butyl ester (23). A 0° C. solution of 4-(3-phenylpropyl)-imidazole-2-carboxylic (13d) (150 mg, 0.65 mmol) and N-(2-phenethyl)glycine tert-butyl ester (140 mg, 0.59 mmol) in 5 ml of anhydrous dimethylformamide was treated with diisopropylethylamine (154 µl, 0.89 mmol), hydroxy-benzotriazole (160 mg, 1.18 mmol), and 1-(3-dimethylaminopropyl)-3-ethyl carbodiimide hydrochloride (136 mg, 0.71 mmol). After stirring for 36 h, the reaction was poured onto saturated aqueous sodium chloride and extracted with ethyl acetate (3×50 ml) The combined organic extracts were washed twice with saturated aqueous sodium bicarbonate (2×) and saturated aqueous sodium chloride (1×), dried (Na$_2$SO$_4$), filtered, and concentrated in vacuo to give a brown oil. Chromatography (flash, SiO$_2$, 30% ethyl acetate/hexane) to give 160 mg (61%) of 23 as a white solid: $^1$H NMR (CDCl$_3$) δ 7.38–7.14 (10H, m), 6.85–6.8 (1H, m), 4.84–4.76 (1H, d), 4.5–4.42 (1H, m), 4.07–4.0 (1H, d), 3.78–3.72 (1H, m), 3.12–2.94 (2H, 2×m), 2.75–2.55 (4H, m), 2.1–1.95 (2H,m), 1.5–1.45 (9H, 3×s).

(3S)-(2-Phenethyl-[5-(3-phenylpropyl)-1H-imidazole-2-carbonyl]amino}acetyl amino) 4-oxobutanoic acid tert-butyl ester semicarbazone (24). The ester 23 (160 mg, 0.357 mmol) was treated with 25% trifluoroacetic acid/dichloromethane (7 ml) for 4 h. The reaction was concentrated in vacuo to afford 180 mg of the acid. The acid (180 mg, 0.357 mmol) was coupled to (3S)-3-amino-4-oxobutanoic acid tert-butyl ester semicarbazone (161 mg, 0.357 mmol) as describe for the preparation of 5a and 5b to give 86 mg (33%) of 24 (one diastereomer) as a white solid: $^1$H NMR (CDCl$_3$) δ 10.9–10.3 (1H, 2 d), 10.08–9.78 (1H, 2 d), 9.25–9.15 (1H,m), 8.35–8.10 (1H, 2 m), 7.9–7.85 (1H, 2 s), 7.40–7.05 (10H, m), 6.9–6.75 (1H,m), 6.3–5.8 (1H, br s), 5.2–4.65 (2H,m), 4.35–3.5 (3H,m), 3.25–3.0 (2H, m), 2.9–2.45 (6H,m), 2.05–1.8 (2H,m), 1.4 (9H,s).

(3S)-(2-{Phenethyl-[5-(3-phenylpropyl)-1H-imidazole-2-carbonyl]amino}acetylamino)-4-oxobutanoic acid trifluoroacetic acid salt (25) was prepared by the method described for 7a to afford 32 mg (82%) as a white solid: $^1$H NMR (CD$_3$OD) δ 7.05–7.35 (m, 11H), 4.65 (m, 1H), 4.4 (m, 1H), 4.3 (s, 2H), 3.6–4.0 (m, 2H), 2.5–2.95 (m, 8H), 2.05 (m, 2H).

7-[5-(3-Phenylpropyl)-1H-imidazole-2-carbonyl]-1,4-dithia-7-azaspiro[4.4]nonane-8(S)-carboxylic acid methyl ester (26). 4-(3-Phenylpropyl)imidazole-2-carboxylic acid (13d) was coupled to 1,4-dithia-7-azaspiro[4.4]nonane-8 (S)-carboxylic acid methyl ester hydrobromide (Smith et. al., J. Med. Chem., 31, pp. 875–85 (1988)) by the method described for 23 to afford 140 mg (65%) as a yellow gum: $^1$H NMR (CDCl$_3$) δ 7.34–7.15 (5H, m), 6.98–6.8 (1H, 3 s), 5.7–5.65 (0.5 H, m), 5.2–5.1 (1H,m), 4.82–4.75 (0.5H, m), 4.4–4.35 (1H, m), 4.05 (1H,d), 3.75–3.7 (3H, 2 s), 3.4–3.3 (4H,m), 2.95–2.45 (8H, m), 2.05–1.95 (2H,m).

(3S)-({7-[5-(3-Phenylpropyl)-1H-imidazole-2-carbonyl]-1,4-dithia-7-azaspiro[4.4]nonane-8(S)-carbonyl}-amino)-4-oxobutanoic acid tert-butyl enter semicarbazone (27). Following the procedure described for 4, the ester 26 was converted to its acid which was subsequently coupled to (3S)-3-amino-4-oxobutanoic acid tert-butyl ester semicarbazone as described for 24 to give 70 mg (33%) as a brown solid. $^1$H NMR (CD$_3$OD) δ 7.28–7.10 (5H,m), 6.90 (1H, br s), 4.94 (1H, m), 3.96–3.86 (2H,q), 3.35–3.25 (4H,d), 3.0 (2H, s), 2.73–2.59 (6H, m), 2.0–1.92 (2H, m),1.44 (9H,s).

(3S)-({7-[5-(3-Phenylpropyl)-1H-imidazole-2-carbonyl]-1,4-dithia-7-azaspiro[4.4]nonane-8(S)-carbonyl}-amino)-4-oxobutanoic acid (28) was prepared by the method described for 7a to afford 17 mg (26%) as a light brown solid: $^1$H NMR (CD$_3$OD) δ 7.4 (s, 1H), 7.1–7.25 (m, 5H), 4.9 (m, 1H), 4.6 (m, 1H), 4.3 (m, 1H), 3.95 (s, 2H), 3.25–3.4 (m, 4H), 3.0 (d, 2H), 2.6–2.8 (m, 5H), 2.45 (m, 1H), 2.05 (m, 2H).

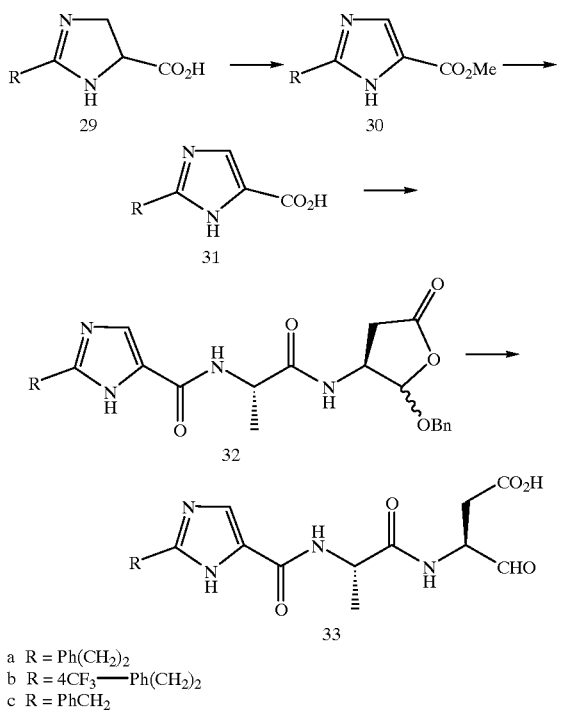

a R = Ph(CH$_2$)$_2$
b R = 4CF$_3$—Ph(CH$_2$)$_2$
c R = PhCH$_2$ 4,5-Dihydroimidazole-4-carboxylic esters (29) were prepared by a modification of the procedure described by Jones et al., *Tetrahedron Lett.*, 29, pp. 3853–56 (1988).

(4R,S) Methyl 2-(2-phenylethyl)-4,5-dihydroaimdazole-4-carboxylate (29a). Dry hydrogen chloride was bubbled into a solution of hydrocinnamonitrile (3.28 ml, 25 mmol) in methanol (125 ml) at 0° C. for 45 mins. The solvents were removed to give the imidate salt which was dissolved in methanol (125 ml) along with methyl 2,3-diaminopropionate (25 mmol) (Jones et al., supra). The mixture was kept at room temperature for 2.5 h, then concentrated to a yellow oil. The crude product was purified by column chromatography (10–20% methanol/dichloromethane) to afford 3.52 g (61%) of a colorless glass: $^1$H NMR(CDCl$_3$) δ 7.30–7.15 (5H, m), 4.63 (1H, t, J=9.7), 3.96 (2H, d, J=9.7), 3.72 (3H, s), 3.10 (4H, m), $^{13}$C NMR (CDCl$_3$) δ 171.3, 168.8, 138.3, 128.4, 128.2, 126.6, 57.3, 53.0, 47.7, 31.7, 27.9.

(4R,S) Methyl 2-[2-(4-trifluoromethylphenyl)ethyl]-4,5-dihydroimidazole-4-carboxylate (29b), was prepared by the method described for 29a to yield 6.80 g (78%) of a colorless solid: mp. 136–141° C.; $^1$H NMR(CDCl$_3$) δ 7.45 (4H, s), 4.71 (1H, dd, J=8.6,10.8), 4.02 (2H, m), 3.73 (3H, s), 3.19 (4H, m).

Imidazole-4-carboxylic esters 30 were prepared by a modification of the procedure described by Martin et al., *J. Org. Chem.*, 33, pp. 3758–61 (1968).

Methyl 2-(2-phenylethyl)imidazole-4-carboxylate (30a). A mixture of (4R,S) methyl 2-(2-phenylethyl)-4,5-dihydroimidazole-4-carboxylate (29a) (3.40 g, 14.64 mmol), chloroform (75 ml) and manganese (IV) oxide (13.0 g, 150 mmol) was heated under reflux for 21 h then filtered hot. The solids were washed with chloroform and methanol. The combined filtrates were concentrated to leave a yellow-brown solid, which was purified by column chromatography (2–5% methanol/dichloromethane) to afford 1.46 g (43%) of a pale yellow solid: mp. 151–155° C.; IR (KBr) 3028, 2946, 1720, 1533, 1433, 1348, 1195, 1166; $^1$H NMR(CDCl$_3$) δ 7.62 (1H, s), 7.26–7.02 (5H, m), 3.82 (3H, s), 3.03 (4H, brs), $^{13}$C NMR(CDCl$_3$) δ 162.9, 150.2, 140.3, 128.5, 128.2, 126.3, 51.5, 34.5, 30.4. Anal. Calcd for C$_{13}$H$_{14}$N$_2$O$_2$: C, 67.81; H, 6.13; N, 12.16. Found: C, 67.70; H, 6.15; N, 12.16.

Methyl 2-[2-(4-trifluoromethylphenyl)ethyl]imidazole-4-carboxylate (30b), was prepared by the method described for 30a. It was recrystallised from ethyl acetate to afford 1.88 g (33%) of cream crystals: mp. 225–26° C.; IR (KBr) 3239, 2951, 1715, 1532, 1331, 1158, 1105, 1068; $^1$H NMR (CDCl$_3$) δ 7.61 (1H, s), 7.54 (2H, d, J=8.1), 7.26 (2H, d, J=8.1), 3.89 (3H, s), 3.10 (4H, m). Anal. Calcd for C$_{14}$H$_{13}$F$_3$N$_2$O$_2$: C, 56.38; H, 4.39; N, 9.39; F, 19.11. Found: C, 56.23; H, 4.44; N, 9.33; F, 19.08.

2-(2-Phenylethyl)imidazole-4-carboxylic acid (31a). A mixture of methyl 2-(2-phenylethyl)imidazole-4-carboxylate (30a) (1.38 g, 6 mmol), methanol (30 ml) and 1M aqueous sodium hydroxide (30 ml) was heated under reflux for 16 h. The methanol was removed under reduced pressure, and the resulting aqueous solution was neutralized with 4M hydrochloric acid, whereupon a pale yellow solid precipitated. The precipitate was collected, washed with water, and dried to afford 1.18 g (91%) of a pale yellow solid: mp. 117–120° C.; IR (KBr) 3375, 3131, 2616, 2472, 1638, 1592, 1551, 1421, 1388, 1360; $^1$H NMR(d$_6$-DMSO) δ 7.59 (1H, s), 7.26 (5H, m), 2.99 (4H, m). Anal. Calcd for C$_{12}$H$_{12}$N$_2$O$_2$ 0.25H$_2$O: C, 65.29; H, 5.71; N, 12.69. Found: C, 65.00; H, 5.64; N, 12.58.

2-[2-(4-Trifluoromethylphenyl)ethyl]imidazole-4-carboxylic acid (31b), was prepared by the method described for 31a to afford 1.09 g (76%) of a pale yellow solid: mp. 126–130° C.; IR (KBr) 3339, 2640–2467, 1638, 1589, 1545, 1383, 1323; $^1$H NMR(d$_6$-DMSO) δ 7.69 (2H, d, J=8.0), 7.59 (1H, s), 7.47 (2H, d, J=8.0), 3.06 (4H, m).

(2R,S, 3S) N$^2$-[2-(2-Phenylethyl)imidazole-4-carbonyl]-N-(tetrahydro-2-benzyl-oxy-5-oxo-3-furanyl)-L-alaninamide (32a). To a solution of (2R,S, 3S) N$^2$-tert-butoxycarbonyl-N-(tetrahydro-2-benzyloxy-5-oxo-3-furanyl)-L-alaninamide (14) (1.59 g, 4.20 mmol; Chapman, *Biorg. Med. Chem. Lett.*, 2, pp. 613–18 (1992)) in dichloromethane (15 ml), cooled to 0° C., was added trifluoroacetic acid (15 ml). The mixture was stirred at 0° C. for 1 h and then concentrated. The residue was treated with ether and then the ether was removed under vacuum. This procedure was repeated twice to yield a pale yellow glass. The solid was dissolved in DMF (20 ml), then diisopropylethylamine (2.19 ml, 12.6 mmol), 2-(2-phenylethyl)imidazole-4-carboxylic acid (31a) (1.0 g, 4.62 mmol), 1-(3-dimethylaminopropyl)-3-ethyl carbodiimide hydrochloride (0.89 g, 4.62 mmol) and hydroxybenzotriazole (1.14 g, 8.40 mmol) were added to the solution. The reaction mixture was stirred at room temperature for 20 h then poured into brine. The mixture was extracted with ethyl acetate (3×50 ml). The combined organic extracts were washed with saturated aqueous sodium bicarbonate (3×100 ml) then brine (3×100 ml), dried (MgSO$_4$) and concentrated. The residue was purified by column chromatography (2–10% isopropanol in dichloromethane then 0–6% isopropanol in ethyl acetate) to yield 1.10 g (55%) of 32a as a mixture of diastereomers: IR (KBr) 3278, 3065, 1790, 1641, 1577, 1545, 1499, 1454, 1120; $^1$H NMR (CDCl$_3$) δ 10.26 (1H, s), 8.14 (1H, s), 7.66 (d, J=7.0), 7.56 (d, J=7.0), 7.43 (1H, s), 7.31–7.11 (10H, m), 5.49 (d, J=5.6), 5.48 (s), 4.83–4.41 (4H, m), 3.04–2.41 (2H, m), 2.99 (4H, s), 1.45 (d, J=7.0), 1.44 (d, J=7.0).

(2R,S, 3S) N$^2$-{2-[2-(4-Trifluoromethylphenyl)ethyl] imidazole-4-carbonyl}-N-(tetrahydro-2-benzyloxy-5-oxo-3-furanyl)-L-alaninamide (32b), was prepared by the method described for 32a to afford 1.08 g (62%) of a pale yellow glass: IR (KBr) 3376, 3284, 3070, 2938, 1791, 1642, 1578, 1546, 1327, 1165, 1122, 1068; $^1$H NMR(CDCl$_3$) δ 7.95 (0.5H, m), 7.55–7.25 (11.5H, m), 5.53 (s), 5.49 (d, J=5.3), 4.88–4.48 (4H, m), 3.11–2.96 (4H, m), 2.91 (1H, m), 2.51 (1H, m), 1.47 (3H, d, J=7.1).

(2R,S, 3S) N$^2$-(2-Benzylimidazole-4-carbonyl)-N-(tetrahydro-2-benzyloxy-5-oxo-3-furanyl)-L-alaninamide (32c), was prepared by the method described for 32a from 2-benzylimidazole-4-carboxylic acid (Ger. Offen. DE 3427136) to afford 1.13 g (83%) of a yellow glass: IR (CH$_2$Cl$_2$) 3433, 3062, 2990, 1803, 1693, 1584, 1504, 1429, 1285, 1258; $^1$H NMR(CDCl$_3$) δ 9.50 (s), 9.37 (s), 7.86 (0.5H, d, J=6.1), 7.56–7.21 (10.5H, m), 7.48 (1H, s), 5.51 (d, J=5.2), 5.48 (s), 4.87–4.41 (4H, m), 4.08 (s), 4.07 (s), 3.03–2.39 (2H, m), 1.46 (3H, d, J=7.0).

(3S) 3-{N-[2-(2-Phenylethyl)imidazole-4-carbonyl]-L-alaninyl}amino-4-oxobutanoic acid (33a; A). A mixture of (2R,S, 3S) N$^2$-[2-(2-phenylethyl)imidazole-4-carbonyl]-N-(tetrahydro-2-benzyloxy-5-oxo-3-furanyl)-L-alaninamide (32a) (1.0 g, 2.10 mmol) and 10% palladium on activated carbon (1.0 g) in methanol (50 ml) was stirred under a hydrogen atmosphere for 4.5 h. The resulting mixture was filtered and concentrated to yield a colorless glass. Recrystallization from methanol-diethyl ether afforded 510 mg (63%) of a colorless solid: mp. 127° C.; IR (KBr) 3360, 3279, 2981, 1781, 1732, 1646, 1577, 1547; $^1$H NMR (CD$_3$OD) δ 7.54 (1H, s) 7.29–7.12 (5H, m), 4.60–4.47 (2H, m), 4.28 (1H, m), 3.01 (4H, s), 2.76–2.39 (2H, m), 1.43 (3H, 2xd, J=7.0, J=7.0), $^{13}$C NMR (CD$_3$OD) δ 176.2, 176.0, 174.7, 174.6, 164.4, 164.3, 150.5, 141.9, 134.8, 129.5, 129.3, 127.3, 122.3, 98.8, 98.4, 52.3, 52.0, 50.3, 35.6, 31.2, 18.8, 18.7. Anal. Calcd for C$_{19}$H$_{22}$N$_4$O$_5$·H$_2$O: C, 56.43; H, 5.98; N, 13.85. Found: C, 56.78; H, 5.70; N, 13.77.

(3S) 3-{N-[2-(2-[4-Trifluoromethylphenyl]ethyl) imidazole-4-carbonyl]-L-alaninyl}-amino-4-oxobutanoic acid (33b; C), was prepared by the method described for 33a to afford 612 mg (73%) of a colorless solid: mp. 120–124° C.; [α]$_D^{23}$+14.3° (c 0.5, MeOH); IR (KBr) 3287, 2985, 2937, 1782, 1732, 1646, 1579, 1547, 1327; $^1$H NMR (CD$_3$OD) δ 7.56 (2H, d, J=8.0), 7.54 (1H, s), 7.36 (2H, d, J=8.0), 4.60–4.48 (2H, m), 4.28 (1H, m), 3.08 (4H, m), 2.75–2.41 (2H, m), 1.43 (3H, d, J=7.0). Anal. Calcd for C$_{20}$H$_{21}$F$_3$N$_4$O$_5$·0.5H$_2$O: C, 51.84; H, 4.78; N, 12.09; F, 12.30. Found: C, 51.83; H, 4.72; N, 12.14; F, 12.36.

(3S) 3-[N-(2-Benzylimidazole-4-carbonyl)-L-alaninyl]amino-4-oxobutanoic acid (33c; B), was prepared by the method described for 33a to afford 426 mg (64%) of a colorless solid: [α]$_D^{23}$+13.4° (c 0.407, MeOH). IR (KBr) 3260, 3150, 2980, 1779, 1727, 1649, 1573, 1547; $^1$H NMR (CD$_3$OD) δ 7.58 (1H, s), 7.34–7.22 (5H, m), 4.59–4.47 (2H, m), 4.28 (1H, m), 4.07 (2H, s), 2.74–2.41 (2H, m), 1.42 (3H, d, J=6.7); $^{13}$C NMR (CD$_3$OD) δ 175.6, 175.5, 175.0, 164.6, 164.5, 150.1, 138.7, 135.3, 130.0, 129.9, 128.2, 122.9, 98.9, 98.5, 52.5, 52.2, 35.5, 35.1, 35.0, 19.0, 18.9. Anal. Calcd for C$_{18}$H$_{20}$N$_4$O$_5$·H$_2$O: C, 55.37; H, 5.68; N, 14.35. Found C, 55.83; H, 5.75; N, 13.96. MS(FAB, m/z): 373 ((M$^+$), 228, 185, 91.

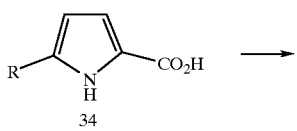

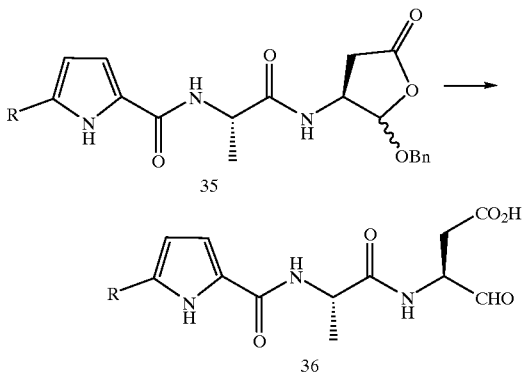

(a) R = H
(b) R = CH$_2$Ph

5-Benzylpyrrole-2-carboxylic acid (34b). A mixture of Ethyl 5-benzylpyrrole-2-carboxylate (0.7 g, 3.05 mmol; Elder et al., *Synthetic Communications*, 19, 763–767 (1989)), ethanol (20 ml) and 1M sodium hydroxide (9.2 ml, 9.2 mmol) was stirred and heated under reflux for 3 h. The major part of the ethanol was removed and the remaining liquid was diluted with water, washed with ether, cooled in ice and acidified with concentrated hydrochloric acid. The mixture was extracted with ether. The combined extracts were washed with brine, dried (Na$_2$SO$_4$) and concentrated to afford 0.567 g (92%) of an off white solid: mp. 130–134° C.; $^1$H NMR(CDCl$_3$) δ 8.87 (1H, brs), 7.37–6.95 (5H, m), 6.97 (1H, m), 6.07 (1H, m), 4.00 (2H, s).

(2R,S, 3S) N$^2$-(Pyrrole-2-carbonyl)-N-(tetrahydro-2-benzyloxy-5-oxo-3-furanyl)-L-alaninamide (35a). A solution of (2R,S, 3S) N$^2$-tert-butoxycarbonyl-N-(tetrahydro-2-benzyloxy-5-oxo-3-furanyl)-L-alaninamide (14) (756 mg, 2.0 mmol) in dry dichloromethane (8 ml) at 0° C. was treated with trifluoroacetic acid (8 ml) for 1 h and then evaporated to dryness. Dry ether was added to the residue and the mixture concentrated to give a viscous oil. The oil was dissolved in dry DMF (10 ml). Pyrrole-2-carboxylic acid (34a) (244 mg, 2.2 mmol) was added and the solution was cooled in an ice bath before the addition of N,N-diisopropylamine (0.78 g, 6.0 mmol), 1-hydroxybenzotriazole (0.54 g, 4.0 mmol) and ethyl dimethylaminopropyl carbodiimide hydrochloride (0.42 g, 2.2 mmol). The resulting mixture was stirred at 25° C. for 17 h and then saturated aqueous sodium chloride (30 ml) was added. The mixture was extracted with ethyl acetate (3×20 ml) and the combined organic extracts were washed with 5% aqueous sodium bicarbonate (3×10 ml) and brine (10 ml), dried (MgSO$_4$) and concentrated. Flash chromatography (25% hexane-ethyl acetate) afforded 557 mg (75%) of a 1:1 mixture of diastereomers as a white glassy solid: mp. 85–90° C.; IR (KBr) 3288, 1789, 1665, 1629, 1557 and 1122; $^1$H NMR(d$_6$-DMSO) δ 11.46 (1H, bs), 8.55 (0.5H, d, J=7.0), 8.30 (0.5H, d, J=7.6), 8.06 (0.5H, d, J=7.0), 8.04 (0.5H, d, J=7.6), 7.36–7.30 (5H, m), 6.88–6.85 (2H, m), 6.10–6.07 (1H, m), 5.63 (0.5H, d, J=5.0), 5.42 (0.5H, s), 4.72 (2H, q, J=12.2), 4.74–4.25 (2H, m), 3.14–2.35 (2H, m), 1.29, 1.25 (3H, 2xd, J=7.2).

(2R, S, 3S) N$^2$-(5-Benzylpyrrole-2-carbonyl)-N-(tetrahydro-2-benzyloxy-5-oxo-3-furanyl)-L-alaninamide (35b), was prepared from 5-benzylpyrrole-2-carboxylic acid (34b) by the method described for compound 35a (65%). Data is given for a single diastereomer. $^1$H NMR (d$_6$-DMSO) δ 11.37 (1H, brs,), 8.27 (1H, d, J=7.4), 7.93 (1H, d, J=7.6), 7.33–7.16 (10H, m), 6.76 (1H, m), 5.82 (1H, m), 5.62 (1H, d, J=5.2), 4.76 (1H, d, J=12.0), 4.65 (1H, m), 4.62 (1H, d, J=12.2), 4.47 (1H, m), 3.88 (2H, s), 2.77 (1H, dd, J=9.0,18.0), 2.5 (dd), 1.23 (3H, d, J=7.0).

(3S) 3-[N-(Pyrrole-2-carbonyl)-L-alaninyl]amino-4-oxobutanoic acid (36a; D). A mixture of (35a) (612 mg; 1.65 mmol), methanol (40 ml) and 10% palladium on carbon (500 mg) was vigorously stirred under an atmosphere of hydrogen for 4 h. The mixture was filtered through a 0.2 μM nylon membrane then concentrated. The residue was purified by flash chromatography (5–10% methanol in methylene chloride) to afford the hemihydrate of (36a) (223 mg, 48%) as a white solid after precipitation from an ethyl acetate-ether mixture. There were traces of solvent in the product: mp. 96–100° C.; IR (KBr) 3381, 1774, 1729 (EtOAc), 1632, 1558, 1523, 1123; $^1$H NMR(CD$_3$OD) δ 6.94–6.85 (2H, m), 6.17 (1H, dd, J=3.8 and 2.6), 4.58 (0.5H, d, J=3.94), 4.56 (0.5H, d, J=4.24), 4.51 (1H, q, J=7.16), 4.35–4.20 (1H, m), 2.74–2.40 (2H, m), 1.42 and 1.41 (3H, 2×d, J=7.13).

(3S) 3-[N-(5-Benzylpyrrole-2-carbonyl)-L-alaninyl]amino-4-oxobutanoic acid (36b), was prepared (41%) from 35b by the method described for compound 36a, to afford an off white solid: mp. 109–112° C.; [α]$_D^{25}$+6.3° (c 0.3, methanol); IR (KBr) 3368, 1724, 1630, 1530, 1453, 1414, 1233, 1049; $^1$H NMR(d$_4$ methanol) δ 7.25–7.11 (5H, m), 6.76 (1H, d, J=3.5), 5.84 (1H, d, J=3.5), 4.51 (1H, m), 4.43 (1H, q, J=7.1), 4.23 (1H, m), 2.5 (2H, m),1.35 (3H, d, J=7.0). Anal. Calcd for C$_{19}$H$_{21}$N$_3$O$_5$. 1.75 H$_2$O: C, 56.64; H, 6.13; N, 10.43. Found: C, 56.34; H, 5.72; N, 10.00.

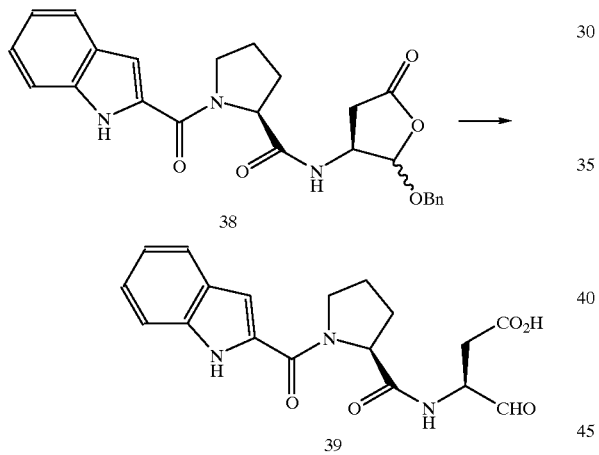

purified by column chromatography (ethyl acetate) to afford 518 mg (77%) of a mixture of diastereomers: IR (KBr) 3314, 1780, 1677, 1609, 1524, 1435, 1406, 1344; 1H NMR (d$_6$-DMSO), δ 11.58 (1H, m), 8.81–8.41 (1H, m), 7.71–6.67 (10H, m), 5.70 (d, J=5.2), 5.48 (s), 4.89–4.29 (4H, m), 3.99–3.74 (2H, m), 3.20–2.44 (2H, m), 2.39–1.77 (4H, m).

(3S) 3-[1-(Indole-2-carbonyl)-L-prolinyl]amino-4-oxobutanoic acid (39). A mixture of (2R,S, 3S) 1-(indole-2-carbonyl)-N-(tetrahydro-2-benzyloxy-5-oxo-3-furanyl)-L-prolinamide (38) (478 mg, 1.07 mmol) and 10% palladium on carbon (475 mg) and methanol (150 ml) was stirred under a hydrogen atmosphere for 6 h. The resulting mixture was filtered and concentrated to yield a colorless glass. Recrystallization from a mixture of methanol and diethyl ether afforded 202 mg (53%) of a colorless solid: mp. 135–138° C.; [α]$_D^{24}$–44° (c 0.25, CH$_3$OH); IR (KBr) 3287, 2977, 2879, 1781, 1725, 1716, 1667, 1662, 1600, 1529, 1441, 1346; $^1$H NMR(CD$_3$OD) δ 7.65 (1H, d, J=8.0), 7.44 (1H, d, J=8.4), 7.22 (1H, m), 7.09–6.84 (2H, m), 4.62 (2H, m), 4.29 (1H, m), 4.15–3.73 (2H, m), 2.74–1.72 (6H, m).

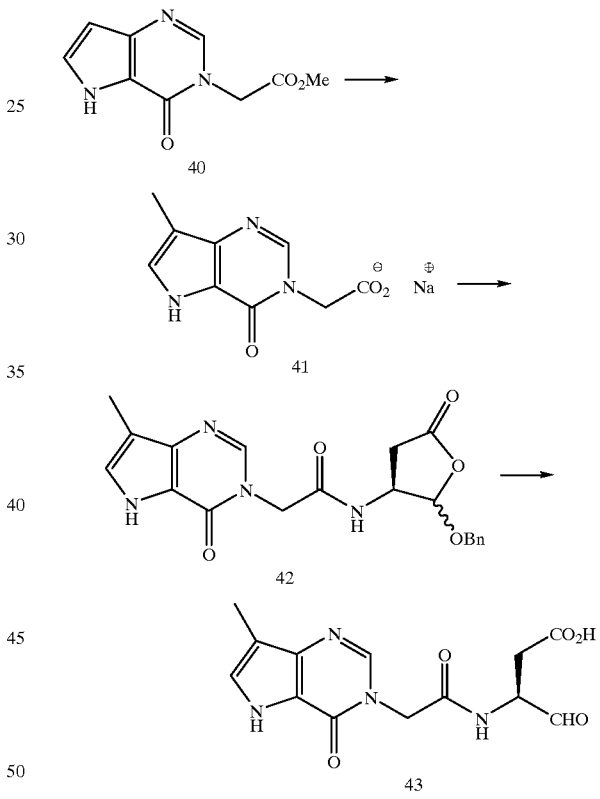

(2R,S, 3S) 1-(Indole-2-carbonyl)-N-(tetrahydro-2-benzyloxy-5-oxo-3-furanyl)-L-prolinamide (38). Trifluoroacetic acid (4 ml) was added to a solution of (2R,S, 3S) 1-tert-butoxycarbonyl-N-(tetrahydro-2-benzyloxy-5-oxo-3-furanyl)-L-prolinamide (15) (0.607 g, 1.5 mmol) in dichloromethane (4 ml) at 0° C. The mixture was stirred at 0° C. for 75 min. The mixture was concentrated, and the residue treated with diethyl ether, then the ether was removed under vacuum. This procedure was repeated twice to yield a yellow oil, which was dissolved in DMF (12 ml). Diisopropyl-ethylamine (0.78 ml, 4.5 mmol) followed by indole-2-carboxylic acid (266 mg, 1.65 mmol), 1-(3-dimethylaminopropyl)-3-ethyl carbodiimide hydrochloride (316 mg, 1.65 mmol) and hydroxybenzotriazole (405 mg, 3 mmol) were then added to the solution. The mixture was stirred at room temperature for 20 h then poured into brine. The mixture was extracted with ethyl acetate (3×30 ml). The combined organic extracts were washed with saturated aqueous sodium bicarbonate (2×60 ml) then brine (2×60 ml), dried (MgSO$_4$), filtered and concentrated. The residue was Methyl 2-(3,5-dihydro-7-methyl-4-oxo-4H-pyrrolo [3,2-d] pyrimidin-3-yl)acetate (40). Freshly prepared methyl glycinate (1.25 g, 14 mmol) was added to a stirred solution of ethyl 3-[N-(dimethylamino) methylene]amino-4-methylpyrrole-2-carboxylate (1.56 g, 7.0 mmol; Lim et al., J. Org. Chem., 44, pp. 3826–29 (1979)) in dry methanol (60 ml). The resulting mixture was kept at 70° C. Two further batches of methyl glycinate (1.25, 14.0 mmol) were added after 18 h and 42 h heating. The mixture was cooled and filtered 24 h after the final addition. The filtrate was concentrated and the residue purified by flash chromatography (2–5% methanol/chloroform) to afford 0.54 g (35%) of a white crystalline solid: mp. 233–235° C. (recrystallized from ethyl acetate); IR (KBr) 3135, 2958, 1745, 1675, 1254; $^1$H NMR (d$_6$-DMSO) δ 11.90 (1H, s), 8.07 (1H, s), 7.23 (1H, s), 4.83 (2H, s), 3.69 (3H, s), 2.16 (3H, s). Anal. Calcd for C$_{10}$H$_{11}$N$_3$O$_3$ 0.1H$_2$O: C, 53.85; H, 5.07; N, 18.84. Found: C, 53.85; H, 4.96; N, 18.81; MS(70eVE.I.) m/e 222, 221 (M$^+$, 100%), 189, 162, 133, 105.

2-(3,5-Dihydro-7-methyl-4-oxo-4H-pyrrolo[3,2-d] pyrimidin-3-yl)acetic acid, sodium salt (41). A suspension of 40 (354 mg, 1.6 mmol) in methanol (15 ml) was treated with 0.5N sodium hydroxide (4.8 ml) and the resulting mixture was stirred at 25° C. for 1 h. The reaction mixture was filtered to afford the hemihydrate of 41 (354 mg, 97%) as a white crystalline solid: mp.>340° C. (recrystallized from methanol); IR (KBr) 3461, 3143, 1676, 1666, 1605, 1415; $^1$H NMR(d$_6$ DMSO) δ 11.63 (1H, s), 7.83 (1H, s), 7.11 (1H, d, J=2.0), 4.24 (2H, s), 2.14 (3H, s). Anal. Calcd for C$_9$H$_8$N$_3$O$_3$Na. 0.5H$_2$O: C, 45.39; H, 3.81; N, 17.64. Found: C, 45.57; H, 4.05; N, 17.39.

(2R,S, 3S) 2-(3,5-Dihydro-7-methyl-4-oxo-4H-pyrrolo[3,2-d]pyrimidin-3-yl)-N-(tetrahydro-2-benzyloxy-5-oxo-3-furanyl)acetamide (42). A suspension of the sodium salt 41 (344 mg, 1.5 mmol) in dry DMF (15 ml) was treated with ethyl dimethylaminopropyl carbodiimide hydrochloride (373 mg, 1.95 mmol) and 1-hydroxybenzo-triazole (405 mg, 3.0 mmol). The mixture was kept at 25° C. for 1 h then (2R,S, 3S) N-allyloxycarbonyl-3-amino-2-benzyloxy-5-oxotetrahydrofuran (437 mg, 1.5 mmol; Chapman, *Biorg. Med. Chem. Lett.*, 2, pp. 613–18 (1992)) and (Ph$_3$P)$_2$PdCl$_2$ (25 mg) were added followed by the dropwise addition of n-tributyltin hydride (0.6 ml, 2.25 mmol). The resulting mixture was stirred at 25° C. for 1 h then water (20 ml) was added. The mixture was extracted with ethyl acetate (3×15 ml), and the combined organic extracts were washed with water (5 ml), dried (MgSO$_4$), and concentrated to afford a mixture of diastereomers. Evaporation of the aqueous phase and purification of the residue by flash chromatography (5% methanol/chloroform) gave an additional quantity affording a total 182 mg of 42 (31%): m.p. 240–244° C.; IR (KBr) 3274, 1772, 1691, 1664, 1562; $^1$H NMR (d$_6$-DMSO) δ 11.81 (1H, s), 8.85 (0.6H, d, J=6.6), 8.72 (0.4H, d, J=7.4), 7.98 (0.6H, s), 7.95 (0.4H, s), 7.40–7.30 (5H, m), 7.20 (1H, d, J=2.2), 5.61 (0.4H, d, J=5.0), 5.46 (s), 4.85–4.60 (m), 4.28 (m), 3.20–2.35 (2H, m), 2.16 (3H, s).

(3S)-3-[2-(3,5-Dihydro-7-methyl-4-oxo-4H-pyrrolo[3,2-d] pyrimidin-3-yl)-1-oxo-ethylamino]-4-oxobutanoic acid (43). A mixture of 42 (131 mg, 0.33 mmol), in methanol (50 ml) and 10% palladium on carbon (100 mg) was stirred vigorously under an atmosphere of hydrogen for 2 h. An additional quantity of catalyst (100 mg) was added and the mixture hydrogenated for a further 2 h. The mixture was filtered through a 0.2 µM nylon membrane, and concentrated. The residue was recrystallized from methanol/diethyl ether to afford 79 mg (78%) of 43 as a hygroscopic white solid: mp. 222–226° C.; (decomp.); [α]$_D^{32}$+0.5 (c 0.02, MeOH); IR (KBr) 3282, 1680, 1558, 1425 1275; $^1$H NMR (CD$_3$OD) δ 8.03 (1H, s), 7.18 (1H, d, J=0.7), 4.79–4.74 (2H, m), 4.63–4.59 (1H, 2×d, J=3.6), 4.36–4.25 (1H, m), 2.78–2.39 (2H, m), 2.24 (3H, d, J=0.7). Anal. Calcd for C$_{13}$H$_{14}$N$_4$O$_5$. 1.4H$_2$O: C, 47.10; H, 5.12; N, 16.90. Found: C, 47.00; H, 4.79; N, 16.59. FABMS m/e 307, 306 (M$^+$), 244, 207, 190, 152, 115 (100%)

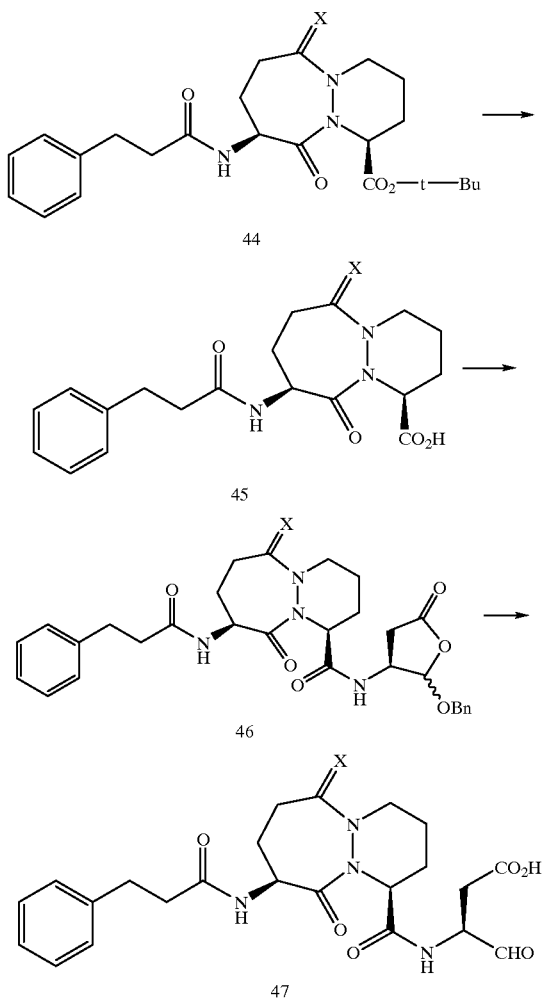

(a) X = O
(b) X = H$_2$ (1S,9S) t-Butyl 6,10-dioxo-octahydro-9-(3-phenylpropionylamino)-6H-pyridazino [1,2-a] [1,2] diazepine-1-carboxylate (44a). To a solution of (1S,9S)t-butyl 9-amino-6,10-dioxo-octahydro-6H-pyridazino [1,2-a] [1,2]diazepine-1-carboxylate (690 mg; 2.32 mmol; GB 2128984) in dioxane (16 ml) and water (4 ml) at 0° C. was added solid sodium bicarbonate (292 mg; 3.48 mmol) followed by dropwise addition of 3-phenylpropionyl chloride (470 mg; 2.78 mmol). The mixture was stirred at room temperature for 2 h then more sodium bicarbonate (200 mg; 2.38 mmol) and 3-phenylpropionyl chloride (100 mg; 0.6 mmol) was added. The mixture was stirred for a further 2 h at room temperature, diluted with ethyl acetate (50 ml), washed with saturated sodium bicarbonate (2×25 ml) then dried (MgSO$_4$) and concentrated. The residue was purified by flash chromatography (0–50% ethyl acetate/chloroform) and finally crystallized by trituration with ether to afford 860 mg (86%) of a white solid: mp. 137–138° C.; [α]$_D^{23}$–95.1° (c 0.549, CH$_2$Cl$_2$); IR (KBr) 3327, 1736, 1677, 1664, 1536, 1422, 1156; $^1$H NMR (CDCl$_3$) δ 7.24 (5H, m), 6.50 (1H, d, J=7.5), 5.24 (1H, m), 4.90 (1H, m), 4.60 (1H, m), 3.44 (IR, m), 2.93 (2H, m), 2.84 (1H, m), 2.64 (1H, m), 2.54 (2H, m), 2.26 (2H, m), 1.70 (4H, m), 1.70 (9H, s). MS(FAB, m/z): 430 (M$^+$+1), 374, 242, 105, 91.

(1S,9S)t-Butyl octahydro-10-oxo-9-(3-phenylpropionylamino)-6H-pyridazino-[1,2-a] [1,2]

diazepine-1-carboxylate (44b), was prepared from (1S, 9S)-t-butyl 9-amino-octahydro-10-oxo-6H-pyridazino[1,2-a][1,2]diazepine-1-carboxylate (Attwood et al., *J. Chem. Soc. Perkin* 1, pp. 1011–19 (1986)) as for 44a, to afford 810 mg (81%) of a colorless oil: $[\alpha]_D^{23}$–33.5° (c 0.545, $CH_2Cl_2$); IR (film) 3334, 2935, 1737, 1728, 1659, 1642; $^1$H NMR ($CDCl_3$) δ 7.24 (5H, m), 6.75 (1H, d, J=6.7), 5.27 (1H, m), 4.92 (1H, m), 3.39 (1H, m), 3.03 (4H, m), 2.55 (3H, m), 2.33 (1H, m), 2.17 (1H, m), 1.80 (5H, m), 1.47 (9H, s), 1.39 (1H, m). MS(FAB, m/z): 416 ($M^+$+1), 360, 211, 143, 97.

(1S,9S) 6,10-Dioxo-octahydro-9-(3-phenylpropionylamino)-6H-pyridazino[1,2-a] [1,2]diazepine-1-carboxylic acid (45a). To a solution of (1S,9S) t-butyl 6,10-dioxo-octahydro-9-(3-phenylpropionylamino)-6H-pyridazino[1,2-a] [1,2]diazepine-1-carboxylate (44a) (800 mg; 1.863 mmol) in dry dichloromethane (5 ml) at 0° C. was added trifluoroacetic acid (5 ml). The solution was stirred at room temperature for 3 h then concentrated. Dry ether (10 ml) was added to the residue then removed under vacuum. This process was repeated three times to afford a crystalline solid. The solid was triturated with ether and filtered to afford 590 mg (85%) of a white crystalline solid: mp. 196–197.5° C.; $[\alpha]_D^{23}$–129.5° (c 0.2, $CH_3OH$); IR (KBr) 3237, 1729, 1688, 1660, 1633, 1574, 1432, 1285, 1205; $^1$H NMR ($CD_3OD$) δ 8.28 (1H, d, J=7.4), 7.22 (5H, m), 5.32 (1H, dd, J=5.9, 2.9), 4.75 (1H, m), 4.51 (1H, m), 3.50 (1H, m), 3.01 (1H, m), 2.91 (2H, m), 2.55 (2H, m), 2.29 (3H, m), 1.95 (2H, m), 1.71 (2H, m). Anal. Calcd for $C_{19}H_{23}N_3O_5$: C, 61.12; H, 6.21; N, 11.25. Found: C, 60.80; H, 6.28; N, 10.97. MS(FAB, m/z) 374 ($M^+$+1), 242, 105, 91.

(1S, 9S) Octahydro-10-oxo-9-(3-phenylpropionylamino)-6H-pyridazino[1,2-a]-[1,2]diazepine-1-carboxylic acid (45b), was prepared from (1S, 9S) t-butyl octahydro-10-oxo-9-(3-phenylpropionylamino)-6H-pyridazino[1,2-a][1,2]diazepine-1-carboxylate (44b) by the method described for compound 45a to afford 657 mg (96%) of 45b as a crystalline solid: mp. 198–202° C.; $[\alpha]_D^{23}$–86.2° (c 0.5, $CH_3OH$); IR (KBr) 3294, 2939, 1729, 1645, 1620, 1574, 1453, 1214; $^1$H NMR ($CD_3OD$) δ 7.92 (1H, d, J=7.9), 7.20 (5H, m), 5.29 (1H, m), 4.90 (1H, m), 3.47 (1H, m), 3.08 (2H, m), 2.90 (2H, m), 2.55 (3H, m), 2.36 (1H, m), 1.81 (5H, m), 1.43 (2H, m). MS(FAB, m/z) 360 ($M^+$+1), 211,143,91.

[3S, 2R,S, (1S, 9S)]N-(2-Benzyloxy-5-oxotetrahydrofuran-3-yl)-6,10-dioxo-octahydro-9-(3-phenylpropionylamino)-6H-pyridazino[1,2-a][1,2]diazepine-1-carboxamide (46a). To a solution of (1S, 9S) 6,10-dioxo-octahydro-9-(3-phenyl-propionylamino)-6H-pyridazino[1,2-a] [1,2]diazepine-1-carboxylic acid (45a) (662 mg; 1.773 mmol) in dry dichloromethane (9 ml) and dry dimethyl formamide (3 ml) at room temperature was added bis(triphenylphosphine) palladium chloride (30 mg) and (3S, 2R,S)-3-allyloxycarbonylamino-2-benzyloxy-5-oxotetrahydrofuran (Chapman, *Biorg. Med. Chem. Lett.*, 2, pp. 613–18 (1992)) (568 mg; 1.95 mmol) followed by dropwise addition of tri-n-butyltin hydride (1.19 g; 4.09 mmol). 1-Hydroxybenzotriazole (479 mg; 3.546 mmol) was added to the mixture and the mixture was cooled to 0° C. before addition of 1-(3-dimethylaminopropyl)-3-ethylcarbodiimide hydrochloride (408 mg; 2.128 mmol). The mixture was stirred at room temperature for 3.25 h then diluted with ethyl acetate (50 ml), washed twice with dilute hydrochloric acid (20 ml), twice with saturated sodium bicarbonate (20 ml), once with brine then dried ($MgSO_4$) and concentrated. The resulting oil was purified by flash chromatography (0–100% ethyl acetate/chloroform) to afford 810 mg (81%) of 46a as a mixture of anomers: mp. 92–94° C.; IR (KBr) 3311, 1791, 1659, 1651, 1536; $^1$H NMR($CDCl_3$) δ 7.49, 6.56 (1H, 2d, J=6.7, 7.8), 7.29 (10H, m), 6.37, 6.18 (1H, 2d, J=7.7,7.6), 5.56, 5.34 (1H, d, s, J=5.2), 5.08–4.47 (6H), 3.18–2.80 (5H), 2.62–2.28 (5H), 2.04–1.53 (5H). MS(FAB, m/z), 563 ($M^+$+ 1), 328, 149, 91.

[3S, 2R,S, (1S, 9S)] N-(2-Benzyloxy-5-oxotetrahydrofuran-3-yl)-octahydro-10-oxo-9-(3-phenylpropionylamino)-6H-pyridazinot[,2-a] [1,2]diazapine-1-carboxamide (46b), was prepared from 45b by the method described for 46a to yield 790 mg (96%) of a glass: m.p. 58–60° C.; IR (KBr) 3316, 2940, 1793, 1678, 1641, 1523, 1453, 1120; $^1$H NMR ($CDCl_3$) δ 7.28 (10H, m), 6.52, 6.42 (1H, 2d, J=7.2, 7.1), 5.53, 5.44 (1H, d, s, J=5.2), 5.35 (1H, m), 4.6–4.9, 4.34 (4H, m), 3.1–2.8 (6H, m), 2.6–2.1 (7H), 1.95–1.05 (5H). MS(FAB, m/z), 549 ($M^+$+1), 400, 310, 279, 91.

[3S, (1S, 9S)] 3-(6,10-Dioxo-octahydro-9-(3-phenylpropionylamino)-6H-pyridazino[1,2-a] [1,2]diazepine-1-carboxamido)-4-oxobutanoic acid (47a). A mixture of [3S, 2R,S, (1S, 9S)] N-(2-benzyloxy-5-oxotetrahydrofuran-3-yl)-6,10-dioxo-octahydro-9-(3-phenylpropionylamino)-6H-pyridazino[1,2-a] [1,2]diazepine-1-carboxamide (46a) (205 mg; 0.364 mmol), 10% palladium on carbon (200 mg) and methanol (20 ml) was stirred under hydrogen at atmospheric pressure for 5 h. The mixture was filtered then concentrated to yield 154 mg (90%) of a glass: mp. 116–118° C.; $[\alpha]_D^{23}$–140° (c 0.1, $CH_3OH$); IR (KBr) 3323 (br), 1783, 1731, 1658, 1539, 1455, 1425; $^1$H NMR ($CD_3OD$) δ 7.21 (5H, m), 5.17 (1H, m), 4.73 (1H, m), 4.50 (2H, m), 4.23 (1H, m), 3.38 (1H, m), 3.06 (1H, m), 2.91 (2H, m), 2.73–2.18 (6H, m) and 2.01–1.59 (5H, m). Anal. Calcd for $C_{23}H_{27}N_4O_7$ +$H_2O$: C, 56.32; H, 6.16; N, 11.42. Found: C, 56.29; H, 6.11; N, 11.25. MS(FAB, m/z) 473 ($M^+$+1), 176, 149, 105, 91.

[3S, (1S,9S)]3-(Octahydro-10-oxo-9-(3-phenylpropionylamino)-6H-pyridazino-[1,2-a] [1,2]diazepine-1-carboxamido)-4-oxobutanoic acid (47b), was prepared from 46b by the method described for 47a. The residue was purified by flash chromatography (0–10% methanol/chloroform) to afford 65 mg (52%) of a glass; m.p. 87–90° C.; $[\alpha]_D^{23}$–167.0° (c 0.1, methanol); IR (KBr) 3329, 2936, 1786, 1727, 1637; $^1$H NMR ($CD_3OD$) δ 7.23 (5H, m), 5.29 (1H, m), 4.83 (1H, m), 4.59 (1H, d, J=3.6), 4.29 (1H, m), 3.3–3.0 (3H, m), 2.91 (2H, m), 2.70–2.34 (5H, m), 2.19 (2H, m), 1.75 (4H, m), 1.36 (2H, m). Anal. Calcd for $C_{23}H_{30}N_4O_6$ +$0.5H_2O$: C, 59.09; H, 6.68; N, 11.98. Found: C, 58.97; H, 6.68; N, 11.73. MS(FAB, m/z) 459 ($M^+$+1), 310, 149, 105, 91.

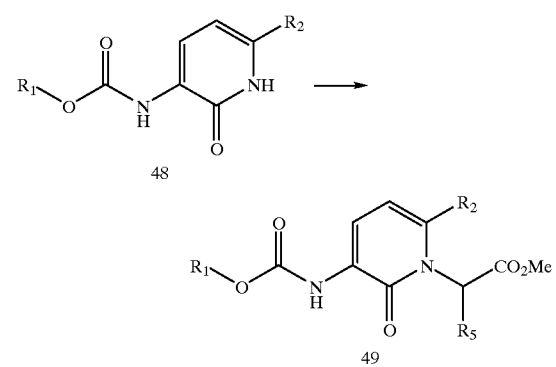

|     | R₁        | R₂       | R₃     |
| --- | --------- | -------- | ------ |
| (a) | PhCH₂     | H        | (S)Me  |
| (b) | PhCH₂     | CH₂Ph    | H      |
| (c) | PhCH₂     | (CH₂)₂Ph | H      |
| (d) | PhCH₂     | nBu      | H      |
| (e) | PhCH₂     | Me       | H      |
| (f) | PhCH₂     | Ph       | H      |
| (g) | PhCH₂     | H        | H      |
| (h) | PhCH₂     | CH₂Ph    | (S)-Me |
| (i) | Ph(CH₂)₂  | CH₂Ph    | H      |

Pyridones 48 were prepared by the method described by Damewood et al., *J. Med. Chem.*, 37, pp. 3303–12 (1994)). Compound 48d is new.

3-Benzyloxycarbonylamino-6-butyl-pyrid-2-one (48d), was isolated as a cream solid: mp. 158–160° C.; IR (KBr) 3382, 2953, 2930, 2866, 1729, 1643, 1524, 1468, 1202, 1044; $^1$H NMR (d₆-DMSO) δ 8.26 (1H, s), 7.72 (1H, d), 7.39 (5H, m), 6.00 (1H, d), 5.14 (2H, s), 2.41 (2H, t), 1.52 (2H, m), 1.24 (2H, m), 0.87 (3H, t). Anal. Calcd for $C_{17}H_{20}N_2O_3$: C, 67.98; H, 6.71; N, 9.33. Found: C, 67.69; H, 6.68; N, 9.20. MS CI M⁺=300 (m)) 28%.

(2S) Methyl 2-[3-benzyoxycarbonylamino-1,2-dihydro-2-oxo-1-pyridyl]propionate (49a). Sodium hydride (80% oil dispersion) (0.35 g, 11.64 mmole) was added to a stirred mixture of 3-(benzyloxycarbonylamino)pyrid-2-one (48a) (2.58 g, 10.58 mmol) and tetrahydrofuran (100 ml) at room temperature. The mixture was stirred for 10 mins. The resulting solution was added to a solution of 2(R) methyl-2((trifluoromethane) sulphonyloxy)propionate (2.5 g, 10.58 mmole; Feenstra et al., *Tetrahedron Lett.*, 28, pp. 1215–18 (1987)) in tetrahydrofuran (5 ml) at room temperature during 10 mins. The mixture was stirred at room temperature for 80 mins then poured into ethyl acetate. The mixture was washed twice with 1M HCl, twice with aqueous sodium bicarbonate then brine. It was dried (MgSO₄) and concentrated. The residue was purified by flash chromatography (30% ethyl acetate/hexane) to afford 2.945 g (84%) of a colorless solid: mp. 96–7°; $[\alpha]_D^{20}$ –71.36 (c 2.5, CHCl₂); IR (KBr) 3370, 1764, 1729, 1648, 1602, 1564, 1523, 1515, 1503, 1449, 1359, 1203, 1064; $^1$H NMR(CDCl₃) δ 8.04 (1H, d, J=7.2), 7.86 (1H, s), 7.36 (5H, m), 6.98 (1H, dd, J=7.1, J=1.7), 6.30 (1H, t, J=7.2), 5.46 (1H, q, J=7.4), 5.20 (2H, s), 3.74 (3H, s), 1.66 (3H, d, J=7.4). Anal. Calcd for $C_{17}H_{18}N_2O_5$: C, 61.81; H, 5.49; N, 8.48. Found: C, 61.49; H, 5.51; N, 8.41. MS(FAB, m/z) 331 (M⁺+1), 299, 223, 196, 163, 91.

Methyl [6-benzyl-3-benzyloxycarbonylamino-1,2-dihydro-2-oxo-1-pyridyl]-acetate (49b). Sodium hydride (80% oil dispersion) (0.65 g, 26.2 mmole) was added to a stirred mixture of 6-benzyl-3(benzyloxycarbonylamino) pyrid-2-one (48b) (7.3 g, 2.18 mmol) and tetrahydrofuran (150 ml) at room temperature. The mixture was stirred for 10 mins, treated with methyl bromoacetate (2.5 ml, 26.2 mmol) and kept for 3 h. The resulting mixture was poured onto a mixture of ice and 1M HCl. The resulting solid was filtered off then dissolved in dichloromethane. The resulting solution was dried (MgSO₄), decolourised with charcoal and concentrated. The residue was purified by chromatography (2–5% ethyl acetate/dichloromethane) to afford 7.2 g (81%) of colorless crystals: mp. 117–9°; IR (KBr) 3375, 1753, 1730, 1651, 1605, 1513, 1384, 1223, 1185, 1071; $^1$H NMR (CDCl₃) δ 8.02 (1H, d, J=7.5), 7.78 (1H, s), 7.31 (8H, m), 7.10 (2H, m), 6.15 (1H, d, J=7.5), 5.20 (2H, s), 4.70 (2H, s), 3.88 (2H, s), 3.66 (3H, s).

The following compounds were prepared in a similar manner:

Mothyl [3-benzyloxycarbonylamino-1,2-dihydro-2-oxo-6-phonothyl-1-pyridyl]-acetate (49c). 97% yield: m.p. 102–4° C. IR (KBr) 3245, 3232, 1741, 1725, 1648, 1600, 1526, 1216; $^1$H NMR (d₆-DMSO) δ 8.45 (1H, s), 7.76 (1H, d, J=7.6), 7.35 (10H, m), 6.15 (1H, d, J=7.6), 5.15 (2H, s), 4.85 (2H, s), 3.68 (3H, s), 2.86 (4H, s).

Methyl [3-benzyloxycarbonylamino-6-butyl-1,2-dihydro-2-oxo-1-pyridyl]-acetate (49d). 90% yield: mp. 111–112° C.; IR (KBr) 3393, 1738, 1731, 1645, 1598, 1517, 1225, 1208; $^1$H NMR (d₆-DMSO) δ 8.39 (1H, s), 7.78 (1H, d, J=7.7), 7.35 (5H, m), 6.17 (1H, d, J=7.7), 5.15 (2H, s), 4.80 (2H, s), 3.67 (3H, s), 1.38 (6H, m), 0.89 (3H, t).

Methyl [3-benzyloxycarbonylamino-1,2-dihydro-6-methyl-2-oxo-1-pyridyl]-acetate (49e). 84% yield as a colorless solid: mp. 115–6° C.; IR (KBr) 3246, 1740, 1725, 1649, 1598, 1573, 1535, 1417, 1365, 1259, 1219, 1193, 1090, 1068, 1006; $^1$H NMR (d₆-DMSO) δ 8.40 (1H, s), 7.75 (1H, d, J=7.6), 7.38 (5H, m), 6.20 (1H, d, J=7.6), 5.15 (2H, s), 4.85 (2H, s), 3.68 (3H, s), 2.26 (3H, s).

Methyl [3-benzyloxycarbonylamino-1,2-dihydro-6-phenyl-1-pyridyl]-acetate (49f). 67% yield as a colorless oil: IR (KBr) 3266, 1739, 1727, 1646, 1606, 1566, 1517, 1490, 1365, 1213, 1163, 1075; $^1$H NMR (CDCl₃) δ 8.15 (1H, d), 7.85 (1H, s), 7.39 (10H, m), 6.22 (1H, d), 5.22 (2H, s), 4.57 (2H, s), 3.74 (3H, s).

Methyl [3-benzyloxycarbonylamino-1,2-dihydro-2-oxo-1-pyridyl]-acetate (49 g). 80% yield as a colorless crystalline solid: m.p. 110–111° C. IR (KBr) 3385, 1745, 1726, 1650, 1601, 1512, 1502, 1378, 1369, 1358, 1215, 1195, 1162, 1067; $^1$H NMR (CDCl₃) δ 8.06 (1H, d), 7.84 (1H, s), 7.36 (5H, m), 6.88 (1H, dd), 6.27 (1H, t), 5.20 (2H, s), 4.68 (2H, s), 3.78 (3H, s). Anal. Calcd for $C_{16}H_{16}N_2O_5$: C, 60.75; H, 5.10; N, 8.85. Found: C, 60.65; H, 5.15; N, 8.85. MS FAB (+)M+=317 (M+1).

2(S) Methyl 2-methyl-[6-benzyl-(3-benzyloxycarbonylamino)-1,2-dihydro-2-oxo-1-pyridyl]-acetate (49 h), was prepared by the method used in the preparation of compound 49a to afford (58%) an oil; $[\alpha]_D^{25}$ –25.0° (c 1, CH₂Cl₂); IR (KBr) 3381, 1736, 1650, 1604, 1513, 1218, 1190, 1068; $^1$H NMR (CDCl₃) δ 7.97 (1H, d), 7.78 (1H, s), 7.4–7.14 (10H, m), 6.17 (1H, d), 5.19 (2H, s), 4.64 (1H, q), 3.98 (2H, s), 3.62 (3H, s), 1.31 (3H, d).

Methyl [6-benzyl-1,2-dihydro-2-oxo-3-(2-phenylethoxy)-carbonylamino-1-pyridyl]acetate (49i), was isolated (88%) as a colorless solid: mp. 130–133° C.; IR (KBr) 3363, 1746, 1732, 1651, 1604, 1515, 1368, 1231, 1212, 1185; $^1$H NMR (CDCl₃) δ 8.00 (1H, d, J=7.0), 7.68 (1H, s), 7.36–7.10 (10H, m), 6.15 (1H, d, J=7.6), 4.7 (2H, s), 4.38 (2H, t, J=7.0), 3.88 (2H, s), 3.67 (3H, s), 2.98 (2H, t, J=7).

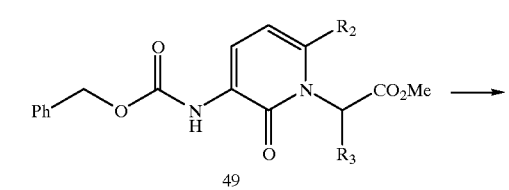

49

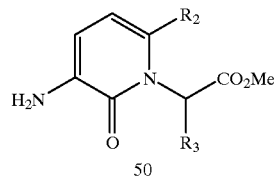

50

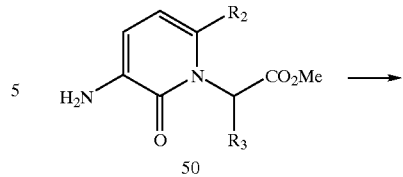

50

2(S) Methyl 2[3-amino-1,2-dihydro-2-oxo-1-pyridyl] propionate (50a). A mixture of 2(S) methyl-2[3-benzyloxycarbonylamino-1,2-dihydro-2-oxo-1-pyridyl) propionate (49a) (2.75 g, 8.33 mmol), methanol (100 ml), and 10% palladium on carbon (300 mg) was stirred under an atmosphere of hydrogen for 30 min. The mixture was filtered and concentrated to afford 1.63 g (100%) of a colorless solid: $^1$H NMR ($d_6$-DMSO) δ 8.35 (1H, brs), 7.46 (1H, d), 7.22 (1H,d), 6.29 (1H, t), 5.22 (1H, q), 3.63 (3H, s), 1.55 (3H, d).

The following compounds were prepared in a similar manner:

Methyl [3-amino-6-benzyl-1,2-dihydro-2-oxo-1-pyridyl] acetate (50b). 100% yield as a grey solid: mp. 134–6° C.; IR (KBr) 3418, 3312, 1723, 1658, 1596, 1548, 1435, 1290, 1245, 1011; $^1$H NMR ($d_6$-DMSO) δ 7.25 (5H, m), 6.45 (1H, d, J=7.4), 5.92 (1H, d, J=7.4), 5.00 (2H, s), 4.63 (2H, s), 3.88 (2H, s), 3.51 (3H, s).

Methyl[3-amino-1,2-dihydro-2-oxo-6-phenethyl-1-pyridyl] acetate (50c). 99% yield as a viscous oil: IR (KBr) 3456, 341, 2953, 1745, 1649, 1600, 1548, 1219; $^1$H NMR (CDCl$_3$) δ 7.25 (5H, m), 6.51 (1H, d, J=7.4), 5.92 (1H, d, J=7.4), 4.79 (2H, s), 3.77 (3H, s), 2.80 (4H, m).

Methyl[3-amino-6-butyl-1,2-dihydro-2-oxo-1-pyridyl] acetate (50d). 97% as a brown solid: mp. 75–7° C.; IR (KBr) 3437, 3342, 2955, 1745, 1655, 1609, 1550, 1432, 1301, 1222, 1200; $^1$H NMR (CDCl$_3$) δ 6.53 (1H, d, J=6.8), 5.93 (1H, d, J=6.8), 4.81 (2H, s), 3.77 (3H, s), 2.44 (2H, t), 1.45 (4H, m), 0.93 (3H, t).

Methyl[3-amino-1,2-dihydro-6-methyl-2-oxo-1-pyridyl] acetate (50e), was isolated (100%) as a colorless crystalline solid: mp. 87–9° C.; IR (KBr) 3442, 3326, 1735, 1647, 1600, 1549, 1434, 1407, 1383, 1366, 1225, 1209; $^1$H NMR ($d_6$-DMSO) δ 6.40 (1H, d, J=7.3), 5.93 (1H, d, J=7.3), 4.86 (2H, s), 4.79 (2H, s), 3.67 (3H, s), 2.15 (3H, s).

Methyl[3-amino-1,2-dihydro-2-oxo-6-phenyl-1-pyridyl] acetate (50f), was isolated (86%) as a grey solid: mp. 207–9° C.; IR (KBr) 3473, 3345, 1750, 1644, 1600, 1536, 1443, 1366, 1309, 1212, 1184, 1156; $^1$H NMR ($d_6$-DMSO) δ 7.30 (5H, m), 6.54 (1H, d), 6.03 (1H, d), 5.25 (2H, s), 4.49 (2H, s), 3.61 (3H, s).

Methyl[3-amino-1,2-dihydro-2-oxo-1-pyridyl]acetate (50 g), was obtained as a colorless oil and used immediately in the next step.

2(S) Methyl 2-methyl-[3-amino-6-benzyl-1,2-dihydro-2-oxo-1-pyridyl]acetate (50h), was isolated (69%) as a colorless oil: IR (film) 3354, 1743, 1646, 1600, 1548, 1494, 1455, 1309, 1268, 1227, 113; $^1$H NMR ($C_6D_6$) δ 7.29–6.76 (5H, m), 5.86 (1H, d, J=7.2), 5.51 (1H, d, J=7.2), 4.43 (1H, q, J=6.7), 3.69 (2H, s), 3.41 (2H, s), 3.36 (3H, s), 1.43 (3H, d, J=6.7).

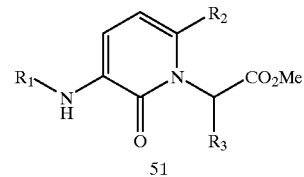

51

| | $R_1$ | $R_2$ | $R_3$ |
|---|---|---|---|
| (a) | Ph(CH$_2$)$_2$CO | H | (S)Me |
| (b) | Ph(CH$_2$)$_2$CO | CH$_2$Ph | H |
| (c) | Ph(CH$_2$)$_2$CO | (CH$_2$)$_2$Ph | H |
| (d) | Ph(CH$_2$)$_2$CO | nBu | H |
| (e) | Ph(CH$_2$)$_2$CO | Me | H |
| (f) | Ph(CH$_2$)$_2$CO | Ph | H |
| (g) | Ph(CH$_2$)$_2$CO | H | H |
| (h) | Ph(CH$_2$)$_2$CO | CH$_2$Ph | (S)-Me or (R, S)-Me |
| (i) | AcTyr | CH$_2$Ph | H |
| (j) | Ph(CH$_2$)$_2$SO$_2$ | CH$_2$Ph | H |
| (k) | Ph(CH$_2$)$_2$OCO | CH$_2$Ph | H |
| (l) | Ph(CH$_2$)$_3$CO | CH$_2$Ph | H |

2(S) Methyl 2-[1,2-dihydro-2-oxo-3-(3-phenylpropionyl) amino-1-pyridyl]-propionate (51a). 3-Phenylpropionyl chloride (1.5 g, 9 mmol) was added dropwise to a stirred mixture of 2S methyl-2-[3-amino-1,2-dihydro-2-oxo-1-pyridyl]propionate (50a) (1.63 g, 8.33 mmol), dioxane (60 ml), water (15 ml) and sodium bicarbonate (1.54 g, 16.7 mmol). The mixture was kept for 1 h then extracted with ethyl acetate. The extracts were washed with aqueous sodium bicarbonate, dried (MgSO$_4$) and concentrated. The resulting red oil was purified by flash chromatography to afford 2.54 g (93%) of an oil: $[\alpha]_D^{20}$ –68° C. (1, CH$_2$Cl$_2$); IR (CH$_2$Cl$_2$) 3369, 1747, 1690, 1650, 1602, 1512, 1267, 1260, 1217; $^1$H NMR (CDCl$_3$) δ 8.41 (1H, dd), 8.36 (1H, s), 7.24 (5H, m), 7.02 (1H, dd), 6.32 (1H, t), 5.44 (1H, q), 3.75 (3H, s), 3.03 (2H, t), 2.70 (2H, t), 1.66 (3H, d). FAB M+=329 (M+1), 197, 165, 131, 110, 91.

The following compounds were prepared in a similar manner:

Methyl [6-benzyl-1,2-dihydro-2-oxo-3-(3-phenylpropionyl) amino-1-pyridyl]-acetate (51b), was isolated (93%) as crystals: mp. 95–7° C.; IR (KBr) 3265, 1747, 1686, 1642, 1590, 1563, 1511, 1454, 1401, 1220, 1183, 1133; $^1$H NMR (CDCl$_3$) δ 8.39 (1H, d, J=7.7), 8.27 (1H, s), 7.21 (10H, m), 6.17 (1H, d, J=7.7), 4.70 (2H, s), 3.89 (2H, s), 3.67 (3H, s), 3.02 (2H, m), 2.70 (2H, m).

Methyl [1,2-dihydro-2-oxo-6-phenethyl-3-(3-phenylpropionyl)amino-1-pyridyl]-acetate (51c), was isolated (81%) as colorless crystals: mp. 105–8° C.; IR (KBr) 3378, 1746, 1680, 1646, 1597, 1517, 1221; $^1$H NMR (CDCl$_3$) δ 8.34 (1H, d, J=7.7), 8.25 (1H, s), 7.23 (10H, m), 6.11 (1H, d, J=7.7), 4.77 (2H, s), 3.78 (3H, s), 2.88 (8H, m).

Methyl [6-butyl-1,2-dihydro-2-oxo-3-(3-phenylpropionyl) amino-1-pyridyl]-acetate (51d), was isolated (88%) as colorless crystals: mp. 84–5° C.; IR (KBr) 3345, 2958, 2930, 1756, 1693, 1650, 1602, 1510, 1227, 1180, 1137; $^1$H NMR (CDCl$_3$) δ 8.34 (1H, d, J=7.7), 8.22 (1H, s), 7.26 (5H, m), 6.12 (1H, d, J=7.7), 4.80 (2H, s), 3.79 (3H, s), 3.03 (2H, t), 2.68 (2H, t), 2.50 (2H, t), 1.46 (4H, m), 0.95 (3H, t).

Methyl[1,2-dihydro-6-methyl-2-oxo-3-(3-phenylpropionyl) amino-1-pyridyl]-acetate (51e), was isolated (100%) as a pale yellow oil: IR (film) 3264, 1745, 1691, 1644, 1587, 1566, 1518, 1495, 1400, 1215, 1183, 1136; $^1$H NMR (CDCl$_3$) δ 8.33 (1H, d, J=7.6), 7.26 (5H, m), 6.13 (1H, d, J=7.6), 4.83 (2H, s), 3.79 (3H, s), 3.03 (2H, m), 2.69 (2H, m), 2.28 (3H, s).

Methyl[1,2-dihydro-2-oxo-6-phenyl-3-(3-phenylpropionyl) amino-1-pyridyl]-acetate (51f), was isolated (99%) as a pale yellow oil: IR (film) 3365, 3299, 1751, 1689, 1643, 1600, 1563, 1519, 1493, 1419, 1370, 1224; $^1$H NMR (CDCl$_3$) δ 8.46 (1H, d, J=7.7), 8.32 (1H, s), 7.32 (10H, m), 6.24 (2H, d, J=7.7), 4.57 (2H, s), 3.73 (3H, s), 3.06 (2H, m), 2.72 (2H, m).

Methyl [1,2-dihydro-2-oxo-3-(3-phenylpropionyl)amino-1-pyridyl]-acetate (51g), was isolated (81%) as an oil: IR (film) 3330, 1753, 1689, 1650, 1600, 1560, 1517, 1374, 1225, 1208; $^1$H NMR (CDCl$_3$) δ 8.43 (1H, dd, J=7.4, 1.7), 8.33 (1H, s), 7.28 (5H, m), 6.92 (1H, dd, J=6.9, 1.7), 6.29 (1H, t), 4.67 (2H, s), 3.79 (3H, s), 3.04 (2H, m), 2.70 (2H, m). MS FAB (+) M+=315 (M+1).

2(S) Methyl 2-methyl-[6-benzyl-1,2-dihydro-2-oxo-3-(3-phenylpropionyl)amino-1-pyridyl]-acetate (51h), was isolated (93%) as a colorless oil; [α]$_D^{30}$–19° (c 1, CH$_2$Cl$_2$); IR (film) 3354, 3313, 3028, 2950, 1745, 1687, 1645, 1600, 1567, 1514, 1454, 1225; $^1$H NMR (CDCl$_3$) δ 8.35 (1H, d, J=7.5), 8.26 (1H, s), 7.27 (10H, m), 6.20 (1H, d, J=7.5), 4.65 (1H, q, J=6.8), 3.99 (2H, s), 3.71 (3H, s), 3.03 (2H, m), 2.68 (2H, m), 1.31 (3H, d, J=6.8).

Methyl [3-(N-acetyl-O-benzyl-L-tyrosine)amino-6-benzyl-1,2-dihydro-2-oxo-pyridyl3acetate (51i). A stirred mixture of methyl [3-amino-6-benzyl-1,2-dihydro-2-oxo-1-pyridyl] acetate (100 mg, 0.367 mmol), Boc-Tyr(Bn)—OH (136 mg, 0.367 mmol), dimethylformamide (1 ml), diisopropylethylamine (0.25 ml, 1.468 mmol) and 2-(1H-benzotriazol-1-yl)-1,1,3,3-tetramethyluronium hexafluorophosphate (118 mg, 0.367 mmol) was kept overnight at room temperature. The mixture was diluted with ethyl acetate, washed twice with 1M hydrochloric acid, twice with aqueous sodium bicarbonate, once with brine, then dried (MgSO$_4$) and concentrated. The residue was purified by flash chromatography (10% ethyl acetate/dichloromethane) to afford a 162 mg (70%) of a is colorless oil. The oil (160 mg, 0.255 mmol) was dissolved in dichloromethane (1 ml) and treated with trifluoroacetic acid (1 ml) at 0° C. The resulting solution was allowed to reach room temperature during 40 min then evaporated to dryness at 30° C. The residue was dissolved in dichloromethane then evaporated to dryness again. This procedure was repeated three times. The residue was dissolved in pyridine (0.5 ml) and treated with acetic anhydride (0.03 ml, 0.3 mmol) at 0° C. The resulting mixture was allowed to reach room temperature and kept for 3.5 h. It was diluted with ethyl acetate, washed twice with 1M hydrochloric acid, twice with aqueous sodium bicarbonate, dried (MgSO$_4$) and concentrated to afford 128 mg (86%) of a colorless oil: IR (film) 3290, 1751, 1649, 1602, 1568, 1513, 1455, 1438, 1375, 1224, 1179; $^1$H NMR (CDCl$_3$) δ 8.78 (1H, s), 8.33 (1H, d, J=7.6), 7.33 (8H, m), 7.11 (4H, m), 6.86 (2H, d, J=8.5), 6.47 (1H, d, J=7.6), 6.12 (1H, d, J=7.6), 4.99 (2H, s), 4.85 (1H, m), 4.69 (2H, s), 3.87 (2H, s), 3.62 (3H, s), 3.08 (2H, m), 1.96 (3H, s).

Methyl[6-benzyl-1,2-dihydro-2-oxo-3-(2-phenylethanesulphonyl)amino-1-pyridyl]-acetate (51j). 2-Phenylethanesulphonyl chloride (Zhong et al., J. Am. Chem. Soc., 113, pp. 2259–63 (1991)) was added to a stirred mixture of methyl [3-amino-6-benzyl-2-oxo-1,2-dihydro-1-pyridyl]-acetate (49b) (1.0 g, 3.67 mmol), dichloromethane (15 ml) and triethylamine (1.0 ml, 7.34 mmol). The mixture was kept overnight then poured into ethyl acetate. The resulting mixture was washed twice with aqueous sodium bicarbonate, three times with 1M hydrochloric acid, then brine. It was dried (MgSO$_4$) and concentrated. The resulting pale brown solid was purified by flash chromatography (10% ethyl acetate/dichloromethane) to afford 1.25 g (77%) of a pale yellow solid: m.p. 92–4° C.; IR (KBr) 3181, 1737, 1646, 1595, 1565, 1454, 1241, 1220, 1150; $^1$H NMR (CDCl$_3$) δ 7.53 (1H, d, J=7.5), 7.29 (10H, m), 6.10 (1H, d, J=7.5), 4.75 (2H, s), 3.89 (2H, s), 3.67 (3H, s), 3.34 (2H, m), 3.14 (2H, m).

Methyl [6-benzyl-1,2-dihydro-2-oxo-3-(4-phenylbutyryl) amino-1-pyridyl]-acetate (51l), was isolated (74%) as colorless crystals: mp. 93–95° C.; IR (KBr) 3285, 1747, 1683, 1642, 1591, 1563, 1512, 1455, 1220, 1181; $^1$H NMR (CDCl$_3$) δ 8.39 (1H, d, J=7.6), 8.24 (1H, s), 7.2 (10H, m), 6.18 (1H, d, J=7.6), 4.7 (2H, s), 3.90 (2H, s), 3.67 (3H, s), 2.69 (2H, t), 2.40 (2H, t), 2.04 (2H, m).

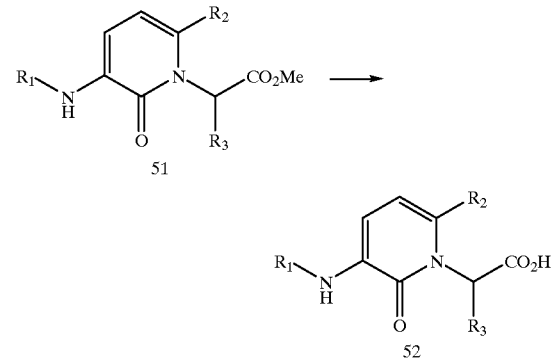

2(S) 2-[1,2-Dihydro-2-oxo-3-(3-phenylpropionyl)amino)-1-pyridyl]propionic acid (52a). 1M Sodium hydroxide (15 ml, 15 mmol) was added to a stirred solution of 2(5) methyl 2-(1,2-dihydro-2-oxo-3(3-phenylpropionyl)amino-1-pyridyl]propionate (51a) (2.39 g, 7.3 mmol) in methanol (30 ml) at 0° C. The mixture was kept at this temperature for 2 h, acidified with 1M hydrochloric acid (15.1 ml) and extracted with ethyl acetate. The extracts were washed with brine, dried (MgSO$_4$) and concentrated to afford 1.98 g (87%) of a colorless solid: [α]$_D^{20}$–75° (1, CH$_2$Cl$_2$); IR (KBr) 3301, 1724, 1693, 1637, 1563, 1523, 1453, 1233, 1216, 765; $^1$H NMR (CDCl$_3$) δ 8.47 (2H, m), 7.20 (5H, m), 7.03 (1H, d), 6.36 (1H, t), 5.35 (1H, q), 3.01 (2H, m), 2.70 (2H, m), 1.69 (3H, m).

The following compounds were prepared in a similar manner:

[6-Benzyl-1,2-dihydro-2-oxo-3-(3-phenylpropionyl)amino-1-pyridyl]acetic acid (52b), was isolated (100%) as a pale amber oil: IR (film) 3291, 1738, 1686, 1644, 1591, 1554, 1519, 1496, 1454, 1403, 1215, 1182; $^1$H NMR (CDCl$_3$) δ 8.44 (1H, d, J=7.8), 8.4 (1H, s), 7.21 (10H, m), 6.19 (1H, d, J=7.8), 4.71 (2H, s), 3.90 (2H, s), 2.99 (2H, m), 2.71 (2H, m).

[1,2-Dihydro-2-oxo-6-phenethyl-3-(3-phenylpropionyl) amino-1-pyridyl]acetic acid (52c), was isolated (94%) as a beige solid: mp. 214–6° C.; IR (KBr) 3289, 1740, 1680, 1640; $^1$H NMR (d$_6$-DMSO) δ 9.24 (1H, s), 8.14 (1H, d, J=7.7), 7.22 (10H, m), 6.11 (1H, d, J=7.8), 4.78 (2H, s), 2.81 (8H, m).

[6-Butyl-1,2-dihydro-2-oxo-3-(3-phenylpropionyl)amino-1-pyridyl]acetic acid (52d), was isolated (99%) as a pale brown solid: mp. 132–4° C.; IR (KBr) 3286, 1739, 1676, 1641, 1584, 1555, 1535, 1455, 1414, 1249, 1227, 1204; $^1$H NMR (CDCl$_3$) δ 8.42 (1H, d, J=7.8), 8.37 (1H, s), 7.24 (5H, m), 6.19 (1H, d, J=7.8), 4.82 (2H, s), 3.55 (1H, s), 3.00 (2H, t), 2.67 (2H, t), 2.53 (2H, t), 1.41 (4H, m), 0.94 (3H, t).

[1,2-Dihydro-6-methyl-2-oxo-3-(3-phenylpropionyl)amino-1-pyridyl]acetic acid (52e), was isolated as a solid (100%): mp. 159–61° C.; IR (KBr) 3335, 1731, 1686, 1642, 1536, 1516, 1430, 1420, 1401, 1222, 1195; $^1$H NMR (d$_6$-DMSO) δ 9.21 (1H, s), 8.13 (1H, d, J=7.6), 7.20 (5H, m), 6.15 (1H, d, J=7.6), 4.77 (2H, s), 2.87 (2H, m), 2.70 (2H, m), 2.25 (3H, s).

[1,2-Dihydro-2-oxo-6-phenyl-3-(3-phenylpropionyl)amino-1-pyridyl]acetic acid (52f), was isolated (100%) as a pale yellow foam: IR (KBr) 3271, 1747, 1683, 1634, 1580, 1536, 1490, 1406, 1392, 1365, 1235, 1219; $^1$H NMR (CDCl$_3$) δ 8.52 (1H, d, J=7.7), 7.31 (10H, m), 6.48 (2H, s), 6.30 (1H, d, J 7.7), 4.60 (2H, s), 3.03 (2H, m), 2.71 (2H, m).

[1,2-Dihydro-2-oxo-3-(3-phenylpropionyl)amino-1-pyridyl]acetic acid (52 g), was isolated (94%) as a colorless solid: mp. 195–7° C.; IR (KBr) 3324, 1724, 1693, 1644, 1569, 1555, 1512, 1427, 1370, 1240; $^1$H NMR (d$_6$-DMSO) δ 9.31 (1H, s), 8.23 (1H, d, J=6.8), 7.36 (1H, dd, J=6.8, 1.71), 7.25 (5H, m), 6.25 (1H, t), 4.66 (2H, s), 2.84 (4H, m).

2(R,S) 2-16-Benzyl-1,2-dihydro-2-oxo-3-(3-phenylpropionyl)amino-1-pyridyl]-propionic acid (52h), was prepared by hydrolysis of compound 51 h in aqueous tetrahydrofuran during 5 h at 40° C. to afford (95%) as a yellow oil: IR (film) 3330, 1734, 1686, 1643, 1600, 1587, 1553, 1524, 1498, 1208; $^1$H NMR (d$_6$-DMSO) δ 9.29 (1H, s), 8.18 (1H, d, J=7.6), 7.21 (10H, m), 6.22 (1H, d, J=7.6), 4.82 (1H, q, J=6.6), 4.08 (2H, m), 2.76 (4H, m), 1.05 (3H, d, J=6.6).

[3-(Acetyl-Tyr(Bn))amino-6-benzyl-1,2-dihydro-2-oxo-1-pyridyl]acetic acid (52i), was isolated (93%) as a foam: IR (KBr) 3302, 1731, 1646, 1603, 1562, 1512, 1454, 1428, 1379, 1231, 1178; $^1$H NMR (CDCl$_3$) δ 9.48 (1H, s), 8.36 (1H, d, J=7.6), 7.30 (8H, m), 7.10 (2H, m), 6.85 (2H, d, J=8.3), 6.91 (2H, d, J=8.3), 6.71 (1H, d, J 7.6), 4.95 (1H, m), 4.90 (2H, s), 4.68 (2H, s), 3.92 (2H, s), 3.17–2.83 (2H, m), 1.92 (3H, s).

[6-Benzyl-1,2-dihydro-2-oxo-3-(2-phenylethanesulphonyl)amino-1-pyridyl]acetic acid (52j), was isolated (100%) as a colorless solid: mp. 165–7° C.; IR (KBr) 3174, 1760, 1646, 1593, 1567, 1497, 1453, 1424, 1326, 1225, 1140, 1127; $^1$H NMR (d$_6$-DMSO) δ 13.09 (1H, s), 9.08 (1H, s), 7.30 (11H, m), 6.02 (1H, d), 4.68 (2H, s), 4.99 (2H, s), 3.29 (2H, m), 3.03 (2H, m).

[6-Benzyl-1,2-dihydro-2-oxo-3-(2-phenylethoxy)carbonylamino-1-pyridyl]acetic acid (52%), was prepared (70%) by hydrolysis of compound 49i during 1 h at 60° C.: IR (CH$_2$Cl$_2$) 1797, 1689, 1649, 1601, 1512, 734; $^1$H NMR (CDCl$_3$) δ 8.39 (1H, s), 8.03 (1H, d), 7.81 (1H, s), 7.33–7.07 (10H, m), 6.13 (1H, d, J=7.8), 4.72 (2H, s), 4.33 (2H, t, J=7.0), 3.86 (2H, s), 2.93 (2H, t, J=7.0).

[6-Benzyl-1,2-dihydro-2-oxo-3-(4-phenylbutyryl)amino-1-pyridyl]acetic acid (52l), was isolated (100%) as a white foam: m.p. 159–161° C.; IR (KBr) 3373–3310, 1787, 1726, 1691, 1649, 1599, 1567, 1517, 1367, 1215; $^1$H NMR (CDCl$_3$) δ 8.43 (1H, d, J=7.7), 8.25 (1H, s), 7.37–7.09 (10H, m), 6.21 (1H, d, J=7.7), 4.73 (2H, s), 4.15 (3H, s), 3.91 (2H, s), 2.67 (2H, t), 2.39 (2H, t), 2.02 (2H, m).

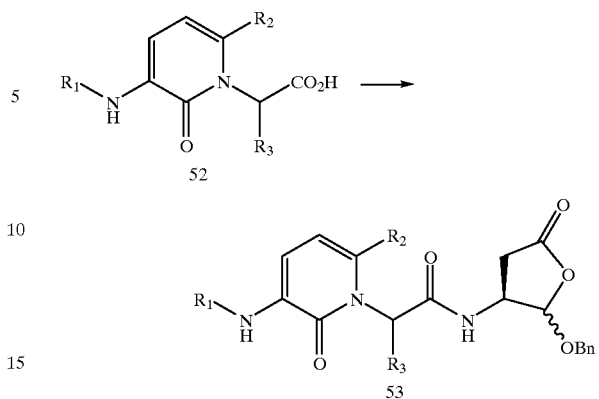

2(S), N-3(S) 2-[1,2-Dihydro-2-oxo-3-(3-phonylpropionyl)amino-1-pyridyl]-N-(2-benzyloxy-5-oxotetrahydrofuran-3-yl)propionamide (53a). Tri-n-butyltin hydride (1.7 ml, 6.3 mmol) was added dropwise to a stirred mixture of 2(S)-2-[1,2-dihydro-2-oxo-3(3-phenylpropionyl)amino-1-pyridyl] propionic acid (52a) (1.1 g, 3.49 mmol), 3(S), 2(R,S) 3-allyloxycarbonylamino-2-benzyloxy-5-oxotetrahydrofuran (1.02 g, 3.49 mmol; Chapman, Biorg. Med. Chem. Lett., 2, pp. 613–18 (1992)), bis (triphenylphosphine)palladium (II) chloride (55 mg), dichloromethane (35 ml) and dimethylformamide (1 ml). The resulting mixture was stirred for 5 min. then 1-hydroxybenzotriazole (946 mg, 7 mmol) was added. The mixture was cooled to 0° C. before the addition of 1-(3-dimethylaminopropyl)-2-ethylcarbodiimide hydrochloride (740 mg, 3.84 mmol). The mixture was kept overnight at room temperature then poured into ethyl acetate. The mixture was washed twice with 1M hydrochloric acid, twice with aqueous sodium bicarbonate, then brine. The mixture was dried (MgSO$_4$) and concentrated. The residue was triturated with pentane. The remaining solid was purified by flash chromatography (40–60% ethyl acetate/hexane) to afford 1.28 g (73%) of colorless solid: IR (KBr) 1796, 1692, 1647, 1595, 1557, 1512, 1119; $^1$H NMR (d$_6$-DMSO) δ 9.28, 9.26 (1H, 2×s), 8.77, 8.69 (1H, 2×d), 8.24, 8.20 (1H, 2×dd), 7.20 (11H, m), 6.31, 6.26 (1H, 2×t), 5.65 (0.5H, d), 5.46 (0.5H, d), 5.41, 5.28 (1H, 2×q), 4.7 (2.5H, m), 4.24 (0.5H, t), 3.24 (2H, m), 2.80 (4H, m), 1. 51, 1.46 (3H, 2×d).

The following compounds were prepared in a similar manner:

N(3(S)) 2[6-Benzyl-1,2-dihydro-2-oxo-3-(3-phenylpropionyl)amino-1-pyridyl]-N-(2-benzyloxy-5-oxotetrahydrofuran-3-yl)acetamide (53b), was obtained (86%) as a foam: IR (KBr) 3345, 3297, 1807, 1791, 1688, 1679, 1650, 1602, 1554, 1525, 1497, 1453, 1372, 1257, 1119; $^1$H NMR (d$_6$-DMSO) δ 9.25 (0.5H, s), 9.23 (0.5H, s), 8.75 (0.5H, d, J=6.5), 8.67 (0.5H, d, J=7.4), 8.18 (1H, 2d), 7.21 (15H, m), 6.07 (1H, 2d), 5.65 (0.5H, d, J=5.0), 5.38 (0.5H, s), 4.83–4.45 (4.5H, m), 4.19 (0.5H, m), 3.94, 3.83 (2H, m), 3.10–2.31 (6H, m).

N(3(S)) 2[1,2-Dihydro-2-oxo-6-phenethyl-3-(3-phenylpropionyl)amino-1-pyridyl]-N-(2-benzyloxy-5-oxotetrahydrofuran-4-yl)acetamide (53c), was obtained (74%) as a mixture of anomers: $^1$H NMR (d$_6$-DMSO) δ 9.71 (1H, d), 9.41 (0.5H, d), 9.25 (0.5H, d), 8.64 (1H, d, J=7.7), 7.75 (15H, m), 6.61 (1H, 2d), 6.11 (0.5H, d), 5.93 (0.5H, s), 5.17 (5H, m), 4.77 (0.5H, d), 3.68–2.94 (2H, m), 3.32 (8H, m).

N(3(S)) 2[6-Butyl-1,2-dihydro-2-oxo-3-(3-phenylpropionyl)amino-1-pyridyl]-N-(2-benzyloxy-5- oxotetrahydrofuran-3-yl)acetamide (53d), was obtained (74%) as a mixture of anomers: IR (KBr) 3300, 1791, 1689, 1645, 1597, 1566, 1546, 1514, 1454, 1417, 1378; $^1$H NMR (CDCl$_3$) δ 8.38 (1H, d, J=7.7), 8.13 (1H, s), 7.30 (10H, m), 6.18 (1H, t), 5.47 (0.5H, d, J=5.2), 5.43 (0.5H, s), 4.75 (4.5H, m), 4.38 (0.5H, m), 3.08–2.35 (8H, m), 1.43 (4H, m), 0.95 (3H, t).

N(3(S)) 2[1,2-Dihydro-6-methyl-2-oxo-3-(3-phenylpropionyl)amino-1-pyridyl]-N-(2-benzylaxy-5-oxotetrahydrofuran-3-yl)acetamide (53e), was obtained (67%) as a mixture of anomers: IR (KBr) 3282, 1774, 1667, 1651, 1596, 1561, 1556, 1498, 1265, 1254, 1236, 1199, 1143; $^1$H NMR (d$_6$-DMSO) δ 9.17 and 9.15 (1H, 2xs), 8.89 (0.5H, d, J=6.5), 8.73 (0.5H, d, J=7.4), 7.25 (10H, m), 6.13 (1H, t), 5.64 (0.5H, d, J=5.0), 5.45 (0.5H, s), 4.89–4.61 (4.5H, m), 4.26 (0.5H, m), 3.17–2.36 (6H, m), 2.23 and 2.15 (3H, 2s).

N(3(S)) 2-[1,2-Dihydro-2-oxo-6-phenyl-3(3-phenylpropionyl)amino-1-pyridyl]-N-(2-benzyloxy-5-oxotetrahydrofuran-3-yl)acetamide (53f), was obtained (73%) as a mixture of anomers: IR (KBr) 3296, 1792, 1691, 1643, 1595, 1561, 1514, 1489, 1453, 1420, 1373, 1230, 1118; $^1$H NMR (d$_6$-DMSO) δ 9.40, 9.36 (1H, 2s), 8.70 (0.5H, d, J=7.6), 8.52 (0.5H, d, J=7.5), 8.29 (1H, dd), 7.25 (15H, m), 6.20 (1H, d, J=7.6), 5.61 (0.5H, d, J=5.0), 5.28 (0.5H, s), 4.78–4.20 (5H, m), 3.12–2.24 (6H, m).

N(3(S)) 2-[1,2-Dihydro-2-oxo-3-(3-phenylpropionyl) amino-1-pyridyl]-N-(2-benzyloxy-5-oxotetrahydrofuran-3-yl)acetamide (53 g), was obtained (70%) as a mixture of anomers: IR (KBr) 3336, 3290, 1791, 1691, 1646, 1595, 1582, 1556, 1518, 1454, 1376, 1351, 1150, 1122; $^1$H NMR (d$_6$-DMSO) δ 9.26 (1H, 2s), 8.86 (0.5H, d, J=6.4), 8.67 (0.5H, d, J=7.5), 8.23 (1H, m), 7.40–7.13 (11H, m), 6.24 (1H, 2t, J=7.2), 5.61 (0.5H, d, J=5.0), 5.44 (0.5H, s), 4.83–4.59 (2.5H, m), 4.25 (0.5H, m), 3.15–2.34 (2H, m), 2.91–2.70 (4H, m). Anal. Calc. for C$_{27}$H$_{27}$N$_3$O$_6$ H$_2$O: C, 63.90; H, 5.76; N, 8.28. Found: C 63.70; H, 5.68; N, 8.22. MS FAB M$^+$=490 (M+1).

2(R, S), N(3(S)) 2-[6-Benzyl-1,2-dihydro-2-oxo-3-(3-phenylpropionyl)amino-1-pyridyl]-N(2-benzyloxy-5-oxotetrahydrofuran-3-yl)propionamide (53h), was obtained (89%) as a mixture of diastereomers. Data is given for a single diastereomer: IR (film) 3356, 1788, 1677, 1645, 1602, 1517, 1455, 1377, 1203, 1167, 1120; $^1$H NMR (CDCl$_3$) δ 8.34 (1H, d, J=7.6), 8.19 (1H, s), 7.38–7.13 (10H, m), 6.26 (1H, d, J=. 7.6), 5.58 (1H, t), 5.31, 5.24 (1H, 2xs), 4.62 (2H, 2q), 4.60 (1H, m), 4.27 (1H, m), 2.98, 2.68 (4H, 2m), 3.0–2.0 (2H, m), 1.42 (3H, d).

N(3(S)) 2-[6-Benzyl-1,2-dihydro-2-oxo-3-(N-acetyl-O-benzyltyrosinyl)amino-1-pyridyl]-N-(2-benzyloxy-5-oxotetrahydrofuran-3-yl)acetamide (53i), was obtained (76%) as a mixture of anomers: IR (KBr) 1794, 1698, 1651, 1612, 1514, 1454, 1374, 1247, 1177, 1126; $^1$H NMR (d$_6$-DMSO) δ 9.34, 9.31 (2x0.5H, 28), 8.71 (1H, 2d), 8.38 (1H, m), 8.17 (1H, d), 7.48–6.88 (19H, m), 6.08 (1H, 2d), 5.65 (0.5H, d, J=5.0), 5.40 (0.5H, s), 5.04 (2H, s), 4.68 (5.5H, m), 4.15 (0.5H, m), 3.95, 3.84 (2H, s+abq), 3.20–2.40 (4H, m), 1.78 (3H, s).

N(3(S)) 2-[6-Benzyl-1,2-dihydro-2-oxo-3-(2-phenylethanesulphonyl)amino-1-pyridyl]-N-(2-benzyloxy-5-oxotetrahydrofuran-3-yl)acetamide (53j), was obtained (78%) as a mixture of anomers: IR (KBr) 3344, 1792, 1691, 1647, 1599, 1566, 1454, 1365, 1150, 1121, 973; $^1$H NMR (d$_6$-DMSO) δ 9.02, 8.99 (1H, 2s), 8.80 (0.5H, d, J=6.4), 8.70 (0.5H, d, J=7.4), 7.26 (15H, m), 6.00 (1H, dd), 5.63 (0.5H, d, J=5.0), 5.39 (0.5H, s), 4.68 (4.5H, m), 4.18 (0.5H, m), 3.90 (2H, m), 3.30–2.30 (6H, m).

N(3(S)) 2-[6-Benzyl-1,2-dihydro-2-oxo-3-(2-phenylethoxy)carbonyl]amino-1-pyridyl]-N-(2-benzyloxy-5-oxotetrahydrofuran-3-yl)acetamide (53%), was obtained (78%) as a mixture of anomers: IR (KBr) 3386, 1794, 1726, 1650, 1603, 1518, 1366, 1214, 699; $^1$H NMR (CDCl$_3$) δ 8.03 (1H, bd), 7.63, 7.61 (1H, 2xs), 7.34–7.04 (15H, m), 6.21, 6.18 (1H, 2d), 5.44 (0.5H, d, J=5.4), 5.37 (0.5H, s), 4.85, 4.83 (1H, 2d, J=11.6, 11.5), 4.61–4.48, 4.32 (4H, 2m), 4.4 (2H, t), 4.08, 4.03 (2H, 2bs), 3.07–2.78 (3H, m), 2.47–2.30 (1H, m).

N(3(S)) 2-[6-Benzyl-1,2-dihydro-2-oxo-3-(4-phenylbutyryl)amino-1-pyridyl]-N-(2-benzyloxy-5-oxotetrahydrofuran-3-yl)acetamide (53l), was obtained (86%) as a colorless oil: IR (CH$_2$Cl$_2$) 1797, 1689, 1649, 1601, 1512, 734; $^1$H NMR (CDCl$_3$) δ 8.42, 8.40 (1H, 2d, J=7.6), 7.35–7.07 (15H, m), 6.21, 6.19 (1H, 2d, J=7.6), 5.44 (0.5H, d), 5.37 (0.5H, s), 4.84, 4.81 (1H, 2d, J=11.7, 11.4), 4.73–4.48, 4.34 (4H, 2m), 4.05 (2H, m), 3.05–2.63, 2.46–2.30 (6H, 2m), 2.01 (2H, m).

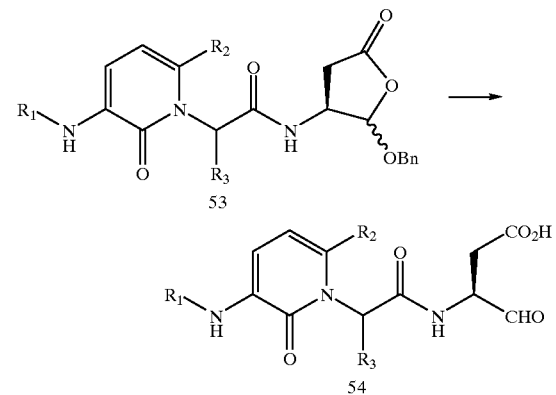

| | R$_1$ | R$_2$ | R$_3$ |
|---|---|---|---|
| (a) | Ph(CH$_2$)$_2$CO | H | (S)Me |
| (b) | Ph(CH$_2$)$_2$CO | CH$_2$Ph | H |
| (c) | Ph(CH$_2$)$_2$CO | (CH$_2$)$_2$Ph | H |
| (d) | Ph(CH$_2$)$_2$CO | nBu | H |
| (e) | Ph(CH$_2$)$_2$CO | Me | H |
| (f) | Ph(CH$_2$)$_2$CO | Ph | H |
| (g) | Ph(CH$_2$)$_2$CO | H | H |
| (h) | Ph(CH$_2$)$_2$CO | CH$_2$Ph | (R,S)-Me |
| (i) | AcTyr | CH$_2$Ph | H |
| (j) | Ph(CH$_2$)$_2$SO$_2$ | CH$_2$Ph | H |
| (k) | Ph(CH$_2$)$_2$OCO | CH$_2$Ph | H |
| (l) | Ph(CH$_2$)$_3$CO | CH$_2$Ph | H |

3(S), N(2(S)) 3-(2-(1,2-Dihydro-2-oxo-3-(3-phenylpropionylamino-1-pyridyl)-propionylamino)-4-oxo-butanoic acid (54a; F). A mixture of 2(S), N(3(S)) 2-[1,2-dihydro-2-oxo-3-(3-phenylpropionyl)amino-1-pyridyl]-N (2-benzyloxy-5-oxotetrahydro-furan-3-yl)propionamide 53a (1.28 g, 2.5 mmol), methanol (140 ml) ethyl acetate (60 ml) and 10% palladium on carbon (1.4 g) was stirred under an atmosphere of hydrogen. After 2.5 h more catalyst (300 mg) was added and hydrogenation continued for 1 h. The mixture was filtered through Celite™ and then refiltered through 0.2 μM nylon filter and concentrated. The residual oil triturated with a mixture of methanol and ether to afford 916 mg (87%) of colorless crystals: mp. 198–200° C.; [α]$_D^{28}$–120° (0.1, CH$_3$OH); IR (KBr) 3330, 1794, 1688, 1644, 1583, 1556, 1515, 1427; $^1$H NMR (CD$_3$OD) δ 8.28 (1H, d), 7.35 (1H, d), 7.20 (5H, m), 6.36 (1H, t), 5.49 (1H, q), 4.59 (1H, t), 4.25 (1H, m), 2.98, 2.74 (2×2H, 2×m), 2.59 (2H, m), 1.57 (3H, d). Anal. Calcd for $C_{21}H_{23}N_3O_6$ 0.75 $H_2O$: C, 59.08; H, 5.78; N, 9.84. Found: C 59.24; H, 5.96; N, 9.84. FAB M+=414 (M+1), 297, 165, 91.

The following compounds were prepared in a similar manner:

3(S) 3-(6-Benzyl-1,2-dihydro-2-oxo-3-(3-phenylpropionyl) amino-1-pyridyl)acetylamino-4-oxobutanoic acid, (54b; M), was isolated (59%) as colorless crystals: mp. 115° C. (decomp);. IR (KBr) 3440, 3297, 1718, 1646, 1598, 1565, 1526, 1496, 1260; $^1$H NMR ($CD_3OD$) 8.25 (1H, d, J=7.7), 7.25 (10H, m), 6.15 (1H, 2d, each J=7.7), 4.73 (2H, 2q), 4.59 (1H, m), 4.30 (1H, m), 3.95 (2H, s), 2.98 (2H, m), 2.75 (2H, m), 2.8–2.42 (2H, m). Anal. Calcd for $C_{27}H_{27}N_3O_6$. 0.7 $H_2O$: C, 64.58; H, 5.70; N, 8.37. Found: C, 64.51; H, 5.63; N, 8.38. MS FAB+ M+=490 (M+1).

3(S) 3-(1,2-Dihydro-2-oxo-6-phenethyl-3(3-phenylpropionyl)amino-1-pyridyl)acetylamino-4-oxobutanoic acid (54c), was isolated (46%) as a white solid: IR (KBr) 3375, 1694, 1643, 1586, 1561, 1515, 1377, 1254, 1188, 1070; $^1$H NMR ($CD_3OD$) 8.18 (1H, d, J=7.8), 7.22 (10H, m), 6.15 (1H, d, J=7.8), 4.75 (2H, s), 4.58 (1H, m), 4.30 (1H, m), 3.01–2.28 (10H, m); MS FAB+ M+=504 (M+1).

3(S) 3-(6-Butyl-1,2-dihydro-2-oxo-3-(3-phenylpropionyl) amino-1-pyridyl)acetylamino-4-oxobutanoic acid (54d), was isolated (90%) as colorless crystals: m.p. 120–5° C.; IR (KBr) 3315, 1784, 1679, 1644, 1589, 1561, 1556, 1520, 1415, 1379, 1186; $^1$H NMR ($CD_3OD$) 8.22 (1H, d, J=7.8), 7.24 (5H, m), 6.22 (1H, d, J=7.8), 4.80 (2H, m), 4.60 (1H, s), 4.28 (1H, m), 2.98 (2H, m), 2.72 (2H, m), 2.58 (4H, m), 1.48 (4H, m), 0.97 (3H, t, J=7.1). Anal. Calcd for $C_{24}H_{29}N_3O_6$ 0.5 $H_2O$. C, 62.06; H, 6.51; N, 9.05. Found: C, 62.08; H, 6.43; N, 9.01. MS FAB+ M+=456 (M+1).

3(S) 3-(1,2-Dihydro-6-mothyl-2-oxo-3-(3-phenylpropionyl) amino-1-pyridyl)acetylamino-4-oxobutanoic acid (54e), was isolated (85%) as a colorless solid: mp. 129–138° C.; IR (KBr) 327, 3294, 1710, 1695, 1682, 1554, 1525, 1379, 1272, 1240; $^1$H NMR ($CD_3OD$) δ 8.19 (1H, d, J=7.6), 7.19 (5H, m), 6.21 (1H, d, J=7.6), 4.80 (2H, m), 4.59 (1H, m), 4.30 (1H, m), 2.98 (2H, m), 2.72 (2H, m), 2.80–2.40 (2H, m), 2.30 (3H, s). Anal. Calcd for $C_{21}H_{22}N_3O_6$. $H_2O$: C, 58.46; H, 5.84; N, 9.74. Found C: 58.82; H, 60.5; N, 9.42.

3(S) 3-(1,2-Dihydro-2-oxo-6-phenyl-3-(3-phenylpropionyl)amino-1-pyridyl)acetylamino-4-oxobutanoic acid (54f), 73% as an off-white solid: m.p. 140° C. (decomp). [$\alpha_D^{24}$=-8.5° (c 0.1, MeOH). IR (KBr) 3302, 1796, 1726, 1679, 1643, 1590, 1560, 1516, 1490, 1449, 1420, 1398, 1376, 1231; $^1$H NMR ($CD_3OD$) δ 8.36 (1H, d), 7.49–7.14 (10H, m), 6.27 (1H, dd), 4.54 (3H, m), 4.30 (1H, m), 3.0, 2.73 (2×2H, 2×m), 2.7–2.29 (2H, m).

3(S) 3-(1,2-Dihydro-2-oxo-3-(3-phenylpropionyl)amino-1-pyridyl)acetylamino-4-oxobutanoic acid (54 g; G), was isolated (73%) as a foam: mp. 140–5° C. (decomp); IR (KBr) 3352, 3314, 1719, 1700, 1668, 1649, 1600, 1559, 1514, 1379, 1261; $^1$H NMR ($CD_3OD$) δ 8.32 (1H, d, J=7.5) 7.19 (6H, m), 6.34 (1H, t), 5.1–4.6 (3H, m), 4.32 (1H, m), 2.7 (6H, m). Anal. Calcd for $C_{20}H_{21}N_3O_6$. 0.6$H_2O$: C, 58.50, H, 5.45, N, 10.24. Found: C, 58.43, H, 5.35, N. 9.85. MS FAB+ M+=400 (M+1).

3(S), N(2(R,S)) 3-(2-(6-Benzyl-1,2-dihydro-2-oxo-3-(3-phenylpropionyl)amino-1-pyridyl)propionylamino)-4-oxobutanoic acid (54h), was obtained (69%) as a colorless foam: m.p. 120° C.; [$\alpha$]$_D^{20}$–16.0° (c, 0.11, $CH_2Cl_2$). IR (KBr) 3315, 1783, 1727, 1666, 1644, 1599, 1564, 1517, 1454, 1379; $^1$H NMR ($CD_3OD$) δ 8.23 (1H, m), 7.27 (10H, m), 6.28 (1H, m), 4.84 (1H, m), 4.53 (1H, m), 4.22 (1H, m), 4.10 (2H, m), 2.96 (2H, m), 2.72 (2H, m), 2.39 (2H, m), 1.21 (3H, m). Anal. Calcd for $C_{28}H_{29}N_3O_6$. 1.25$H_2O$: C, 63.93, H, 6.03, N, 7.99. Found: C, 63.98, H, 5.85, N, 7.86. MS FAB (+) M+=504 (M+1).

3(S) 3-(3-(2-Acetyl-L-tyrosinyl)amino-6-benzyl-1,2-dihydro-2-oxo-1-pyridyl)acetylamino-4-oxobutanoic acid (54i), was isolated (79%) as colorless crystals: mp. 193–6° C. (decomp.); IR (KBr) 3284, 1644, 1599, 1565, 1519, 1455, 1429, 1407, 1375, 1267, 1251; $^1$H NMR ($d_6$-DMSO/$CDCl_3$) δ 8.16 (1H, d, J=7.7), 7.26 (5H, m), 7.03 (2H, d, J=8.4), 6.61 (2H, d, J=8.4), 6.03 (1H, d, J=7.7), 4.58 (3H, m), 4.44 (1H, m), 4.13 (1H, m), 3.84 (2H, s), 3.07–2.30 (4H, m). Anal. Calcd for $C_{29}H_{30}N_4O_8$. 2$H_2O$: C, 58.19; H, 5.72; N, 9.36. Found: C, 58.11; H, 5.63; N, 9.29. MS FAB+ M+=563 (M+1).

3(S) 3-(6-Benzyl-1,2-dihydro-2-oxo-3-(2-phenylethane-sulphonyl)amino-1-pydridyl)acetylamino-4-oxobutanoic acid (54j), was isolated (85%) as a colorless solid: mp. 102–5° C.; [$\alpha$]$_D^{23}$–9.9° (c 0.1, MeOH); IR (KBr) 3452, 3328, 3155, 1719, 1679, 1645, 1594, 1567, 1453, 1425, 1357, 1307, 1225, 1148, 1132; $^1$H NMR ($CD_3OD$) δ 7.52 (1H, d, J=7.6), 7.33 (10H, m), 6.12 (1H, d, J=7.6), 4.73 (2H, m), 4.58 (1H, d, J=3.7), 4.34 (1H, m), 3.97 (2H, s), 3.29 (2H, m), 3.08 (2H, m), 2.75–2.37 (2H, m). Anal. Calcd for $C_{26}H_{27}N_3O_7S$. 1.7$H_2O$: C, 56.14; H, 5.51; N, 7.55. Found: C, 56.20; H, 5.49; N, 7.29. MS FAB+ M+=526 (M+1).

3(S) 3-(6-Benzyl-1,2-dihydro-2-oxo-3-(2-phenylethoxy) carbonylamino-1-pyridyl)acetylamino-4-oxobutanoic acid (54%), was isolated (54%) as an off-white solid: mp. 84–86° C.; IR (KBr) 3373–3310, 1787, 1726, 1691, 1649, 1599, 1567, 1517, 1367, 1215; $^1$H NMR ($CD_3OD$) δ 7.93 (1H, bd, J=7.4), 7.37–7.18 (10H, m), 6.15 (1H, d, J=7.4), 4.77 (1H, d, J=3.7), 4.67 and 4.58 (2H, 2m), 4.35 (2H, t, J=6.9), 4.35 (1H, m), 3.94 (2H, s), 2.98 (2H, t, J=6.9), 2.76–2.39 (2H, m).

3(S) 3-(6-Benzyl-1,2-dihydro-2-oxo-3-(4-phenylbutyryl) carbonylamino-1-pyridyl)acetylamino-4-oxobutanoic acid (54l), was isolated (50%) as a white solid: mp. 89–93° C.; IR (KBr) 3369–3302, 1678, 1645, 1594, 1565, 1517, 1379, 1258; $^1$H NMR ($d_4$-methanol) δ 8.25 (1H, d, J=7.6), 7.37–7.18 (10H, m), 6.15 (1H, d, J=7.4), 4.74 (2H, m), 4.60 (1H, m), 4.30 (1H, m), 3.97 (2H, s), 2.76–2.37 (2H, m), 2.67 (2H, t), 2.45 (2H, t), 1.98 (2H, m). Anal. Calcd for $C_{28}H_{29}N_3O_6$. 1.5$H_2O$: C, 63.39; H, 6.08; N, 7.92. Found C: 63.69; H, 5.74; N, 7.83.

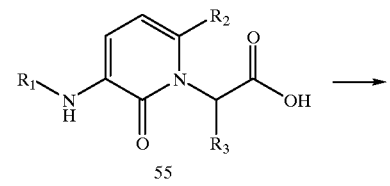

55

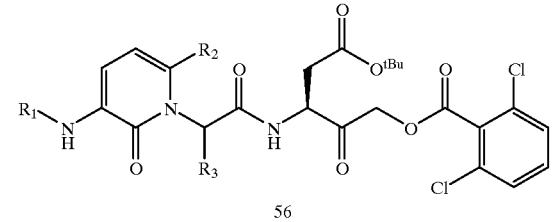

56

|   | $R_1$ | $R_2$ | $R_3$ |
|---|---|---|---|
| (a) | Ph-CH₂—O—C(=O)— | H | H |
| (b) | Ph-CH₂-CH₂—C(=O)— | —CH₂-Ph | H | t-Butyl N-2-(3-benzyloxycarbonylamino-1,2-dihydro-2-oxo-1-pyridyl)acetyl-3-amino-5-(2,6-dichlorobenzoyloxy)-4-oxo-pentanoate (56a). The acetic acid (55a) (WO 93 21213) in THF (2 ml) was stirred at room temperature and treated with 1-hydroxybenzotriazole (60 mg, 0.448 mmol) and dimethylaminopropyl-3-ethylcarbodiimide hydrochloride (47 mg, 0.246 mmol). After 5 mins water (2 drops) was added and stirring continued for 20 minutes. Bis(triphenylphosphine) palladium II chloride (6 mg) was added followed by a solution of t-butyl 3-(allyloxycarbonylamino)-4-oxo-5-(2,6-dichlorobenzoyloxy)pentanoate (WO 93 16710) (103 mg, 0.224 mmol) in THF (1 ml). Tributyltin hydride (0.09 ml, 0.336 mmol) was added dropwise over 1 hour at room temperature. The mixture was stirred for a further 3 hours and poured onto ethyl acetate, washed with 1M HCl, aqueous NaHCO₃, brine, dried over MgSO₄ and concentrated in vacuo. The residue was triturated with pentane and the supernatant discarded. The remaining solid was purified by flash chromatography (50% ethyl acetate/hexane) to afford the title compound 92 mg (63%) as a colorless oil: $[\alpha]_D^{26}$–29.6° (c 1.1, CH₂Cl₂); IR (film) 3377, 3365, 3332, 3312, 1733, 1691, 1650, 1599, 1515, 1366, 1261, 1153, 1068, 747; ¹H NMR (CDCl₃) δ 8.09 (1H, d, J=6.8), 7.84 (1H, s), 7.58 (1H, d, J=8.3), 7.33 (8H, m), 7.02 (1H, dd, J=6.9, 1.7), 6.33 (1H, t, J=7.2), 5.20 (2H, s), 5.12 (2H, m), 4.89 (1H, dt), 4.65 (2H, m), 2.80 (2H, m), 1.38 (9H, s).

t-Butyl N-2-(6-benzyl-1,2-dihydro-2-oxo-3-(3-phenylpropionyl)amino-1-pyridyl)acetyl-3-amino-5-(2,6-dichlorobenzyloxy)-4-oxo-pentanoate (56b), was prepared by the method described for (56a) which afforded the title compound (66%) as a colorless oil: IR (film) 3364, 3313, 1738, 1688, 1648, 1600, 1566, 1514, 1433, 1369, 1254, 1152; ¹H NMR (CDCl₃) δ 8.40 (1H, d, J 7.6), 8.30 (1H, s), 7.28 (13H, m), 6.20 (1H, d, J=7.6), 5.12 (2H, q), 4.86 (1H, m), 4.65 (2H, q), 4.06 (2H, s), 3.07–2.61 (6H, m), 1.39 (9H, s).

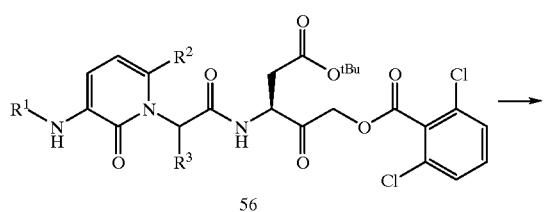

56

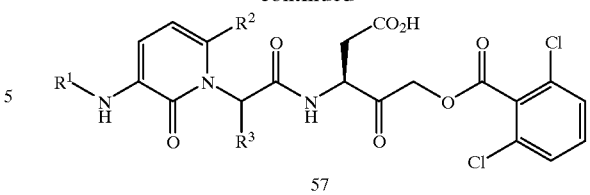

57

|   | $R^1$ | $R^2$ | $R^3$ |
|---|---|---|---|
| (a) | PhCH₂O—C(=O)— | H | H |
| (b) | PhCH₂CH₂—C(=O)— | —CH₂-Ph | H |

N-2(3-Benzyloxycarbonylamino-1,2-dihydro-2-oxo-1-pyridyl)acetyl-3-amino-5-(2,6-dichlorobenzoyloxy)-4-oxo-pentanoic acid (57a; O). The ester (56a) (210 mg, 0.356 mmol) in dichloromethane (0.5 ml) was cooled to 0° C. and treated with trifluoroacetic acid (0.5 ml), stirred and warmed to 20° C. over 30 minutes. The solution was evaporated to dryness under reduced pressure, redissolved in dichloromethane and concentrated (×3). The residue was triturated with ethyl acetate and diluted with ether to afford the title compound 162 mg (85%) as a colorless solid: m.p. 165–8° C. (decomposition); $[\alpha]_D^{23}$–38.8° (c 0.1, CH₃OH); IR (KBr) 3332, 3275, 1723, 1658, 1649, 1597, 1581, 1562, 1526, 1432, 1385, 1258, 1218, 1206; ¹H NMR (d₆-DMSO) δ 8.96 (1H, d, J=7.3), 8.34 (1H, s), 7.85 (1H, dd, J=7.3), 7.58 (3H, m), 7.35 (5H, m), 6.29 (1H, t, J=7.3), 5.26 (2H, m), 5.15 (2H, s), 4.69 (3H, m), 2.75 (2H, m). Anal. Calcd. C₂₇H₂₃N₃O₉Cl₂: C, 53.66; H, 3.84; N, 6.95. Found: C, 53.36; H, 3.90; N, 6.81. M.S. (+FAB); 604 (M⁺+1), 285, 241, 195, 173, 149, 91.

N-2-(6-Benzyl-1,2-dihydro-2-oxo-3-(3-phenylpropionyl)amino-1-pyridyl)acetyl-3-amino-5-(2,6-dichlorobenzoyloxy)-4-oxo-pentanoic acid (57b; P), was prepared by the method described for 57a which afforded the title compound (78%) as colorless crystals: m.p. 116–120° C. (decomposition); $[\alpha]_D^{26}$–41.1° (c 0.1, CH₃OH); IR (KBr) 3299, 1739, 1715, 1689, 1666, 1645, 1598, 1563, 1518, 1432, 1209, 1151; ¹H NMR (d₆-DMSO) δ 9.24 (1H, s), 8.88 (1H, d, J=7.6), 8.18 (1H, d, J=7.7), 7.60 (3H, m), 7.26 (10H, m), 6.06 (1H, d, J=7.7), 5.23 (2H, ABq), 4.69 (3H, m), 3.93 (2H, s), 2.78 (6H, m). Anal. Calcd. for C₃₅H₃₁N₃O₈Cl₂·H₂O: C, 59.16; H, 4.68; N, 5.91. Found: C, 59.38; H, 4.53; N, 5.84. M.S. (+FAB); 694, (Cl=35, 37), (M⁺+1); 692 (Cl=35, 35), (M⁺+1).

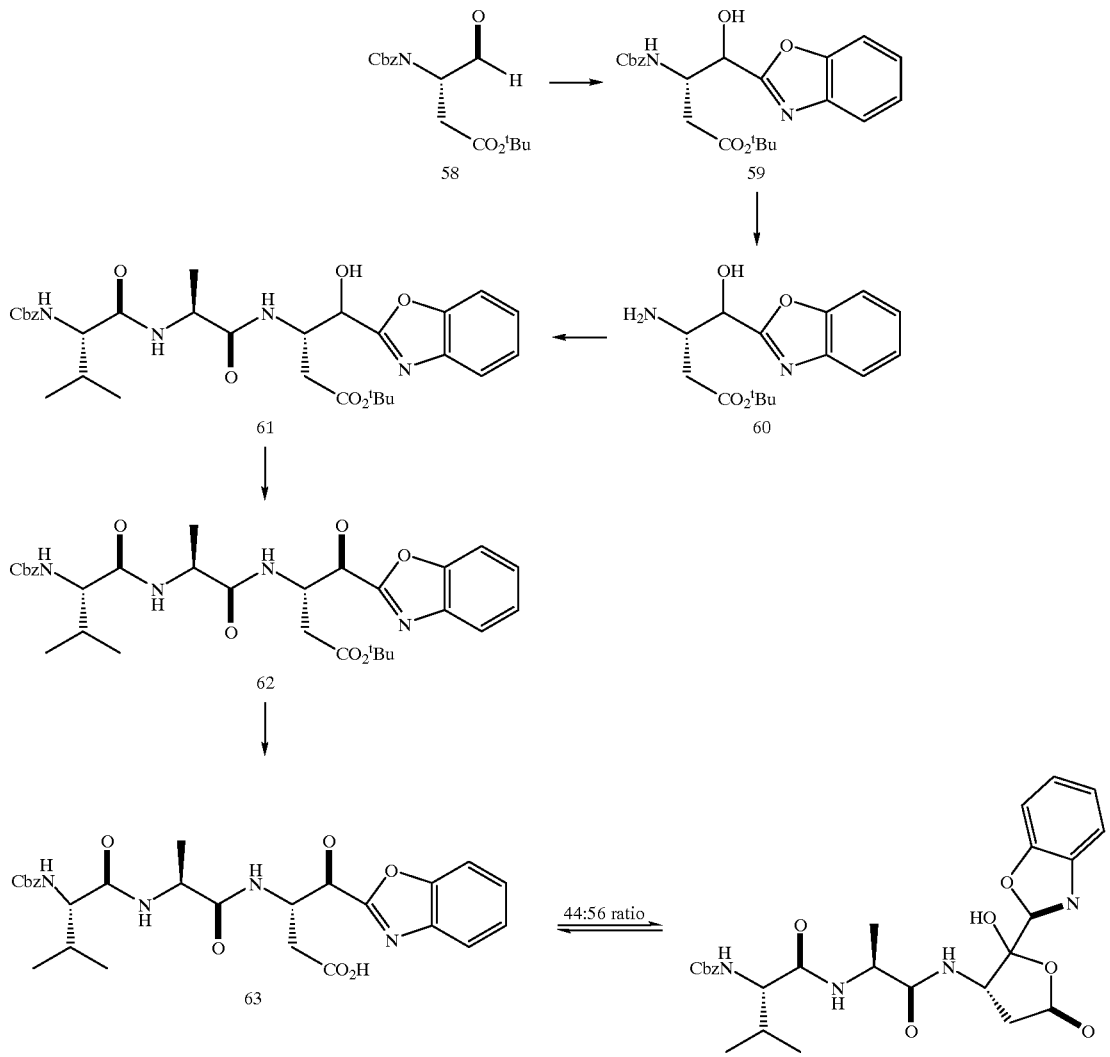

(3S, 4R,S) t-Butyl N-(benzyloxycarbonyl)-3-amino-4-(2-benzoxazolyl)-4-hydroxy-butanoate (59). To a stirred solution of benzoxazole (250.2 mg, 2.1 mmol) in anhydrous THF (10.5 ml) at −78° C. under $N_2$ was added 2.3M n-butyl lithium in hexanes (0.96 ml, 2.2 mmol) dropwise. After stirring at −78° C. for 20 min, dry $MgBr_2OEt_2$ (594.0 mg, 2.3 mmol) was added as a solid. The resulting heterogeneous mixture was warmed to −45° C. and stirred for 15 min. The reaction mixture was then recooled to −78° C. and a solution of aldehyde 58 (Graybill et al., Int. J. Peptide Protein Res., 44, pp. 173–182 (1993)) (644.6 mg, 2.1 mmol) in THF (10.5 ml) was added dropwise. The reaction was stirred at −78° C. for 30 min, warmed to 0° C. for 1 h, and then stirred at room temperature for 16 h. The reaction was quenched with 5% sodium bicarbonate (2.0 ml) and the THF was removed in vacuo. The resulting aqueous residue was extracted four times with methylene chloride. The combined extracts were washed with brine, dried ($MgSO_4$), filtered and reduced in vacuo to give 880.0 mg of crude product. Flash chromatography (45:55 ethyl acetate/hexane) afforded 567.2 mg (63%) of the title compound, an oil, as a mixture of diastereoisomers at C-4. IR (film) 3324, 2976, 1726, 1517, 1455, 1368, 1243, 1159, 1048, 747; $^1$H NMR ($CDCl_3$) δ 7.71–7.64 (1H, m), 7.52–7.48 (1H, m), 7.37–7.20 (7H, m), 5.91 (1H, brd, J=9.0), 5.79 (1H, d, J=9.0), 5.41–4.78 (4H, m), 4.75–4.54 (1H, m), 2.91–2.51 (2H, m), 1.42 (9H, s), 1.37 (9H, s).

(3S, 4R,S) t-Butyl 3-amino-4-(2-benzoxazolyl)-4-hydroxybutanoate (60). A solution of the ester 59 (189.0 mg, 0.44 mmol) in ethanol (5.0 ml) was treated with 10% Palladium on carbon (20.5 mg) and stirred under an atmosphere of $H_2$ for 21 h. The mixture was filtered through Celite®, and the solvent was evaporated to afford 125.0 mg (98%) of crude amine 60 as an oil. This was used without further purification. $^1$H NMR ($CDCl_3$) δπ7.73–7.64 (1H, m), 7.51–7.42 (1H, m), 7.35–7.22 (2H, m), 6.48 (3H, brs), 5.58 (1H, d, J=3.0), 5.27 (1H, d, J=6.5), 4.23–4.05 (1H, m), 2.92–2.63 (2H, m), 1.36 (9H, s), 1.33 (9H, s).

(3S, 4R,S) t-Butyl N-(N-benzyloxycarbonyl-(S)-valinyl-(S)-alaninyl)-3-amino-4-(2-benzoxazolyl)-4-hydroxybutanoate (61). A solution of the amine 60 (261.4 mg, 0.89 mmol), Z-Val-Ala-OH (286.9 mg, 0.89 mmol) (prepared by standard peptide synthetic procedures) and hydroxybenzotriazole (120.3 mg, 0.89 mmol) in DMF (3.0 ml) at 0° C. was treated with 1-ethyl-3-[3-(dimethylamino)propyl]carbodiimide hydrochloride (179.2 mg, 0.93 mmol). The reaction was warmed to room temperature and stirred for 16 h. The reaction was diluted with ethyl acetate and washed twice with 1M sodium hydrogensulphate, twice with saturated sodium bicarbonate, then water, and brine. The organic layer was dried (MgSO₄), filtered and reduced in vacuo to afford 494.8 mg of crude product. Flash chromatography (95:5 methylene chloride/methanol) gave 480.9 mg (91%) of the title compound as a yellow solid: mp. 81–83° C.; IR (KBr) 3312, 2974, 1723, 1709, 1529, 1455, 1368, 1243, 1156, 747; ¹H NMR (CDCl₃) δ 7.79 (0.5H, d, J=8.0), 7.73–7.20 (9.5H, m), 6.15 (1H, t, J=8.5), 5.74 (0.5H, brd, J=5.5), 5.45 (1H, brd, J=7.5), 5.28–5.20 (0.5H, m), 4.82–4.11 (3.5H, m), 4.78–4.55 (1H, m), 4.40–4.22 (1H, m), 2.95–2.51 (2H, m), 2.12–1.95 (1H, m), 1.45–1.32 (12H, m), 1.11–0.81 (6H, m), ¹³C NMR (CDCl₃) δ 173.14, 172.94, 171.82, 171.03, 170.78, 165.98, 165.45, 157.29, 157.17, 151.23, 151.10, 140.92, 140.82, 136.83, 136.79, 128.91, 128.52, 125.75, 124.97, 120.60, 120.40, 111.38, 81.82, 81.68, 70.27, 68.97, 67.44, 60.43, 50.74, 50.55, 49.18, 49.07, 36.87, 36.57, 32.37, 28.51, 19.88, 19.80, 18.53. Anal. Calcd. for C₃₁H₄₀N₄O₈. H₂O: C, 60.57; H, 6.89; N, 9.11. Found: C, 60.84; H, 6.64; N, 9.09. M.S. (+FAB); 597 (M⁺+1); 541, 91.

(3S) t-Butyl N-(N-benzyloxycarbonyl-(S)-valinyl-(S)-alaninyl)-3-amino-4-(2-benzoxazolyl)-4-oxobutanoate (62). The alcohol 61 (100.3 mg, 0.17 mmol) was dissolved in methylene chloride (2.0 ml) and Dess-Martin reagent (142.6 mg, 0.34 mmol) was added (Ireland et al., *J. Org. Chem.*, 58, p. 2899 (1993); Dess et al., *J. Org. Chem.*, 48, pp. 4155–4156 (1983)). The resulting mixture was stirred for 22 min and then partitioned between saturated sodium thiosulphate: saturated sodium bicarbonate (1:1, 10 ml), and ethyl acetate (10 ml). The resulting organic phase was washed with saturated sodium thiosulphate, saturated sodium bicarbonate (1:1), saturated sodium bicarbonate, and brine. The organic phase was dried (MgSO₄), filtered and reduced in vacuo to give 111.3 mg of crude product. Flash chromatography (95:5 methylene chloride/methanol) afforded 97.3 mg (96%) of the title compound as an oil: [α]$_D^{23}$–11.74° (c 0.95, CH₂Cl₂); IR (CH₂Cl₂) 3419, 2974, 1721, 1677, 1501, 1369, 1221, 1156; ¹H NMR (CDCl₃) δ 7.89–7.84 (1H, m), 7.73–7.22 (10H, m), 5.98 (1H, d, J=9.0), 5.72 (1H, m), 5.10 (2H, q, J=12.5), 4.73 (2H, m), 4.20 (1H, dd, J=7.0, 8.5), 3.30 (1H, dd, J=5.0, 16.5), 3.03 (1H, dd, J=5.5, 16.5), 2.18–1.97 (1H, m), 1.39 (3H, d, J=7.0), 1.34 (9H, s), 0.93 (3H, d, J=6.0), 0.90 (3H, d, J=6.0), ¹³C NMR (CDCl₃) δ 186.46, 172.73, 171.90, 170.13, 157.17, 156.28, 151.16, 140.99, 136.99, 129.39, 129.08, 128.66, 128.59, 126.49, 123.06, 112.55, 82.73, 67.60, 60.84, 53.75, 49.41, 38.58, 32.05, 28.52, 19.85, 19.32, 18.51. M.S. (+FAB); 595 (M⁺+1); 539, 91.

(3S) N-(N-Benzyloxycarbonyl-(S)-valinyl-(S)-alaninyl)-3-amino-4-(2-benzoxazolyl)-4-oxobutanoate (63; O). A solution of the ester 62 (95.0 mg, 0.16 mmol) in a 1:1 mixture of methylene chloride and trifluoroacetic acid (10.0 ml) was stirred for 1 h under a dry atmosphere of N₂. The solution was then reduced in vacuo, taken up in ether and reduced again. This process was repeated six times to afford the crude product as an off white solid. Flash chromatography (95:5 methylene chloride/methanol) gave 60.0 mg (69%) of the title compound as a white solid. The product existed as a mixture of three isomers in CD₃OD, consisting of the ketone form (one isomer, c 44%), and its acyloxy ketal form (two isomers at C-4, c. 56%): m.p. 156–159° C. [α]$_D^{26}$–45.6° (c 0.13, methanol); IR (KBr) 3440, 2967, 1713, 1703, 1638, 1531, 1427; ¹H NMR (CD₃OD) δ 7.93–7.24 (9H, m), 5.59 (1H, brt), 5.16–5.00 (2H, m), 5.0–4.78 (1H, m), 4.50–4.22 (1H, m), 3.95–3.81 (1H, m), 3.11 (2H, d, J=6.5), 3.05–2.92 (1H, m), 2.70–2.39 (1H, m), 2.08–1.89 (1H, m), 1.19–0.78 (9H, m). Anal. Calcd. for C₂₇H₃₀N₄O₈. 0.5H₂O: C, 59.22; H, 5.71; N, 10.23. Found: C, 59.48, H, 5.36, N, 10.17. M.S. (+FAB); 539 (M⁺+1), 91.

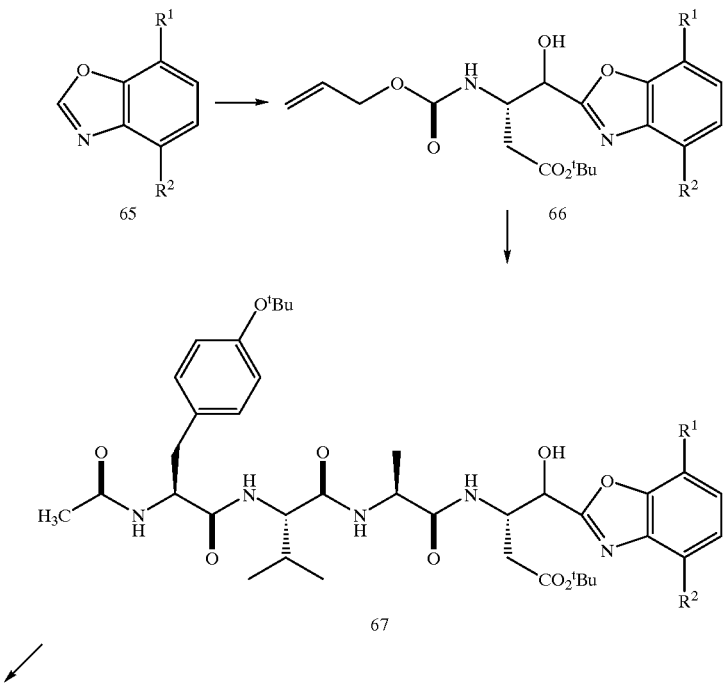

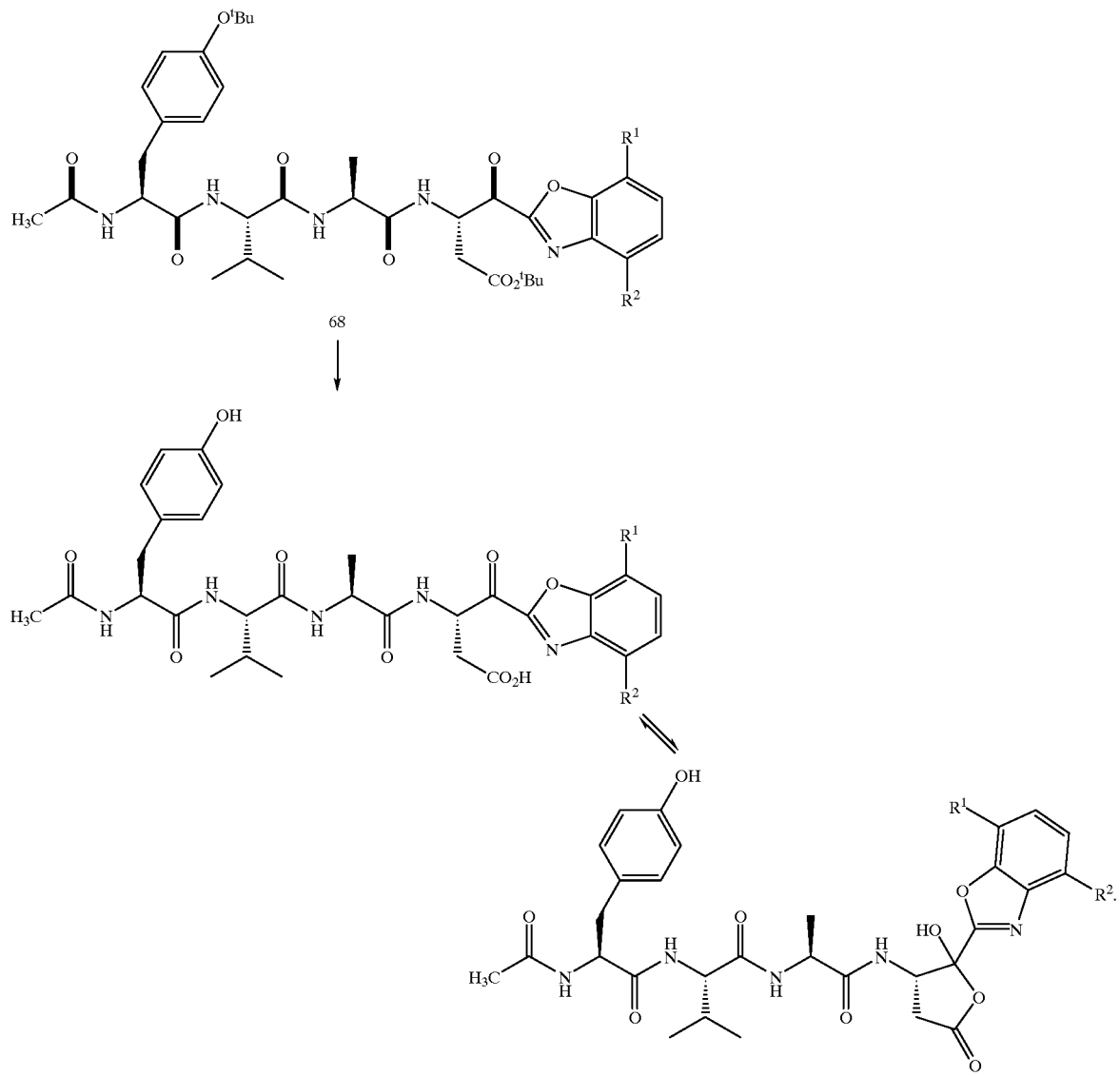

(a) R$^1$ = OCH$_3$, R$^2$ = H
(b) R$^1$ = H, R$^2$ = OCH$_3$

7-Methoxybenzoxazole (65a). A mixture of 2-nitro-6-methoxyphenol (2.62 g, 15.5 mmol) (EP 333176) and 10% Palladium on carbon (130 mg) in ethanol (50 ml) was stirred under an atmosphere of H$_2$ for 75 min. The mixture was filtered through Celite® then immediately treated with p-toluenesulphonic acid (32.0 mg) and triethylorthoformate (6.45 ml, 38.8 mmol) then heated under reflux under an atmosphere of N$_2$. After 20 h p-toluenesulphonic acid (30.0 mg) and triethylorthoformate (6.45 ml, 38.8 mmol) were added. After a total of 44 h heating, the reaction was allowed to cool and reduced in vacuo. The resulting residue was purified by flash chromatography (25:75 ethyl acetate/hexane) to give 1.97 g (85%) of the title compound as a yellow solid: m.p. 28–31° C.; IR (film) 1629, 1497, 1434, 1285, 1097; $^1$H NMR (CDCl$_3$) δ 8.09 (1H, s), 7.40 (1H, d, J=8.0), 7.28 (1H, t, J=8.0), 6.89 (1H, d, J=8.0), 4.02 (3H, s); $^{13}$C NMR (CDCl$_3$) δ 152.84, 145.82, 142.50, 139.99, 125.75, 113.42, 108.80, 56.97. Anal. Calcd. for C$_8$H$_7$N$_1$O$_2$. 0.1H$_2$O: C, 63.65; H, 4.81; N, 9.29. Found: C, 63.43, H, 4.88, N, 9.05. M.S. (+FAB); 150 (M$^+$+1).

4-Methoxybenzoxazole (65b). To a suspension of 4-hydroxybenzoxazole (2.00 g, 14.8 mmol) (Musser et al.,J. Med. Chem., 30, pp. 62–67 (1987)) in acetone (80.0 ml) was added dried K$_2$CO$_3$ (2.25 g, 16.3 mmol) followed by iodomethane (1.38 ml, 22.2 mmol). The reaction was heated under reflux under N$_2$ for 4.5 h, then filtered and reduced in vacuo to afford the crude product. The resulting residue was purified by flash chromatography (25:75 ethyl acetate/hexane) to give 2.0 g (91%) of the title compound as a white crystalline solid: m.p. 72–74° C.; IR (KBr) 3089, 1619, 1610, 1503, 1496, 1322, 1275, 1090, 1071, 780, 741; $^1$H NMR (CDCl$_3$) δ 8.02 (1H, s), 7.32 (1H, t, J=8.0), 7.18 (1H, d, J=8.0), 6.81 (1H, d, J=8.0), 4.04 (3H, s). Anal. Calcd. for C$_8$H$_7$NO$_2$: C, 64.42; H, 4.73; N, 9.39. Found: C, 64.40; H, 4.84; N, 9.31; m/z (EI) 149 (M$^+$+1, 100%).

(3S, 4R,S) t-Butyl N-(allyloxycarbonyl)-3-amino-4-hydroxy-4-(2-(7-methoxybenzoxazolyl))butanoate (66a). To a stirred solution of 7-methoxybenzoxazole 65a (548.6 mg, 3.68 mmol) in anhydrous THF (18.5 ml) at −78° C. under N$_2$ was added 1.56M n-butyl lithium in hexanes (2.47 ml, 3.86 mmol) dropwise, to produce a yellow colored solution. After stirring at −78° C. for 20 min, dry MgBr$_2$OEt$_2$ (1.045 g, 4.05 mmol) was added as a solid. The resulting heterogeneous mixture was warmed to −45° C. and stirred for 15 min. The reaction mixture was then recooled to −78° C. and a solution of (S)-Alloc-Asp(t-Bu)H[1b] (946.4 mg, 3.68 mmol) in THF (18.5 ml) was added dropwise. The reaction was stirred at −78° C. for 30 min, warmed to 0° C. and stirred for 1 h. The resulting homogeneous reaction was warmed to room temperature and stirred for 16 h. The reaction was quenched with 5% sodium bicarbonate (3.5 ml) then THF was removed in vacuo. The resulting aqueous residue was extracted with methylene chloride (×6). The combined extracts were washed with brine, dried (MgSO$_4$), filtered and reduced in vacuo to give 1.8 g of crude product. Flash chromatography (40:60 ethyl acetate/hexane) gave 1.21 g (81%) of the title compound, an oil, as a mixture of diastereoisomers at C-4: IR (CH$_2$Cl$_2$) 3425, 2983, 1725, 1504, 1290, 1157, 1101; $^1$H NMR (CDCl$_3$) δ 7.35–7.19 (2H, m), 6.89–6.81 (1H, m), 6.00–5.57 (2H, m), 5.32–5.05 (3H, m), 4.68–4.35 (3H, m), 4.01 (3H, s), 2.86–2.59 (2H, m), 1.45 (9H, s), 1.41 (9H, s); $^{13}$C NMR (CDCl$_3$) δ 171.18, 171.09, 165.80, 165.30, 156.71, 156.60, 145.65, 142.76, 142.71, 140.82, 140.72, 133.23, 125.81, 125.72, 118.41, 118.21, 113.07, 112.87, 108.95, 82.16, 70.28, 69.98, 66.52, 66.39, 57.03, 52.57, 52.29, 37.83, 36.86, 28.65. Anal. Calcd. for C$_{20}$H$_{26}$N$_2$O$_7$. 0.6H$_2$O: C, 57.57; H, 6.57; N, 6.72. Found: C, 57.49, H, 6.34, N, 6.60. M.S. (+FAB); 407 (M$^+$+1); 351, 307, 154.

(3S,4R,S) t-Butyl N-(allyloxycarbonyl)-3-amino-4-hydroxy-4-(2-(4-methoxybenzoxazolyl))butanoate (66b), was prepared according to the method described for 66a which afforded 1.29 g (26%, 68% based on recovered starting material) of the title compound as an oil and as a mixture of diastereoisomers at C-4: IR (CH$_2$Cl$_2$) 3400, 1725, 1625, 1505, 1369, 1354, 1281, 1263, 1226, 1158, 1092, 1048; $^1$H NMR (CDCl$_3$) δ 7.34–7.24 (1H, m), 7.16 (1H, d, J=8.2), 6.79 (1H, d, J=7.9), 6.00–5.50 (2H, m), 5.30–5.05 (3H, m), 4.70–4.35 (4H, m), 4.02 (3H, s), 2.90–2.45 (2H, m), 1.45–1.41 (9H, 2×s). Anal. Calcd. for C$_{20}$H$_{26}$N$_2$O$_7$. 0.4H$_2$O: C, 58.07; H, 6.53; N, 6.77. Found: C, 58.09; H, 6.41; N, 6.63. M.S. (+FAB); 407 (M$^+$+1, 88%); 351 (100).

(3S, 4R,S) t-Butyl N-(N-acetyl-(S)-(O-tert-butyl-tyrosinyl)-(S)-valinyl-(S)-alaninyl)-3-amino-4-hydroxy-4-(2-(7-methoxybenzoxazolyl))butanoate (67a). To a stirred solution of the benzoxazole 66a (481.9 mg, 1.19 mmol) and Ac-Tyr ($^t$Bu)-Val-Ala-OH (586.3 mg, 1.30 mmol) in methylene chloride (3.5 ml) and DMF (3.5 ml) was added bis(triphenylphosphine) palladium (II) chloride (18.0 mg), followed by tributyltinhydride (0.80 ml, 2.96 mmol) dropwise. Hydroxybenzotriazole (320.4 mg, 2.37 mmol) was added and the mixture cooled to 0° C. 1-Ethyl-3-[3-(dimethylamino)propyl]carbodiimide hydrochloride (278.2 mg, 1.42 mmol) was added and the mixture was allowed to warm to room temperature and stirred for 16.5 h. The reaction was diluted with ethyl acetate and washed twice with 1M sodium hydrogensulphate, twice with saturated sodium bicarbonate, water, and brine. The organic layer was dried (MgSO$_4$), filtered and reduced in vacuo to yield 2.0 g of crude product. Flash chromatography (95:5 methylene chloride/methanol) gave 844.0 mg (94%) of the title compound as a white solid: m.p. 205° C.; IR (KBr) 3399, 3304, 2977, 1729, 1643, 1506, 1367, 1290, 1161; $^1$H NMR (d$_6$-DMSO) δ 8.24–7.78 (4H, m), 7.43–7.32 (2H, m), 7.23 (2H, d, J=8.5), 7.16–7.07 (1H, m), 6.93 (2H, d, J=8.5), 6.52, 6.40 (1H, 2×d, J=5.5, J=5.0) 5.03, 4.78–4.49, 4.45–4.16 (5H, brt, 2×m), 4.05, 4.04 (3H, 2×s), 3.08–2.35 (14H, m), 2.11–1.89 (1H, m), 1.83 (3H, s), 1.49–1.32, 1.15, 1.0–0.81 (27H, s, 2×m, J=7.0); $^{13}$C NMR (d$_6$-DMSO) δ 175.55, 175.18, 173.88, 173.75, 173.05, 169.23, 157.28, 148.55, 146.16, 143.21, 136.63, 133.55, 128.87, 127.17, 115.78, 111.92, 84.02, 81.50, 71.40, 61.15, 60.05, 57.79, 53.39, 51.62, 43.76, 40.52, 34.58, 32.52, 31.60, 26.35, 23.11, 22.71, 21.76. Anal. Calcd. for C$_{39}$H$_{55}$N$_5$O$_{10}$. 0.5H$_2$O: C, 61.40; H, 7.40; N, 9.18. Found: C, 61.43; H, 7.31; N, 9.07. M.S. (+FAB); 754 (M$^+$+1); 698, 338, 267.

(3S, 4R, S) t-Butyl N-(N-acetyl-(S)-(O-tert-butyl-tyrosinyl)-(S)-valinyl-(S)-alaninyl)-3-amino-4-hydroxy-4-(2-(4-methoxybenzoxazolyl))butanoate (67b), was prepared according to the method described for 67a which afforded 1.05 g (94%) of the title compound as a fine white powder: m.p. 210–213° C. (dec); IR (KBr) 3284, 2977, 1736, 1691, 1632, 1536, 1505, 1452, 1392, 1367, 1258, 1236, 1161, 1091; $^1$H NMR (d$_6$-DMSO) δ 8.20–7.75 (4H, m), 7.40–7.10 (4H, m), 7.00–6.80 (3H, m), 6.45, 6.34 (1H, 2×d, J=5.3, J=5.0), 5.00–4.10 (5H, m), 4.00, 3.99 (3H, 2×s), 3.00–2.25 (4H, m), 1.95 (1H, m), 1.78 (3H, s), 1.39–0.80 (27H, m). Anal. Calcd. for C$_{39}$H$_{55}$N$_5$O$_{10}$. 0.5H$_2$O: C, 61.40; H, 7.40; N, 9.18. Found: C, 61.58; H, 7.38; N, 8.91. M.S. (+FAB); 754 (M$^+$+1, 30%); 72 (100).

(3S) t-Butyl N-(N-acetyl-(S)-(O-tert-butyl-tyrosinyl)-(S)-valinyl-(S)-alaninyl)-3-amino-4-(2-(7-methoxybenzoxazolyl))-4-oxobutanoate (68a). The Dess-Martin reagent (1.082 g, 2.55 mmol) (Ireland et al., *J. Org. Chem.*, 58, p. 2899 (1993); Dess et al.,*J. Org. Chem.*, 48, pp. 4155–4156 (1983)) was added to a stirred suspension of the alcohol 67a (641.0 mg, 0.85 mmol) in methylene chloride (46.0 ml). The resulting mixture was stirred for 1 h before being partitioned between saturated sodium thiosulphate: saturated sodium bicarbonate (1:1, 86.0 ml) and ethyl acetate (86.0 ml). The resultant organic phase was washed in turn with saturated sodium thiosulphate: saturated sodium bicarbonate (1:1), saturated sodium bicarbonate, and brine. The organic phase was dried (MgSO$_4$), filtered and reduced in vacuo to give 660.0 mg of crude product. Flash chromatography (94:6 methylene chloride/methanol) gave 636.0 mg (100%) of the title compound as a white solid: m.p. 209° C.; [α]$_D^{24}$−21.8° (c 0.16, methanol); IR (KBr) 3395, 3294, 2977, 1722, 1641, 1535, 1505, 1161; $^1$H NMR (CDCl$_3$) δ 8.43–8.16 (1H, m), 7.97–7.62 (2H, m), 7.49–7.14 (3H, m), 7.08–6.95 (3H, m), 6.89–6.73 (2H, m), 5.81–5.68 (1H, m), 5.16–4.86 (2H, m), 4.53 (1H, brt), 4.03 (3H, s), 3.16–2.84 (4H, m), 2.11–1.84 (4H, m), 1.46–1.14 (21H, m), 0.92–0.78 (6H, m); $^{13}$C NMR (CDCl$_3$) δ 186.28, 173.39, 171.90, 171.19, 171.03, 169.89, 156.43, 154.75, 146.32, 142.88, 140.98, 132.31, 130.54, 126.98, 124.73, 114.95, 111.42, 82.44, 78.71, 58.92, 57.20, 54.91, 53.47, 48.77, 39.43, 38.15, 32.79, 29.44, 28.60, 23.55, 20.27, 19.70, 19.34. M.S. (+FAB); 752 (M$^+$+1); 696, 336, 265.

(3S) t-Butyl N-(N-acetyl-(S)-(O)-tert-butyl-tyrosinyl)-(S)-valinyl-(S)-alaninyl)-3-amino-4-(2-(4-methoxybenzoxazolyl))-4-oxobutanoate (68b), was prepared according to the method described for the ketone 68a which afforded 420 mg (55%) of the title compound as a white solid: m.p. 211–213° C. (dec); [α]$_D^{24}$−23.9° (c 0.82, methanol); IR (KBr) 3277, 3075, 1723, 1690, 1632, 1530, 1506, 1392, 1366, 1269, 1234, 1160, 1094; $^1$H NMR (CDCl$_3$) δ 8.15 (1H, brs), 7.7 (2H, brs), 7.46 (1H, t, J=8.3), 7.24 (2H, d, J=8.3), 7.10 (1H, brs), 7.03 (2H, d, J=8.3), 6.83 (3H, m), 5.74 (1H, q, J=6.9), 5.00 (2H, m), 4.51 (1H, t, J=7.0), 4.07 (3H, s), 3.20–2.95 (4H, m), 2.00 (4H, m), 1.42 (3H, d, J=6.8), 1.35 (9H, s), 1.23 (9H, s), 0.86 (6H, d, J=6.7). M.S. (+FAB); 752 (M$^+$+1, 7%); 72 (100).

(3S) N-(N-Acetyl-(S)-tyrosinyl-(S)-valinyl-(S)-alaninyl)-3-amino-4-(2-(7-methoxybenzoxazolyl))-4-oxobutanoate (69a; R). A solution of the ester 68a (600.0 mg, 0.80 mmol) in a 1:1 mixture of methylene chloride and trifluoroacetic acid (65.0 ml) was stirred for 1 h under a dry atmosphere of $N_2$. The solution was then reduced in vacuo, taken up in ether and reduced again. This process was repeated six times to afford the crude product as an off white solid. Flash chromatography (gradient 95:5 to 80:20 methylene chloride/methanol) gave 420.8 mg (83%) of the title compound as a hygroscopic white solid. The product existed as a mixture of three isomers in $CD_3OD$, consisting of the keto form (c 50%), and its acyloxy keto form (two isomers at C-4, c 50%): m.p. decomposes above 150° C.; $[\alpha]_D^{24}$-33.2° (c 0.17, methanol); IR (KBr) 3300, 1715, 1658, 1650, 1531, 1517, 1204; $^1$H NMR ($CD_3OD$) δ 7.46–7.19 (2H, m), 7.16–6.91 (3H, m), 6.70–6.59 (2H, m), 5.62–5.49 (1H, m), 5.00–4.72 (1H, obscurred m), 4.69–4.51 (1H, m), 4.49–4.08 (2H, m), 4.05–3.89 (3H, m), 3.16–2.47 (4H, m), 2.05–1.78 (4H, m), 1.41–1.11, 1.05–0.70 (9H, 2×m). Anal. Calcd. for $C_{31}H_{37}N_5O_{10}$·$3H_2O$: C, 53.67; H, 6.25; N, 10.10. Found: C, 53.76; H, 5.56; N, 10.28. M.S. (+FAB); 640 ($M^+$+1); 435, 147.

(3S) t-Butyl N-(N-acetyl-(S)-tyrosinyl-(S)-valinyl-(S)-alaninyl)-3-amino-4-(2-(4-methoxybenzoxazolyl))-4-oxobutanoate (69b; S), was prepared according to the method described for the acid 69a which afforded the hygroscopic title compound 252 mg (96%). The product existed as a mixture of three isomers in $CD_3OD$, consisting of the keto form, and its acyloxy ketal form (two isomers at C-4). The product existed as a single isomer in d-6 DMSO: m.p. 200–203° C. (dec.); $[\alpha]_D^{24}$-38.0° (c 0.23, methanol); IR (KBr) 3289, 2968, 1718, 1713, 1658, 1634, 1548, 1517, 1506, 1461, 1453, 1393, 1369, 1268, 1228, 1174, 1092; $^1$H NMR ($d_6$-DMSO) δ 9.20 (1H, brs), 8.71 (1H, d, J=6.2), 8.10 (2H, m), 7.83 (1H, d, J=8.7), 7.61 (1H, t, J=8.2), 7.46 (1H, d, J=8.2), 7.08 (3H, m), 6.65 (2H, d, J=8.3), 5.50 (1H, q, J=6.5), 4.50 (1H, m), 4.37 (1H, m), 4.20 (1H, m), 4.05 (3H, s), 3.09–2.77 (4H, m), 1.94 (1H, m), 1.79 (3H, s), 1.23 (3H, d, J=7.0), 0.82 (6H, m). Anal. Calcd. for $C_{31}H_{37}N_5O_{10}$·$1.5H_2O$: C, 55.85; H, 6.05; N, 10.51. Found: C, 55.21; H, 5.69; N, 10.13. M.S. (+FAB); 640 ($M^+$+1, 22%); 107 (100).

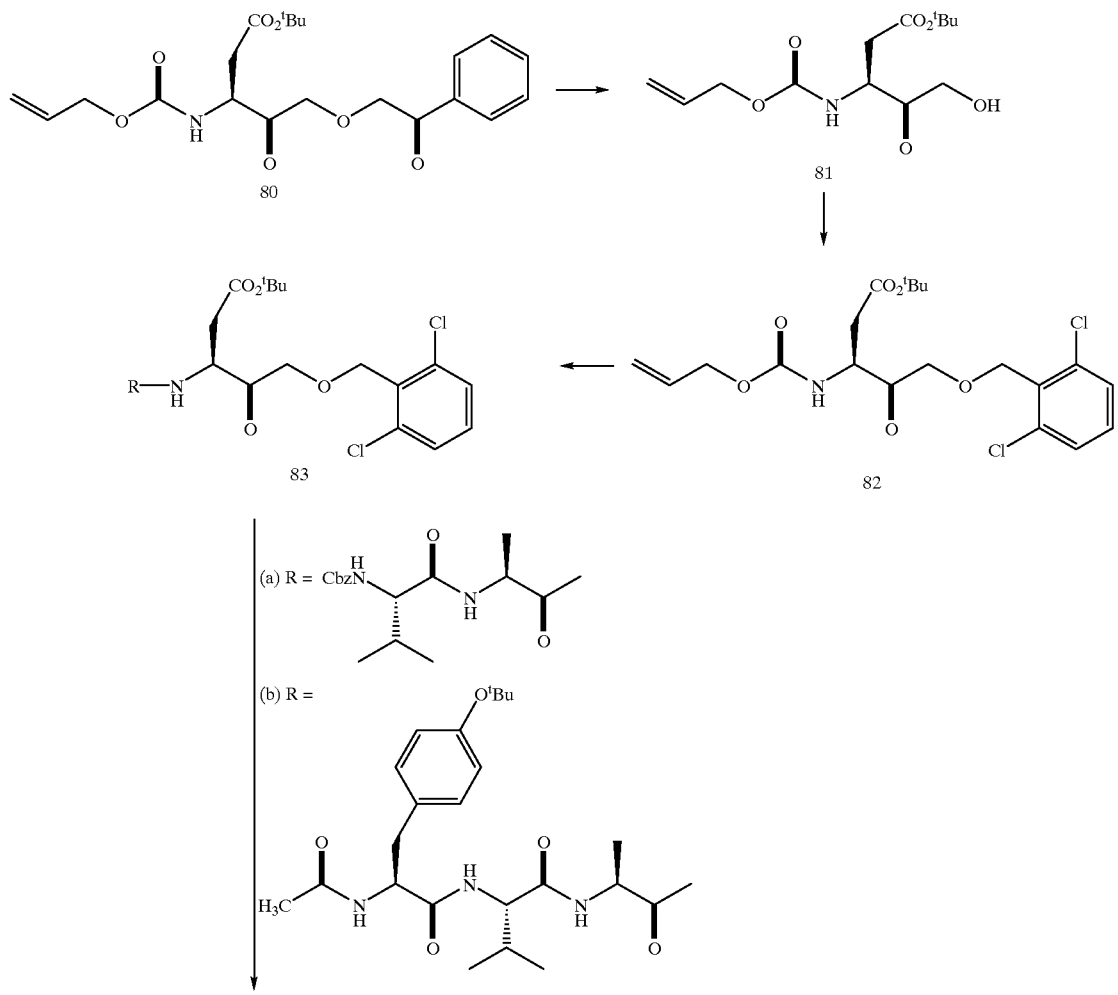

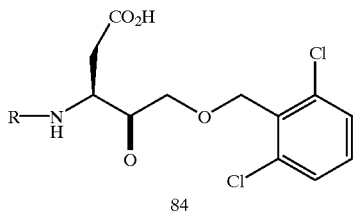

84

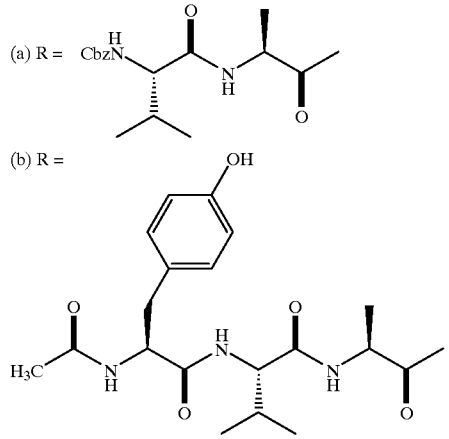

(a) R =

(b) R =

20

3S) t-Butyl N-(allyloxycarbonyl)-3-amino-4-oxo-5-(1,2-dioxo-2-phenylethyloxy)-pentanoate (80). Potassium fluoride (792 mg, 13.6 mmol) and then benzoyl formic acid (1.02 g, 6.82 mmol) were added to a stirred solution of (3S) t-butyl N-(allyloxycarbonyl)-3-amino-5-bromo-4-oxo-pentanoate (WO 93 16710) (2.17 g, 6.20 mmol) in dimethylformamide (30 ml). The mixture was stirred for 140 mins, quenched with water (50 ml) and extracted with ethyl acetate (2×50 ml). The combined organic extracts were washed with water (4×50 ml) then brine (50 ml). They were dried (MgSO$_4$) and concentrated to afford an oil which was purified by flash chromatography (20–45% ethyl acetate in hexane) to afford 2.44 g (94%) of a colorless oil: $[\alpha]_D^{20}$-35.0° (c 1.41, CH$_2$Cl$_2$); IR (film) 3359, 2981, 2938, 1752, 1740, 1726, 1712, 1512, 1369, 1285, 1177, 1053, 991, 939, 688; $^1$H NMR (CDCl$_3$) δ 8.15 (2H, m), 7.66 (1H, m), 7.53 (2H, m), 5.90 (2H, m), 5.33 (2H, m), 5.31 (1H, d, J=16.9), 5.18 (1H, d, J=16.9), 4.63 (3H, m), 3.03 (1H, dd, J=17.3, 4.6), 2.74 (1H, dd, J=17.3, 4.9), 1.44 (9H, s). MS (C.I.) 420 (M$^+$+1 20%); 364 (100).

(3S) t-Butyl N-(allyloxycarbonyl)-3-amino-5-hydroxy-4-oxo-pentanoate (81). A mixture of the ester 80 (2.40 g, 5.71 mmol), tetrahydrofuran (200 ml) and 1M aqueous potassium bicarbonate (200 ml) was vigorously stirred at room temperature for 18 h. The layers were separated and the aqueous portion extracted with ethyl acetate (100 ml). The combined organic extracts were washed with brine (100 ml), dried (MgSO$_4$) and concentrated. The residue was purified by flash chromatography (10–60% ethyl acetate in hexane) to afford 1.48 g (90%) of pale yellow oil: $[\alpha]_D^{20}$-5.9 (c 1.06, CH$_2$Cl$_2$); IR (film) 3345, 2981, 2936, 1739, 1725, 1712, 1692, 1515, 1368, 1259, 1158, 1051; $^1$H NMR (CDCl$_3$) δ 5.92 (2H, m), 5.30 (2H, m), 4.36–4.69 (5H, m), 3.05 (1H, dd, J=17.4, 4.3), 2.93 (1H, t), 2.70 (1H, dd, J=17.4, 4.9), 1.43 (9H, s). Anal. Calcd for C$_{18}$H$_{21}$N$_1$O$_6$. 0.25H$_2$O: C, 53.51; H, 7.43; N, 4.80. Found: C, 53.61; H, 7.18; N, 4.71. MS (C.I.) 280 (M$^+$+1, 87%); 232 (100).

(3S) t-Butyl N-(allyloxycarbonyl)-3-amino-5-(2,6-dichlorophenyl-methoxy)-4-oxo-pentanoate (82). A stirred mixture of alcohol 81 (1.44 g, 5.0 1mmol), 2,6-dichlorobenzyl iodide (Abraham et al., J. Chem. Soc., pp. 1605–1607 (1936)) (4.31 g, 15.0 mmol), silver oxide (2.32 g, 10.0 mmol) and dichloromethane (25 ml) was heated under reflux for 45 h. The mixture was allowed to cool to room temperature then diluted with water (50 ml) then extracted with ethyl acetate (50 ml, 25 ml). The organic layer was washed with water (50 ml) then brine (50 ml), dried (MgSO$_4$), and concentrated. The residue was purifed by flash chromatography (10–100% ethyl acetate in hexane) to afford 1.65 g (74%) of a colorless oil: $[\alpha]_D^{20}$+8.8° (c 1.13, CH$_2$Cl$_2$); IR (film) 3339, 2980, 2935, 1724, 1712, 1503, 1438, 1368, 1246, 1156, 1106, 770; $^1$H NMR (CDCl$_3$) δ 7.33 (2H, m), 7.22 (1H, dd), 5.92 (2H, m), 5.28 (2H, m), 4.87 (2H, m), 4.67 (1H, m), 4.58 (2H, br d), 4.56 (1H, d, J=16.9), 4.31 (1H, d, J=16.9), 3.04 (1H, dd, J=16.7, 4.5), 2.77 (1H, dd, J=16.7, 4.9), 1.40 (9H, s). Anal. Calcd. for C$_{20}$H$_{25}$Cl$_2$N$_1$O$_6$. 0.25H$_2$O: C, 53.28; H, 5.70; N, 3.11. Found: C, 53.15; H, 5.52; N, 2.98. M.S. (C.I.); 446 (M$^+$, 27%); 390 (100).

(3R,S) t-Butyl N-[N-phenylmethyloxycarbonylvalaninyl-alaninyl]-3-amino-5-(2,6-dichlorophenylmethyloxy)-4-oxo-pentanoate (83a). 1-(3-Dimethylamino-propyl)-3-ethylcarbodiimide hydrochloride (379 g, 1.98 mmol) and 1-hydroxybenzotriazole (486 mg, 3.60 mmol) were added to a stirred solution of N-phenyl-methyloxycarbonylvalinyl-alanine (637 mg, 1.98 mmol) in tetrahydrofuran (40 ml) and water (1 ml). The mixture was stirred for 15 mins and then the ether 82 (802 mg, 1.80 mmol) and bis (triphenylphosphine)palladium (II) chloride (ca 5 mg) were added. Tributyltin hydride (785 mg, 725 1, 2.70 mmol) was then added dropwise during 20 mins and the resulting solution was stirred for 3.75 h and then quenched with 1M hydrochloric acid (50 ml). The mixture was extracted twice with ethyl acetate. The combined organic extracts were washed with 1M hydrochloric acid, twice with aqueous sodium bicarbonate, water and then brine, dried (MgSO$_4$) and concentrated. The residue was purified by flash chromatography (10–30% ethyl acetate—dichloromethane) to afford 941 mg (79%) of pale yellow solid: m.p. 148–52° C.; IR (KBr) 3287, 3070, 1730, 1691, 1641, 1536, 1369, 1289, 1247, 1156; $^1$H NMR (CDCl$_3$) δ 7.33 (8H, m), 7.23 (1H, dd), 6.61 (1H, br, d), 5.42 (1H, br, d), 5.11 (2H, s), 4.85 (3H, m), 4.50 (1H, m), 4.40 (1H, d, J=16.9), 4.26 (1H, d, J=16.9), 4.02 (1H, m), 2.99 (1H, dd, J=16.8, 4.7), 2.73 (1H, dd, J=16.8, 5.0), 2.09 (1H, m), 1.37 (12H, m), 0.96 (3H, d, J=6.9), 0.91 (3H, d, J=6.8). Anal. Calcd. for C$_{32}$H$_{41}$Cl$_2$N$_3$O$_8$. 0.25H$_2$O: C, 57.25; H, 6.23; Cl, 10.57; N, 6.26. Found: C, 57.18; H, 6.23; Cl, 10.58; N, 5.95. M.S. (+FAB); 667 (M$^+$1, 1%); 666 (3), 159 (25), 91 (100).

(3R, S) t-Butyl N-[(N-acetyl-O-t-butyltyrosinyl)-valaninyl-alaninyl]-3-amino-5-(2,6-dichlorophenylmethyloxy)-4-oxo-pentanoate (83b), was prepared by the method described for 83a to afford 554 mg (64%) of colorless solid: m.p. 184–6° C.; IR (KBr) 3282, 3075, 1736, 1690, 1633, 1536, 1508, 1366, 1236, 1161; $^1$H NMR (d$_6$-DMSO) δ 8.49 (1H, d), 8.14 (1H, d), 8.08 (1H, d), 7.84 (1H, d), 7.43 (3H, m), 7.14 (2H, d), 6.83 (2H, d), 4.71 (2H, s), 4.51 (2H, m), 4.36 (2H, dd), 4.17 (2H, m), 2.93 (1H, m), 2.73 (1H, m), 1.94 (1H, m), 1.74 (3H, s), 1.37 (9H, s), 1.23 (12H, m), 0.83 (6H, m). M.S. (+FAB); 793 (M$^+$1, 4%); 737 (5), 681 (1), 178 (40), 159 (45), 136 (100), 107 (40). MS. (-FAB); 792 (20), 791 (40), 447 (100).

(R,S) N-[N-(Phenylmethyloxy)carbonyl-valinyl-alaninyl]-3-amino-5-(2,6-dichlorophenylmethyloxy)-4-oxo-pentanoic acid (84a; V). Trifluoroacetic acid (5 ml) was added to a stirred solution of the ester 83a, (918 mg, 1.38 mmol) in dichloromethane (20 ml). The mixture was stirred for 2.5 h then evaporated to dryness. The residue was treated with ether (25 ml) and evaporated to dryness. This procedure was repeated three times. The resulting product was triturated with ether (10 ml) and then dried to afford 730 mg (87%) of light brown powder: m.p. 156–60° C.; IR (KBr) 3282, 2965, 1702, 1694, 1642, 1536, 1438, 1246, 1230; $^1$H NMR (d$_6$-DMSO) δ 8.48 (1H, d), 8.09 (1H, d), 7.47 (9H, m), 5.02 (2H, s), 4.70 (2H, s), 4.49 (1H, m), 4.37 (2H, dd), 4.27 (1H, m), 3.88 (1H, m), 2.75 (1H, dd), 2.54 (1H, dd), 1.96 (1H, m), 1.19 (3H, s), 0.84 (6H, m). Anal. Calcd. for C$_{28}$H$_{33}$Cl$_2$N$_3$O$_8$·0.5H$_2$O: C, 54.27; H, 5.53; Cl, 11.45; N, 6.78. Found: C, 54.49; H, 5.39; Cl, 11.33; N, 6.73. M.S. (+FAB); 610 (M$^+$1, 10%); 91 (100).

(R,S) N-[N-(Acetyl)tyrosinyl-valinyl-alaninyl]-3-amino-5-(2,6-dichlorophenylmethyloxy)-4-oxo-pentanoic acid (84b; W), was obtained as a colorless powder (95%) by the method used for 84a. m.p. 165–8° C.: IR (KBr) 3295, 2968, 1733, 1642, 1517, 1438, 1231, 1105; $^1$H NMR (d$_6$-DMSO) 9.2 (1H, br, s), 8.48 (1H, br, d), 8.14 (1H, br, d), 8.02 (1H, br, d), 7.81 (1H, br, d), 7.45 (3H, m), 7.02 (2H, d), 6.62 (2H, d), 4.70 (2H, s), 4.12–4.53 (3H, m), 3.60 (3H, m), 2.51–2.92 (4H, m), 1.96 (1H, m), 1.75 (3H, s), 1.21 (3H, d), 0.83 (6H, m). Anal. Calcd. for C$_{31}$H$_{38}$Cl$_2$N$_4$O$_9$·H$_2$O: C, 53.22; H, 5.76; Cl, 10.14; N, 8.09. Found: C, 53.33; H, 5.54; Cl, 10.02; N, 7.85. M.S. (+FAB); 682 (M$^+$2, 30%); 681 (67), 158 (100). (-FAB); 680 (45), 679 (100).

EXAMPLE 6

We obtained inhibition constants (K$_i$) and IC$_{50}$ values for several compounds of this invention using enzyme assays with UV-visible substrate, fluorescent substrate, and cell assays as described in Example 2. The following K$_i$ and IC$_{50}$ values were determined for compounds 22e, 54b, 54j, 54k, 57b, 85, 86, 87, 88, 89, 90, 91, 92, 98, 102a–c, 106a–c, 108a–c, 114a, 114b, 115, 121, 125a, 125b, 126, 127, 128, 129, 130, 131, 132a, 132b, 133, 135a, 135b, 136, 137, 138, 139, 140, 141, 142, 144, 145, 146, 147, 148, 149, 150, 151, 152, 153, 154, 155, 156, 157, 158, 159, 160, 161, 162, and 163 using the indicated assays. The structures of compounds 22e, 54b, 54j, 54k, and 57b are shown in Example 5. The other compound structures are shown in Example 7.

| | Assay | |
|---|---|---|
| Compound | UV-visible K$_i$ (μM) | Cell IC$_{50}$ (μM) |
| 22e | 0.19 | >20 |
| 54b | | 20 |
| 54j | | 10 |
| 54k | | 6.6 |
| 57b | | 2.2 |

-continued

| | Assay | |
|---|---|---|
| Compound | UV-visible K$_i$ (μM) | Cell IC$_{50}$ (μM) |
| 85 | 0.0035 | 9.8 |
| 86 | 0.175 | 4.0 |
| 87 | 7.2 | 35.0 |
| 88 | 0.9 | |
| 89 | 0.018 | |
| 90 | 0.42 | 6.2 |
| 91 | 0.26 | >25 |
| 92 | 3.8 | |
| 98 | 0.535 | 4.0 |
| 102a | | 4.0 |
| 102b | 0.29 | 1.75 |
| 102c | 0.68 | |
| 106a | 2.3 | 30.0 |
| 106b | 0.2 | 2.9 |
| 106c | 3.8 | >30.0 |
| 108a | | 17.5 |
| 108b | 0.4 | 25.0 |
| 108c | 0.43 | |
| 114a | 0.12 | 3.8 |
| 114b | 3.7 | |
| 115 | 0.345 | 6.0 |
| 121 | 4.3 | |
| 125a | 0.39 | >30.0 |
| 125b | 0.060 | 0.30 |
| 126 | 0.45 | 1.5 |
| 127 | 0.39 | 8.0 |
| 128 | 0.04 | 7.5 |
| 129 | 0.59 | 25.0 |
| 130 | | 1.20 |
| 131 | 12.0 | 30.0 |
| 132a | 5.0 | >30.0 |
| 132b | 12.5 | |
| 133 | 50.0 | >30.0 |
| 135a | 0.090 | 0.90 |
| 135b | 0.32 | 0.95 |
| 136 | | 1.0 |
| 137 | 0.04 | 0.25 |
| 138 | | 0.375 |
| 139 | 0.350 | 2.0 |
| 140 | 0.87 | >30.0 |
| 141 | 0.670 | |
| 142 | | 1.75 |
| 144 | 0.32 | >20.0 |
| 145 | 0.34 | 8.5 |
| 146 | 0.16 | 3.8 |
| 147 | 0.26 | 8.5 |
| 148 | 6.3 | 30.0 |
| 149 | 14.0 | >30.0 |
| 150 | 10.0 | 30.0 |
| 151 | 13.0 | 30.0 |
| 152 | 8.8 | |
| 153 | 0.24 | |
| 154 | 0.042 | 2.4 |
| 155 | 0.023 | |
| 156 | 0.001 | 2.7 |
| 157 | 0.26 | |
| 158 | 1.1 | |
| 159 | 0.0017 | 8.0 |
| 160 | 0.145 | 2.25 |
| 161 | 0.011 | |
| 162 | 0.0025 | |
| 163 | 0.0028 | 1.2 |

EXAMPLE 7

Compounds 126, 127, 128, 129, 135a, 135b, 137 144, 145, 146, 147, 148, 149, 150, 151, 152, 153, 154, 155, 156, 157, 159, 160, 162, and 163 were synthesized by a method similar to the method used in the synthesis of 69a.

126
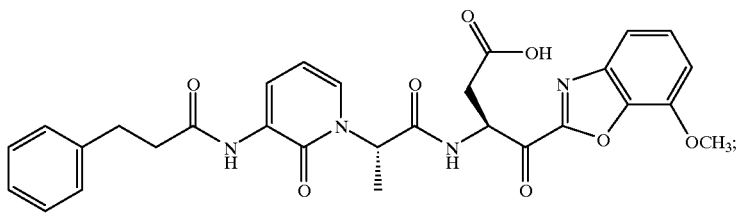
127
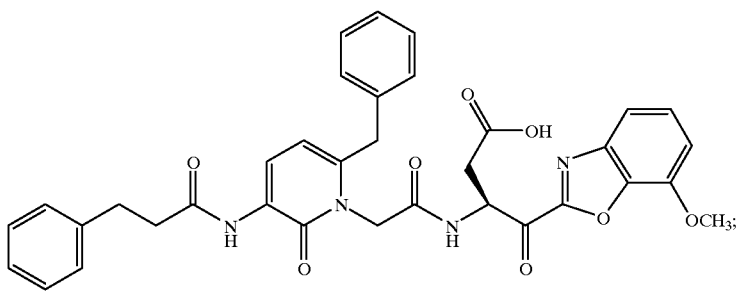
128
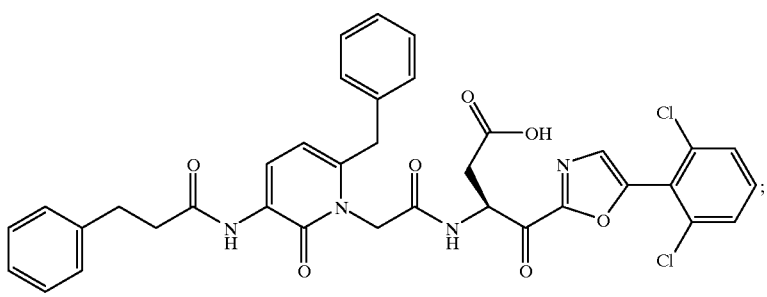
129
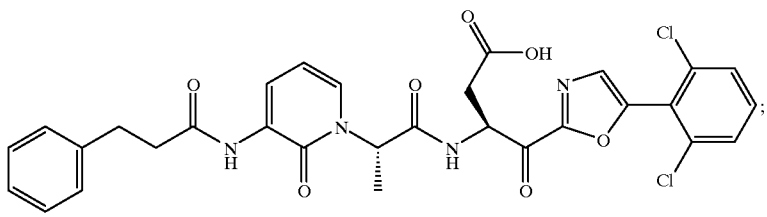
135a
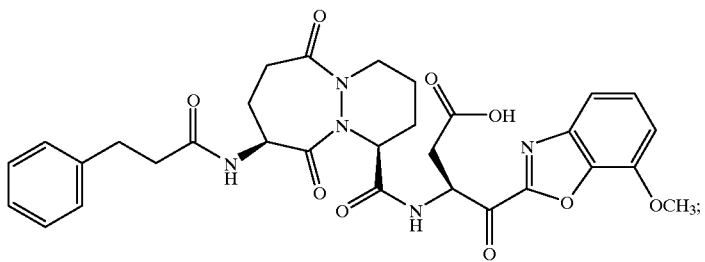
135b
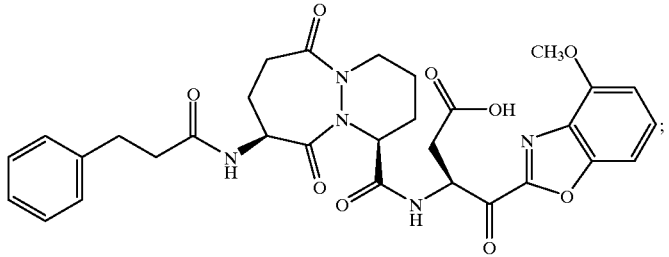

137
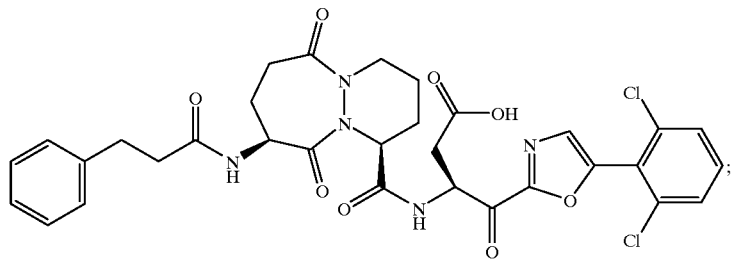
144
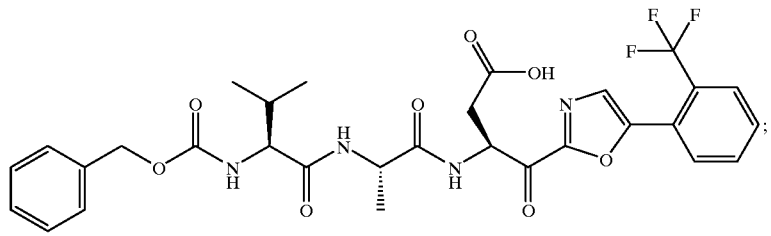
145
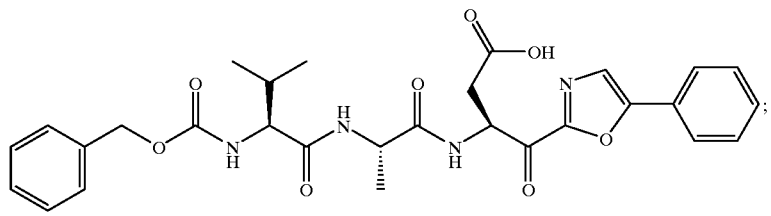
146
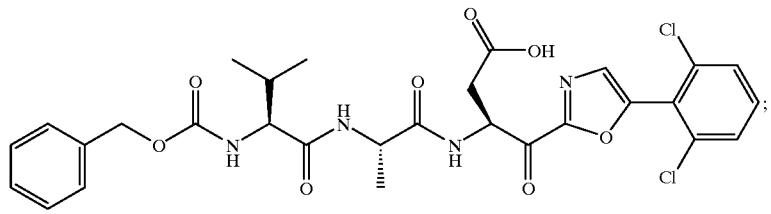
147
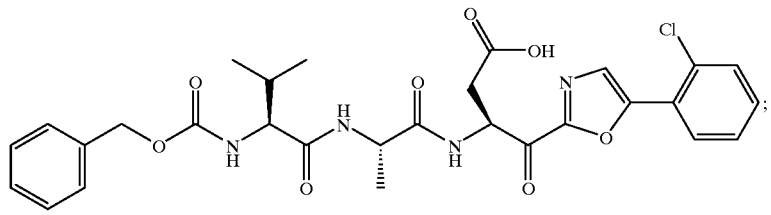
148
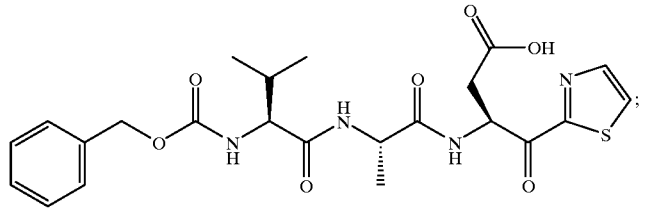

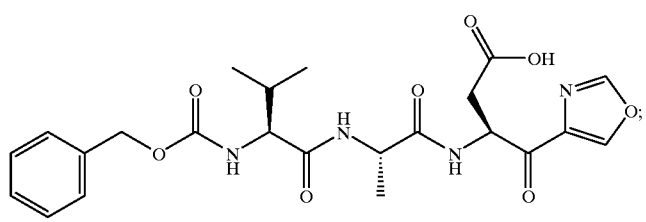
149
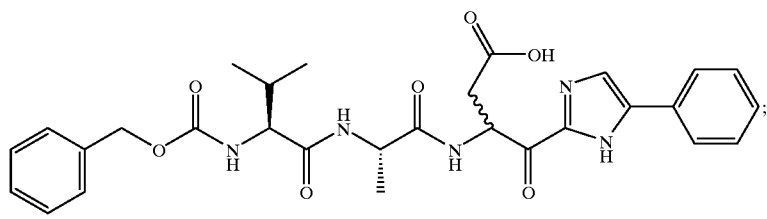
150
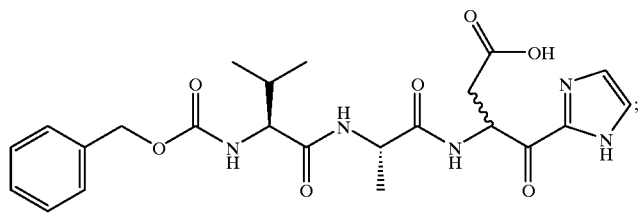
151
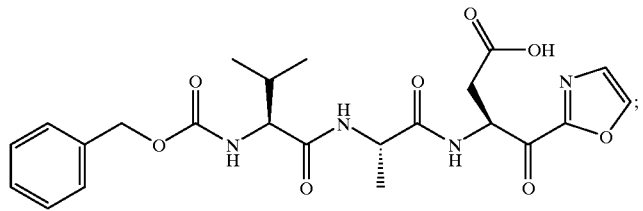
152
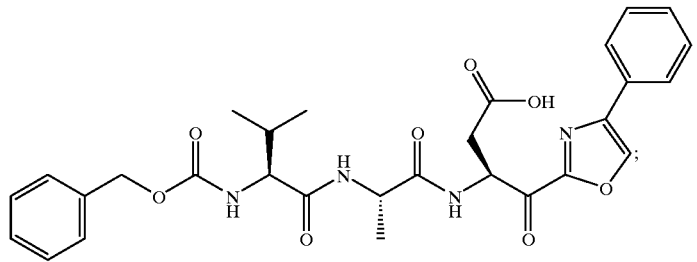
153
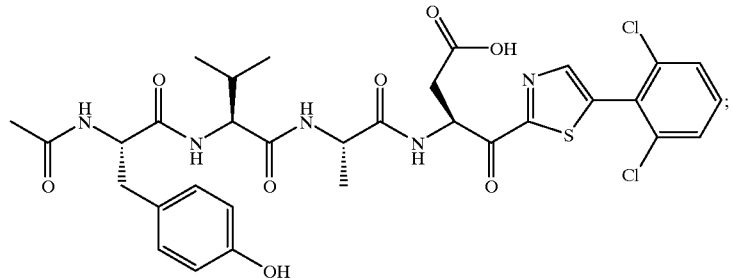
154

155
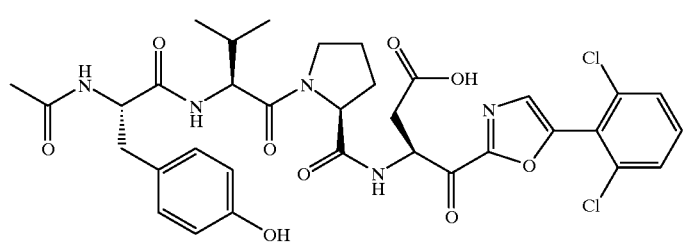
156
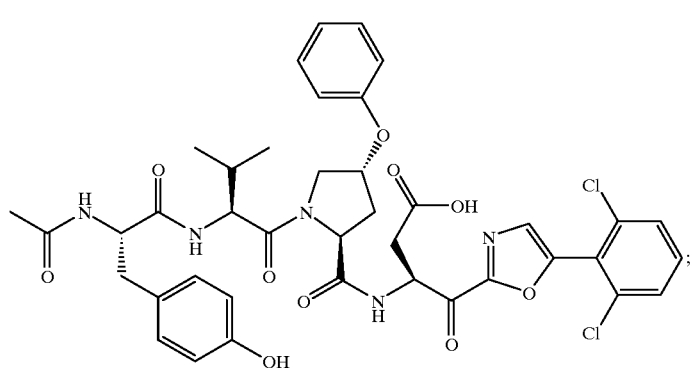
157
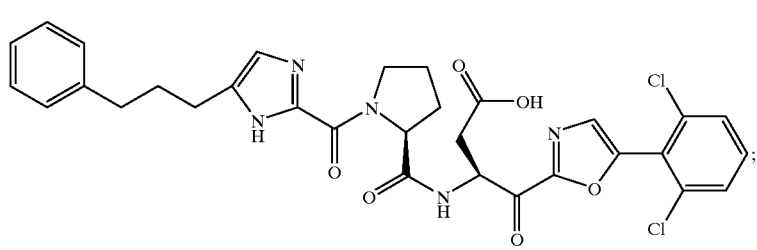
159
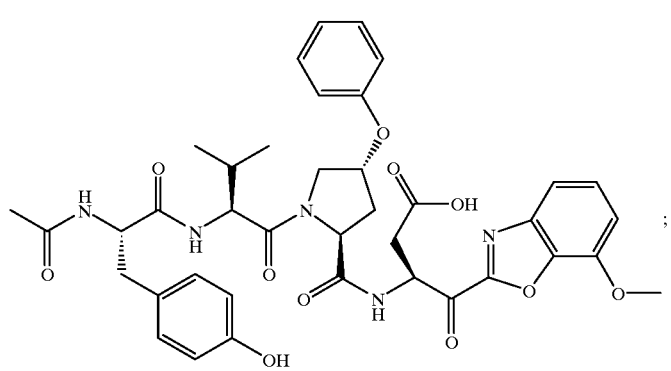
160
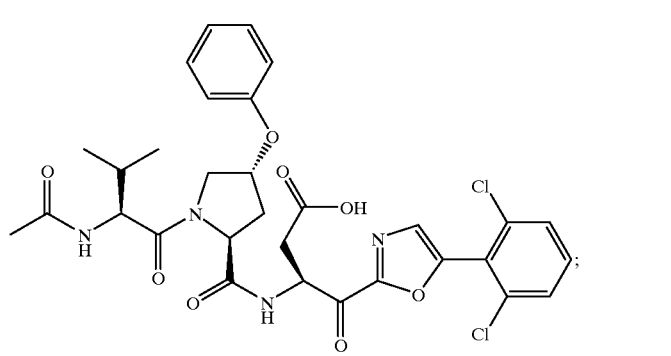

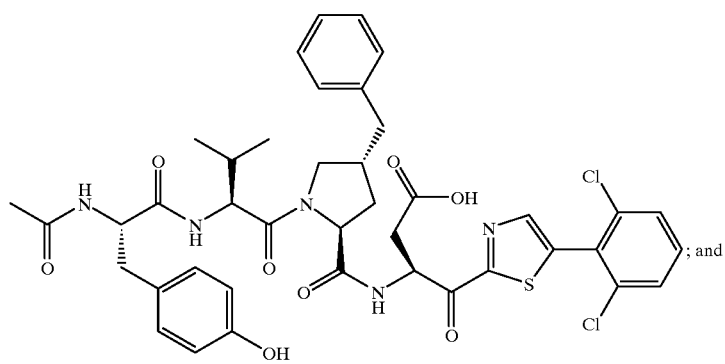
162
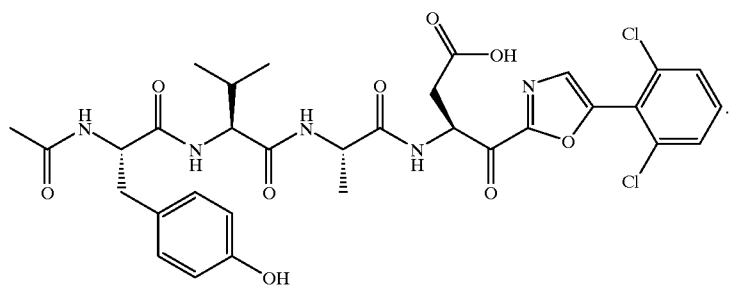
163
Compound 158 was synthesized by a method similar to the method used in the synthesis of (K).
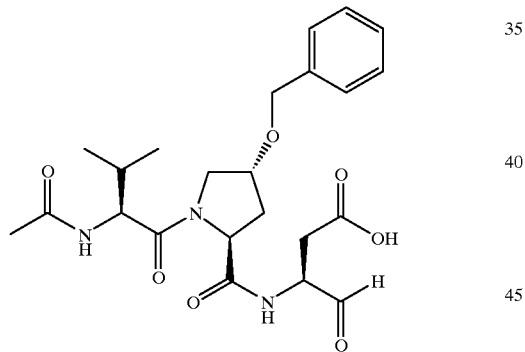
158
Compound 130 was synthesized by a method similar to the method used in the synthesis of 56b.
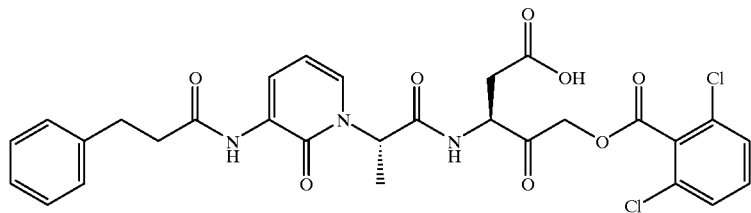
130
Compounds 131, 136, 138, and 142 were synthesized by a method similar to the method used in the synthesis of 57b.

131
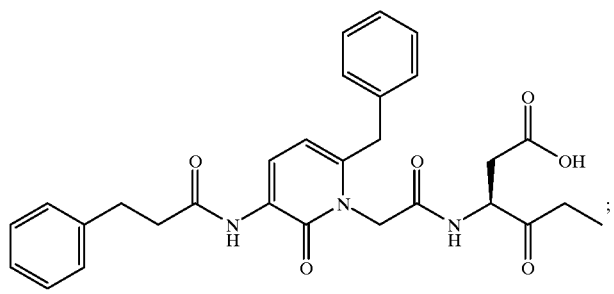
136
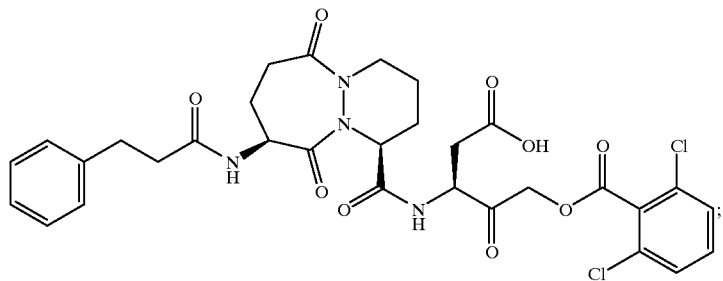
138
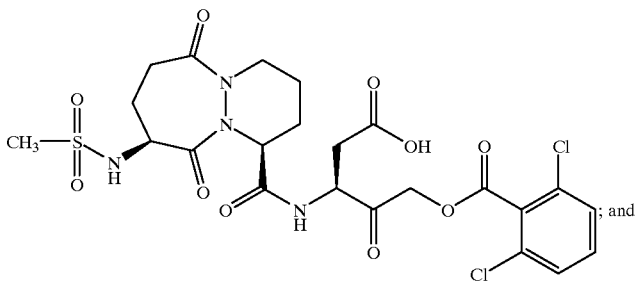
; and
142
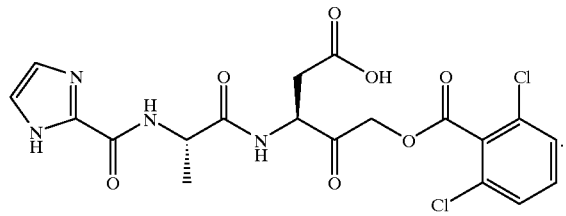
Compounds 132a, 132b, 139, 140, and 141 were synthesized by a method similar to the method used in the synthesis of 47a. The starting material for compound 140 was obtained as described in: Robl, et al., *J. Am. Chem. Soc.*, 116, pp. 2348–2355 (1994). The starting material for compound 141 was obtained as described in: Wyvratt, et al., *Pept. Struct: Funct. Proc.* (*8th Am. Pept. Symp.*), (1983) or U.S. Pat. No. 4,415,496.
132a
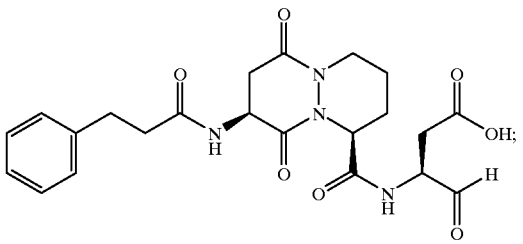

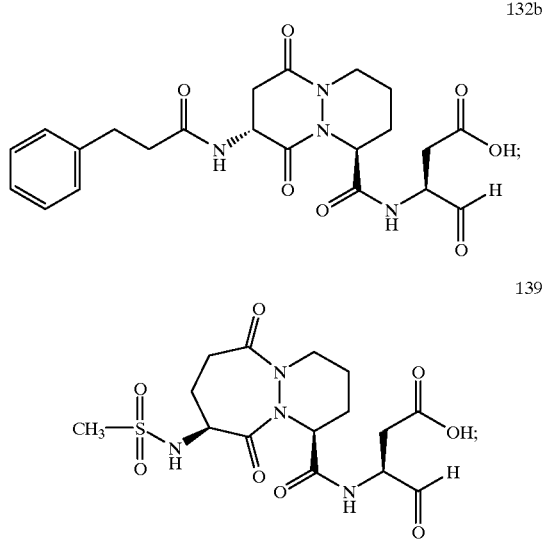
132b
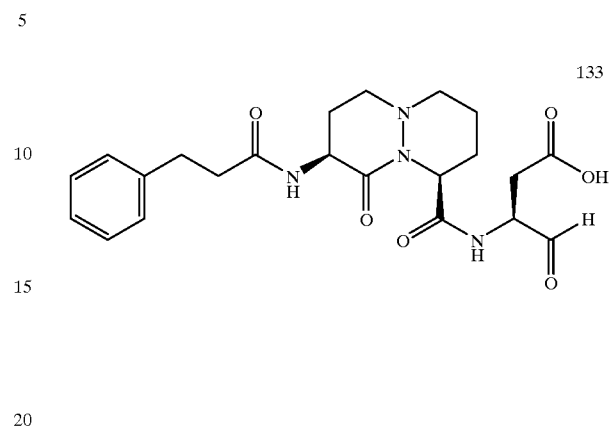
133
Compound 133 was synthesized by a method the method used in the synthesis of 47b.
139
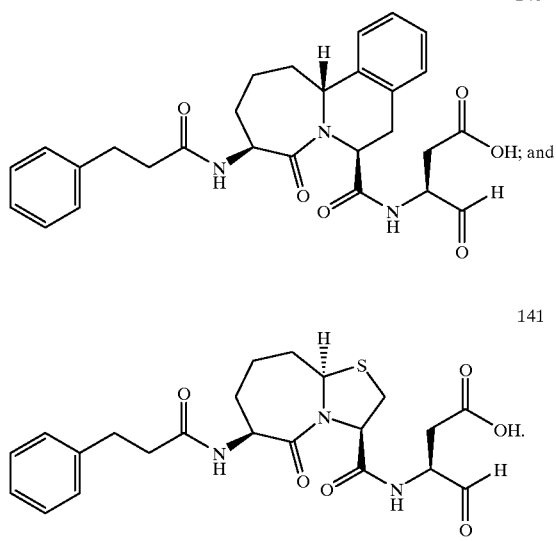
Compound 161 was synthesized by a method the method used in the synthesis of 125a.
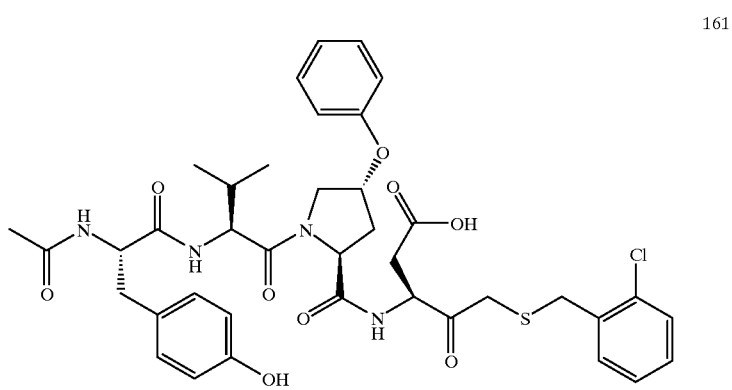
161
-continued
140
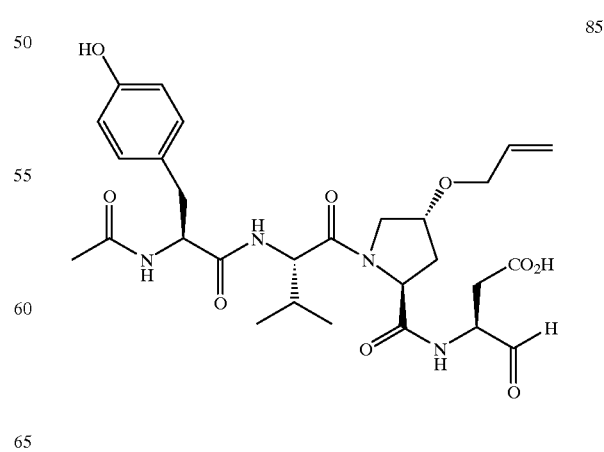
141
Compounds 22e, 54b, 54j, 54k, and 57b were synthesized as described in example 5.
Compounds 85, 86, 87, 88, 89, 90, 91, 92, 98, 102a, 102b, 102c, 106a, 106b, 106c, 108a, 108b, 108c, 114a, 114b, 115, 121, 125a, and 125b were synthesized as follows.
85
N-(N-Acetyl-tyrosinyl-valinyl-(4(R)-allyloxy prolinyl))-3(S)-amino-4-oxobutanoic acid (85).

Step A. N-tert-Butoxycarbonyl-4(R)-allyloxyproline. N-tert-Butoxycarbonyl(4R)-hydroxyproline (9.25 g, 40 mmol) was added to a solution of 60% sodium hydride (3.36 g, 84 mmol) in 100 ml of anhydrous tetrahydrofuran and stirred for 2 hours at room temperature. Allyl bromide (6.9 ml, 80 mmol) was added to the mixture and refluxed for 6 hours. The mixture was quenched with the addition of ice chips, then additional water was added and the mixture was washed with hexane. The aqueous layer was acidified with 10% sodium hydrogen sulfate and extracted with ethyl acetate (2×150 ml). The combined extracts were dried over anhydrous sodium sulfate, filtered and evaporated to give 5 g of the title product with no further purification.

$^1$H NMR (CDCl$_3$; exist as rotamers) δ 5.92–5.82 (1H, m), 5.3–5.14 (2H, m) 4.5–4.31 (1H, m), 4.16–4.05 (1H, m), 4.04–3.9 (1H, m), 3.79–3.5 (3H, m), 2.43–2.2 (1.5H, m), 2.15–2.10 (0.5H, m), 1.45 (4.5H, s), 1.35 (4.5H, s).

Step B. 4(R)-Allyloxyproline methyl ester hydrochloride. N-tert-Butoxycarbonyl-4(R)-allyloxyproline (5 g, 18.4 mmol) was refluxed in 50 ml of saturated methanolic hydrogen chloride for 6 hours. The mixture was evaporated in vacuo to give 3.78 g of a yellow gum as the title compound: $^1$H NMR (CDCl$_3$) δ 5.83–5.72 (1H, m), 5.24–5.14 (1H, d), 5.13–5.08 (1H, d), 4.55–4.3 (3H, m), 4.25–4.15 (1H, m), 3.9 (1.5H, s), 3.78 (1.5H, s), 3.7–3.28 (3H, m), 2.45–2.32 (1H, m), 2.2–2.05 (1H, m).

Step C. N-Acetyl-tyrosinyl-valinyl-(4(R)-allyloxyproline) methyl ester. 4(R)-Allyloxyproline methyl ester hydrochloride (1.05 g, 4.75 mmol) and N-acetyl-Tyr-Val-OH (1.68 g, 5.21 mmol) were dissolved in 10 ml of a 1:1 mixture of dichloromethane and dimethylformamide and cooled to 0° C. Diisopropylethylamine (1 ml, 5.93 mmol) was added to the cooled mixture followed by the addition of N-hydroxybenzotriazole (0.769 g, 5.69 mmol) and 1-(3-Dimethylaminopropyl)-3-ethylcarbodiimide hydrochloride (1.18 g, 6.2 mmol). After stirring for 2 hours, the mixture was warmed to room temperature and stirred for 16 hours. The reaction was poured into 150 ml of ethyl acetate and washed with 50 ml each of water, 10% sodium hydrogen sulfate, and 10% sodium bicarbonate. The organic layer was dried over sodium sulfate, filtered, and evaporated to give a light yellow solid. This was purified by flash chromatography eluting with dichloromethane/methanol/pyridine (100:3:0.5) to give 780 mg of the title compound. $^1$H NMR (CD$_3$OD) δ 7.02–6.96 (2H, d), 6.67–6.63 (2H, d), 5.95–5.85 (1H, m), 5.34–5.27 (1H, d), 5.16–5.13 (1H, d), 4.53–4.38 (3H, m), 4.28–4.22 (1H, m), 4.12–3.97 (3H, m), 3.82–3.73 (1H, m), 3.72 (3H, s), 3.04–2.88 (2H, m), 2.85–2.72 (2H, m), 2.45–2.34 (1H, m), 2.08–1.95 (2H, m), 1.92 (3H, s), 1.00–0.92 (6H, 2×d).

Step D. N-(N-Acetyl-tyrosinyl-valinyl-(4(R)-allyloxyprolinyl))-3(S)-amino-4-oxobutanoic acid tert-butyl easter semicarbazone. N-Acetyl-tyrosinyl-valinyl-(4-allyloxyproline) methyl ester (770 mg, 1.57 mmol) was dissolved in 20 ml of tetrahydrofuran and 4 ml of methanol. Lithium hydroxide (145 mg, 3.46 mmol) was added to the mixture and stirred at room temperature. After two hours, 1 ml of 10% hydrogen chloride was added and the mixture evaporated in vacuo to give a solid residue then partitioned between 5 ml of water and 50 ml of ethyl acetate and the organic layer separated and evaporated in vacuo to give 430 mg of the acid that waa used immediately in the next step.

N-Acetyl-tyrosinyl-valinyl-4-allyloxyproline (420 mg, 0.88 mmol) and 3-amino-4-oxobutyric acid tert-butyl ester semicarbazone (184 mg, 0.8 mol, Graybill et al., *Int. J. Protein Res.*, 44, pp. 173–82 (1994)) to give 100 mg (20%) of the title compound as a white amorphous solid: $^1$H NMR (CD$_3$OD) δ 7.24–7.2 (1H, m), 7.04–6.97 (2H, d), 6.73–6.65 (2H, d), 5.98–5.86 (1H, m), 5.35–5.24 (1H, d), 5.17–5.12 (1H, m), 4.12–3.98 (2H, m), 3.72–3.67 (1H, m), 2.98–2.92 (3H, m), 2.38–2.32 (1H, m), 2.1–2.02 (2H, m), 1.92 (3H, s), 0.98–0.89 (6H, 2×d).

Step E. N-(N-Acetyl-tyrosinyl-valinyl-(4(R)-allyloxyprolinyl))-3(S)-amino-4-oxobutanoic acid (85). N-(N-Acetyl-tyrosinyl-valinyl-(4(R)-allyloxyprolinyl))-3(S)-amino-4-oxobutanoic acid tert-butyl ester semicarbazone (100 mg) was deprotected as described (Example 3, compound K, Step C) to give 44.2 mg (53%) of the title compound: $^1$H NMR (CD$_3$OD) δ 7.04–6.97 (2H, d), 6.72–6.65 (2H, d), 5.97–5.86 (1H, m), 5.32–5.25 (1H, d), 5.17–5.12 (1H, d), 4.62–4.40 (3H, m), 4.30–4.13 (2H, m), 4.12–3.96 (3H, m), 3.75–3.68 (1H, m), 2.99–2.92 (1H, m), 2.78–2.70 (1H, m), 2.70–2.48 (2H, m), 2.35–2.30 (1H, m), 2.17–1.95 (2H, m), 1.92 (3H, S), 0.98–0.88 (6H, 2×d).

Compounds 86 and 87 were prepared by a similar method described for the synthesis of 69a in example 5:

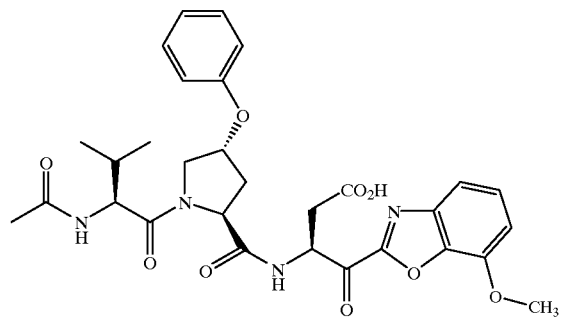

86

N-Acetyl-(S)-valinyl-(4-(S)-phenoxy)prolinyl-3(S)-amino-4-(7-methoxybenzoxazol-2-yl)-4-oxo-butanoic acid (86). N-Acetyl-(S)-valinyl-(S)-(4-(S)-phenoxy)proline was converted to 86 as a white powder: $^1$H NMR (DMSO-d$_6$) δ 8.75(d, 1H), 7.6–7.2(m, 4H), 7.0–6.8(m, 4H), 5.5(m, 1H), 5.05(s, 1H), 4.5(t, 1H), 4.29(t, 1H), 4.0(s, 3H), 4.0–3.8(m, 2H), 3.0–2.8(dd, 2H), 2.3(m, 1H), 2.09(m, 1H), 1.95–1.8(m, 2H), 1.78(s, 3H), 1–0.7(dd, 6H).

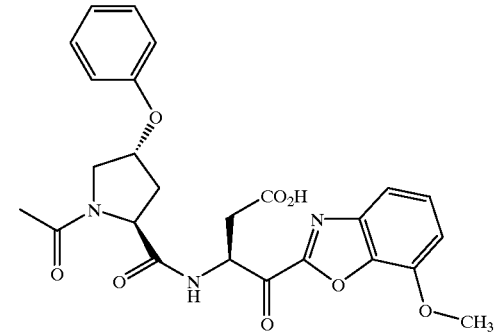

87

N-Acetyl(4-(R)-phenoxy)prolinyl-3(S)-amino-4-(7-methoxybenzoxazol-2-yl)-4-oxo-butazoic acid (87): N-Acetyl-(S)-(4-(S)-phenoxy)proline was converted to 87 as a white powder: $^1$H NMR (DMSO-d$_6$) δ 9.1(d, 1H), 8.76(d, 1H), 7.6–7.2(m, 4H), 7.0–6.9(m, 4H), 5.55(m, 1H), 5.45(m, 1H), 5.0(m, 2H), 4.56(t, 1H), 4.40(t, 1H), 4.0(s, 3H), 3.9(dd, 1H), 3.76(d, 1H), 3.64(d, 1H), 3.1–2.9(m, 1H), 2.8(m, 1H), 2.50(m, 1H), 2.3–2.2(m, 1H), 2.09(m, 1H), 1.95 and 1.75(2×s, 3H, rotamers)

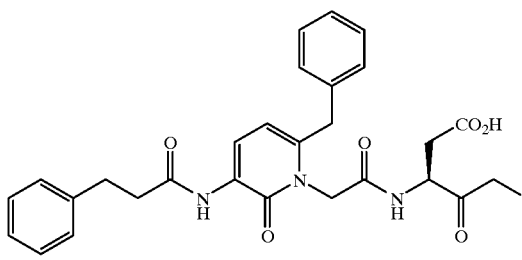

N-2-(6-Benzyl-1,2-dihydro-2-oxo-3-(3-phenylpropionyl) amino-1-pyridyl) acetyl-3(S)-amino-5-hydroxy-4-oxo-pentanoic acid (88). N-2-(6-Benzyl- 1,2-dihydro-2-oxo-3-(3-phenylpropionyl)amino-1-pyridyl) acetyl-3(S)-amino-5-hydroxy-4-oxo-pentanoic acid tert-butyl ester was prepared from 52b and 81 following the method described for the synthesis of 83a to give a white solid (45%): $^1$H NMR (CDCl$_3$) δ 8.40(d, 1H), 8.20(s, 1H), 7.4–7.1(m, 11H), 6.18(s, 1H), 4.72(m, 1H), 4.65–4.5(q, 2H), 4.4–4.2(dd, 2H), 4.0(s, 2H), 3.04(t, 2H), 2.9(dd, 1H), 2.76(t, 2H), 2.55(dd, 1H), 1.39(s, 9H).

The resulting product was converted to 88 by method described-in example 5, compound 84a to give the title compound (42%) as a white solid: $^1$H NMR(CDCl$_3$) δ 8.5(d, 1H), 8.1(d, 1H), 8.0(m, 1H), 7.4–7.1(m, 11H), 6.3(d, 1H), 4.9–4.8(m, 2H), 4.6–4.4(m, 2H), 4.3(dd, 1H), 4.1(s, 2H), 3.3(t, 1H), 3.05(t, 2H), 2.8–2.6(m, 3H).

Compounds 89 and 90 were prepared by a similar method the preparation of 84a in example 5.

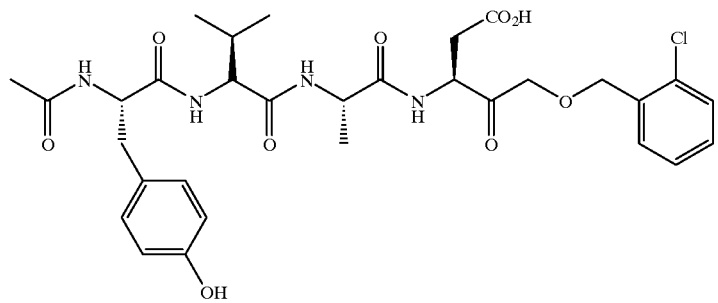

N-Acetyl-(S)-tyrosinyl-(S)-valinyl-(S)-alaninyl-3(S)-amino-5-(2-chlorobenzyloxy)-4-oxo-pentanoic acid (89) was prepared from Ac-Tyr-Val-Ala-OH and (3S) t-butyl N-(allyloxycarbonyl)-3-amino-5-(2-chlorophenyl-methoxyl)-4-oxo-pentanoate (prepared by a similar method as 82) to give a white solid: $^1$H NMR (DMSO-d$_6$) δ 9.15(s, 1H), 8.5(d, 1H), 7.98(d, 1H), 7.75(d, 1H), 7.55–7.3(m, 4H), 7.0(d, 1H), 6.6(d, 2H), 4.6–4.3(m, 6H), 4.3–4.1(m, 2H), 2.9(d, 1H), 2.76(dd, 1H), 2.7–2.5(m, 2H), 1.95(m, 1H), 1.75(s, 3H), 1.2(d, 3H), 0.9–0.7(dd, 6H).

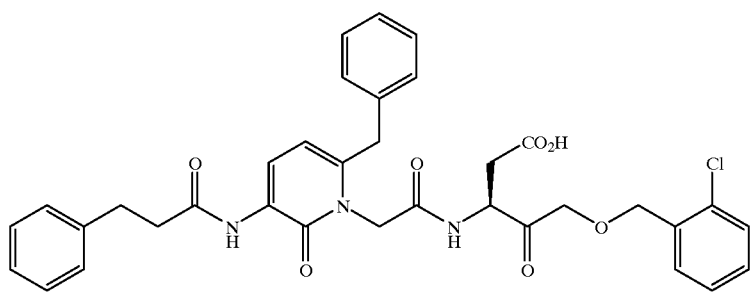

N-2-(6-Benzyl-1,2-dihydro-2-oxo-3-(3-phenylpropionyl) amino-1-pyridyl) acetyl-3-amino-5-(2-chlorobenzyloxy)-4-oxo-pentanoic acid (90) was prepared from 52b and (3S) t-butyl N-(allyloxycarbonyl)-3-amino-5-(2-chlorophenyl-methoxyl)-4-oxo-pentanoate (prepared by a similar method as 82) to give a white solid: $^1$H NMR(DMSO-d$_6$) δ 9.2(s, 1H), 8.75(d, 1H), 7.7–7.1(m, 14H), 6.4(d, 1H), 4.65(d, 6H), 4.56(s, 1H), 4.6–4.35(dd, 1H), 3.9(s, 2H), 2.9–2.6(m, 6H).

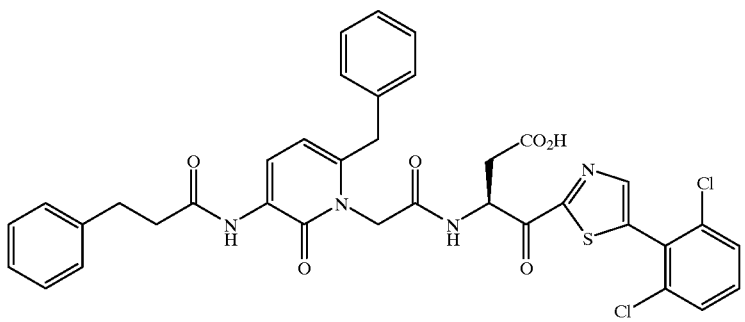

91

N-2-(6-Benzyl-1,2-dihydro-2-oxo-3-(3-phenylpropionyl) amino-1-pyridyl) acetyl-3(S)-amino-5-(5-(2,6-dichlorophenyl)thiazol-2-yl)-4-oxo-pentanoic acid (91) was prepared from 52b and 3-(Allyloxycarbonyl)-amino-4-[(2,6-dichloro-phenyl)-thiazol-2-yl]-4-hydroxy-butyric acid tert-butyl ester (99) as described for the preparation of 69a to give an off-white powder: $^1$H NMR(DMSO-d$_6$) δ 9.32(s, 1H), 9.05(d, 1H), 8.27(d, 1H), 8.18(d, 1H), 7.7(d, 1H), 7.6(t, 1H), 7.4–7.1(m 11H), 6.1(d, 1H), 5.64(m, 1H), 4.8–4.6(dd, 2H), 3.85(s, 2H), 3.02(m, 1H), 2.9–2.7(m, 4H).

prepared from 2-(3[3-(S)-(4-Hydroxy-phenyl)-propionylamino]-2-oxo-azepan-1-yl)-acetic acid and N-allyloxycarbonyl-4-amino-5-benzyloxy-2-oxotetrahydrofuran (Chapman, *Biorg. Med. Chem. Lett.*, 2, pp. 613–18 (1992)) by a similar method described for the synthesis of 54a to give the title compound as a white solid: $^1$H NMR(DMSO-d$_6$) δ 9.10–9.20(s, 1H), 8.40(s, 1H), 7.88 (d, 1H), 7.0(d, 2H), 6.64(d, 2H), 4.60(t, 1H), 4.10(q, 2H),

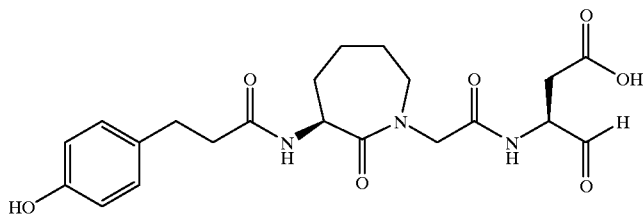

92

3-(S)-(2-(3[3-(S)-(4-Hydroxy-phenyl)-propionylamino]-2-oxo-azepan-1-yl)-acetylamino)-4-oxo-butyric acid (92) was 3.9–4.2(m, 2H), 3.6(m, 1H), 3.18(d, 2H), 2.70(t, 2H), 2.40 (m, 2H), 1.85–1.40(m, 8H).

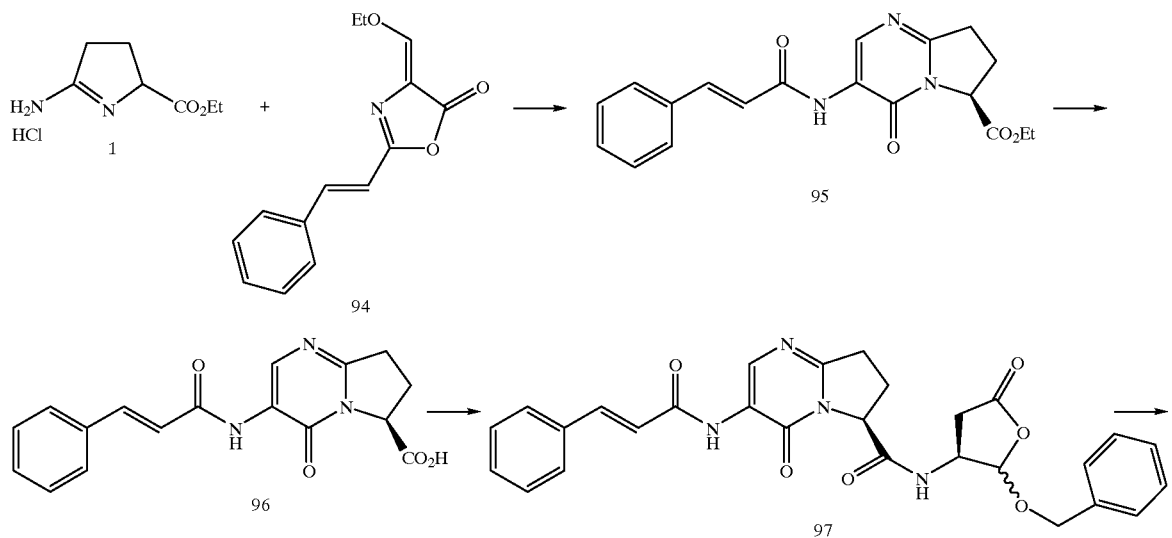

4-Ethoxymethylene-2-styryl-4H-oxazol-5-one (94) was prepared according to Cornforth, The Chemistry of *Penicillin*, Clarke, Johnson, Robinson, (eds.) Princeton University Press, p. 804 (1949).

4-Oxo-3-(3-phenyl-acryloylamino)-4,6,7,8-tetrahydro-pyrrolo[1,2-a]pyrimidine-(6S)-carboxylic acid ethyl ester (95) was prepared from 94 by the procedure in example 5 for compound 3 to give 4.5 g (30%) of the title compound: $^1$H NMR (CD$_3$OD) δ 1.3 (t, 3H), 2.35 (m, 1H), 2.65 (m, 1H), 3.1 (m, 1H), 3.15 (m, 1H), 4.25 (q, 2H), 5.15 (dd, 1H), 6.95 (d, 1H), 7.4 (m, 3H), 7.6 (m, 2H), 7.65 (d, 1H), 8.95 (s, 1H).

4-Oxo-3-(3-phenyl-acryloylamino)-4,6,7,8-tetrahydro-pyrrolo[1,2-a]pyrimidine-(6S)-carboxylic acid (96) A mixture of 4-Oxo-3-(3-phenyl-acryloylamino)-4,6,7,8-tetrahydro-pyrrolo[1,2-a]pyrimidine-(6S)-carboxylic acid ethyl ester (95, 3.1 g, 8.8 mmol) and aqueous 1N lithium hydroxide (8.8 mL, 8.8 mmol) in methanol (10 mL) was stirred 18 h at room temperature. The reaction was diluted with water and washed with ethyl ether (1×20 mL). The aqueous layer was acidified with conc. hydrochloric acid. The solid was collected by filtration and washed with water. The solid was dried in a vacuum oven at 50° C. for 18 h to give 2.2 g (75%) of the title compound as a tan solid: $^1$H NMR(CD$_3$OD) δ 2.4(m 1H), 2.7(m, 1H), 3.1(m, 1H), 3.2(m, 1H), 5.15(dd, 1H), 7.0(d, 1H), 7.4(m, 3H), 7.6(m, 2H), 7.65(d, 1H), 8.95(s, 1H).

4-Oxo-3-(3-phenyl-acryloylamino)-4,6,7,8-tetrahydro-pyrrolo]1,2-a]pyrimidine-(6S)-carboxylic acid (2-benzyloxy-5-oxo-tetrahydro-furan-(3S)-yl)-amide (97) was prepared from 96 by the method described in example 3 for compound H, step A to give 0.52 g (75%) of the title compound as a mixture of diastereomers: $^1$H NMR(CDCl$_3$) δ 2.3–2.7(m, 3H), 2.9(dd, 1H), 3.05(m, 1H), 3.3(m, 1H), 4.4–4.8(m, 2H), 4.9(2×d, 1H), 5.05(m, 1H), 5.55(2×s, 1H), 6.6(2×d, 1H), 7.4(m, 6H), 7.55(m, 4H), 7.65(2×d, 1H), 8.0(m, 2H), 9.2(s×2, 1H).

4-Oxo-(3S)-{[4-oxo-3-(3-phenyl-propionylamino)-4,6,7,8-tetrahydro-pyrrolo[1,2-a]pyrimidine-(6S)-carbonyl]-amino}-butyric acid (98) was prepared by the procedure in example 3 for compound H, step D to give 0.13 g (45%) of the title compound: $^1$H NMR(CD$_3$OD) δ 2.35(m, 1H), 2.45–2.75(m, 3H), 2.8(t, 2H), 3.0(t, 2H), 3.1(m, 1H), 3.25 (m, 1H), 4.3(m, 1H), 6.65(dd, 1H), 5.15(m, 1H), 7.15(m, 1H), 7.3(m, 4H), 8.8(a,1H).

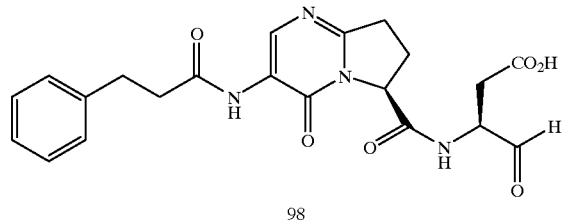

98

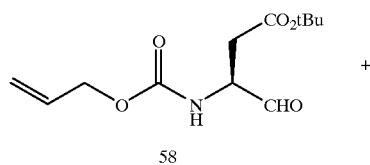

58

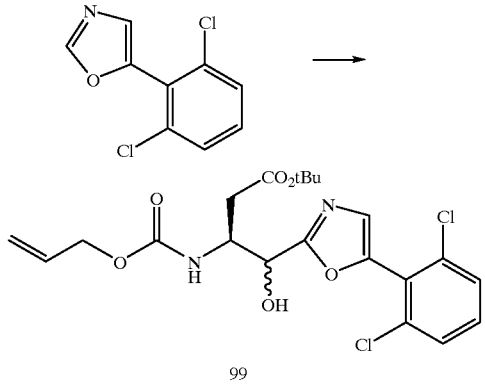

99

3(S)-(Allyloxycarbonyl)-amino-4-[(2,6-dichloro-phenyl)-oxazol-2-yl]-4(R,S)-hydroxy-butyric acid tert-butyl eter (99). A solution of 5-(2,6-Dichlorophenyl)oxazole (2.71 g, 12.7 mmol; prepared by a similar method described in Tet. Lett. 23, p2369 (1972)) in tetrahydrofuran (65 mL) was cooled to −78° C. under a nitrogen atmosphere. To this solution was added n-butyl lithium (1.5M solution in hexanes, 8.5 mL, 13.3 mmol) and stirred at −78° C. for 30 min. Magnesium bromide etherate (3.6 g, 13.9 mmol) was added and the solution was allowed to warm to −45° C. for 15 min. The reaction was cooled to −78° C. and aldehyde 58 (3.26 g, 12.7 mmol; Graybill et al., Int. *J. Protein Res.*, 44, pp. 173–182 (1993)) in tetrahydrofuran (65 mL) was added dropwise. The reaction was stirred for 25 min., then allowed to warm to −40° C. and stirred for 3 h, and then at room temperature for 1 h. The reaction was quenched with 5% NaHCO$_3$ (12 mL) and stirred for 3 h. The tetrahydrofuran was removed in vacuo and the resulting residue was extracted with dichloromethane. The organic layer was washed with saturated sodium chloride solution and dried over magnesium sulfate, filtered, and concentrated to yield 6.14 g of the title compound. Purification gave 4.79 g (80%) of 99: $^1$H NMR (CDCl$_3$) δ 1.45(s, 9H), 2.7–2.5(m, 2H), 2.8(dd, 1H), 4.2, 4.4(2×d, 1H), 4.7–4.5(m, 3H), 5.35–5.1(m, 2H), 5.6, 5.7(2×d, 1H), 6.0–5.8(m, 1H), 7.2(d, 1H), 7.3(m, 1H), 7.4(m, 2H).

4-Oxo-3-(3-phenyl-propionylamino)-4,6,7,8-tetrahydro-pyrrolo [1,2-a]pyridine-(6S)-carboxylic acid (100). A mixture of 4-Oxo-3-(3-phenyl-acryloylamino)-4,6,7,8-tetrahydro-pyrrolo[1,2-a]pyrimidine-(6S)-carboxylic acid (96; 2.1 g, 6.5 mmol) and 20% palladium hydroxide on carbon (0.5 g) in methanol (50 mL) was stirred under a hydrogen atmosphere for 4 h. The resulting mixture was filtered and concentrated to yield 2.1 g (100%) of the title compound as a white solid: $^1$H NMR(CD$_3$OD) δ 2.35(m, 1H), 2.65(m, 1H), 2.75(m, 2H), 3.0(t, 2H), 3.1(m, 1H), 3.15(m, 1H), 5.1(dd, 1H), 7.15(m, 1H), 7.25(m, 4H), 8.75(s, 1H)

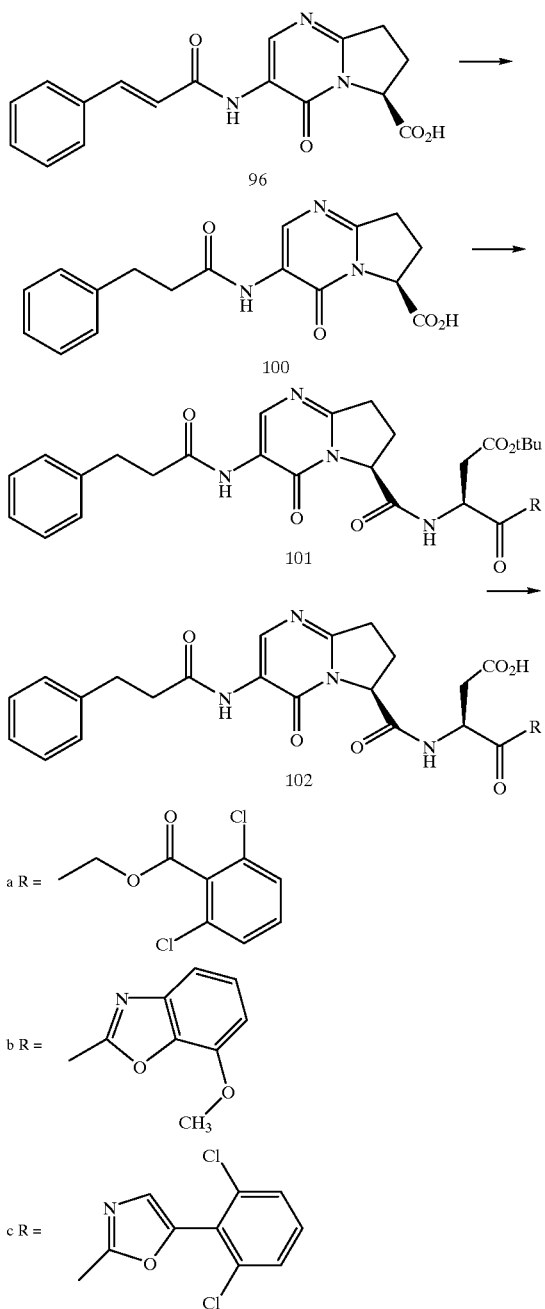

2,6-Dichloro-benzoic acid 4-tert-butoxycarbonyl-2-oxo-(3S)-{[4-oxo-3-(3-phenyl-propionylamino)-4,6,7,8-totrahydro-pyrrolo[1,2-a]pyrimidine-(6S)-carbonyl]-amino}-butyl ester (101 a) was prepared by the procedure in example 5 for compound 56a to give 0.16 g (20%) of the title compound: $^1$H NMR(CD$_3$OD) δ 1.45(s, 9H), 2.3(m, 1H), 2.6(m,1H), 2.7(m, 3H), 2.95(m, 3H), 4.8(m, 1H), 5.1(m, 1H), 5.2(q, 2H), 7.1(m, 1H), 7.2(m, 4H), 7.4(m, 3H), 8.75(s, 1H).

4-(7-methoxy-benzoxazol-2-yl)-4-oxo-(3S)-{[4-oxo-3-(3-pheny 1-propionylamino)-4,6,7,8-tetrahydro-pyrrolo[1,2-a]pyrimidine-(6S)-carbonyl]-amino}-butric acid tert-butyl ester (101b). 4-Hydroxy-4-(7-methoxy-benzoxazol-2-yl)-(3S)-{[4-oxo-3-(3-phenyl-propionylamino)-4,6,7,8-tetrahydro-pyrrolo[1,2-a]pyrimidine-(6S)-carbonyl]-amino}-butyric acid tert-butyl ester was prepared from 100 and 66a by the procedure in example 5 for compound 67a to give 0.95 g (quantitative) of the product as a mixture of diastereomers: $^1$H NMR(CD$_3$OD) δ 1.45(2×s, 9H), 2.2(2×m, 1H), 2.35–3.0(m, 9H), 4.0(m, 3H), 4.75(m,1H), 4.85(m, 1H), 5.05(2×dd, 1H), 7.1(2×dd, 1H), 7.15–7.3(m, 4H), 7.5 (2×t, 1H), 7.8(2×d, 1H), 8.55(2×dd, 1H), 8.7(2×s, 1H).

The resulting product was converted to 101b by the procedure in example 5 for compound 68a to give 0.36 g (50%) of the title compound: $^1$H NMR(CD$_3$OD) δ 1.4(s, 9H), 2.35(m, 1H), 2.55(m, 1H), 2.75(t, 2H), 2.95(t, 2H), 3.00(m,1H), 3.1(dd, 2H), 3.15(m, 1H), 5.15(dd, 1H), 5.65(t, 1H), 7.1(m, 2H), 7.2(m, 4H), 7.4(m, 2H), 8.7(s, 1H).

4-[5-(2,6-Dichloro-phenyl)-oxazol-2-yl]-4-oxo-(3S)-{[4-oxo-3-(3-phenyl-propionylamino)-4,6,7,8-tetrahydro-pyrrolo[1,2-a]pyrimidine-(6S)-carbonyl]-amino}-butyric acid tert-butyl ester (101c). 4-[5-(2,6-Dichloro-phenyl)-oxazol-2-yl]-4-hydroxy-(3S)-{[4-oxo-3-(3-phenyl-propionylamino)-4,6,7,8-tetrahydro-pyrrolo[1,2-a]pyrimidine-(6S)-carbonyl]-amino}-butyric acid tert-butyl ester from 100 and 99 using the method described in example 5, compound 67a to give 0.09 g (60%) of the product as a mixture of diastereomers: $^1$H NMR(CD$_3$OD) δ1.45(2×s, 9H), 2.2(m, 1H), 2.5(m, 2H), 2.7(2×dd, 1H), 2.75(t, 2H), 2.9–3.1(m, 4H), 4.7(m, 1H), 5.1(m, 2H), 7.1(m, 1H), 7.1–7.25(m, 4H), 7.4(t, 1H), 7.5(t, 1H), 8.55(d, 1H), 8.75(s, 1H).

The resulting product was converted to 101c by the method described in example 5, compound 68a to give 0.04 g (45%) of the title compound: $^1$H NMR(CD$_3$OD) δ 1.4(s, 9H), 2.3(m, 1H), 2.6(m, 1H), 2.75(t, 2H), 2.95(t, 2H), 2.9–3.2(m, 4H), 5.2(dd, 1H), 5.55(t, 1H), 7.1(m, 1H), 7.25 (m, 4H), 7.55(m, 3H), 8.75(s, 1H).

2,6-Dichloro-benzoic acid 4-carboxy-2-oxo-(3S)-{[4-oxo-3-(3-phenyl-propionylamino)-4,6,7,8-tetrahydro-pyrrolo[1,2-a]pyrimidine-(6S)-carbonyl]-amino}-butyl ester (102a) was prepared from 101a by the procedure in example 5 for compound 57a to give 0.12 g (80%) of the title compound: $^1$H NMR(CD$_3$OD) δ2.35(m, 1H), 2.65(m, 1H), 2.75(m, 2H), 2.85(dd, 1H), 2.95(m, 2H), 3.0(dd, 1H), 3.15(m, 1H), 3.25 (m, 1H), 4.55(dd, 1H), 5.15(m, 1H), 5.25(q, 2H), 7.15(m, 1H), 7.25(m, 4H), 7.45(m, 1H), 8.8(s, 1H).

4-(7-methyoxy-benzoxazol-2-yl)-4-oxo-(3S)-{[4-oxo-3-(3-phenyl-propionylamino)-4,6,7,8-tetrahydro-pyrrolo [1,2-a] pyrimidine-(6S)-carbonyl]-amino}-butric acid (102b) was prepared from 101b by the procedure described in example 5 for compound 69a to give 0.12 g (35%) of the title compound: $^1$H NMR(DMSO-d$_6$) δ 2.1(m, 1H), 2.55(m, 1H), 2.7–3.1(m, 8H), 4.05(s, 3H), 5.1(dd, 1H), 5.55(t, 1H), 7.2(m, 1H), 7.25(m, 5H), 7.5(t, 1H), 7.55(d, 1H), 8.7(s, 1H), 9.2(d, 1H), 9.4(s, 1H), 12.7(br, 1H).

4-[5-(2,6-Dichloro-phenyl)-oxazol-2-yl]-4-oxo-(3S)-{[4-oxo-3-(3-phenyl-propionylamino)-4,6,7,8-tetrahydro-pyrrolo[1,2-a] pyrimidine-(6S)-carbonyl]-amino}-butyric acid (102c) was prepared from 101c as 5 described in example 5 for compound 69a to give 0.01 g (40%) of the title compound: $^1$H NMR(CD$_3$OD) δ 2.35(m, 1H), 2.6(m, 1H), 2.75(t, 2H), 2.95(t, 2H), 3.05(m, 1H), 3.15(m, 3H), 5.15(dd, 1H), 5.55(t, 1H), 7.15(m, 1H), 7.2(m, 4H), 7.55(m, 3H), 8.8(s, 1H)

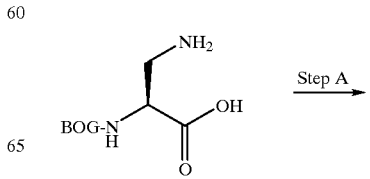

Step A

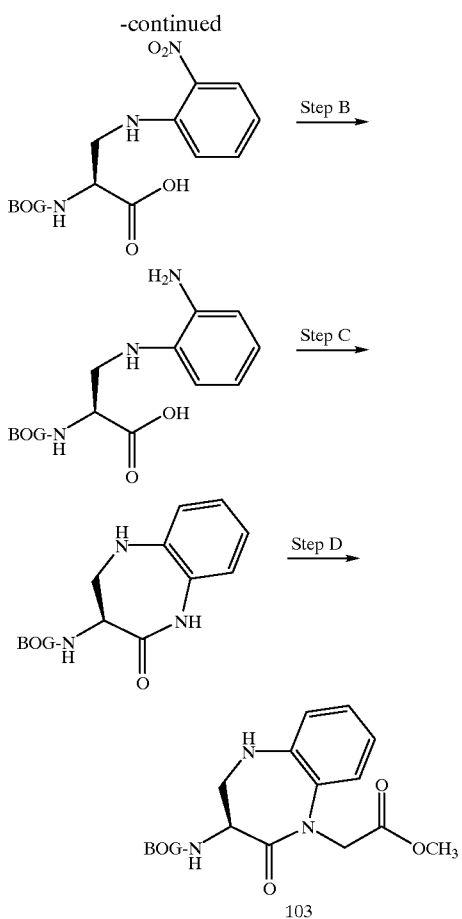

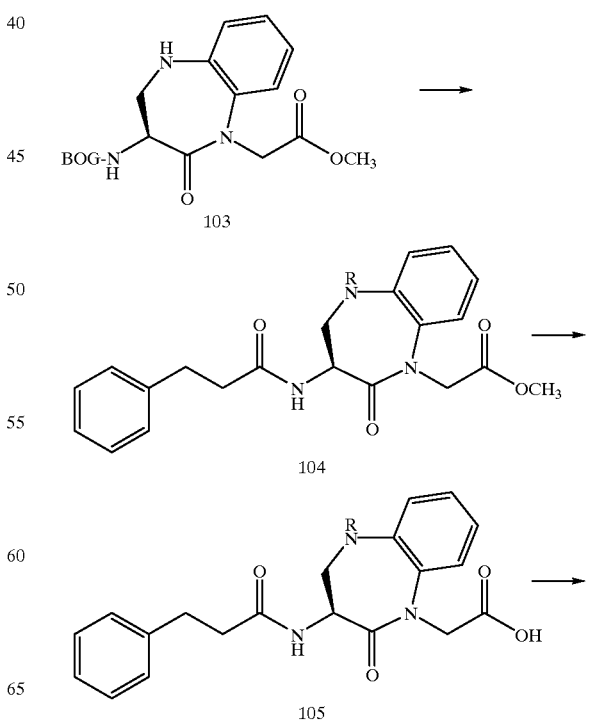

(3-tert-Butoxycarbonylamino-2-oxo-2,3,4,5-tetrahydrobenzo[b][1,4]diazepin-1-yl)acetic acid methyl ester (103).
Step A. 2(S)-tert-Butoxycarbonylamino-3-(2-nitrophenylamino)-propionic acid. 2-tert-Butoxycarbonylamino-3-aminopropionic acid (10 g, 49 mmol), 2-fluoronitrobenzene (5.7 ml, 54 mmol), and sodium bicarbonate (8.25 g, 98 mmol) was taken into 130 ml of dimethylformamide and heated at 80° C. for 18 hours. The reaction was evaporated in vacuo to give a viscous orange residue that was dissolved in 300 ml of water and extracted with diethyl ether (3×150 ml). The aqueous solution was acidified to pH 5 with 10% sodium hydrogen sulfate and extracted with ethyl acetate (3×250 ml). The combined extracts were dried over anhydrous sodium sulfate, filtered, and evaporated to give 12.64 g (83 μ) of the title compound as an orange amorphous solid. ¹H NMR (CD₃OD) δ 8.15–8.10 (1H,d), 7.54–7.48 (1H,t), 7.13–7.08 (1H, d), 6.73–6.65 (1H, t), 4.45–4.35 (1H, m), 3.9–3.8 (1H, dd), 3.65–3.55 (1H, dd), 1.45 (9H, s).
Step B. 2(S)-tert-Butoxycarbonylamino-3-(2-aminophenylamino)-propionic acid. A mixture of 2-tert-Butoxycarbonylamino-3-(2-nitrophenylamino)propionic acid (12.65 g, 40.5 mmol) and 0.5 g of 10% Pd/C in 100 ml of methanol under hydrogen at 1 atmosphere was stirred for 4 hrs. The solution was filtered through Celite 545 and the filtrate evaporated in vacuo to afford 11.95 g of the title compound in quantitative yield as a dark brown solid that was used without purification. ¹H NMR (CD₃OD) δ 6.75–6.70 (3H,m), 6.65–6.58 (1H, m), 4.35–4.3 1H, m), 3.6–3.38 (2H, m), 1.45 (9H, s).
Step C. 3(S)-tert-Butoxycarbonylamino-1,3,4,5-tetrahydrobenzo[b][1,4] diazepin-2-one. 1-(3-Dimethylaminopropyl)-3-ethylcarbodiimide hydrochloride (8.54 g, 44.5 mmol) was added to a cooled (0° C.) solution of 2-tert-butoxycarbonylamino-3-(2-aminophenylamino)propionic acid (11.95 g, 40.5 mmol) in 100 ml of dimethylformamide and stirred for 18 hours. The reaction was poured into 700 ml of ethyl acetate and washed four times with 100 ml of water. The organic layer was dried over anhydrous sodium sulfate, filtered, and evaporated to give a brown solid that was purified by flash chromatography eluting with 3:7 ethyl acetate/hexane to give 8 g (71) of the title compound: ¹H NMR (CDCl₃) 7.78 (1H, s), 7.02–6.95 (1H, m), 6.88–6.82 (1H, m), 6.82–6.78 (1H, m), 6.75–6.70 (1H, m), 5.8–5.7 (1H, d), 4.55–4.45 (1H, m), 3.95 (1H, s), 3.9–3.82 (1H, m), 3.48–3.40 (1H,m), 1.45 (9H,s).

Step D. (3(S)-tert-Butoxycarbonylamino-2-oxo-2,3,4,5-tetrahydrobenzo[b][1,4]diazepin-1-yl)acetic acid methyl ester (103). A 1.0 M solution of lithium bis(trimethylsilyl) amide (3.4 ml, 3.4 mmol) in THF was added dropwise to a –78° C. solution of 3-tert-butoxycarbonylamino-1,3,4,5-tetrahydrobenzo[b][1,4]diazepin-2-one (0.94 g, 3.38 mmol) in 20 ml of anhydrous tetrahydrofuran and stirred for 30 minutes. Methyl bromoacetate (o.44 ml, 4 mmol) was added dropwise to the reaction mixture then warmed to room temperature. The reaction was diluted with 100 ml of ethyl acetate and washed with 0.3N potassium hydrogen sulfate (50 ml), water (2×50 ml), and brine. The combined organics were dried over anhydrous sodium sulfate, filtered, and evaporated to afford a gum that was purified by flash chromatography eluting with 3:7 EtOAc/Hex. to give 0.98 g (83%) of the title compound as a white solid. ¹H NMR (CDCl₃) δ 7.15–7.07 (2H, m), 6.98–6.94 (1H, m), 6.88–6.84 (1H, d), 5.62–5.55 (1H, d), 4.71–4.65 (1H, d), 4.65–4.6 (1H, m), 4.33–4.27 (1H, d), 3.96–3.90 (1H, m), 3.78 (3H, s), 3.44–3.37 (1H, m), 1.4 (9H, s).

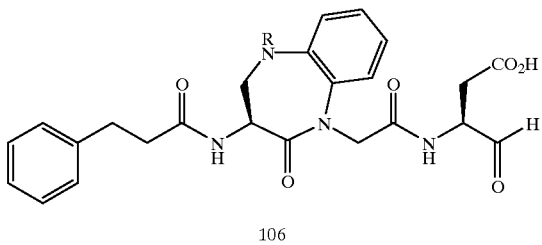

106
a R = H
b R = COCH₂CH₂Ph
c R = CH₂Ph

[2-Oxo-3(S)-(3-phenylpropionylamino)-2,3,4,5-tetrahydrobenzo[b][1,4]diazepin-1-yl]acetic acid methyl ester (104a). Anhydrous hydrogen chloride was bubbled into a solution of (3(S)-tert-butoxycarbonylamino-2-oxo-2,3,4,5-tetrahydrobenzo[b][1,4]diazepin-1-yl)acetic acid methyl ester (103, 1 g, 2.86 mmol) in 25 ml of ethyl acetate for 2 minutes then stirred for 1 hour at room temperature. The reaction was evaporated to give 2-oxo-3(S)-amino-2,3,4,5-tetrahydrobenzo[b][1,4]diazepin-1-yl acetic acid methyl ester hydrochloride as a white solid. The hydrochloride salt and hydrocinnamic acid (0.47 g, 3.15 mmol) was dissolved into 20 ml of dimethylformamide and cooled to 0° C. Diisopropylethylamine (1 ml, 5.72 mmol) was added to the solution followed by the addition of N-hydroxybenzotriazole and 1-(3-dimethylaminopropyl)-3-ethylcarbodiimide hydrochloride. After stirring for 18 hours at room temperature, the mixture was diluted with 150 ml of ethyl acetate and washed with 10% sodium hydrogen sulfate, 10% sodium bicarbonate, and brine. The organic layer was dried over anhydrous sodium sulfate, filtered, and evaporated to a crude solid that was purified by flash chromatography eluting with 7:3 ethyl acetate/dichloromethane to afford 600 mg (55%)of the title compound as a white solid. $^1$H NMR (CDCl$_3$) δ 7.3–6.85 (9H,m), 6.55–6.0 (1H, d), 4.88–4.82 (1H, m), 4.72–4.65 (1H, d), 4.28–4.22 (1H, m), 3.95–3.9 (1H, m), 3.78 (3H, s), 3.65 (1H, br. s), 3.28–3.2 (1H, m), 2.95–2.84 (2H, m), 2.55–2.4 (2H, m).

(3(S)-(3-Phenylpropionylamino)-2-oxo-2,3,4,5-tetrahydrobenzo[b][1,4]diazepin-1-yl)acetic acid (105a). (3(S)-(3-Phenylpropionylamino)-2-oxo-2,3,4,5-tetrahydro-benzo[b][1,4]diazepin-1-yl)acetic acid methyl ester (104a) was dissolved in 90% methanol. Lithium hydroxide hydrate was added to the reaction and the reaction was stirred at room temperature for 4 h. The reaction was evaporated in vacuo to give a white solid. This was dissolved in 20 ml of water and acidified to pH 5 and extracted with ethyl acetate to afford 304 mg (88%) of the title compound as a white solid. $^1$H NMR (CDCl$_3$) δ 7.5–6.9 (11H, m), 4.92–4.8 (1H, m), 4.7–4.58 (1H, d), 4.38–4.25 (1H, d), 3.88–3.78 (1H, m), 3.45–3.25 (1H, m), 3.05–2.85 (2H, m), 2.55–2.45 (2H, m). 4-Oxo-3(S)-{2-[2-oxo-3(S)-(3-phenylpropionylamino)-2,3,4,5-tetrahydro-benzo[b][1,4]diazepin-1-ylacetylamino}butyric acid (106a). N-[1-(2-Benzyloxy-5-oxotetrahydrofuran-3-ylcarbamoyl-methyl)-2-oxo-2,3,4,5-tetrahydro-1H-benzo[b][1,4]diazepin-3-yl]-3-phenylpropionamide was prepared from 105a by the procedure in example 3, compound H (step A) to afford 390 mg (93%) of the product as diastereomers. $^1$H NMR (CD$_3$OD) δ 7.58–7.22 (14H, m), 5.78–5.73 (0.5 H, d), 5.64 (0.5 H, s), 5.0–4.72 (4H, m), 4.54–4.42 (2H, m), 3.82–3.76 (0.5 H, m), 3.68–3.62 (o.5 H, m), 3.28–3.21 (0.5H, m), 3.19–3.12 (0.5H, m), 3.07–2.98 (2H, m), 2.78–2.48 (4H, m).

The resulting product was converted to 106a by the method described in example 3, compound H (StepD) to afford the title compound as a white solid (17%): $^1$H NMR (CD$_3$OD) δ 7.54–6.98 (9H, m), 5.58–5.44 (1H, m), 4.8–4.2 (4H, m), 3.96–3.3 (2H, m), 3.30–3.05 (1H, m), 2.98–2.25 (5H, m).

[2-Oxo-5-(3-phenylpropionyl)-3(S)-(3-phenylpropionylamino)-2,3,4,5-tetrahydrobenzo[b][1,4]diazepin-1-yl]acetic acid methyl ester (104b). Anhydrous hydrogen chloride was bubbled into a solution of (3(S)-tert-butoxycarbonylamino-2-oxo-2,3,4,5-tetrahydro-benzo[b][1,4]diazepin-1-yl)acetic acid methyl ester (103, 1 g, 2.86 mmol) in 25 ml of ethyl acetate for 2 minutes then stirred for 1 hour at room temperature. The reaction was evaporated to give 2-oxo-3(S)-amino-2,3,4,5-tetrahydrobenzo[b][1,4]diazepin-1-yl acetic acid methyl ester hydrochloride as a white solid. The hydrochloride salt was suspended into 20 ml of dichloromethane and cooled to 0° C. Triethylamine (1.6 ml, 11.5 mmol) was added to the suspension followed by the dropwise addition of dihydrocinnamoyl chloride (0.9 ml, 6 mmol). The mixture was warmed to room temperature and stirred for 18 hours. The mixture was diluted with 25 ml of dichloromethane and washed twice with 50 ml of water and once with 50 ml of brine. The organic layer was dried over anhydrous sodium sulfate, filtered, and evaporated to give a viscous, yellow oil that was purified by flash chromatography eluting with 1:1 ethyl acetate/dichloromethane to afford 1.35 g (92%) of the title product as a white solid. $^1$H NMR (CDCl$_3$) δ 7.45–7.02 (14 H, m), 6.37–6.32 (1H, d), 4.78–4.72 (1H, m), 4.52–4.3 (3H, m), 3.82–3.77 (1H,m), 3.74 (3H, s), 3.03–2.87 (4H, m), 2.58–2.45 (2H, m), 2.45–2.35 (1H, m), 2.25–2.16 (1H, m).

[2-Oxo-5-(3-phenylpropionyl)-3-(3(S)-phenylpropionylamino)-2,3,4,5-tetrahydrobenzo[b][1,4]diazepin-1-yl]acetic acid (105b). [2-Oxo-5-(3-phenylpropionyl)-3-(3-phenylpropionylamino)-2,3,4,5-tetrahydrobenzo[b][1,4]diazepin-1-yl]acetic acid methyl ester (104b; 680 mg, 1.32 mmol) was hydrolyzed by the procedure in example 105a to afford 645 mg (98%) of the title compound as a white solid. $^1$H NMR (CDCl$_3$) δ 7.58 (1H, br. s), 7.5–7.42 (1H, m), 7.35–6.95 (14H, m), 4.95–4.88 (1H, m), 4.64–4.55 (1H, d), 4.54–4.45 (1H, t), 4.15–4.05 (1H, d), 3.75 (1H, m), 3.05–2.75 (4H, m), 2.58–2.45 (2H, m), 2.45–2.28 (1H, m), 2.25–2.14 (1H, m).

2-Oxo-3(S)-{2-[2-oxo-5-(3-phenylpropionyl)-3(S)-(3-phenyl-propionyl-amino)-2,3,4,5-tetrahydrobenzo[b][1,4]diazepin-1-yl] acetylamino}butyric acid (106b). [2-Oxo-5-(3-phenylpropionyl)-3-(3-phenylpropionylamino)-2,3,4,5-tetrahydrobenzo[b][1,4]diazepin-1-yl]acetic acid and 3-amino-4-oxobutyric acid tert-butylester semicarbazone were coupled by the procedure in example 3, compound K (step A) to give 350 mg (85%) of a white solid. $^1$H NMR (CDCl$_3$)δ 9.05 (1H, br. s), 7.58–7.55 (1H,d), 7.5–7.35 (1H, m), 7.35–6.95 (14 H, m), 6.75–6.72 (1H, d), 6.25 (1H, br. s), 5.25 (1H, br. s), 4.95–4.88 (1H, m), 4.8–4.72 (1H, m), 4.55–4.4 (2H, m), 3.92–3.88 (1H, d), 3.73–3.68 (1H, m), 2.95–2.8 (4H, m), 2.8–2.72 (1H, m), 2.62–2.55 (1H, m), 2.55–2.45 (2H, m), 2.4–2.32 (1H, m), 2.2–2.12 (1H, m), 1.45 (9H, s).

4-Oxo-3-{2-[2-oxo-5-(3-phenylpropionyl)-3-(3-phenylpropionyl-amino)-2,3,4,5-tetrahydrobenzo[b][1,4]diazepin-1-yl]-acetyl-amino}butyric acid tert-butyl ester semicarbazone was deprotected as described in example 3, compound K (step C) to give 118 mg (47%) of the title compound as a white solid. $^1$H NMR (CD$_3$OD)δ 7.48–6.95 (14 H, m), 4.65–4.15 (6H, m), 3.5–3.4 (1H, m), 2.85–2.72 (4H, m), 2.65–2.5 (1H, m), 2.5–2.34 (3H, m), 2.34–2.15 (2H, m).

189

[5-Benzyl-2-oxo-3(S)-(3-phenylpropionylamino)-2,3,4,5-tetrahydro -benzo[b][1,4]diazepin-1-yl]acetic acid methyl ester (104c). [2-Oxo-3-(3-phenylpropionylamino)-2,3,4,5-tetrahydrobenzo-[b][1,4]diazepin-1-yl]acetic acid methyl ester (104a; 500 mg, 1.31 mmol), calcium carbonate (155 mg, 1.58 mmol), and benzyl bromide (170 μl, 1.44 mmol) were taken into 10 ml of dimethylformamide and heated to 80° C. for 8 hours. The mixture was diluted with 150 ml of ethyl acetate and washed 4 times with 50 ml of water. The organic layer was dried over anhydrous sodium sulfate, filtered, and evaporated to give a viscous, yellow oil that was purified by flash chromatography eluting with dichloromethane/ethyl acetate (8:2) to give 460 mg (75%) of the title compound as a white solid. $^1$H NMR (CDCl$_3$) δ 7.34–7.05 (14 H, m), 6.32–6.28 (1H, d), 4.84–4.76 (1H, d), 4.76–4.70 (1H, m), 4.43–4.37 (1H, d), 4.26–4.18 (1H, d), 4.06–4.00 (1H, d), 3.79 (3H, s), 3.45–3.37 (1H, m), 3.02–2.95 (1H, m), 2.90–2.82 (2H, m), 2.5–2.34 (2H, m).

[5-Benzyl-2-oxo-3(S)-(3-phenylpropionylamino)-2,3,4,5-tetrahydro -benzo[b][1,4]diazepin-1-yl]acetic acid (105c) was prepared by the hydrolysis of the ester (102c) by the procedure reported in example 105a to give 450 mg (98%) of the title compound as a white solid: $^1$H NMR (CD$_3$OD) δ 7.5–7.05 (14 H, m), 6.4 (1H, br. s), 4.85–4.55 (2H,m), 4.5–4.21 (2H, m), 4.12–3.92 (1H, d), 3.45–3.3 (1H, m), 3.1–2.8 (3H, m), 2.55–2.28 (3H, m).

3(S)-{2-[5-Benzyl-2-oxo-3-(3(S)-phenylpropionylamino)-2,3,4,5-tetrahydrobenzo[b][1, 4]diazepin-1-yl]-acetylamino}-4-oxobutyric acid (106c). [5-Benzyl-2-oxo-3 (S)-(3-phenylpropionylamino)-2,3,4,5-tetrahydro-benzo[b [1,4]diazepin-1-yl]acetic acid and 3(S)-amino-4-oxobutyric acid tert-butylester semicarbazone were coupled by the procedure in example 3, compound K (step A) and to afford 260 mg (85%) of a white solid: $^1$H NMR (CD$_3$OD) δ 7.35–7.0 (15 H, m), 4.94–4.88 (1H, m), 4.68–4.58 (1H, d), 4.57–4.52 (1H, m), 4.41–4.34 (1H, d), 4.3–4.23 (1H, d), 4.1–4.04 (1H, d), 3.18–3.11 (1H, m), 3.09–2.98 (1H, m), 2.78–2.72 (2H, t), 2.65–2.57 (1H, m), 2.42–2.33 (3H, m). 3(S)-{2-[5-Benzyl-2-oxo-3(S)-(3-phenylpropionylamino)-2,3,4,5-tetrahydrobenzo[b][1,4]diazepin-1-yl]-acetylamino}-4-oxobutyric acid tert-butyl ester semicarbazone was deprotected as described in example 3, compound K (step C) to give 168 mg (81%) of the title compound as a white solid. $^1$H NMR (CD$_3$OD) δ 7.37–7.0 (14H, m), 4.75–4.62 (1H, m), 4.6–4.45 (2H, m), 4.4–4.21 (2H, m), 4.15–3.95 (2H, m), 3.15–3.0 (2H, m), 2.82–2.67 (2H, m), 2.65–2.52 (1H, m), 2.5–2.32 (3H, m).

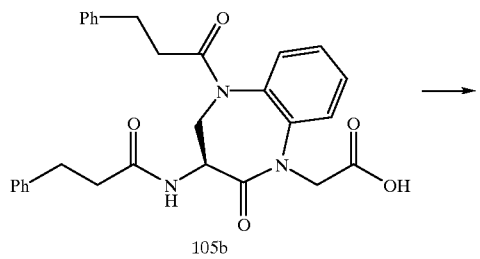

105b

190

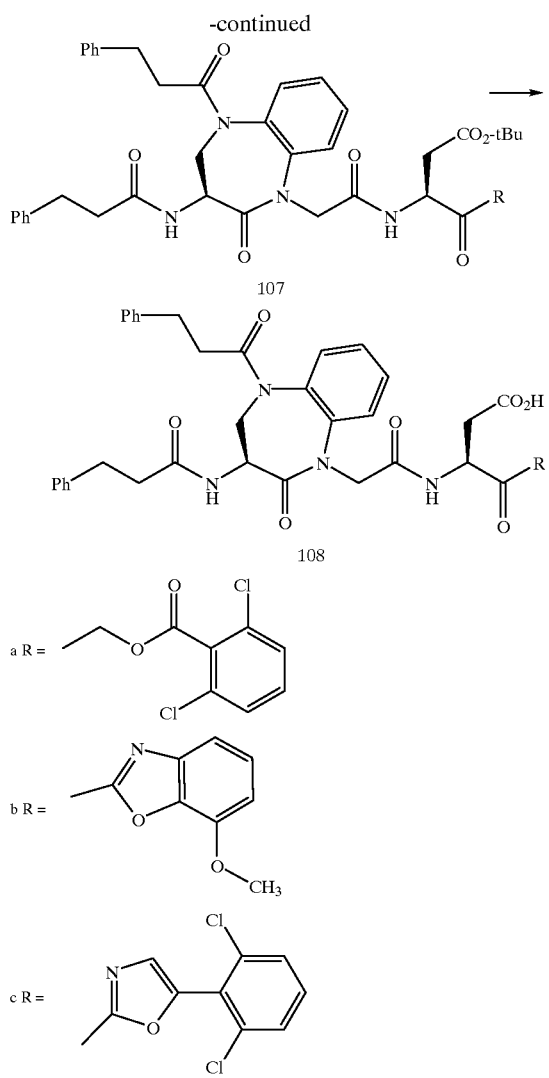

2,6-Dichlorobenzoic acid 4-tert-butoxycarbonyl-2-oxo-3 (S)-{2-[2-oxo-5-(3-phenylpropionyl)-3(S)-(3-phenylpropionylamino)-2,3,4,5-tetrahydro-benzo[b][1,4] diazepin-1-yl]acetyl-amino}butyl ester (107a). The resulting semicarbazone was prepared by the coupling of compound 105b and t-butyl 3-(allyloxycarbonylamino)-4-oxo-5-(2,6-dichlorobenzoyl-oxy)pentanoate (WO 93 16710) as described in compound 56a to give 256 mg (58%) of the title compound as a white solid. $^1$H NMR (CDCl$_3$) δ 7.45–7.04 (17H, m), 6.45–6.34 (2H, m), 5.28–5.21 (1H, m), 5.1–5.0 (1H, m), 4.95–4.90 (1H, m), 4.75–4.70 (1H, m), 4.55–4.44 (1H, m), 4.32–4.22 (1H, dd), 3.99–3.85 (1H, dd), 3.85–3.76 (1H, m), 3.06–2. B3 (5H, m), 2.83–2.74 (1H, m), 2.6–2.44 (2H, m), 2.43–2.33 (1H, m), 2.24–2.15 (1H, m), 1.45 (9H, s).

2,6-Dichlorobenzoic acid 4-carboxy-2-oxo-3(S)-{2-[2-oxo-5-(3-phenylpropionyl)-3(S)-(3-phenylpropionylamino)-2,3,4,5-tetrahydrobenzo[b][1,4]diazepin-1-yl] acetylamino}butyl ester (108a) was prepared from 107a by the method described for compound 57a which afforded 156 mg (68%) of the title compound as a white solid. $^1$H NMR (CD$_3$OD) δ 7.5–6.9 (17H, m), 5.16–5.02 (1H, dd), 4.88–4.71 (2H, m), 4.62–4.44 (2H, m), 4.42–4.28 (2H, m), 4.27–4.18 (1H, m), 3.47–3.41 (1H, m), 2.90–2.60 (5H, m), 2.46–2.4 (2H, m), 2.39–2.18 (2H, m).

4-(7-Methoxybenzoxazol-2-yl)-4-oxo-3(S)-(2-[2-oxo-5-(3-phenylpropionyl)-3(S)-(3-phenylpropionylamino)-2,3,4,5- tetrahydrobenzo[b] [1,4]diazepin-1-yl]-acetylamino) butyric acid tert-butyl ester (107b). 4(R,S)-Hydroxy-4-(7-methoxybenzoxazol-2-yl)-3(S)-{2-[2-oxo-5-(3-phenylpropionyl)-3(S)-(3-phenylpropionylamino)-2,3,4,5-tetrahydro[b][1,4]diazepin-1-yl-acetylamino} butyric acid tert-butyl ester was prepared from 105b and 66a by the method described in example 5, compound 67 to give 56% of a white solid: $^1$H NMR (CDCl$_3$) δ 7.72–6.78 (19H, m), 6.37–6.28 (1H, m), 5.17–5.08 (0.5H, m), 4.92–4.82 (0.5H, m), 4.81–4.6 (1H, m), 4.6–4.35 ((3H,m), 4.05–3.9 (1H, m), 3.95 (3H, s), 3.82–3.7 (1H, m), 2.96–2.05 (10H, m), 1.45 (4.5H, s), 1.38 (4.5H, s).

The resulting product was converted to 107b by the method described in example S, compound 68a to give the title compound (56%) as a white solid. $^1$H NMR (CD$_3$OD) δ 7.62–6.8 (17H, m), 5.64–5.58 (0.5H, t), 5.52–5.46 (0.5H, t), 4.62–4.47 (2H, m), 4.40–4.32 (1H, m), 3.9 (1.5H, s), 3.88 (1.5 H, s), 3.43–3.37 (1H, m), 3.0–2.92 (1H, m), 2.90–2.62 (6H, m), 2.5–2.4 (2H, m), 2.28–2.15 (2H, m), 1.32 (4.5H, s), 1.25 (4.5H, s).

4-(7-Methoxybenzoxazol-2-yl)-4-oxo-3(S)-{2-[2-oxo-5-(3-phenylpropionyl)-3(S)-(3-phenylpropionylamino)-2,3,4,5-tetrahydrobenzo[b][1,4]diazepin-1-yl]-acetylamino} butyric acid (108b) was prepared by the method described in example 5, compound 69a to give the title compound (50%) as a white solid. $^1$H NMR (CD$_3$OD) δ 7.41–6.88 (17H, m), 5.6–5.55 (0.5H, t), 5.48–5.43 (0.5H, t), 4.64–4.45 (2H, m), 4.45–4.30 (1H, m), 3.93 (1.5H, s), 3.90 (1.5H, s), 3.47–3.34 (1H, m), 3.10–2.85 (2H, m), 2.84–2.63 (5H, m), 2.6–2.4 (2H, m), 2.3–2.1 (2H, m).

4-[5-(2,6-Dichlorophenyl)oxazol-2-yl]-4-oxo-3(S)-{2-[2-oxo-5-(3-phenylpropionyl)-3(S)-(3-phenylpropionylamino)-2,3,4,5-tetrahydrobenzotb][1,4] diazepin-1-yl]-acetylamino} butyric acid tert-butyl ester (107c). 4-[5-(2,6-Dichlorophenyl)oxazol-2-yl]-4(R,S)-hydroxy-3(S)-{2-[2-oxo-5-(3-phenylpropionyl)-3(S)-(3-phenylpropionylamino)-2,3,4,5-tetrahydrobenzo[b][1,4]diazepin-1-yl-]-acetylamino} butyric acid tert-butyl ester was prepared from 106c and 99 by a similar method as described for compound 67a in example 5 to give 72% of a white solid. $^1$H NMR (CDCl$_3$)δ 7.71–7.64 (1H, m), 7.58–7.42 (2H, m), 7.42–6.92 (I5H, m), 6.5–6.37 (2H, m), 5.15–5.04 (1H, m), 4.88–4.68 (2H, m), 4.57–4.37 (2H, m), 4.28–4.13 (1H, m), 3.87–3.64 (2H, m), 3.04–2.80 (4H, m), 2.76–2.68 (1H, m), 2.67–2.42 (3H, m), 2.41–2.31 (1H, m), 2.22–2.12 (1H, m), 1.45 (9H, s).

The resulting product was converted to 107c by a similar method as described for compound 68a in example 5 to give the title compound in quantitative yield as a white solid. $^1$H NMR (CDCl$_3$)δ 7.47–6.98 (18H, m), 6.52–6.42 (1H, d), 5.6–5.52 (1H, m), 4.78–4.71 (1H, m), 4.52–4.40 (2H, m), 4.03–3.94 (0.67H, m), 3.94–3.85 (0.33H, m), 3.85–3.75 (1H, m), 3.45–3.33 (1H, m), 3.08–2.98 (1H, m), 2.97–2.84 (4H, m), 2.55–2.43 (2H, m), 2.43–2.32 (1H, m), 2.23–2.13 (1H, m), 1.35 (9H, s).

4-[5-(2,6-Dichlorophenyl)oxazol-2-yl]-4-oxo-3(S)-{2-[2-oxo-5-(3-phenylpropionyl)-3(S)-(3-phenylpropionylamino)-2,3,4,5-tetrahydrobenzo[b][1,4]diazepin-1-yl]-acetylamino} butyric acid (108c) was prepared from 107c by a similar method as described for compound 69a in example 5 to give 72% the title compound as a white solid. $^1$H NMR (CD$_3$OD) δ 7.58–7.0 (18H, m), 5.62–5.53 (0.67H, m), 5.52–5.47 (0.33H, m), 4.68 (3H, m), 3.54–3.42 (1H, m), 3.1–2.92 (2H, m), 2.88–2.68 (5H, m), 2.63–2.45 (2H, m) 2.40–2.22 (2H, m).

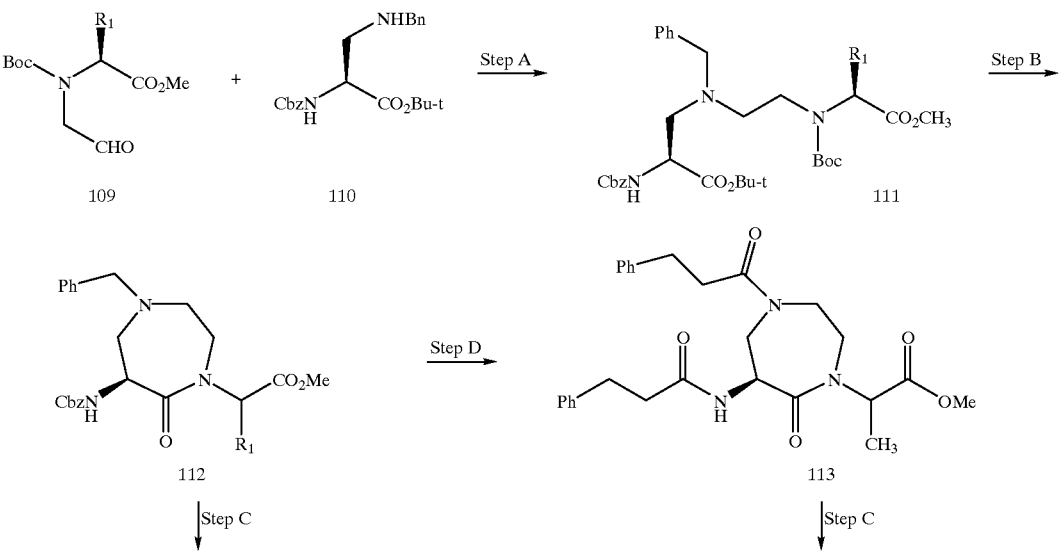

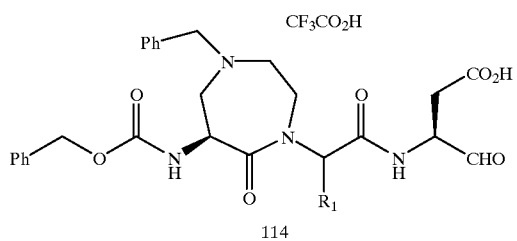

114 a $R_1$ = $CH_3$
b $R_1$ = H

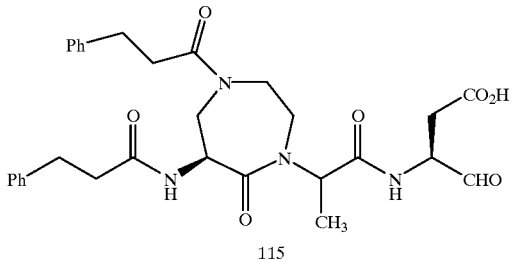

115

3(S)-{2(R,S)-[4-Benzyl-7-oxo-6(S)-(N-benzyloxycarbonylamino)-[1,4]diazepan-1-yl]-propionylamino}-4-oxo-butyric acid trifluoroacetic acid salt (114a):

Step A. To a solution of tert-butyl-2-N-benzyloxycarbonyl-3-N-benzyl-(S)-2,3-diaminopropionate (110; 0.85 g, 2.2 mmol), 3-(N-tert-butoxycarbonyl)amino-2-methyl-5-oxo-pentanoic acid methyl ester (109a; 0.65 g, 2.7 mmol), acetic acid (0.1 mL, 1.8 mmol), sodium acetate (0.36 g, 2 mmol) and 4 Å molecular sieves (1 g) in methanol (45 mL), was added sodium cyanoborohydride (0.33 g, 5.3 mmol). The mixture was stirred overnight at 25° C. then filtered through Celite and concentrated under reduced pressure. The residue was dissolved in 1 N NaOH and extracted with ethyl acetate (3×40 mL). The organic layer was dried (MgSO$_4$), filtered and evaporated to give an oil. Chromatography (silica-gel, 4:1 hexane: ethyl acetate as eluent) gave 0.92 g (68% yield) of 111a as an oil.

Step B. The above material was dissolved in dichloromethane (3 mL) cooled to 0° C. and treated with a 25% solution of trifluoroacetic acid in dichloromethane (20 mL) then allowed to warm to 25° C. and stir until the reaction was judged complete by TLC (4:1 hexane:ethyl acetate). The solvent was removed under reduced pressure and the residue dried under vacuum then dissolved in dichloromethane (40 mL) and treated with 4-methylmorpholine (1 mL, 9 mmol), HOBT (0.2 g, 1.5 mmol) and EDC (0.61 g, 3.2 mmol). The resulting mixture was stirred overnight at 25° C. then diluted with dichloromethane and washed with water. The organic layer was dried (MgSO$_4$), filtered and evaporated to give an oil. Chromatography (silica-gel, 3:2 hexane:ethyl acetate) gave 0.49 g (74% yield) of 112a as a viscous oil.

Step C. A solution of 2(R,S)-[4-benzyl-7-oxo-6(S)-(N-benzyloxycarbonylamino)-[1,4]diazepan-1-yl ]-propionic acid methyl ester (112a; 0.15 g, 0.32 mmol) was dissolved in methanol and treated with 1 M LiOH (0.32 mL) and stirred 5.5 hours at 25° C. then evaporated to dryness. The residue was azeotroped with ethanol (2×10 mL), acetonitrile (2×10 mL), benzene (2×10 mL) then dried under vacuum. The resulting residue was converted to 114a by a method similar to that described in example 3, compound K (steps A, B, and C) and purified by reverse phase (C18 column) HPLC using 0.1% TFA:water/0.1% TFA:acetonitrile as eluent. to give 17 mg (10% yield) of a viscous oil: $^1$H NMR (500 MHz, CD$_3$OD) δ 1.15 (m, 3 H), 2.30–2.70 (m, 6 H), 2.72–2.95 (bm, 6 H), 3.30–3.80 (m, 4 H), 4.10 (m, 1 H), 4.40 (m, 4 H), 4.95 (m, 1H) 6.95–7.10 (bs, 5 H), and 7.12–7.20 ppm (bs, 5 H).

3(S)-{2-[4-Benzyl-7-oxo-6(S)-(N-benzyloxycarbonylamino)-[1,4]diazepan-1-yl]-acetylamino}-4-oxo-butyric acid trifluoroacetic acid salt (114b) was prepared from 109b by a similar method described for the synthesis of 114a to give 85 mg of viscous oil: $^1$H NMR (500 MHz, CD$_3$OD) δ 1.20 (d, J=7 Hz, 3 H), 2.28 (m, 2 H), 2.60 (m, 2 H), 3.18 (bs, 6 H), 3.35–3.45 (m, 2 H), 3.60–3.95 (m, 2 H), 4.15 (m, 1 H), 4.32 (m, 1 H), 4.42 (m, 1 H), 5.00 (bm, 2 H), 7.20 (bs, 5 H), and 7.40 ppm (bs, 5 H); $^{19}$F NMR (470 MHz, CD$_3$OD)δ −10. 72 ppm (s, 3 F).

4-Oxo-3(S)-{2(R,S)-[7-oxo-4-(3-phenyl-propionyl)-6(S)-(3-phenyl-propionylamino)-[1,4]diazepan-1-yl]-propionylamino}-butyric acid (115):

Step D. A suspension of 2(R,S)-[4-benzyl-7-oxo-6(S)-(N-benzyloxycarbonylamino)-[1,4]diazepan-1-yl ]-propionic acid methyl ester (112b; 0.22 g, 0.49 mmol) and 20% Pd(OH)$_2$ on carbon (50 mg) in ethanol was stirred under hydrogen atmosphere for 7 hours. The solvent was evporated under reduced pressure and the residue dissolved in dichloromethane (20 mL) then treated with triethylamine (1 mL) and dihydrocinnamoyl chloride (170 mg, 1 mmol). The resulting mixture was allowed to stir overnight then diluted with ethyl acetate and washed with 1 N NaOH. The organic layer was dried (MgSO$_4$), filtered and evaporated to give an oil. Chromatography (silica-gel, 4:1 hexane: ethyl acetate) gave 0.175 g (75% yield) of 113 as an oil.

Step C. A 0.15 g sample of 113 (0.32 mmol) was dissolved in methanol, treated with 1 M LiOH (0.32 mL), stirred at 40° C. overnight then evaporated to dryness. The residue was azeotroped with ethanol (2×10 mL), acetonitrile (2×10 mL), benzene (2×10 mL) then dried under vacuum. The resulting residue was converted to 115 by a method similar to that described in example 3, compound K (steps A, B, and C).

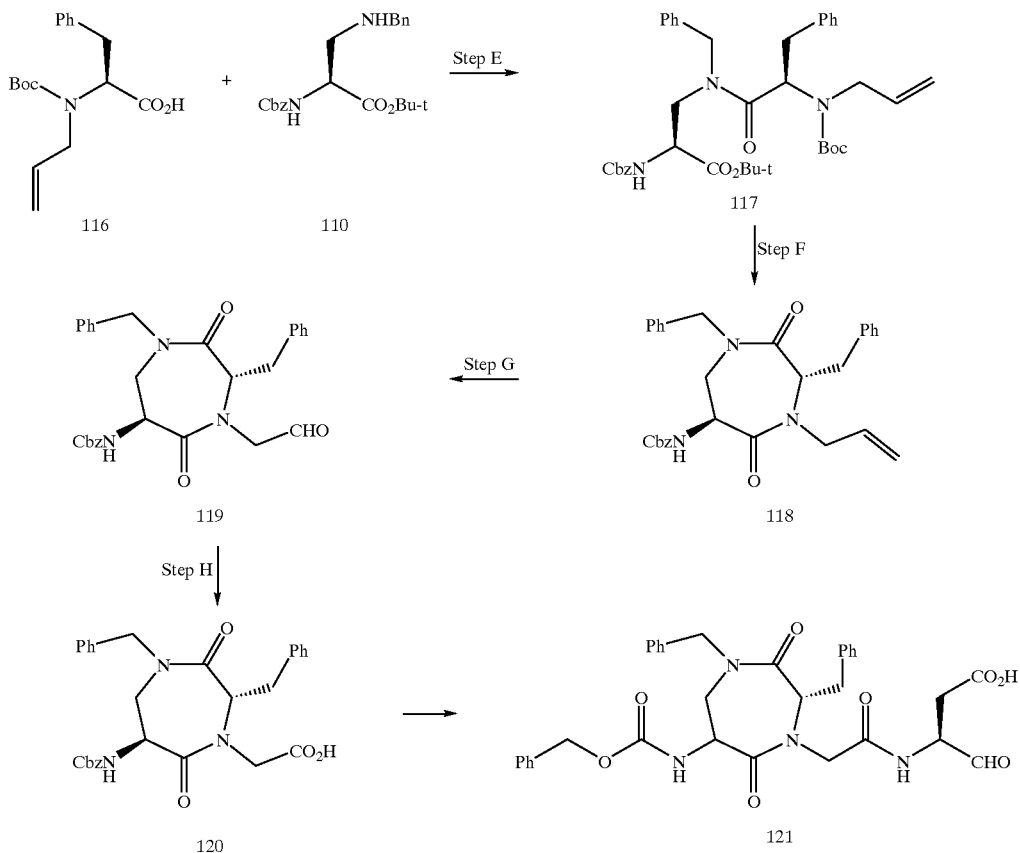

3-{2-[2,4-Dibenzyl-3,7-dioxo-6-(N-benzyloxycarbonylamino)-[1,4]diazepan-1-yl]-acetylamino}-4-oxo-butyric acid (121):

Step E. A solution of tert-butyl-2-N-carbobenzoxy-3-N-benzyl-(S)-2,3-diaminopropionate (110; 1.77 g, 4.6 mmol), N-allyl-N-tert-butoxycarbonyl-(S)-phenylalanine (116; 1.04 g, 4.8 mmol), HOBT (0.74 g, 5.5 mmol) and EDC (1.33 g, 6.9 mmol) in dichloromethane (50 mL) was allowed to stirr at 25° C. for 16 h then diluted with dichloromethane (100 mL) and washed with water. The organic layer was dried (MgSO$_4$), filtered and evaporated to give an oil. Chromatography (silica-gel, 85:15 hexane:ethyl acetate) gave 1.34 g (43% yield) of 117 as a colorless viscous oil.

Step F. A 1.34 g sample of 117 was dissolved in dichloromethane (3 mL) and treated with a 50% solution of trifluoroacetic acid in dichloromethane (20 mL). After 1.5 h, the solvent was removed under reduced pressure and the residue dried under vacuum then dissolved in dichloromethane (50 mL) and combined with 4-methylmorpholine (0.2 mL, 2 mmol), HOBT (0.27 g, 2 mmol) and EDC (0.8 g, 4 mmol). The mixture was stirred overnight at 25° C. then diluted with dichloromethane and washed with water. The organic layer was dried (MgSO$_4$), filtered and evaporated to give an oil. Chromatography (silica-gel, 7:3 hexane:ethyl acetate) gave 0.8 g (80% yield) of 118 as a viscous oil.

Step G. A 0.8 g sample of 118 was dissolved in methanol (40 mL), cooled to -78° C. and saturated with ozone until the solution was blue in color. The excess ozone was removed by purging with argon then dimethylsulfide (5 mL) was added and the mixture allowed to warm to 25° C. and stir 3 h. Solvent removal and chromatography (silica-gel, 1:1 hexane:ethyl acetate ) gave 0.74 g (74% yield) of 119 as a white solid.

Step H. A 0.2 g sample (0.4 mmol) of 119 was dissolved in acetone (25 mL), cooled to 0° C. and treated dropwise with a solution of Jones reagent until the orange color persisted. 2-Propanol (5 mL) was then added to the mixture and the resulting soltuion filtered through Celite and washed with acetone. Solvent removal gave a green-white solid that was dried under vacuum to give 120. The resulting residue was converted to 121 by a method similar to that described in example 3, compound K (steps A, B, and C). Chromatography (SiO$_2$, 95:4.5:0.5 dicholormethane:methanol:acetic acid eluent) gave 85 mg (53% yield) of cream colored solid which was identified as 3-{2-[2,4-dibenzyl-3,7-dioxo-6-(N-benzyloxycarbonylamino)-[1,4]diazepan-1-yl-acetylamino}-4-oxo-butyric acid (121) on the basis of the following spectral data: $^1$H NMR (500 MHz, CD$_3$OD) δ 2.38 (m, 1 H), 2.45 (m, 1 H), 3.21 (bs, 2 H), 3.32–3.39 (bm, 6 H), 3.85 (m, 1 H), 4.05 (m, 1 H), 4.21 (bm, 1 H), 4.31 (bs, 1 H), 4.45 (dm, J=11 Hz, 1 H), 4.95 (bs, 4 H), 7.20 (bs, 5 H), and 7.33–7.45 ppm (m, 5 H); $^{19}$F NMR (470 MHz, CD$_3$OD) d -10.62 ppm (s, 3 F).

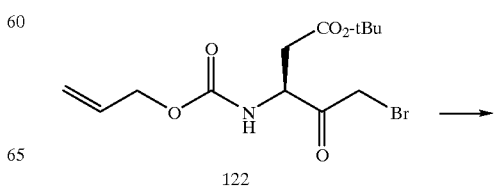

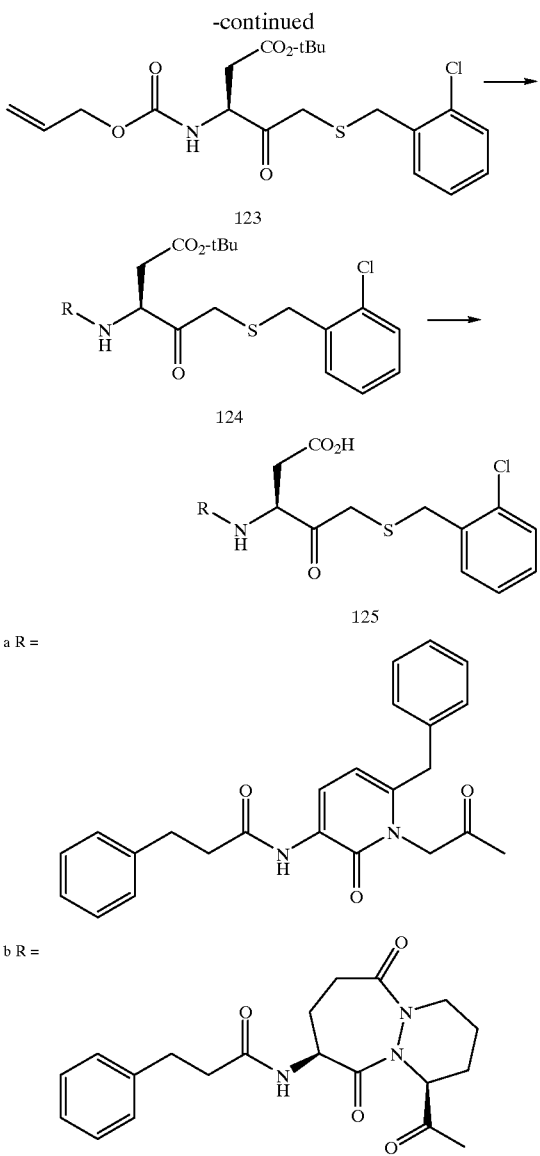

t-Butyl (3S) N-(allyloxycarbonyl)-3-amino-5-(2-chlorophenylmethylthio)-4-oxo-pentanoate (123). Potassium fluoride (273 mg, 4.70 mmol) and then 2-chlorophenylmethyl thiol (373 mg, 2.35 mmol) were added to a stirred solution of (3S) t-butyl N-(allyloxycarbonyl)-3-amino-5-bromo-4-oxo-pentanoate (122; 749 mg, 2.14 mmol; WO 93 16710) in dimethylformamide (20 ml). The mixture was stirred for 3.5 h, quenched with water (50 ml) and extracted with ethyl acetate (2×50 ml). The combined organic extracts were washed with water (4×50 ml) then brine (50 ml). They were dried (MgSO$_4$) and concentrated to afford an oil which was purified by flash chromatography (10–35% ethyl acetate/hexane) to afford 832 mg (91%) of a colourless solid: mp. 45–6° C.; $[\alpha]_D^{20}$ −19.0° (c 1.0, CH$_2$Cl$_2$); IR (film) 3340, 2980, 2935, 1725, 1712, 1511, 1503, 1474, 1446, 1421, 1393, 1368, 1281, 1244, 1157, 1052, 1040, 995, 764, 739; $^1$H NMR (CDCl$_3$) δ 7.36 (2H, m), 7.21 (2H, m), 5.91 (2H, m), 5.27 (2H, m), 4.76 (1H, m), 4.59 (2H, d), 3.78 (2H, s), 3.36 (2H, m), 2.91 (1H, dd), 2.74 (1H, dd), 1.43 (9H, s). Anal. Calcd for C$_{20}$H$_{26}$ClNO$_5$S: C, 56.13; H, 6.12; N, 3.27; S, 7.49. Found: C, 56.08; H, 6.11; N, 3.26; S, 7.54. MS (C.I.) 430/28 (M$^+$+1, 3%), 374/2 (100).

t-Butyl (3S) 3(2(6-benzyl-1,2-dihydro-2-oxo-3(3-phenylpropionylamino)-1-pyridyl)acetylamino-5-(2-chlorophenylmethylthio)-4-oxopentanoate (124a). 6-Benzyl-1,2-dihydro-2-oxo-3-(3-phenylpropionylamino)-pyridyl acetic acid (52b; 300 mg, 0.76 mmol) in THF (7 ml) was stirred with 1-hydroxybenzotriazole (205 mg, 1.52 mmol) and 1-(3-dimethylaminopropy-3-ethylcarbodiimide hydrochloride). After 3 min, water (12 drops) was added and the mixture stirred 10 min then treated with t-butyl (3S) N-(allyloxycarbonyl)-3-amino-5-(2-chlorophenylmethylthio)-4-oxopentanoate (123) (325 mg, 0.76 mmol), bis (triphenylphosphine) palladium II chloride (20 mg) and tributyltin hydride (0.6 ml, 2.28 mmol). The mixture was stirred for 5 h at room temperature, poured into ethyl acetate and washed with aqueous 1M HCl (×2), aqueous sodium bicarbonate, brine, dried (MgSO$_4$) and concentrated. The residue was triturated with pentane and the supernatant discarded. Chromatography (silica gel, 50% ethyl acetate/hexane) afforded a colourless foam (439 mg, 81%): $[\alpha]_D^{21}$ −18.3° (c 0.5, CH$_2$Cl$_2$); IR (KBr) 3356, 3311, 1722, 1689, 1646, 1599, 1567, 1513, 1367, 1154; $^1$H NMR (CDCl$_3$) δ 8.39 (1H, d), 8.23 (1H, s), 7.24 (14H, m), 6.16 (1H, d), 4.95 (1H, m), 4.63 (2H, m), 4.02 (2H, s), 3.74 (2H, s), 3.27 (2H, s), 2.85 (6H, m), 1.40 (9H, s). Anal. Calcd for C$_{39}$H$_{42}$ClN$_3$O$_6$S: C, 65.39; H, 5.91; N, 5.87. Found: C, 65.51; H, 5.99; N,5.77.

t-Butyl[3S(1S,9S)]-3-(6,10-dioxo-1,2,3,4,7,8,9,10-octahydro)-9-(3-phenylpropionylamino)-6H-pyridazine[1,2-a][1,2]diazepine-1-carboxamido-5-(2-chlorophenylmethylthio)-4-oxopentanoate (124b) was prepared by a similar method as 124a from the thioether 123 and 3S(1S,9S)-3-(6,10-dioxo-1,2,3,4,7,8,9,10-octahydro)-9-(3-phenylpropionylamino)-6H-pyridazino[1,2-a][1,2]diazepine-1-carboxylic acid (45a) to afford 452 mg (50%) of colourless foam: mp 55–7° C.; $[\alpha]_D^{22}$ −94.0° (c 0.12, CH$_2$Cl$_2$); IR (KBr) 3288, 2934, 1741, 1722, 1686, 1666, 1644, 1523, 1433, 1260, 1225, 1146, 757; $^1$H NMR (CDCl$_3$) δ 7.35 (3H, m), 7.20 (7H, m), 6.46 (1H, d), 5.21 (1H, m), 4.97 (2H, m), 4.56 (1H, m), 3.75 (2H, s), 3.25 (3H, m), 2.93 (5H, m), 2.71 (1H, dd), 2.55 (2H, m), 2.30 (1H, m), 1.92 (3H, m), 1.66 (2H, m), 1.42 (9H, s). Anal. Calcd for C$_{35}$H$_{43}$ClN$_4$O$_7$S. 0.25H$_2$O: C, 59.73; H, 6.23; Cl, 5.04; N, 7.96; S, 4.56. Found: C, 59.73; H, 6.19; Cl, 5.10; N, 7.79; S, 4.58. MS (−FAB) 697 (M-1, 100).

(3S) 3(2(6-Benzyl-1,2-dihydro-2-oxo-3-(3-phenylpropionylamino)-1-pyridyl)acetylamino-5-(2-chlorphenylmethylthio)-4-oxopentanoic acid (125a). t-Butyl-3(2(6-benzyl-1,2-dihydro-2-oxo-3-(3-phenylpropionylamino)-1-pyridyl)acetyl-amino-5-(2-chlorophenylmethylthio)-4-oxopentanoate (124a) (400 mg, 0.56 mmol) in dichloromethane (3 ml) at 0° C. was treated with trifluoroacetic acid (3 ml) and stirred at 0° C. for 1 h and room temperature for 0.5 h. The solution was concentrated then redissolved in dichloromethane and reconcentrated. This procedure was repeated three times. The residue was stirred in ether for 1 hr and filtered to yield a colourless solid (364 mg, 99%): mp. 165–7° C.; $[\alpha]_D^{22}$ −27.7° (c 0.2, CH$_2$Cl$_2$); IR (KBr) 3289, 1712, 1682, 1657, 1645, 1593, 1562, 1527, 1497, 1416, 1203, 1182; $^1$H NMR (CDCl$_3$) d 8.47 (1H, d), 8.21 (1H, s), 7.70 (1H, d), 7.22 (14H, m), 6.24 (1H, d), 5.03 (1H, m), 4.65 (2H, m), 4.06 (2H, s), 3.69 (2H, m), 3.23 (2H, m), 2.88 (6H, m).

[3S(1S, 9S)]-3-(6,10-dioxo-1,2,3,4,7,8,9,10-octahydro)-9-(3-phenylpropionyl-amino)-6H-pyridazine[1,2-a][1,2]diazepine-1-carboxamido-5-(2-chlorophenyl-methylthio)-4-oxopentanoic acid (125b), was prepared by a similar method as 125a from the t-butyl ester 124b to afford 362 mg (93%)

of colourless powder: mp 76–80° C.; $[\alpha]_D^{21}$ −134° (c 0.10, MeOH); IR (KBr) 3309, 2935, 1725, 1658, 1528, 1445, 1417, 1277, 1219, 1175; $^1$H NMR (D$_6$-DMSO) δ 8.80 (1H, d), 8.19 (1H, d), 7.31 (9H, m), 5.09 (1H, m), 4.74 (1H, m), 4.63 (1H, m), 4.35 (1H, m), 3.76 (2H, m), 3.28 (3H, m), 2.80 (5H, m), 2.52 (4H, m), 2.16 (2H, m), 1.90 (3H, m). Anal. Calcd for $C_{31}H_{35}Cl_2N_4O_7S \cdot 0.25H_2O$: C, 57.49; H, 5.53; N, 8.65; S, 4.95. Found: C, 57.35; H, 5.43; N, 8.45; S, 4.88. MS (−FAB) 641 (M-1, 100).

The data of the examples above demonstrate that compounds according to this invention display inhibitory activity towards IL-1β Converting Enzyme.

Insofar as the compounds of this invention are able to inhibit ICE in vitro and furthermore, may be delivered orally to mammals, they are of evident clinical utility for the treatment of IL-1 mediated diseases. These tests are predictive of the compounds ability to inhibit ICE in vivo.

While we have described a number of embodiments of this invention, it is apparent that our basic constructions may be altered to provide other embodiments which utilize the products and processes of this invention. Therefore, it will be appreciated that the scope of this invention is to be defined by the appended claims, rather than by the specific embodiments which have been presented by way of example.

We claim:

1. A compound represented by the formula:

$$R_1-NH-X_1\begin{matrix}(CJ_2)_{\overline{m}}-T\\(CH_2)_{\overline{g}}-R_3\end{matrix} \qquad \alpha$$

wherein:
 $X_1$ is —CH;
 g is 0 or 1;
 each J is independently —H, —OH, or —F, provided that when a first and second J are bound to a C and said first J is —OH, said second J is —H;
 m is 0, 1, or 2;
 T is —OH, —CO—CO$_2$H, —CO$_2$H, —CO—CH$_2$OH, —CO—NHOH, —SO$_2$—NHR, —SO$_3$H, —PO(OH)NH$_2$, —CONHCN, —OSO$_3$H, —CO—NHSO$_2$R$_{16}$, —PO(OH)$_2$, —PO(OH) (OR$_{16}$), —PO(OH) (R$_{16}$), —OPO(OH)$_2$, —OPO(OH) (OR$_{16}$), —OPO(OH) (R$_{16}$), —NHPO(OH)$_2$, —NHPO(OH) (OR$_{16}$), —NHPO(OH) (R$_{16}$),

[structures shown]

$R_{15}$ is —H, a —C$_{1-6}$ alkyl group, or the bond linking T to (CJ$_2$)$_m$;
 $R_{16}$ is a —C$_{1-6}$ alkyl group;
 $R_1$ is selected from the group consisting of the following formulae, in which any ring may optionally be singly or multiply substituted at any carbon by $Q_1$ at any nitrogen by $R_5$, or at any atom by =O, —OH, —CO$_2$H, or halogen; any saturated ring may optionally be unsaturated at one or two bonds; and wherein $R_1$ (e) is optionally benzofused;

[structure (e) shown]

$R_3$ is:
  —CN,
  —CH=CH—R$_9$,
  —CH=N—O—R$_9$,
  —(CH$_2$)$_{1-3}$—T$_1$—R$_9$,
  —CJ$_2$—R$_9$,
  —CO—R$_{13}$, or $$-CO-CO-N\begin{matrix}R_5\\R_{10}\end{matrix};$$

each $R_4$ is independently:
 —H,
 —Ar$_1$,
 —R$_9$,
 —T$_1$—R$_9$, or
 —(CH$_2$)$_{1,2,3}$—T$_1$—R$_9$;
each $T_1$ is independently:
 CH=CH—,
 —O—,
 —S—,
 —SO—,
 —SO$_2$,
 —NR$_{10}$—,
 —NR$_{10}$—CO—,
 —CO—, —O—CO—,
—CO—O—,
—CO—NR$_{10}$—,
—O—CO—NR$_{10}$—,
—NR$_{10}$—CO—O—,
—NR$_{10}$—CO—NR$_{10}$—,
—SO$_2$—NR$_{10}$—,
—NR$_{10}$—SO$_2$—, or
—NR$_{10}$—SO$_2$—NR$_{10}$—;

each R$_5$ is independently:
—H,
—Ar$_1$,
—CO—Ar$_1$,
—SO$_2$Ar$_1$,
—CO—NH$_2$,
—SO$_2$NH$_2$,
—R$_9$,
—CO—R$_9$,
—CO—O—R$_9$,
—SO$_2$—R$_9$, —CO—N(Ar$_1$)(R$_{10}$), —SO$_2$—N(Ar$_1$)(R$_{10}$), —CO—N(R$_9$)(R$_{10}$), or

—SO$_2$—N(R$_9$)(R$_{10}$);

each R$_9$ is a C$_{1-6}$ straight or branched alkyl group optionally singly or multiply substituted by —OH, —F, or =O and optionally substituted with one or two Ar$_1$ groups;

each R$_{10}$ is independently —H or a C$_{1-6}$ straight or branched alkyl group;

each R$_{13}$ is independently —Ar$_2$, —R$_4$ or

—N(R$_5$)—OH;

each Ar$_1$ is a cyclic group independently selected from an aryl group which contains 6, 10, 12, or 14 carbon atoms and between 1 and 3 rings, a cycloalkyl group which contains between 3 and 15 carbon atoms and between 1 and 3 rings, said cycloalkyl group being optionally benzofused, or a heterocycle group containing between 5 and 15 ring atoms and between 1 and 3 rings, said heterocycle group containing at least one heteroatom group selected from —O—, —S—, —SO—, —SO$_2$—, =N—, and —NH—, said heterocycle group optionally containing one or more double bonds, said heterocycle group optionally comprising one or more aromatic rings, and said cyclic group optionally being singly or multiply substituted by —NH$_2$, —CO$_2$H, —Cl, —F, —Br, —I, —NO$_2$, —CN, =O, —OH, -perfluoro C$_{1-3}$ alkyl,

[oxetane structure with CH$_2$]

each Ar$_2$ is independently selected from the following group, in which any ring may optionally be singly or multiply substituted by —Q$_1$ and —Q$_2$:

(hh) [benzofused 5-ring heterocycle with X, Y]

(ii) [5-membered heterocycle with X, X, Y]

(jj) [5-membered heterocycle with N, X, Y], and (kk) [5-membered heterocycle with N, Y, X];

each Q$_1$ is independently:
—Ar$_1$,
—O—Ar$_1$,
—R$_9$,
—T$_1$—R$_9$, or
—(CH$_2$)$_{1,2,3}$—T$_1$—R$_9$;

each Q$_2$ is independently —OH, —NH$_2$—CO$_2$H, —Cl, —F, —Br, —I, —NO$_2$, —CN, —CF$_3$, or

[oxetane structure with CH$_2$];

provided that when —Ar$_1$ is substituted with a Q$_1$ group which comprises one or more additional —Ar$_1$ groups, said additional —Ar$_1$ groups are not substituted with Q$_1$;

each X is independently =N— or =CH—;
each X$_2$ is independently —O—, —CH$_2$—, —NH—, —S—, —SO—, or —SO$_2$—;
each X$_5$ is independently —CH(|)—   or   —N(|)—;

each Y is independently —O—, —S—, or —NH;
each Z is independently CO or SO$_2$;
each a is independently 0 or 1;
each d is independently 0, 1, or 2; and
each e is independently 0, 1, 2, or 3; provided that when $R_1$ is:
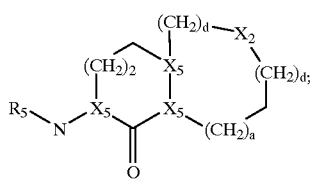
then $R_5$ cannot be:
—$Ar_1$,
—$SO_2$—$Ar_1$,
—CO—$R_9$,
—$SO_2$—$R_9$,
—CO—$NH_2$,
—$SO_2$—$NH_2$,
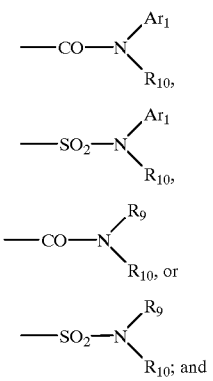
and
when $R_1$ is
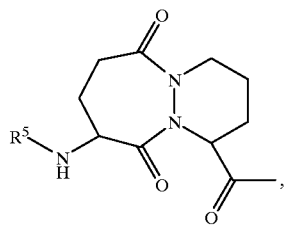
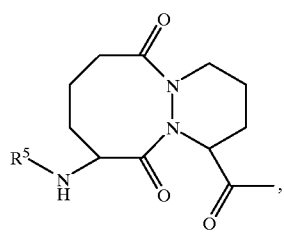
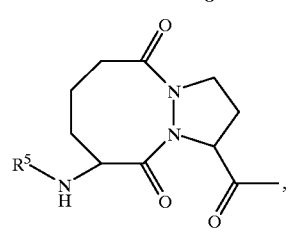
(e)
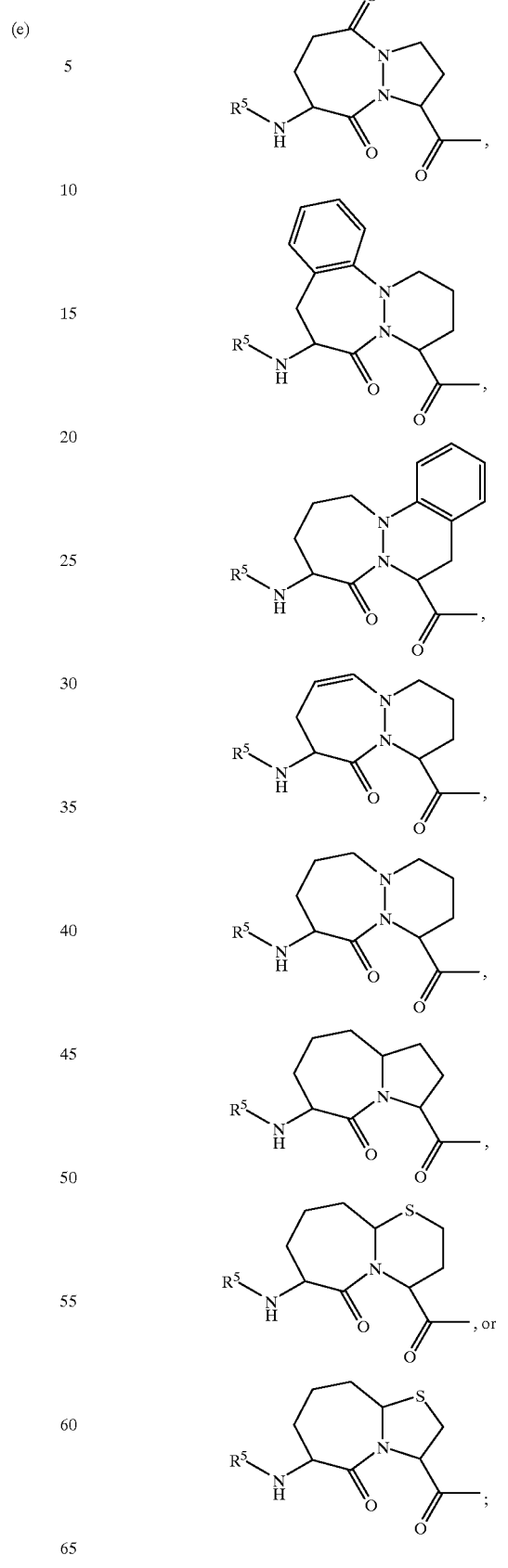
$g$ is 0;

J is —H;
m is 1;
T is —CO$_2$H; and
R$_3$ is —CO—R$_{13}$, wherein R$_{13}$ is:
—H,
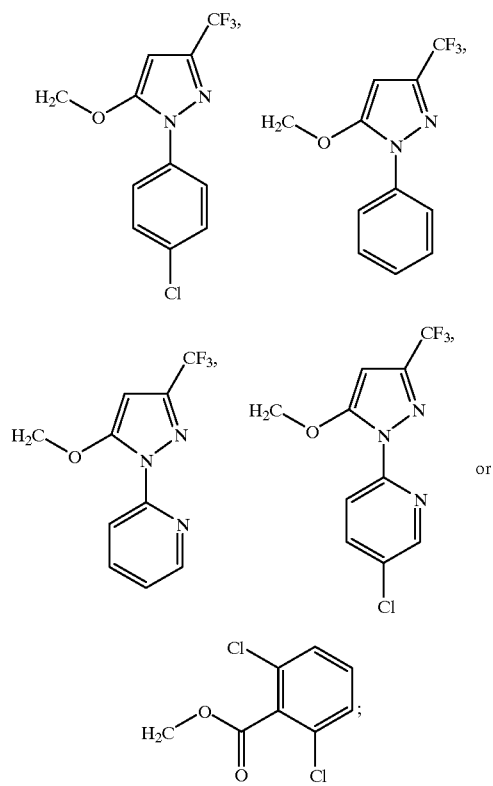
then R$_5$ cannot be:
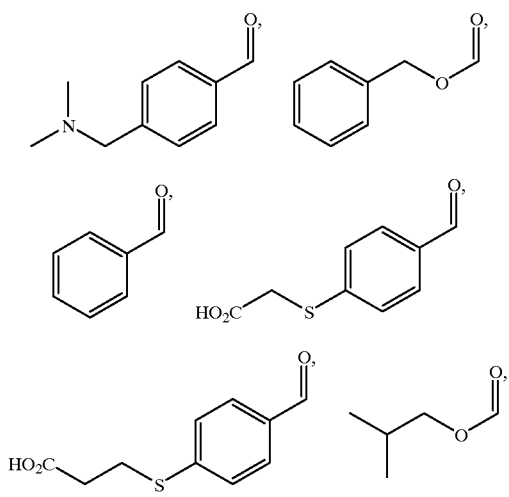
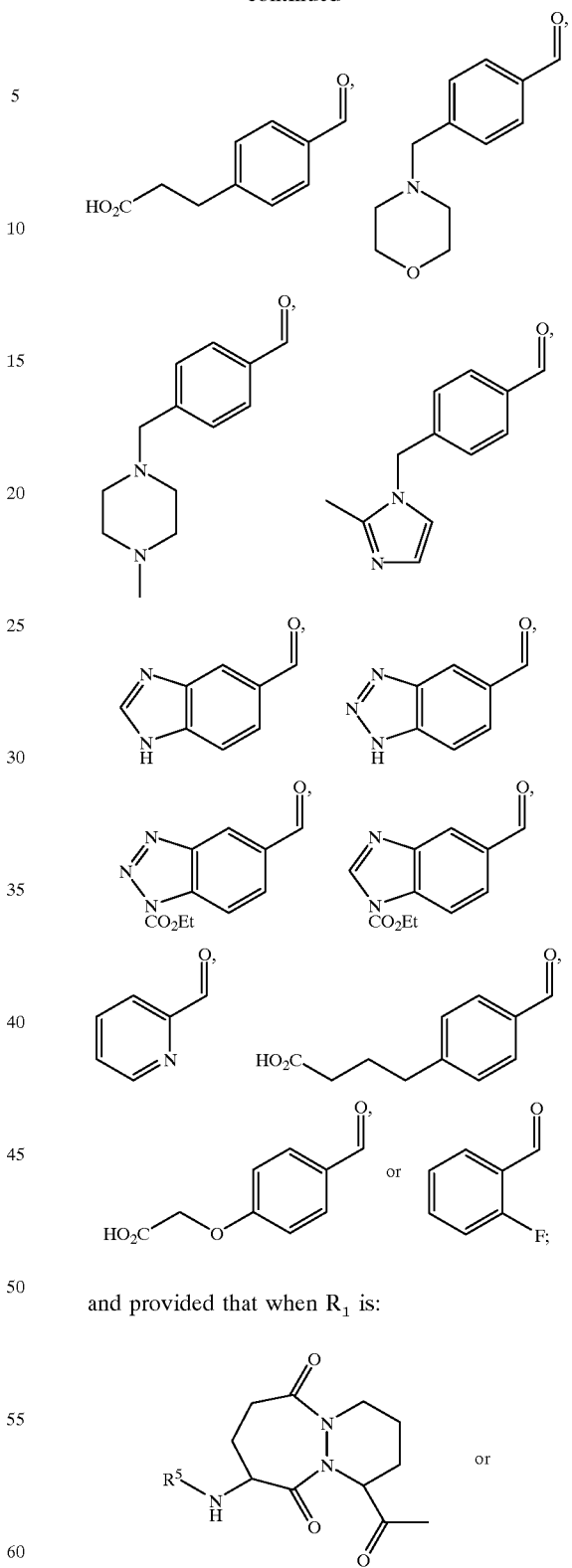
and provided that when R$_1$ is:

-continued

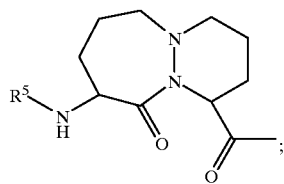

g is 0;

J is —H;

m is 1;

T is —CO$_2$H; and

R$_3$ is —CO—R$_{13}$, wherein R$_{13}$ is H;

then R$_5$ may not be —C(O)—CH$_2$CH$_2$Ph.

2. The compound according to claim 1, wherein R$_5$ is —CO—R$_9$.

3. The compound according to claims 1 or 2, wherein R$_1$ is:

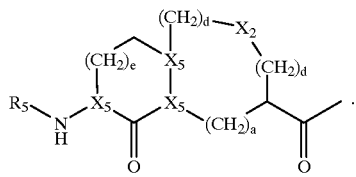 (e)

4. The compound according to claim 1, wherein:

X$_1$ is —CH;

g is 0;

J is —H;

m is 0 or 1 and T is —CO—CO$_2$H, —CO—CH$_2$OH, —CO—NHOH, —SO$_2$—NHR, —SO$_3$H, —PO(OH)NH$_2$, —CONHCN, —OSO$_3$H, —CO—NHSO$_2$R$_{16}$, —PO(OH)$_2$, —PO(OH) (OR$_{16}$), —PO(OH) (R$_{16}$), —OPO(OH)$_2$, —OPO(OH) (OR$_{16}$), —OPO(OH) (R$_{16}$), —NHPO(OH)$_2$, —NHPO(OH) (OR$_{16}$), —NHPO(OH) (R$_{16}$),

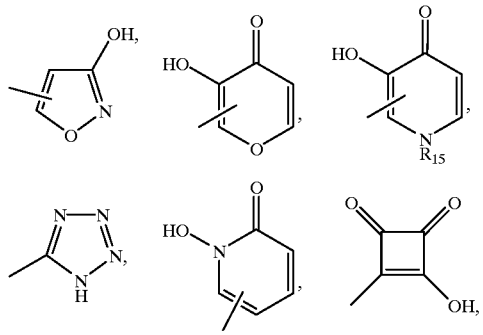

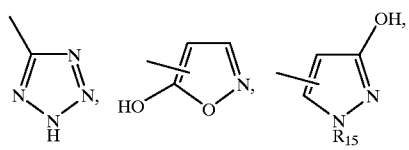

-continued

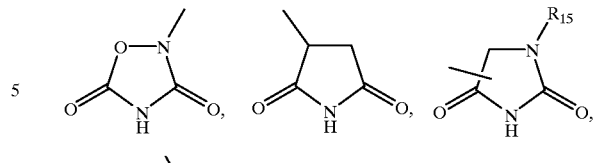

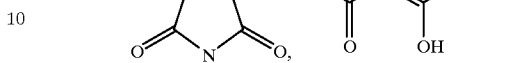

or m is 1 and T is —CO$_2$H;

R$_{15}$ is —H, a —C$_{1-6}$ alkyl group, or the bond linking T to (CJ$_2$)$_m$;

R$_{16}$ is a —C$_{1-6}$ alkyl group;

R$_1$ is selected from the group consisting of the following formulae, in which any ring may optionally be singly or multiply substituted at any carbon by Q$_1$, at any nitrogen by R$_5$, or at any atom by =O, —OH, —CO$_2$H, or halogen, and wherein (e) is optionally benzofused:

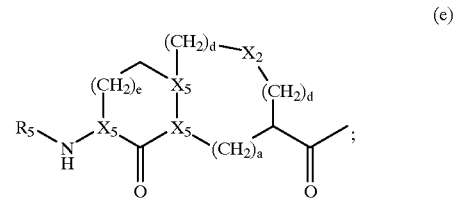 (e)

R$_5$ is —CO—Ar$_1$, —SO$_2$—Ar$_1$, —CO—NH$_2$, —CO—NH—Ar$_1$, —CO—R$_9$, —CO—O—R$_9$, —SO$_2$—R$_9$, or —CO—NH—R$_9$;

R$_6$ is —H, —R$_9$, or —Ar$_1$;

R$_9$ is a C$_{1-6}$ straight or branched alkyl group optionally substituted with =O and optionally substituted with —Ar$_1$;

R$_{10}$ is —H or a —C$_{1-3}$ straight or branched alkyl group;

Ar$_1$ is phenyl, naphthyl, pyridyl, benzothiazolyl, thienyl, benzothienyl, benzoxazolyl, 2-indanyl, or indolyl optionally being singly or multiply substituted with —O—C$_{1-3}$ alkyl, —NH—C$_{1-3}$ alkyl, —N—(C$_{1-3}$ alkyl)$_2$—Cl, —F, —CF$_3$, —C$_{1-3}$ alkyl, or

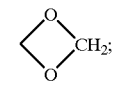

Q$_1$ is R$_9$ or —(CH$_2$)$_{0,1,2}$—T$_1$—(CH$_2$)$_{0,1,2}$—Ar$_1$, wherein T$_1$ is —O— or —S—;

each X is independently =N— or =CH—;
each $X_2$ is independently —O—, —CH$_2$—, —NH—, —S—, —SO—, or —SO$_2$—;
each $X_5$ is independently

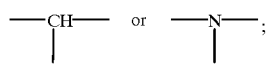

and
Z is C=O.

5. The compound according to claim 4, wherein $R_3$ is:
—CO—$R_{13}$, or

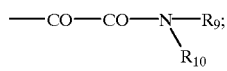

$T_1$ is:
—O— or
—S—;
$R_9$ is a $C_{1-6}$ straight or branched alkyl group optionally substituted with =O and optionally substituted with $Ar_1$; and
$R_{13}$ is:
—H,
—$R_9$,
—$Ar_2$, or
—CH$_2$—$T_1$—$R_9$.

6. The compound according to claim 5, wherein:
$R_{13}$ is H.

7. The compound according to claim 4 or 2, wherein the $R_1$ group is:

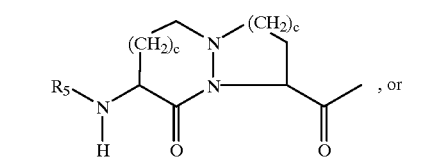
(e1)

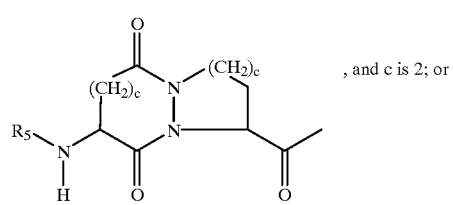
(e2)
, and c is 2; or

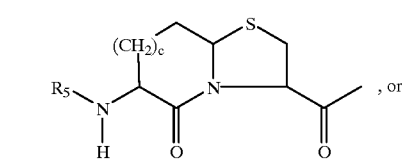
(e4)
, or

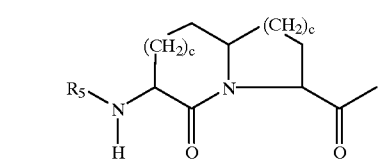
(e7)

which is optionally benzofused, and c is 1 or 2;

provided that when $R_1$ is (e4),
g is 0,
J is —H,
m is 1,
T is —CO$_2$H,
$R_5$ is benzyloxycarbonyl, and
c is 1,
then $R_3$ cannot be —CO—$R_{13}$ when
$R_{13}$ is —CH$_2$—O—$Ar_1$ and
$Ar_1$ is 1-phenyl-3-trifluoromethyl-pyrazole-5-yl, wherein the phenyl is optionally substituted with a chlorine atom; or when
$R_{13}$ is —CH$_2$—O—CO—$Ar_1$, wherein
$Ar_1$ is 2,6-dichlorophenyl,
and when the 2-position of the scaffold ring is substituted with para-fluoro-phenyl; and
also provided that when
$R_1$ is (e7),
g is 0,
J is —H,
m is 1,
T is —CO$_2$H or —CO—NH—OH,
$R_5$ is a protective group for the N atom of an amino acid side chain residue, and
each c is 1,
then $R_3$ cannot be —CO—$R_{13}$ when $R_{13}$ is:
—CH$_2$—O—CO—$Ar_1$,
—CH$_2$—S—CO—$Ar_1$,
—CH$_2$—O—$Ar_1$, or
—CH$_2$—S—$Ar_1$.

8. The compound according to claim 7, wherein:
$R_1$ is:

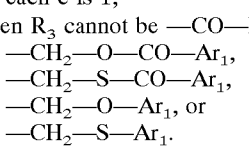
(e1)
, or

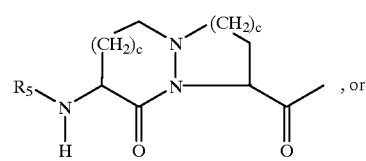
(e2)
and c is 2;

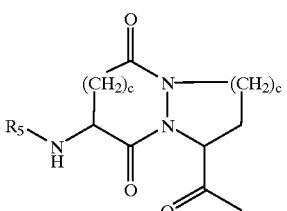

m is 1;
T is —CO$_2$H; and
$R_3$ is —CO—$R_{13}$.

9. A pharmaceutical composition comprising a compound according to any one of claims 3, 1, 4, 7, 5, 6, 8, and 2 in an amount effective for treating an IL-1 mediated disease and a pharmaceutically acceptable carrier.

10. A pharmaceutical composition comprising a compound according to any one of claims 3, 1, 4, 7, 5, 6, 8, and 2 in an amount effective for treating an autoimmune disease and a pharmaceutically acceptable carrier.

11. A pharmaceutical composition comprising a compound according to any one of claims 3, 1, 4, 7, 5, 6, 8, and 2 in an amount effective for treating an inflammatory disease and a pharmaceutically acceptable carrier.

12. A pharmaceutical composition comprising a compound according to any one of claims 1, 3, 4, 7, 5, 6, 8, and 2 in an amount effective for inhibiting a neurodegenerative disease and a pharmaceutically acceptable carrier.

13. A pharmaceutical composition comprising a compound according to any one of claims 1, 3, 4, 7, 5, 6, 8, and 2 in an amount effective for inhibiting an ICE-mediated function and a pharmaceutically acceptable carrier.

* * * * *

```
                         SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
         (A) LENGTH: 4 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (ix) FEATURE:
         (A) NAME/KEY: Modified-site
         (B) LOCATION: 1
         (D) OTHER INFORMATION: /product= "OTHER"
             /note= "tyrosine is succinylated"

(ix) FEATURE:
         (A) NAME/KEY: Modified-site
         (B) LOCATION: 4
         (D) OTHER INFORMATION: /product= "OTHER"
             /note= "aspartic acid residue is derivatized with
             p-nitroanilide"

(xi) SEQUENCE DESCRIPTION: SEQ ID NO:1:

Tyr Val Ala Asp
    1

(2) INFORMATION FOR SEQ ID NO:2:

(i) SEQUENCE CHARACTERISTICS:
         (A) LENGTH: 4 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (ix) FEATURE:
         (A) NAME/KEY: Modified-site
         (B) LOCATION: 1
         (D) OTHER INFORMATION: /product= "OTHER"
             /note= "tyrosine is acetylated"

(ix) FEATURE:
         (A) NAME/KEY: Modified-site
```

(B) LOCATION: 4
(D) OTHER INFORMATION: /product= "OTHER"
    /note= "aspartic acid is derivatized with
    amino-4-methylcoumarin"

(xi) SEQUENCE DESCRIPTION: SEQ ID NO:2:

Tyr Val Ala Asp